US012728132B2

(12) United States Patent
Ke et al.

(10) Patent No.: US 12,728,132 B2
(45) Date of Patent: Sep. 8, 2026

(54) INHIBITORS OF THE PEPTIDYL-PROLYL CIS/TRANS ISOMERASE (PIN1), COMBINATIONS AND USES THEREOF

(71) Applicants: DANA-FARBER CANCER INSTITUTE, INC., Boston, MA (US); BETH ISRAEL DEACONESS MEDICAL CENTER, INC., Boston, MA (US); YEDA RESEARCH AND DEVELOPMENT CO. LTD., Rehovot (IL)

(72) Inventors: Shizhong Ke, Boston, MA (US); Gerburg Wulf, Boston, MA (US); Xiao Zhen Zhou, Newton, MA (US); Nir London, Rehovot (IL); Wenyi Wei, Boston, MA (US); Kun Ping Lu, Newton, MA (US); Nathanael S. Gray, Stanford, CA (US); Behnam Nabet, Boston, MA (US)

(73) Assignees: DANA-FARBER CANCER INSTITUTE, INC., Boston, MA (US); BETH ISRAEL DEACONESS MEDICAL CENTER, INC., Boston, MA (US); YEDA RESEARCH AND DEVELOPMENT CO. LTD., Rehovot (IL)

( * ) Notice: Subject to any disclaimer, the term of this patent is extended or adjusted under 35 U.S.C. 154(b) by 329 days.

(21) Appl. No.: 18/694,557

(22) PCT Filed: Sep. 23, 2022

(86) PCT No.: PCT/US2022/076950
§ 371 (c)(1),
(2) Date: Mar. 22, 2024

(87) PCT Pub. No.: WO2023/049851
PCT Pub. Date: Mar. 30, 2023

(65) Prior Publication Data

US 2025/0127783 A1 Apr. 24, 2025

Related U.S. Application Data

(60) Provisional application No. 63/248,100, filed on Sep. 24, 2021.

(51) Int. Cl.

| | |
|---|---|
| ***A61K 31/519*** | (2006.01) |
| ***A61K 31/203*** | (2006.01) |
| ***A61K 31/381*** | (2006.01) |
| ***A61K 31/506*** | (2006.01) |
| ***A61K 33/36*** | (2006.01) |
| ***A61P 35/00*** | (2006.01) |
| ***C07K 16/28*** | (2006.01) |

(52) U.S. Cl.
CPC .......... *A61K 31/519* (2013.01); *A61K 31/203* (2013.01); *A61K 31/381* (2013.01); *A61K 31/506* (2013.01); *A61K 33/36* (2013.01); *A61P 35/00* (2018.01); *C07K 16/2827* (2013.01)

(58) Field of Classification Search
CPC .. A61K 31/519; A61K 31/203; A61K 31/506; A61K 33/36; A61P 35/00; C07K 16/2827
See application file for complete search history.

(56) References Cited

U.S. PATENT DOCUMENTS

| | | | |
|---|---|---|---|
| 10,265,288 | B2 | 4/2019 | Lu et al. |
| 10,413,548 | B2 | 9/2019 | Lu et al. |
| 2005/0239095 | A1 | 10/2005 | Lu et al. |
| 2017/0202799 | A1 | 7/2017 | Lu et al. |
| 2019/0365710 | A1 | 12/2019 | Fedoriw et al. |

FOREIGN PATENT DOCUMENTS

| | | | |
|---|---|---|---|
| WO | 2015181737 | A1 | 12/2015 |
| WO | 2021133601 | A1 | 7/2021 |

OTHER PUBLICATIONS

Chen et al., "Targeting PIN1 exerts potent antitumor activity in pancreatic ductal carcinoma via inhibiting tumor metastasis," Cancer Science, vol. 110(8), pp. 2442-2455, DOI: 10.1111/cas.14085 (2019), 14 pages.
Cheng et al., "Targeting PIN1 as a Therapeutic Approach for Hepatocellular Carcinoma," Frontiers in Cell and Developmental Biology, vol. 7:369, DOI: 10.3389/fcell.2019.00369 (2019), 12 pages.
Huang et al., "Targeting Pin1 by All-Trans Retinoic Acid (ATRA) Overcomes Tamoxifen Resistance in Breast Cancer via Multifactorial Mechanisms," Frontiers in Cell and Developmental Biology, vol. 7:322, DOI: 10.3389/fcell.2019.00322 (2019), 15 pages.
Koikawa et al., "Targeting Pin1 renders pancreatic cancer eradicable by synergizing with immunochemotherapy," Cell, vol. 184(18):4753-4771, DOI: 10.1016/j.cell.2021.07.020 (2021), 47 pages.
Dubiella et al., "Sulfopin is a covalent inhibitor of Pin1 that blocks Myc-driven tumors in vivo," Nat Chem Biol., vol. 17(9):954-963, DOI:10.1038/s41589-021-00786-7 (2021), 38 pages.

*Primary Examiner* — Kamal A Saeed
(74) *Attorney, Agent, or Firm* — ArentFox Schiff LLP; Daniel W. Clarke

(57) ABSTRACT

Disclosed are methods of treating diseases or disorders mediated by dysregulated CDK4/6 and/or Pin 1 activity comprising co-administering a therapeutically effective amount of one or more CDK4/6 inhibitors, and a therapeutically effective amount of one or more Pin1 inhibitors, or a pharmaceutically acceptable salt or salts thereof.

21 Claims, 106 Drawing Sheets

Specification includes a Sequence Listing.

shCon
shCdh1
shCdc20
shCon
shCdh1
shCdc20
ATRA
Pin1
Cdh1
Cdc20
GAPDH
MCF7
MDA-MB-231

WT
CDH1-KO
AApin
Pin1
Cdh1
β-actin
MEFs

WT
CDH1-KO
Sulfopin
Pin1
Cdh1
β-actin
MEFs

Colocalization rate: 80.84 ± 8.7% (n=24)

Control
HA-Cdh1
+ GST
+ GST-Pin1
+ GST-WW
+ GST-PPI
Cdh1
Bound
Cdh1
Input
GST-Pin1
GST-PPI
GST-WW
GST
Relative Cdh1 intensity
1.0
0.5
0.0
GST
GST-Pin1
GST-WW
GST-PPI Sulfopin-treated
HA-Cdh1
+ GST
+ GST-Pin1
+ GST-WW
+ GST-PPI
Cdh1
Bound
Cdh1
Input
GST-Pin1
GST-PPI
GST-WW
GST
Relative Cdh1 intensity
1.0
0.5
0.0
GST
GST-Pin1
GST-WW
GST-PPI

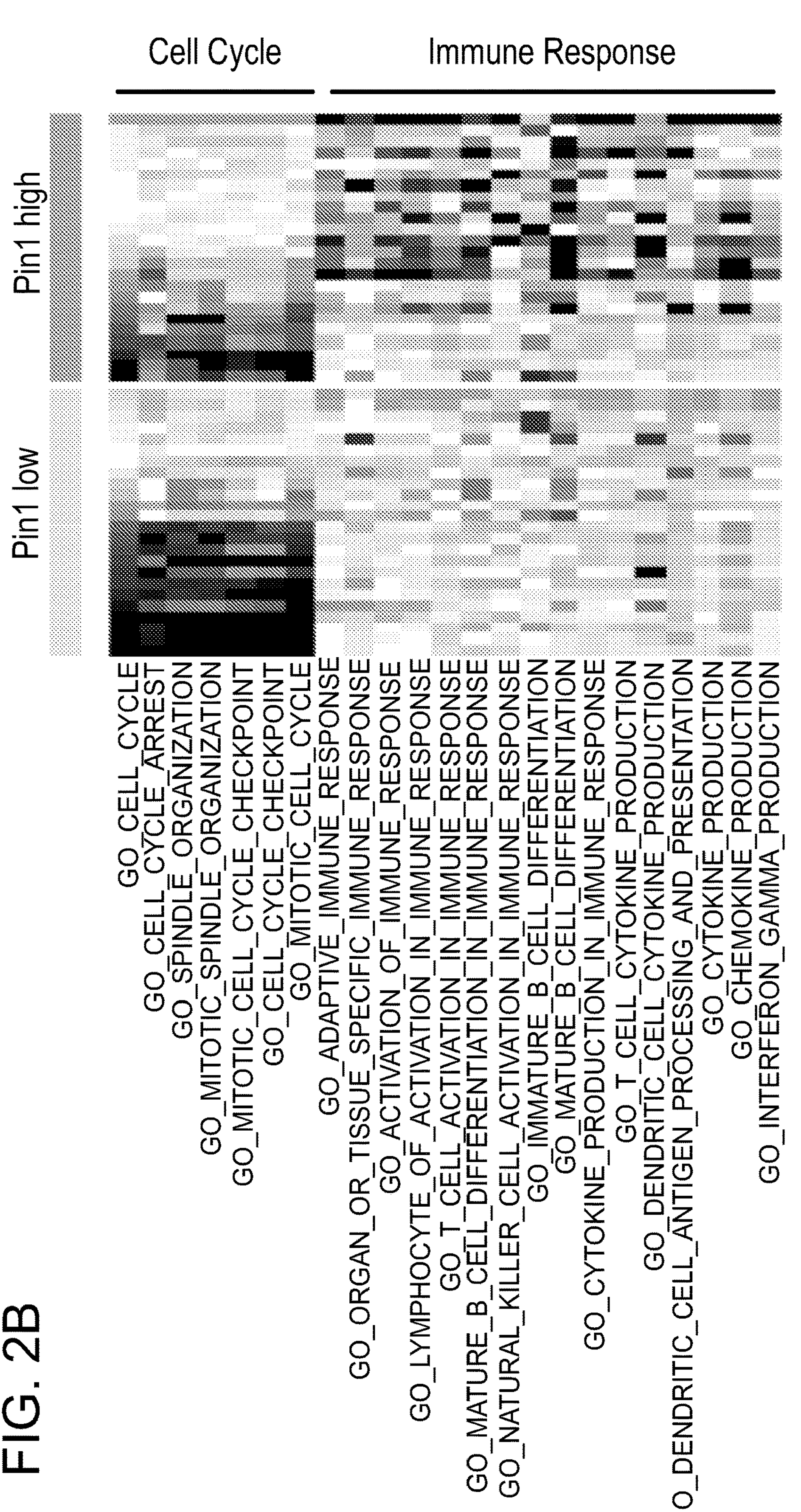
FIG. 2B
Cell Cycle
Immune Response
Pin1 high
Pin1 low
row min
mean
row max
GO_CELL_CYCLE
GO_CELL_CYCLE_ARREST
GO_SPINDLE_ORGANIZATION
GO_MITOTIC_SPINDLE_ORGANIZATION
GO_MITOTIC_CELL_CYCLE_CHECKPOINT
GO_CELL_CYCLE_CHECKPOINT
GO_MITOTIC_CELL_CYCLE
GO_ADAPTIVE_IMMUNE_RESPONSE
GO_ORGAN_OR_TISSUE_SPECIFIC_IMMUNE_RESPONSE
GO_ACTIVATION_OF_IMMUNE_RESPONSE
GO_LYMPHOCYTE_OF_ACTIVATION_IN_IMMUNE_RESPONSE
GO_T_CELL_ACTIVATION_IN_IMMUNE_RESPONSE
GO_MATURE_B_CELL_DIFFERENTIATION_IN_IMMUNE_RESPONSE
GO_NATURAL_KILLER_CELL_ACTIVATION_IN_IMMUNE_RESPONSE
GO_IMMATURE_B_CELL_DIFFERENTIATION
GO_MATURE_B_CELL_DIFFERENTIATION
GO_CYTOKINE_PRODUCTION_IN_IMMUNE_RESPONSE
GO_T_CELL_CYTOKINE_PRODUCTION
GO_DENDRITIC_CELL_CYTOKINE_PRODUCTION
GO_DENDRITIC_CELL_ANTIGEN_PROCESSING_AND_PRESENTATION
GO_CYTOKINE_PRODUCTION
GO_CHEMOKINE_PRODUCTION
GO_INTERFERON_GAMMA_PRODUCTION shRNF149 con 1 2 3 4 5

AApin - + - + - + - + - + - +

Pin1

β-actin shWWP2 con 1 2 3 4

AApin - + - + - + - + - +

Pin1

β-actin

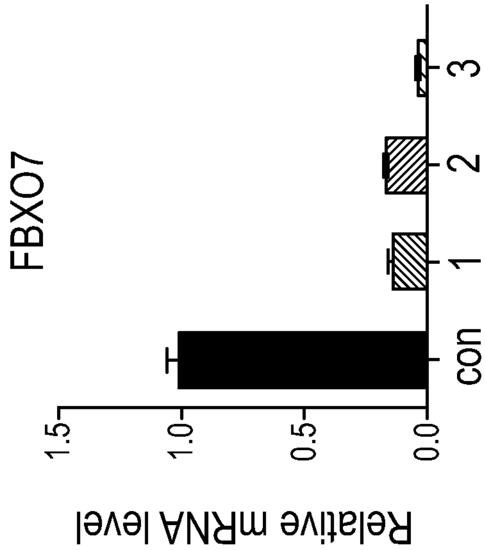
FIG. 3G
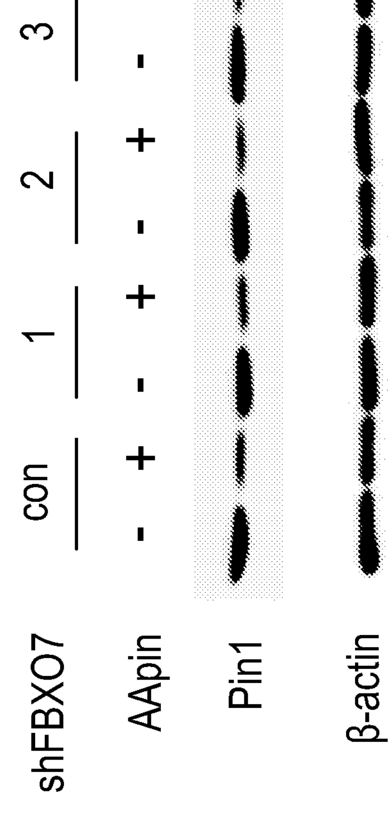

N
C
WW
PPlase
1
39
50
163
hPin1 117 KARGDLGAFSRG 128
mPin1 119 KARGDLGPFSRG 130
Preference for basic residues
Canonical positions
Preference for alanine or proline
Canonical positions
Disfavors bulk residues
Preference for acidic amino acids
Preference for V/I/L
Preference for polar uncharged
Preference for asparagine
X X R X X L X X Ψ X X X
-2 -1 1 2 3 4 5 6 7 8 9 10
Destruction Box

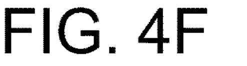
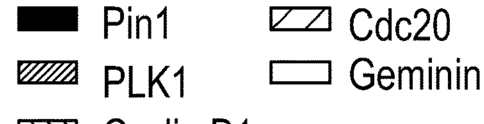
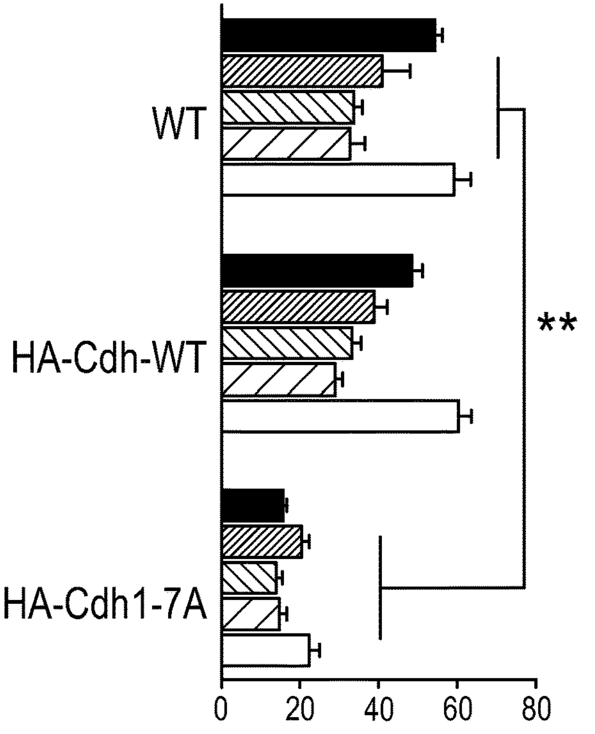
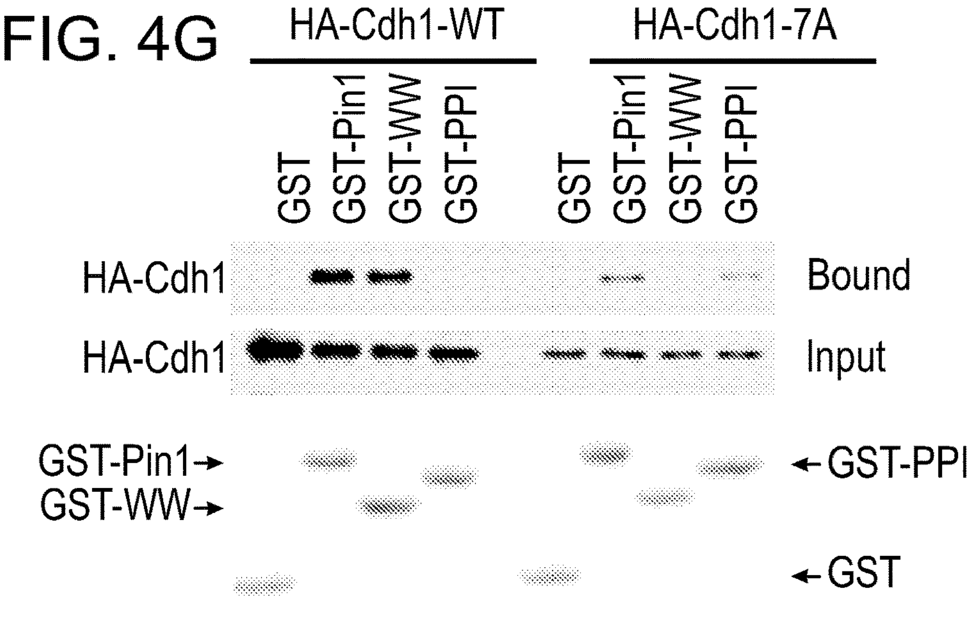
MDA-MB-231

Flag-CDK4 + + -
Flag-CDK6 + - +
HA-Cdh1 - + +
IP: HA
Flag
HA
Input
Flag
HA
293T

HA-Cdh1
PNBM
ATPγS
Cyclin D1-CDK4
ATPγS
HA
WT
S40A
T121A
S151A
S163A

Cdh1-WT
Cdh1-KO
% of cells in S-phase
40
30
20
10
0
0
4
8
12
16
20
24
28
32
Released from serum starvation (h)

Pablo (µM)
1
0.5
0
0
2
4
Sulfopin (µM)

DMSO
Palbo
Sulfopin
AApin
Cells
Time (h)
-24 0 24 48 72
mCherry-Germinin (1-110) intensity
4000 3500 3000 2500 2000 1500 1000 500 0
add drugs
cell divisor
cell death Frequency of G1 arrest (%)
0
20
40
60
80
100
DMSO
Palbo
Sulfopin
AAPin
***
***
***

DMSO
Sulfopin
AApin
Log (mCherry-Geminin)
7
6
5
4
3
2
G1
S
G2/M
2N
4N
DNA Contents
167772
Venus-Pin1
1000

% of cells in G1 phase
80
60
40
20
0
DMSO
Sulfopin
AAPin
*
**
***
mCherry-Geminin
(Relative mean intensity)
1.0
0.8
0.6
0.4
0.2
0.0

AApin
0 12 24 36 48 60 72 84 96
Pin1
Plk1
Cdc20
Cyclin B1
β-actin
MCF-7

Control
CDH1-KO
Palbo
Pin1
Plk1
Cdc20
CyclinB1
Cdh1
β-actin
MCF-7

% of Cells in G1 Phase
Pin1-WT
Pin1-KO
Released from Nocodazole (h)

% Total Cells
EV
Pin1-KO
DNA
2N
4N
Time after double thymidine blocking (hrs)

Distribution (%)
EV
PIN1-KO
G2/M
S
G1
Time after double thymidine blocking (hrs)

Cdh1
RXXL
pEF1α
mCherry
Geminin (1-110)

DMSO
DMSO
Sulfopin
AApin
Frequency (%)
No. of Cell Division
0
50
0
1
2
3
4

DMSO
AApin
Sulfopin
Palbo+AApin
Palbo+Sulfopin
Geminin
Pin1
Merge
0h
24h
48h
72h % Total Cells
0
30
60
90
2N
4N
0
12
24
36
48
60
72
84
96
Duration of Treatment (hrs)

% of Cells in G1
% of Cells in S/G2/M
0
20
40
60
80
0
12
24
36
48
60
72
84
96
Duration of Treatment (hrs)

Control
CDH1-KO
HA-CDH1
Sulfopin
Pin1
Plk1
Cdh1
β-actin
MDA-MB-231

Control
CDH1-KO
Sulfopin
Pin1
Plk1
β-actin
MCF-7

EV
HA-CDH1
Sulfopin
Pin1
Plk1
Cdh1
β-actin
MCF-7

MDA-MB-231

Con
Sulfopin
Palbo
Comb

Cell numbers (X10[4])

8
6
4
2
0

0
1
2
3
4

Days of treatment

**
***

SUM-159

ZIP synergy score: 17.132

40
20
0
-20
-40
δ–score
40
30
20
10
0
-10
-20
-30
-40
0.25
0.1
Palbo (μM)
2
Sulfopin (μM)

MDA-MB-231

ZIP synergy score: 12.111

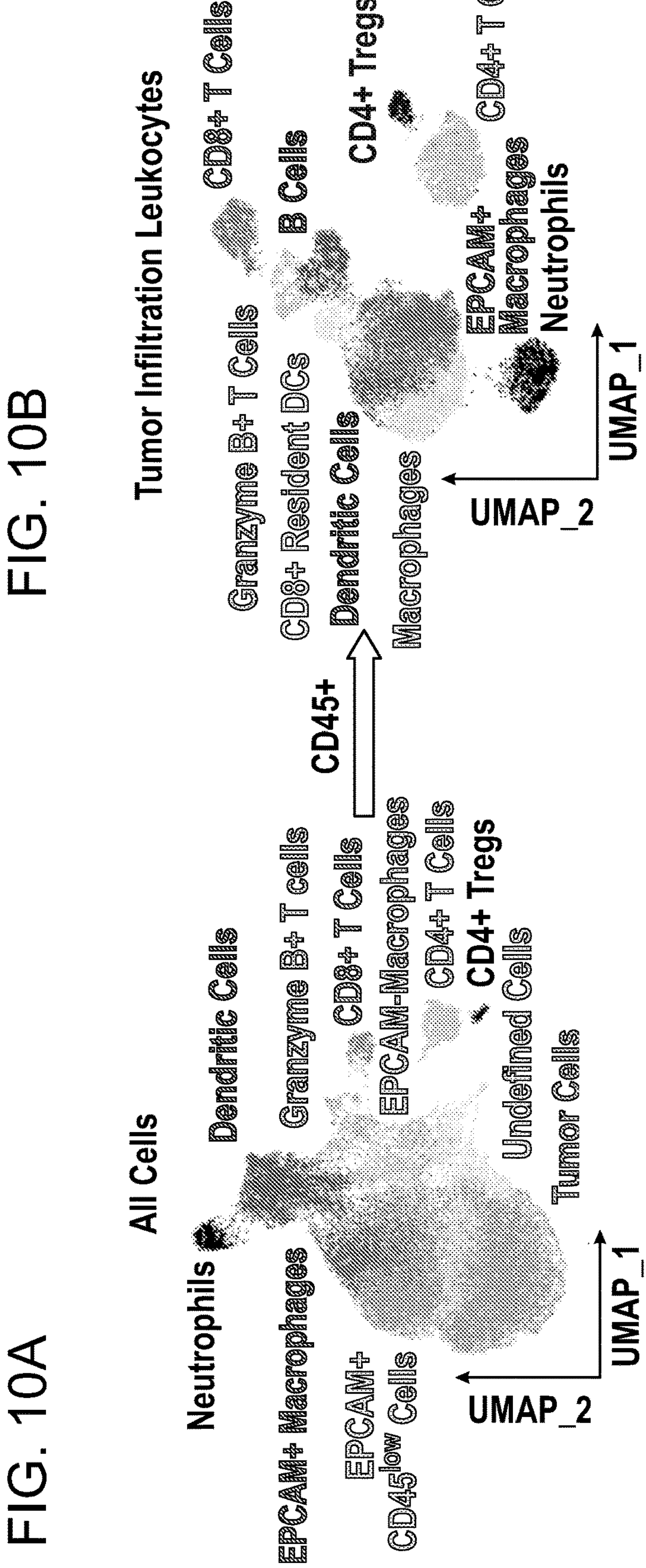
FIG. 10A
All Cells
Neutrophils
EPCAM+ Macrophages
EPCAM+ CD45low Cells
Dendritic Cells
Granzyme B+ T cells
CD8+ T Cells
EPCAM-Macrophages
CD4+ T Cells
CD4+ Tregs
Undefined Cells
Tumor Cells
UMAP_1
UMAP_2
CD45+
FIG. 10B
Tumor Infiltration Leukocytes
Granzyme B+ T Cells
CD8+ T Cells
CD8+ Resident DCs
B Cells
Dendritic Cells
CD4+ Tregs
Macrophages
CD4+ T Cells
EPCAM+ Macrophages
Neutrophils
UMAP_1
UMAP_2

K14cre;Brca1+/-; p53+/-
PD-L1 (n=7)
Sulfopin+PD-L1 (n=12)
Abema+PD-L1 (n=12)
Combination+PD-L1 (n=12)
p=0.0062
p<0.0001
Percent survival
100
50
0
0
20
40
60
Days of treatment Vehicle (n=7)
Tumor volume (mm³)
4000
3000
2000
1000
0
0
20
40
60
Days of treatment Sulfopin (n=12)
4000
3000
2000
1000
0
0
20
40
Days of treatment Abema (n=12)
Tumor volume (mm³)
4000
3000
2000
1000
0
0
20
40
Days of treatment Combination (n=12)
Tumor volume (mm³)
4000
3000
2000
1000
0
0
20
40
Days of treatment PD-L1 (n=7)
Tumor volume (mm3)
4000
3000
2000
1000
0
0
20
40
Days of treatment Sulfopin+PD-L1 (n=12)
Tumor volume (mm3)
4000
3000
2000
1000
0
0
20
40
60
Days of treatment Abema+PD-L1 (n=12)
Tumor volume (mm3)
4000
3000
2000
1000
0
0
20
40
60
Days of treatment Combination+PD-L1 (n=12)
Tumor volume (mm3)
4000
3000
2000
1000
0
0
20
40
60
Days of treatment Cell Cycle Progression Cell Cycle Arrest Neutrophils

NE (K/μL)

6

4

2

0

Vehicle

Sulfopin

Palbo

Sulfopin+Palbo

Abema

Sulfopin+Abema

Vehicle
Sulfopin
Palbo
Sulfopin+Palbo
Abema
Sulfopin+Abema
Pin1/DAPI
Ki67/DAPI

Vehicle
Sulfopin
Palbo
Sulfopin+Palbo
Abema
Sulfopin+Abema
Cyclin B1/ DAPI
Geminin/ DAPI
PIK1/DAPI

ANTIGEN_PROCESSING_AND_PRESENTATION_OF_ENDOGENOUS_ANTIGEN

ENDOTHELIAL_CELL_APOPTOTIC_PROCESS

ENDOTHELIAL_CELL_CYCLE_DNA_REPLICATION

MITOTIC_SISTER_CHROMATID_SEGREGATION

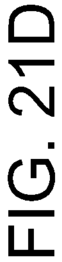
FIG. 21D

PIN1-KO vs PIN1-WT

GO: rRNA processing
GO: cell–cell adhesion
GO: cell division
GO: translational initiation
GO: viral transcription
GO: mRNA splicing, via spliceosome
GO: mitotic nuclear division
GO: cell cycle
GO: DNA replication
GO: protein catabolic process
GO: protein folding
GO: mRNA processing
GO: regulation of mRNA stability
GO: G1/S transition of mitotic cell cycle
GO: transcription elongation
GO: mitotic nuclear envelope disassembly
GO: ribosomal large subunit biogenesis
GO: tRNA export from nucleus
GO: cytoplasmic translation
GO: regulation of glucose transport 1
2
3
4
Gene ratio –log10(pvalue)
40
30
20
10 count
20
40
60
80
100

MDA-MB-231
(Rb-proficient)
WT
PIN1-KO
CHX 0 2 4 8 16 24 0 2 4 8 16 24 hrs
Plk1
Geminin
Cdc20
Emi1
Pin1
β-actin
MDA-MB-468
(Rb-deficient)
WT
PIN1-KO
CHX 0 2 4 8 16 24 0 2 4 8 16 24 hrs
Plk1
Geminin
Cdc20
Cyclin B1
Emi1
Pin1
β-actin

ADAPTIVE_IMMUNE_RESPONSE

LYMPHOCYTE_MEDIATED_IMMUNITY

SISTER_CHROMATID_SEGREGATION

DNA_DEPENDENT_DNA_REPLICATION

INHIBITORS OF THE PEPTIDYL-PROLYL CIS/TRANS ISOMERASE (PIN1), COMBINATIONS AND USES THEREOF

RELATED APPLICATIONS

This application is a national stage application, filed under 35 U.S.C. § 371, of International Application No. PCT/US2022/076950, filed Sep. 23, 2022, which claims the benefit of priority under 35 U.S.C. § 119 (e) to U.S. Provisional Application No. 63/248,100, filed Sep. 24, 2021, each of which is incorporated herein by reference in its entirety.

GOVERNMENT LICENSE RIGHTS

This invention was made with government support under grant number R01 CA205153 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on Sep. 22, 2022, is named 52095-730001WO_ST26.xml and is 28.0 KB bytes in size.

BACKGROUND OF THE DISCLOSURE

Proline is unique among the amino acids because it populates both the cis and trans conformations, providing a backbone conformational switch that is controlled by prolyl isomerization. Due to the high energy barrier associated with cis to trans conversion (25-30 kcal/mol), the intrinsic isomerization process is slow (several minutes) relative to biochemical processes, and therefore catalysis by peptidyl prolyl isomerases (PPIases) is required for efficient isomerization.

Proline (Pro)-directed serine/threonine (Ser/Thr) phosphorylation (pSer/Thr-Pro) serves an essential role in cell signaling networks and is often dysregulated in cancer. Numerous oncogenes and tumor suppressors are regulated by Pro-directed phosphorylation and/or are part of signaling pathways involving such phosphorylation. pSer/Thr-Pro reduces the intrinsically slow cis-trans isomerization process and renders the peptide bonds inaccessible for all known peptidyl-prolyl cis-trans isomerases (PPIases), except for peptidyl-prolyl cis-trans isomerase NIMA-interacting 1 (Pin1) and its homologues. Pin1 contains an N-terminal WW domain, which functions as a phosphorylated Ser/Thr-Pro binding module, and a PPIase domain, which catalyzes the cis-trans isomerization. (Zhou et al., Cell. Mol. Life Sci. 56:788-806 (1999)).

Pin1-catalysed prolyl isomerization regulates the functions of its substrates through multiple different mechanisms, including controlling catalytic activity, turnover, phosphorylation, interactions with DNA, RNA or other proteins, and subcellular localization and processing. Pin1 often functions as a molecular timer that synchronously controls the amplitude and duration of a given cellular process. Pin1 is tightly regulated normally and its deregulation can have a major impact on the development and treatment of cancer and neurodegenerative diseases, such as Alzheimer's disease. (Lu and Zhou, Nat. Rev. Mol. Cell Biol. 8:904-16 (2007)).

Pin1 is widely overexpressed and/or overactivated in cancers which correlate with poor clinical prognosis. (Lu and Hunter, Cell Res. 24:1033-49 (2014)). It has also been shown that Pin1 single nucleotide polymorphisms (SNPs) that reduce Pin1 expression are associated with a reduced risk for multiple cancers, and that Pin1-null mice are highly resistant to tumorigenesis, even after the overexpression of oncogenes or after the mutation or ablation of tumor suppressors. (Li et al., *PLOS ONE* 8: e68148 (2004); Wulf et al., EMBO J. 23:3397-3407 (2004); Girardini et al., Cancer Cell 20:79-91 (2011); Takahashi et al., Oncogene 26:3835-45 (2007)). Further, Pin1-null mice have been shown to develop normally to adulthood with few defects. (Lee et al., Expert Rev. Mol. Med. 13: e21 (2011)). Additionally, Pin1 overexpression disrupts cell cycle coordination and leads to chromosome instability and tumorigenesis. Pin1 activates and inactivates more than 40 oncogenes and 20 tumor suppressors, respectively. Many of these Pin1 substrates have a role in self-renewal, replicative potential and frequency of cancer stem cells (CSCs). (Zhou and Lu, Nat. Rev. Cancer 16:463-78 (2016)). Therefore, Pin1 inhibitors may have the desirable ability to simultaneously block multiple cancer-driving pathways and CSC expansion and differentiation with limited toxicity.

SUMMARY OF THE DISCLOSURE

A first aspect of the present disclosure is directed to a method of treating a disease or disorder mediated by dysregulated cyclin-dependent kinase 4/6 (CDK4/6) activity, in a subject, e.g., a human subject, in need thereof, comprising co-administering a therapeutically effective amount of one or more CDK4/6 inhibitors, and a therapeutically effective amount of one or more peptidyl-prolyl cis-trans isomerase NIMA-interacting 1 (Pin1) inhibitors, or a pharmaceutically acceptable salt or salts thereof.

Another aspect of the present disclosure is directed to a method of reducing the activity of CDK4/6 in a cell, either in vivo or in vitro, comprising co-administering a therapeutically effective amount of one or more CDK4/6 inhibitors, and a therapeutically effective amount of one or more Pinn 1 inhibitors, or a pharmaceutically acceptable salt or salts thereof.

In some embodiments, the co-administering results in greater therapeutic effect than the effect of the one or more CDK4/6 inhibitors when administered as a monotherapy (e.g., alone as a sole active agent), without the one or more Pin1 inhibitors. In some embodiments, the greater therapeutic effect is a synergistic effect. In some embodiments, the greater therapeutic effect is the reduction of tumor growth in triple negative breast cancer.

In some embodiments, the treatment regimen may include administration of the compounds of the disclosure, wherein the one or more CDK4/6 inhibitors and the one or more Pin1 inhibitors is each administered at an amount that is lower than the therapeutically effective amount administered when each of the one or more CDK4/6 inhibitors and the one or more Pin1 inhibitors is administered alone. In some embodiments, administration of the combination of the one or more CDK4/6 inhibitors and the one or more Pin1 inhibitors, each administered at a dose that is lower than the therapeutically effective amount, provides a therapeutic effect.

In some embodiments, the one or more CDK4/6 inhibitors is palbociclib, abemaciclib, ribociclib, or a combination thereof, or a pharmaceutically acceptable salt or stereoisomer thereof. In some embodiments, the one or more CDK4/6 inhibitors is palbociclib. In some embodiments, the one or more CDK4/6 inhibitors is abemaciclib. In some embodiments, the one or more CDK4/6 inhibitors is ribociclib. In some embodiments, the one or more Pin1 inhibitors is sulfopin, all-trans retinoic acid (ATRA), arsenic trioxide (ATO), or a combination thereof, or a pharmaceutically acceptable salt or stereoisomer thereof. In some embodiments, the one or more Pin1 inhibitors is sulfopin. In some embodiments, the one or more Pin1 inhibitors is ATRA and ATO. In some embodiments, the method further comprises administering an immunotherapy. In some embodiments, the immunotherapy is anti-programmed cell death protein 1 (anti-PD-1) or anti programmed death-ligand 1 (anti-PD-L1). In some embodiments, the immunotherapy is anti-PD-L1. In some embodiments, the one or more CDK4/6 inhibitors is palbociclib and the one or more Pin1 inhibitors is sulfopin. In some embodiments, the one or more CDK4/6 inhibitors is palbociclib and the one or more Pin1 inhibitors is ATRA and ATO. In some embodiments, the one or more CDK4/6 inhibitors is abemaciclib and the one or more Pin1 inhibitors is sulfopin. In some embodiments, the one or more CDK4/6 inhibitors is abemaciclib and the one or more Pin1 inhibitors is ATRA and ATO. In some embodiments, the one or more CDK4/6 inhibitors is ribociclib and the one or more Pin1 inhibitors is sulfopin. In some embodiments, the one or more CDK4/6 inhibitors is ribociclib and the one or more Pin1 inhibitors is ATRA and ATO. In some embodiments, the one or more CDK4/6 inhibitors is palbociclib, the one or more Pin1 inhibitors is sulfopin, and the immunotherapy is anti-PD-L1. In some embodiments, the one or more CDK4/6 inhibitors is abemaciclib, the one or more Pin1 inhibitors is sulfopin, and the immunotherapy is anti-PD-L1. In some embodiments, the one or more CDK4/6 inhibitors is ribociclib, the one or more Pin1 inhibitors is sulfopin, and the immunotherapy is anti-PD-L1. In some embodiments, the one or more CDK4/6 inhibitors is palbociclib, the one or more Pin1 inhibitors is ATRA and ATO, and the immunotherapy is anti-PD-L1. In some embodiments, the one or more CDK4/6 inhibitors is abemaciclib, the one or more Pin1 inhibitors is ATRA and ATO, and the immunotherapy is anti-PD-L1. In some embodiments, the one or more CDK4/6 inhibitors is ribociclib, the one or more Pin1 inhibitors is ATRA and ATO, and the immunotherapy is anti-PD-L1.

In some embodiments, the disease is cancer. In some embodiments, the cancer is breast cancer . . . . In some embodiments, the breast cancer is endocrine resistant estrogen receptor positive (ER+) breast cancer or triple negative breast cancer. In some embodiments, the breast cancer is endocrine resistant estrogen receptor positive (ER+) breast cancer. In some embodiments, the endocrine resistant estrogen receptor positive (ER+) breast cancer is either local, locally advanced, or metastatic. In some embodiments, the breast cancer is triple negative breast cancer. In some embodiments, the triple negative breast cancer is either local, locally advanced, or metastatic.

Another aspect of the present disclosure is directed to a pharmaceutical composition, comprising a therapeutically effective amount of one or more CDK4/6 inhibitors, wherein the one or more CDK4/6 inhibitors is palbociclib, abemaciclib, ribociclib, or a combination thereof, and a therapeutically effective amount of one or more Pin1 inhibitors, wherein the one or more Pin1 inhibitors is sulfopin, ATRA, ATO, or a combination thereof, or a pharmaceutically acceptable salt or stereoisomer thereof. In some embodiments, the pharmaceutical composition is in the form of a liquid. In some embodiments, the pharmaceutical composition is in the form of a solid. In some embodiments, the pharmaceutical composition is in the form of a tablet or capsule. In some embodiments, the pharmaceutical composition further comprises a therapeutically effective amount of one or more immunotherapies. In some embodiments, the one or more immunotherapies is anti-PD-1 or anti-PD-L1. In some embodiments, the one or more immunotherapies is anti-PD-L1.

Another aspect of the present disclosure is directed to a kit comprising one or more CDK4/6 inhibitors and one or more Pin1 inhibitors, or a pharmaceutically acceptable salt or stereoisomer thereof, or a pharmaceutical composition of the disclosure, and instructions for administering to a subject or instructions for contacting a biological sample with the one or more CDK4/6 inhibitors and the one or more Pin1 inhibitors or the pharmaceutical composition. In some embodiments, the kit further comprises one or more immunotherapies, wherein the one or more immunotherapies is anti-PD-1 or anti-PD-L1.

BRIEF DESCRIPTION OF THE DRAWINGS

FIG. 1A is a graph of overall survival versus time that shows the overall survival for breast cancer (BC) with low and high Pin1 protein abundance. FIG. 1B is an image that shows an ssGSEA analysis of biological processes in BRCA tumors in TCGA. FIG. 1C shows the coomassie blue stain of Pin1-interacting proteins after immunoprecipitation (IP) resolved by SDS-PAGE. FIG. 1D is a set of immunoblots that shows that Pin1 degradation induced by its inhibitors is blocked by Cdh1, but not Cdc20 knockdown. FIG. 1E is an immunoblot showing the result of the treatment of Cdh1+/+ or Cdh1−/− MEFs with increasing concentrations of AApin for three days. FIG. 1F is an immunoblot showing the result of the treatment of Cdh1+/+ or Cdh1−/− MEFs with increasing concentrations of sulfopin for three days. FIG. 1G is an immunoblot that shows the glutathione S-transferase (GST) pull-down of GST-Pin1 and haemagglutinin (HA)-tagged Cdh1, but not Cdc20. 293T cells were transfected with indicated constructs for 36 hrs and GST-Pin1 were pulled down with glutathione beads. FIG. 1H is an immunoblot that shows the coimmunoprecipitation (Co-IP) of HA-Cdh1 with endogenous Pin1. FIG. 1I is a set of confocal images of the colocalization of Pin1 (red) and Cdh1 (green). FIG. 1J is an immunoblot that shows the interaction of the Pin1 WW domain with Cdh1. FIG. 1K is an immunoblot together with a quantification graph for bound HA-Cdh1 control. FIG. 1L is an immunoblot together with a quantification graph for bound HA-Cdh1 treated with sulfopin.

FIG. 2A-FIG. 2D is a set of box plots, images, and immunoblots that show that the cell cycle regulator APC/$C^{Cdh1}$ is a physiological upstream E3 ubiquitin ligase for Pin1. FIG. 2A is a box plot that shows the distribution of Pin1 mRNA levels across BC tumors (n=1211). FIG. 2B is an image that shows that Pin1 levels correlate with cell cycle signatures and immune response signatures in human BC mRNA dataset in TCGA. FIG. 2C shows a gene ontology (GO) enrichment analysis applied to proteomics of wild-type MDA-MB-231 cells (PIN1-WT) and Pin1 CRISPR Knockout MDA-MB-231 cells (PIN1-KO) cells. FIG. 2D is a set of immunoblots together with the corresponding quantification that shows that Pin1 inhibition promotes its destruction.

FIG. 3A-FIG. 3J is a set of immunoblots and representations that show that the cell cycle regulator APC/$C^{Cdh1}$ is a physiological upstream E3 ubiquitin ligase for Pin1. FIG. 3A-FIG. 3G is a set of immunoblots that show the validation of potential Pin1-interacting E3 ligases identified by mass spectrometry. FIG. 3A is an immunoblot together with the corresponding quantification for shRNF219. FIG. 3B is an immunoblot together with the corresponding quantification for shUBR5. FIG. 3C is an immunoblot together with the corresponding quantification for shRNF149.

FIG. 3D is an immunoblot together with the corresponding quantification for shWWP2. FIG. 3E is an immunoblot together with the corresponding quantification for shUBE3A. FIG. 3F is an immunoblot together with the corresponding quantification for shKEAP1. FIG. 3G is an immunoblot together with the corresponding quantification for shFBXO7. FIG. 3H is an immunoblot that shows the Co-IP of APC7 with Pin1 requires Cdh1 and the Pin1 WW domain. 293T cells were transfected with indicated constructs and treated with 2 μM MG132 for 12 hrs and pulled down using M2 beads. FIG. 3I is an IB analysis of indicated GST pull-down precipitates from MDA-MB-231 cells stably expressing HA-Cdh1 and treated with vehicle or 10 UM sulfopin for 3 days and 10 μM MG132 for the last 12 hrs before harvesting. FIG. 3J is a cartoon representation that shows the domain architecture of Pin1 containing an N-terminal WW domain binding specific pSer/Thr-Pro motifs, and a C-terminal peptidyl-prolyl cis/trans isomerase (PPIase) domain that catalyzes prolyl isomerization of specific pSer/Thr-Pro motifs. For example, hPin1, 117-128, is KARGDLGAFSRG (SEQ ID NO: 28) and mPin1, 119-130 is KARGDLGPFSRG (SEQ ID NO: 29).

FIG. 4A-FIG. 4B is a set of immunoblots that show stabilization of Pin1 and premature S-phase entry in Cdh1-KO MEFs. FIG. 4A is an immunoblot that shows Cdh1-WT and Cdh1-KO MEFs synchronized in G1 phase by serum starvation, followed by releasing back into the cell cycle before harvesting cells at indicated time points. FIG. 4B shows cell-cycle profiles corresponding to FIG. 4A monitored by fluorescence-activated cell sorting (FACS). FIG. 4D-FIG. 4F is a set of images, immunoblots and graphs that show that elimination of the phosphorylation sites in Cdh1 leads to constitutively active Cdh1 with induction of cell senescence (FIG. 4D) and a decrease in the abundance of Pin1 and other Cdh1 substrates (FIG. 4E and FIG. 4F). FIG. 4D is a set of images that shows SA-β-gal stain in MDA-MB-231 and SUM-159 cells infected with the indicated lentiviral constructs. FIG. 4E is an immunoblot analysis for indicated proteins derived from MDA-MB-231 cells stably expressing indicated constructs. FIG. 4F shows quantification of western blot analysis for indicated proteins from FIG. 4E. FIG. 4G-FIG. 4J is a set of immunoblots that show characterization of the Pin1-Cdh1 interaction. FIG. 4G is an immunoblot that shows GST-Pin1 pull-down precipitates derived from MDA-MB-231 cells stably expressing HA-Cdh1 or HA-Cdh1-7A, treated with 10 μM MG132 for 12 hrs. FIG. 4H is a set of immunoblots that shows GST-Pin1 pull-down precipitates from 293T cells transfected with HA-Cdh1 or HA-Cdh1-mutants for 36 hrs. FIG. 4I is an immunoblot of immunoprecipitates from MDA-MB-231 cells stably co-expressing Flag-Pin1-WT or disabling mutations in the WW domain (Flag-Pin1-W34A) or the PPIase/D-box domain (Flag-Pin1-RLAA) (RLAA is defined by replacing two conserved residues within the D-box motif, arginine and leucine, with alanine) or the dual mutant (Flag-Pin1-W34A; RLAA), and HA-Cdh1-WT (left) or the phosphosite-deficient mutant Cdh1-7A (right) treated with 10 μM MG132 for 12 hrs and pulled down using Flag-M2 beads. FIG. 4J is an immunoblot that shows the mutation of the destruction box in Pin1 abolishes Pin1 degradation by Cdh1. FIG. 4K is an IB analysis for indicated proteins derived from 293T cells transfected with indicated constructs for 48 hours. FIG. 4L is an IB analysis of the ubiquitinated proteins derived from 293T cells transfected with the indicated constructs and treated with 2 μM MG132 for 12 hrs and pulled down under denaturing conditions by nickel-nitrilotriacetic acid (Ni-NTA) agarose. FIG. 4M is an IB analysis of immunoprecipitates derived from 293T cells transfected with indicated constructs and treated as in FIG. 4L and pulled down by M2 beads. FIG. 4O is an immunoblot of an in vitro kinase assay showing that CDK4 phosphorylates Cdh1 at Ser163.

FIG. 5A is a graph that shows the percentage of cells in S-phase of Cdh1-WT or Cdh1-KO MEFs from FIG. 6B. FIG. 5B is a graph that shows that Pin1 mRNA fluctuation in Cdh1-WT or Cdh1-KO MEFs released from G0/G1 arrest induced by serum starvation. FIG. 5C is an IB analysis for indicated proteins derived from MCF-7 cells stably expressing shCdh1 or HA-Cdh1 and cultured in 10% serum or serum-free conditions. FIG. 5D is a set of images and an immunoblot that shows the morphology of MCF-7 stably expressing indicated constructs (left panel) and IB analysis for indicated proteins derived from MCF-7 cells stably expressing indicated constructs (right panel). FIG. 5E-FIG. 5G show IB analysis for indicated proteins derived from 293T cells transfected with indicated constructs. FIG. 5H is an image that shows the structure of APC/$C^{Cdh1}$ complex (PDB: 4UI9). FIG. 5I is an IB analysis for indicated proteins derived from MDA-MB-231 cells treated with 2 μM palbociclib (CDK4/6 inhibitor), CDK2-IN-4 (CDK2 inhibitor), PD0325901 (MEK inhibitor), Dasatinib (c-Src inhibitor) or SCH772984 (ERK inhibitor) for 3 days. FIG. 5J is an IB analysis for indicated proteins derived from RB+/+ and RB−/− MDA-MB-231 cells treated with increasing concentrations of palbociclib (0.25, 0.5, 1, 1.5, 2 μM) for 3 days. FIG. 5K and FIG. 5L is a set of images that show long-term colony formation assays (FIG. 5K) and growth inhibition matrices (FIG. 5L) of RB−/− MDA-MB-231 cells treated with indicated concentrations of sulfopin and palbociclib for two weeks. FIG. 5K is a set of images that shows the long-term colony formation assay. FIG. 5L is a quantification growth inhibition matrix. FIG. 5M shows the synergy scores for sulfopin combinations with palbociclib in RB−/− MDA-MB-231 cells from (FIG. 5I) represented as 3D heat maps, with higher scores (darker red) denoting stronger synergy.

FIG. 6A and FIG. 6B show delayed cell cycle entry after Pin1 KO. FIG. 6A is an IB analysis for indicated proteins derived from Cdh1+/+ and Cdh1−/− MDA-MB-231 cells synchronized in M phase by nocodazole and then released back into the cell cycle for the indicated periods of time.

Figure 6A:
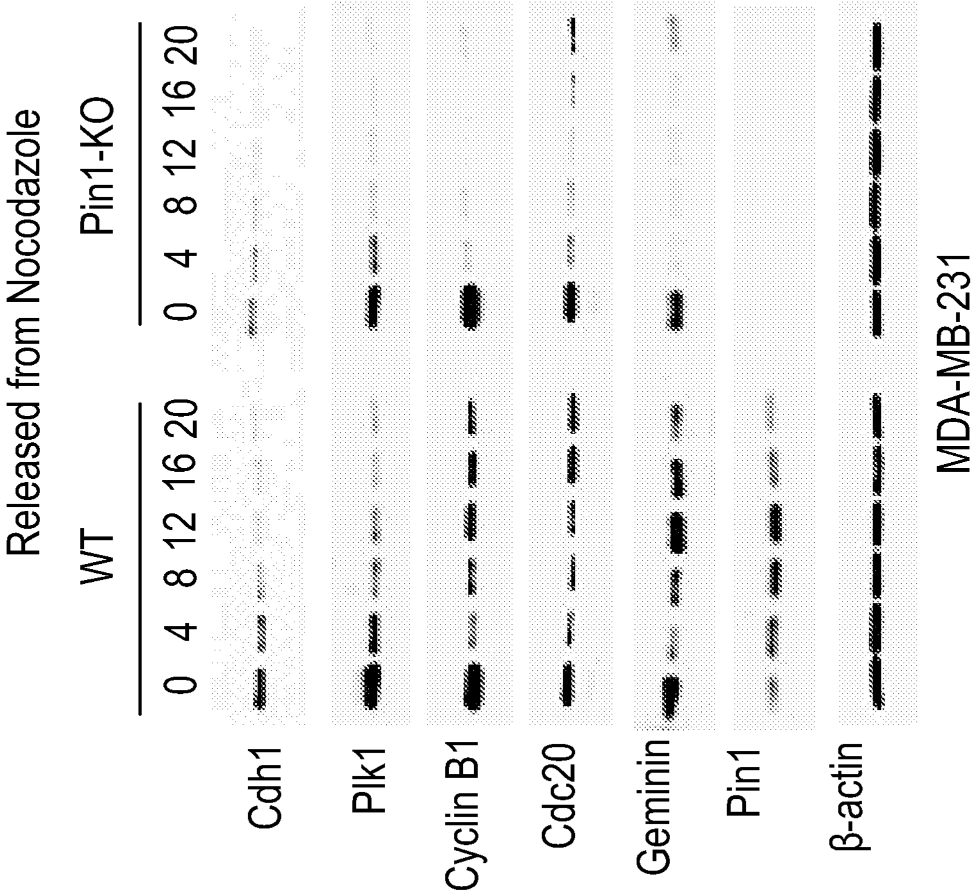
FIG. 6A-FIG. 6O is a set of immunoblots, graphs, images, bar plots and dot plots that show that pharmacologic inhibition of Pin1 and CDK4/6 restores APC/$C^{Cdh1}$ E3 ligase activity.
Figure 6B:
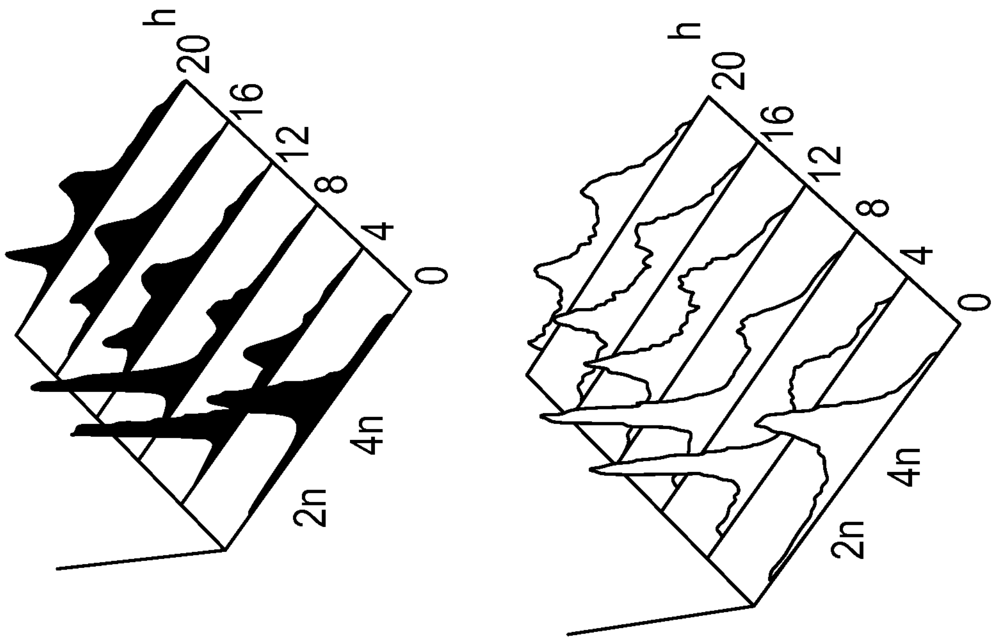
Figure 6C:
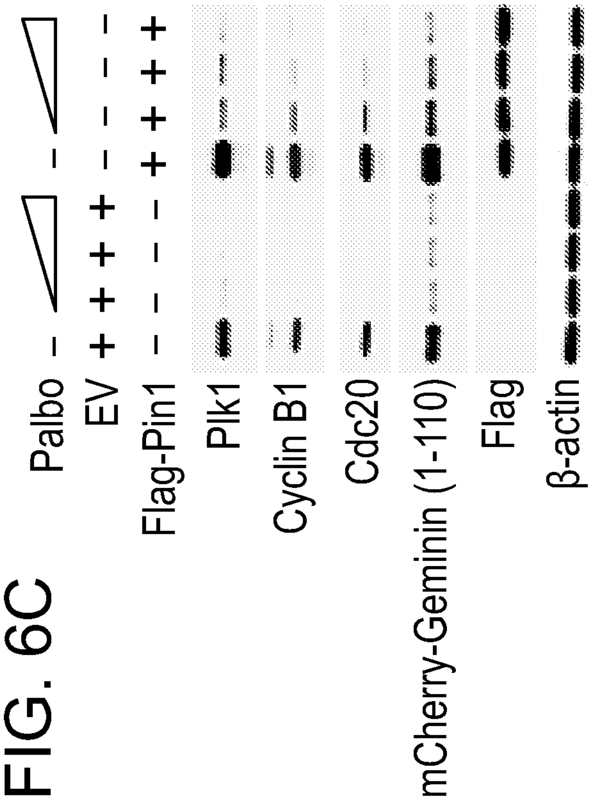
Figure 6D:
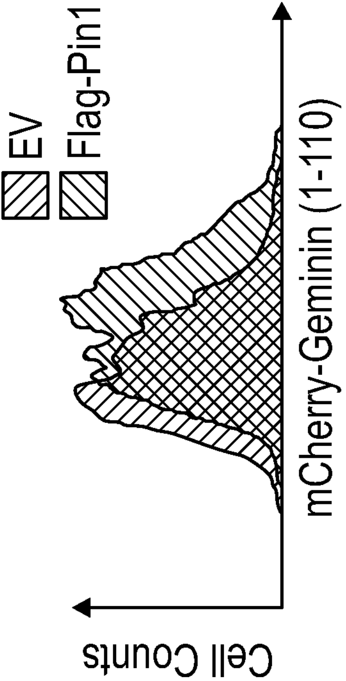
Figure 6E:
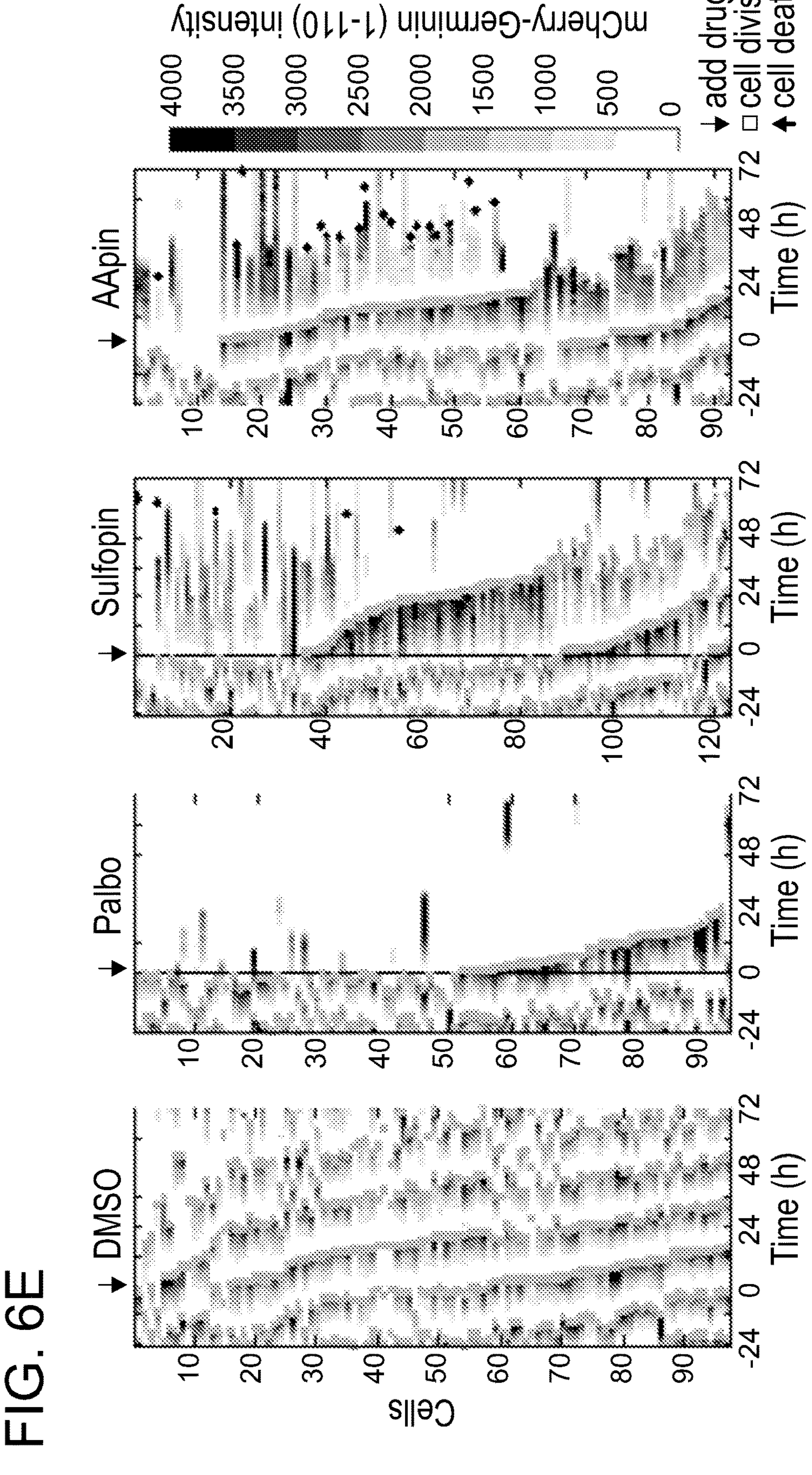
Figures 6F, 6G:
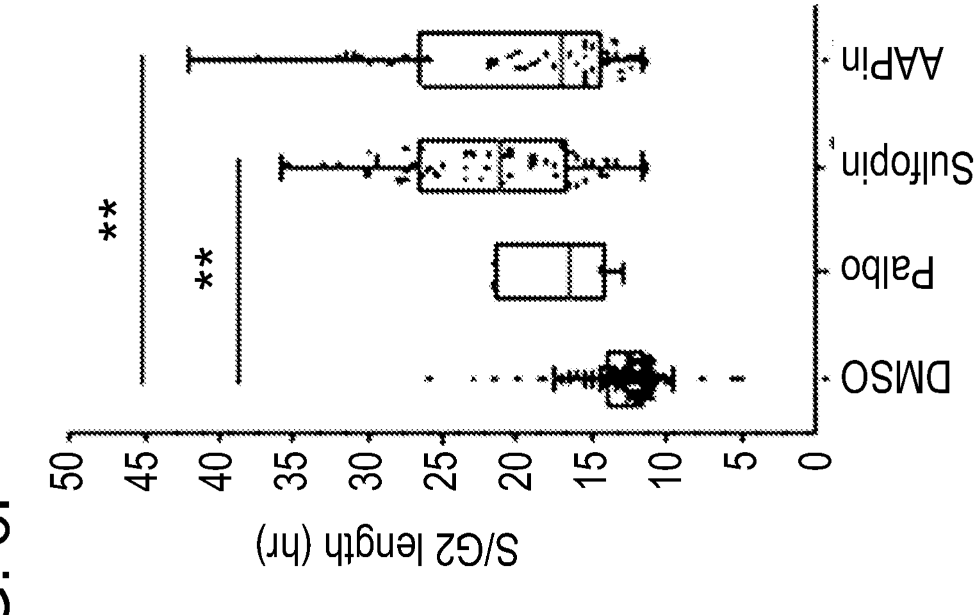
Figures 6H, 6I, 6J:
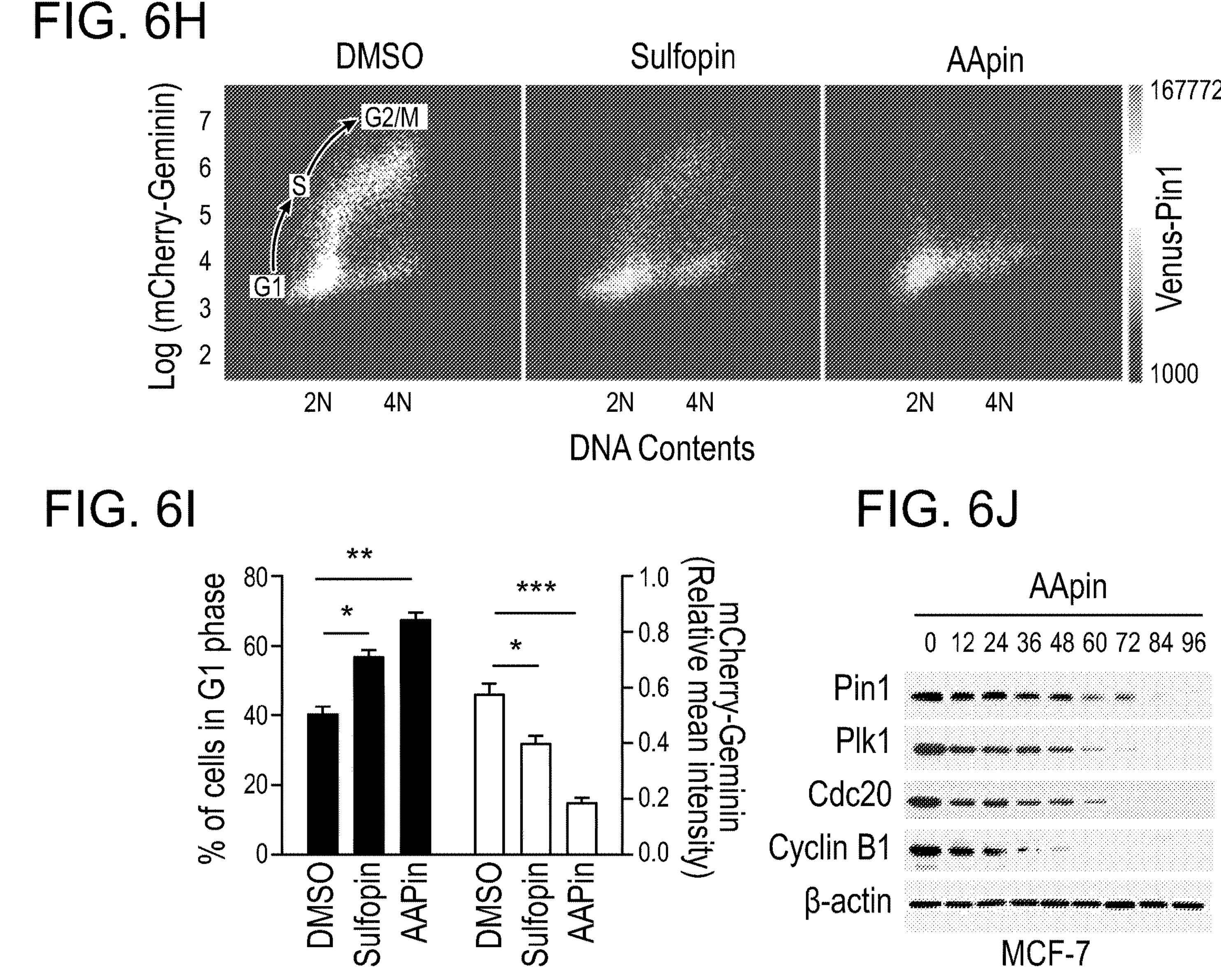
Figure 6K:
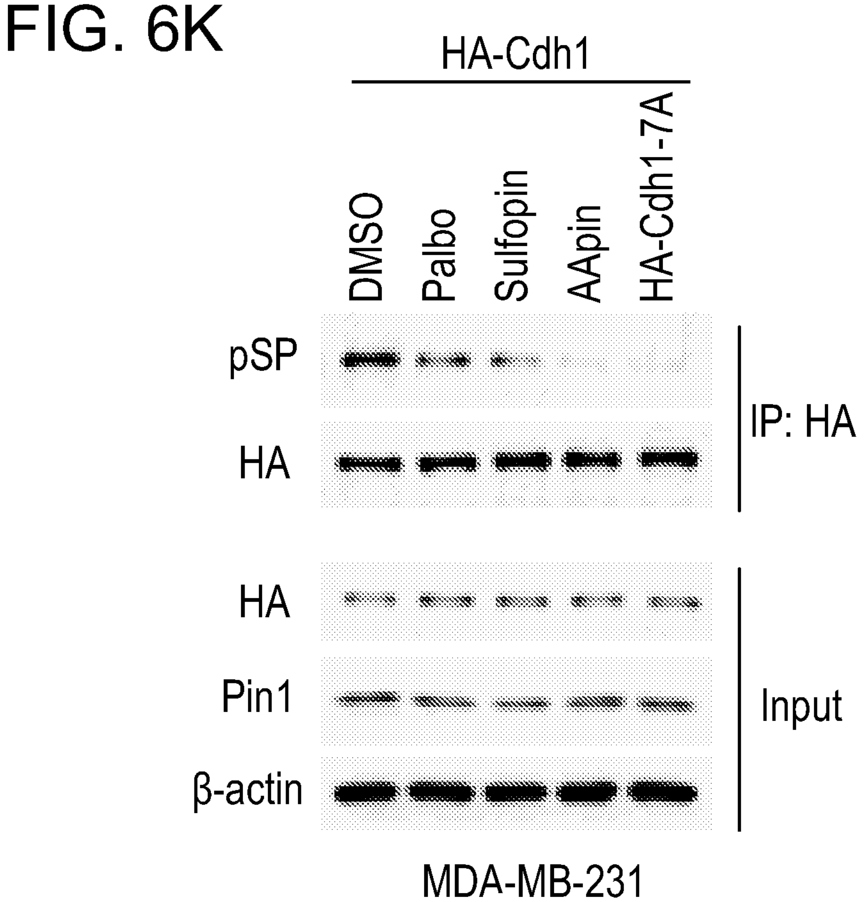
Figure 6M:
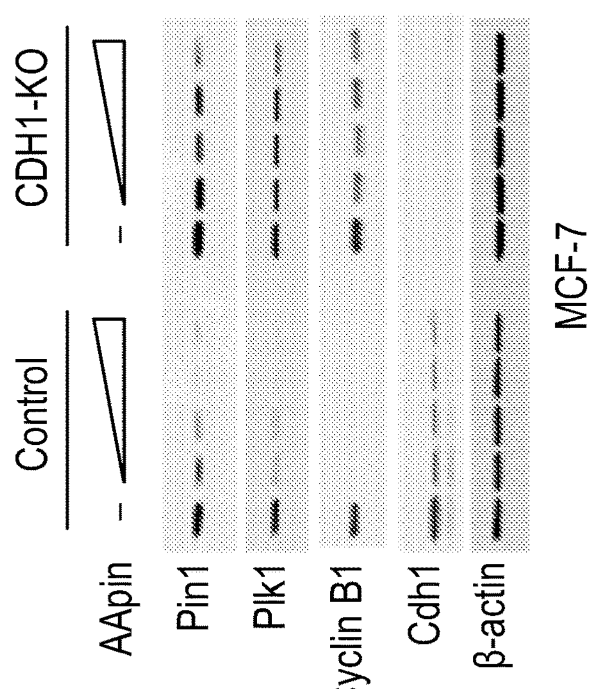
Figure 6L:
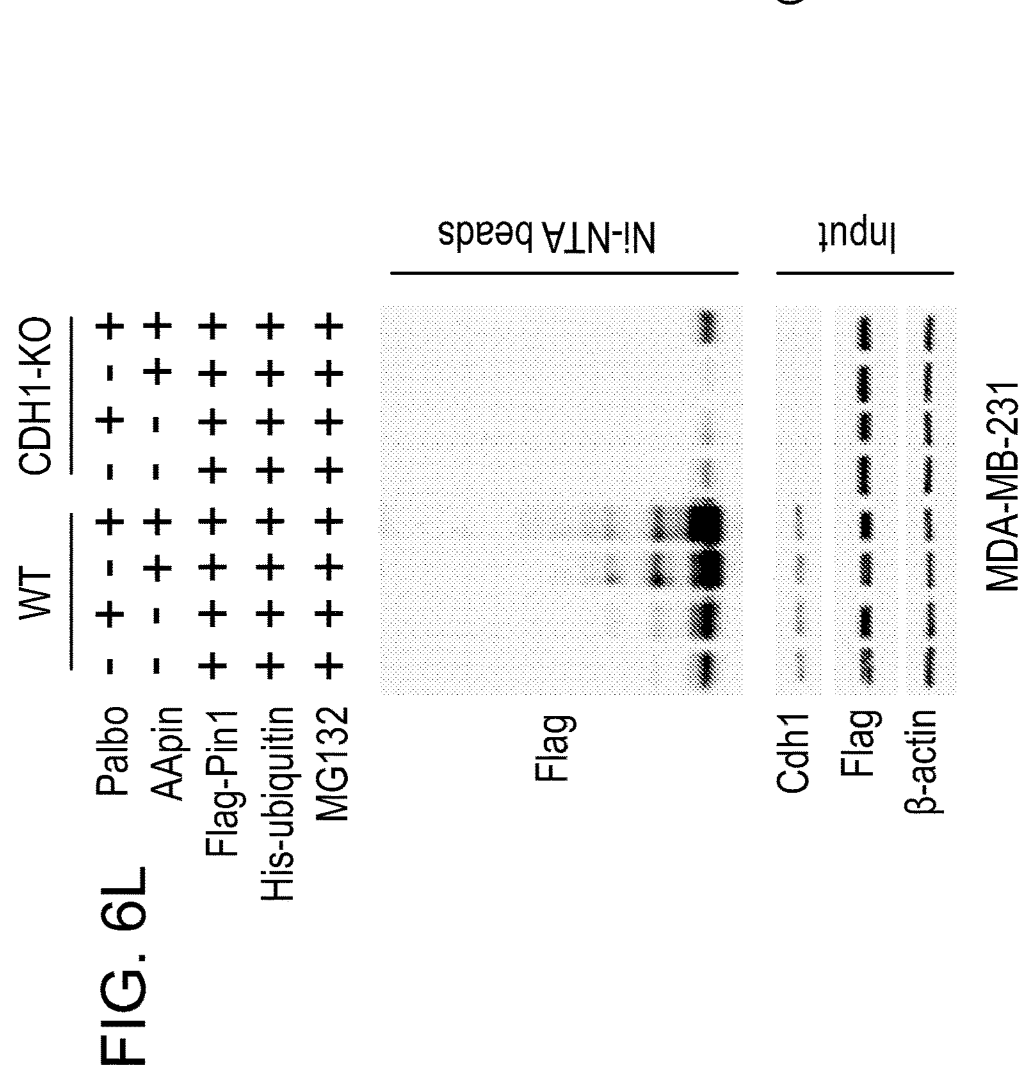
Figures 6N, 6O:
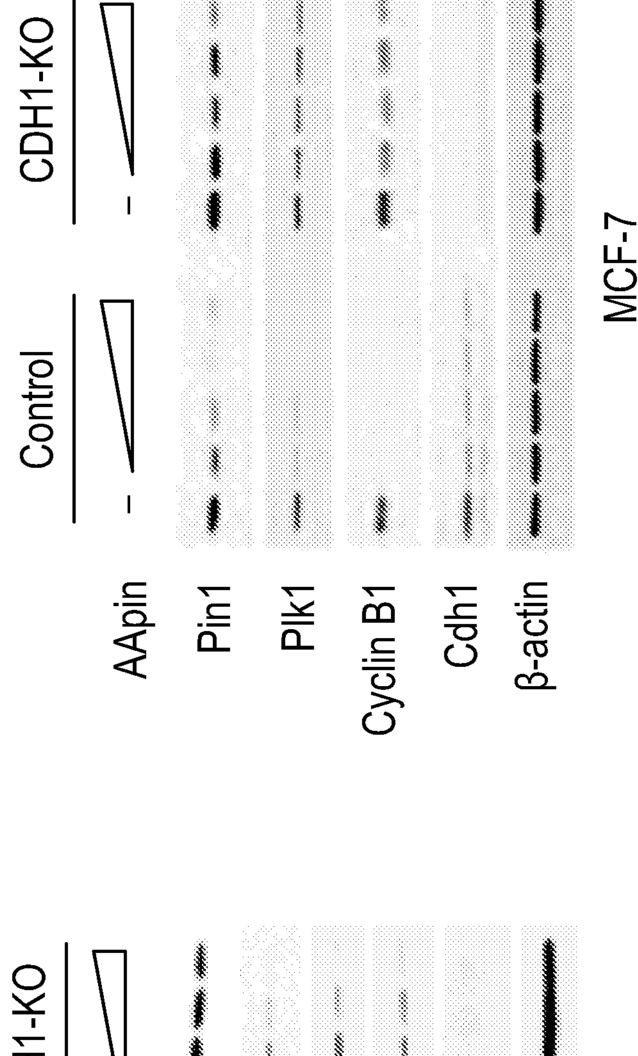

FIG. 6B shows cell-cycle profiles of Pin1-WT (blue) and Pin1-KO (pink) in (FIG. 6A) as determined by FACS. FIG. 6C is an immunoblot that shows enforced expression of Pin1 allows BC cells to overcome CDK4/6-inhibitor induced G1 arrest. FIG. 6D is a graph that shows APC-degron reporter levels in MCF-7 cells stably expressing EV or wild-type Pin1 as determined by FACS. FIG. 6E-FIG. 6J shows the inhibition of Pin1 delays exit from mitosis and ultimately induces G1 arrest. FIG. 6E is a set of images that shows tracking cell division and cell death in response to CDK4/6-inhibition (palbociclib) or Pin1-inhibition (sulfopin, AApin) on the single cell level. FIG. 6F is a graph that shows distributions of S/G2 duration in DMSO-, palbociclib- and Pin1 inhibitors-treated cells. FIG. 6G is a bar plot that shows frequency of G1 arrest (ratio of G1 arrested cells, the last 24 hours, to total cells). FIG. 6H is a set of dot plots of FACS for MDA-MB-231 cells stably expressing the APC-degron reporter (mCherry-Geminin fusion protein) and Pin1 (Venus-Pin1 fusion protein) and treated with DMSO or Pin1 inhibitors for 3 days. FIG. 6I is a graph that shows quantification of cells in G1 and relative mean intensity of mCherry-Geminin from FIG. 6H. FIG. 6J is an immunoblot that shows a time course cell cycle regulator expression in MCF-7 cells treated with AApin (10 μM ATRA plus 1 μM ATO). FIG. 6K is an IB analysis of immunoprecipitates derived from MDA-MB-231 cells stably expressing HA-Cdh1 treated with palbociclib or Pin1 inhibitors and pulled down by anti-HA antibody. FIG. 6L is an IB analysis of ubiquitinated proteins derived from Cdh1+/+ and Cdh1−/− MDA-MB-231 cells transfected with the indicated constructs and treated with 1 μM palbociclib and 10 μM sulfopin for 3 days and 2 μM MG132 for last 12 hrs and pulled down under denaturing conditions by nickel-nitrilotriacetic acid (Ni-NTA) agarose. FIG. 6M-FIG. 6O shows Pin1- and CDK4/6-inhibitors mediated restoration of $APC/C^{Cdh1}$ activity is dependent on Cdh1.

Figures 7A, 7B, 7C, 7D:
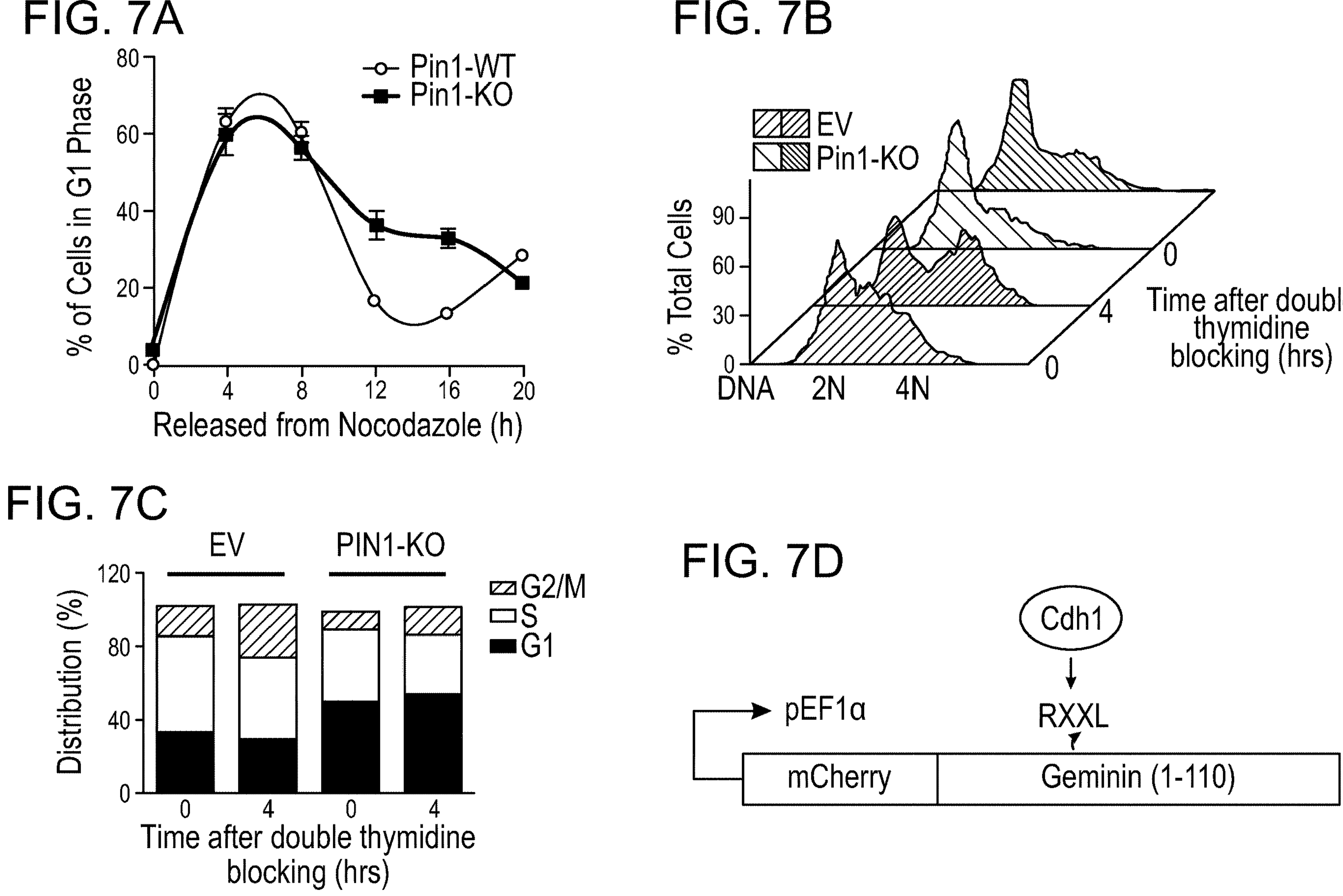
Figure 7E:
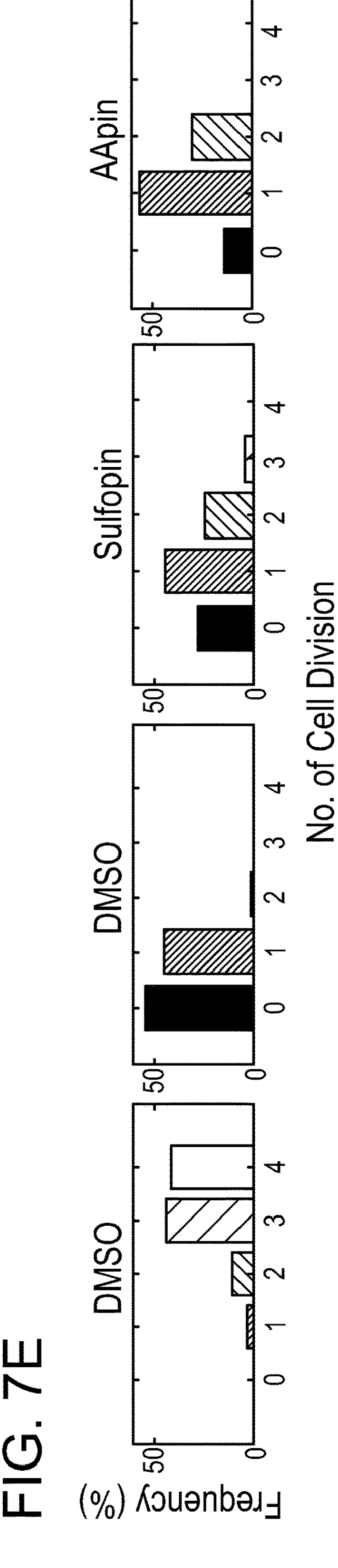
Figures 7F, 7G, 7H:
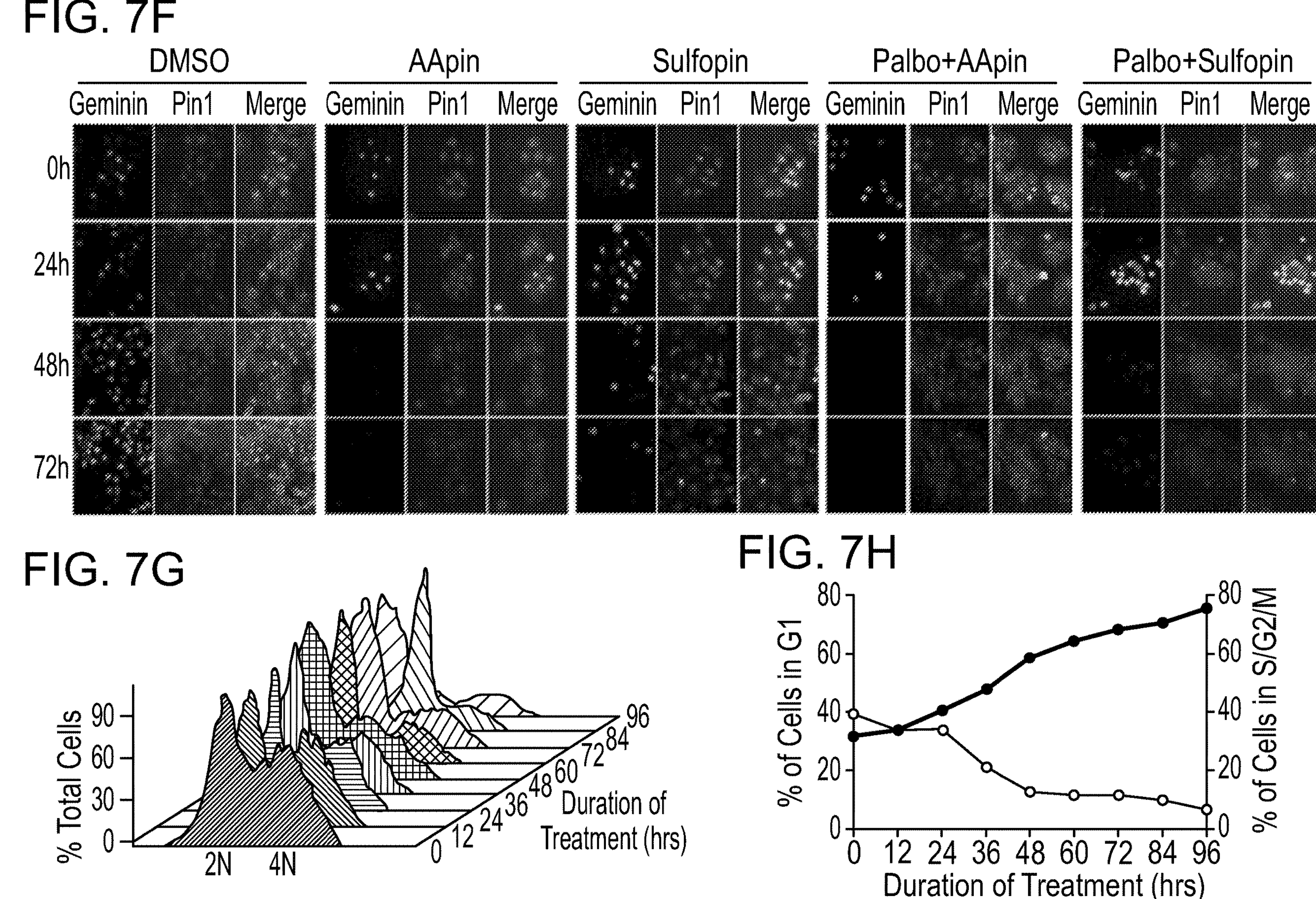
Figures 7I, 7J, 7K:
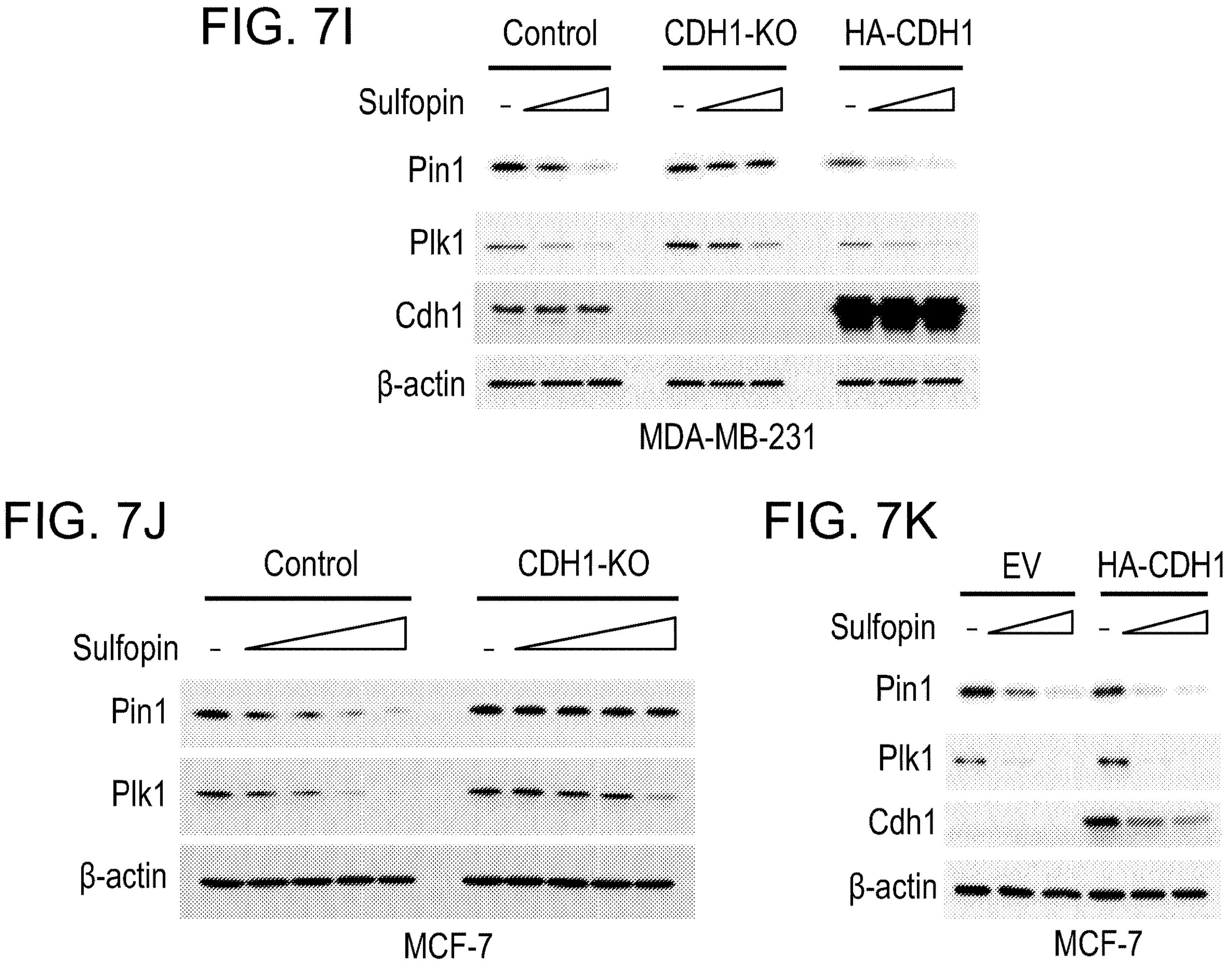
Figure 7L:
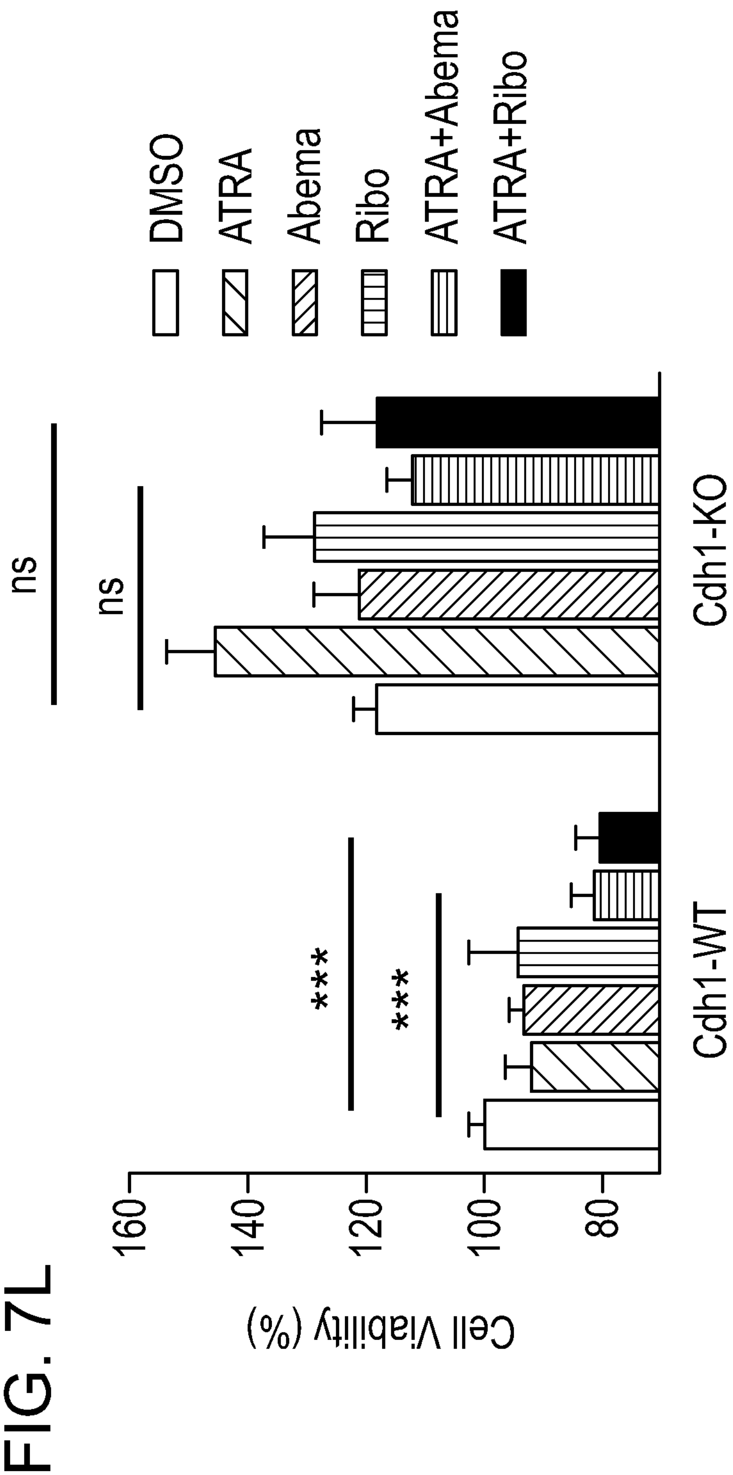

FIG. 7A-FIG. 7L is a set of graphs, images, diagrams and immunoblots that show that pharmacologic inhibition of Pin1 and CDK4/6 restores $APC/C^{Cdh1}$ E3 ligase activity. FIG. 7A is a graph that shows quantification of percentage of Pin1+/+ and Pin1−/− MDA-MB-231 cells from FIG. 8A in G1 phase released from nocodazole. FIG. 7B is a graph that shows release into mitosis after double-thymidine block in the absence or presence of Pin1. FIG. 7C is a graph that shows cell cycle phase distribution of Pin1+/+ and Pin1−/− MDA-MB-231 cells from FIG. 7B. FIG. 7D is a schematic diagram of the APC-degron reporter (Geminin: aa1-110). FIG. 7E is a set of graphs that shows cell division frequency in MCF-7 cells stably expressing the APC-degron reporter from FIG. 8E. FIG. 7F is a set of images that shows immunofluorescence for MDA-MB-231 cells stably expressing the APC-degron reporter (mCherry-Geminin fusion protein) and Pin1 (Venus-Pin1 fusion protein) and treated with different inhibitors for indicated periods. FIG. 7G is a diagram that shows DNA histogram in time course in MCF-7 cells from FIG. 8F. FIG. 7H is a graph that shows the quantification of cells in G1 and S/G2/M. FIG. 7I is an IB analysis for indicated proteins derived from MDA-MB-231 cells. FIG. 7J is an IB analysis for indicated proteins derived from MCF-7 cells stably expressing indicated constructs and treated with increasing concentrations of sulfopin. FIG. 7K is an IB analysis for indicated proteins derived from MCF-7 cells stably expressing indicated constructs and treated with increasing concentrations of sulfopin. FIG. 7L is a graph that shows growth suppression in Cdh1+/+ MEFs, but not Cdh1−/− MEFs by combination of Pin1 inhibitors (ATRA) and CDK4/6 inhibitors.

Figure 8A:
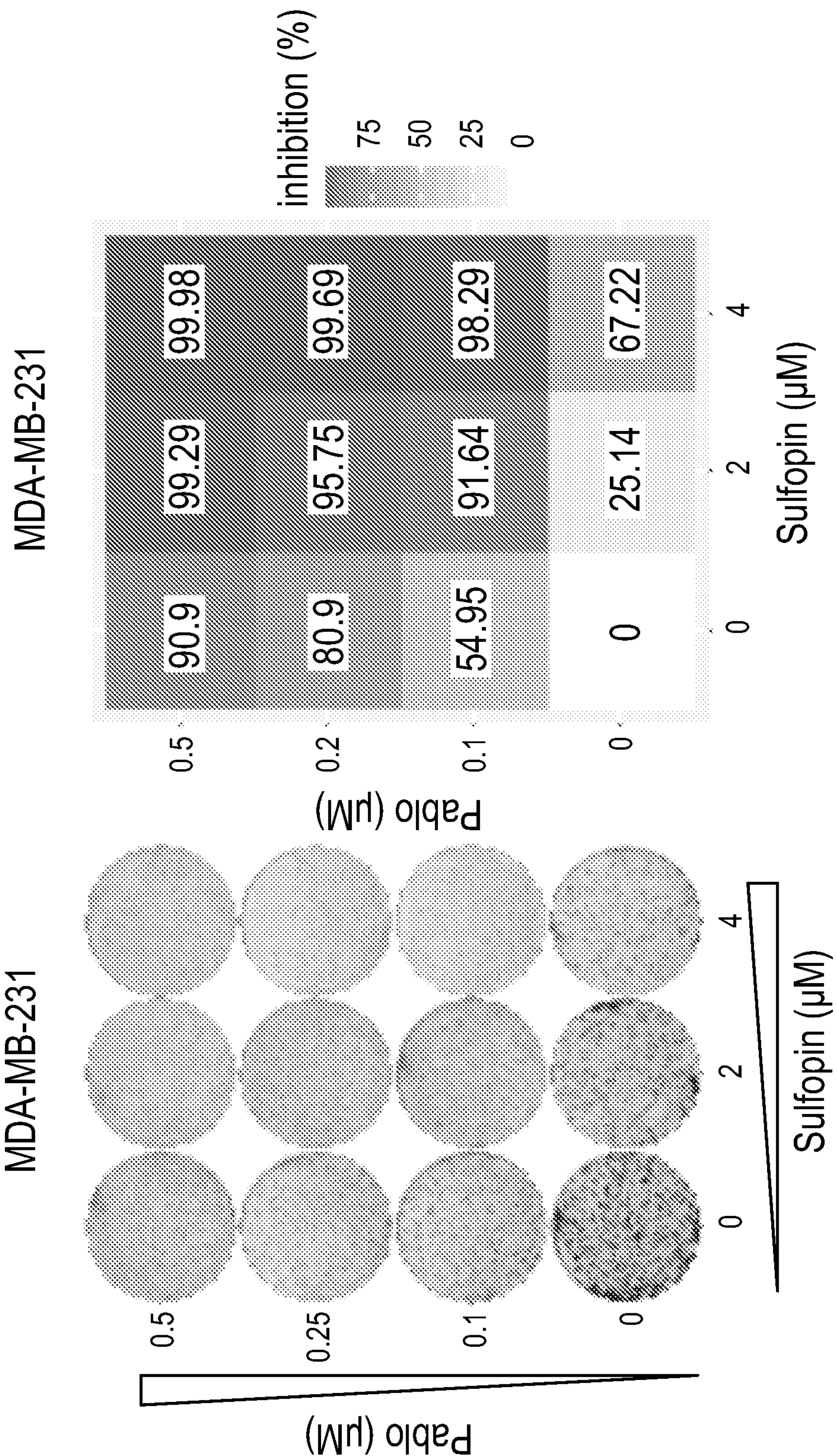
Figure 8B:
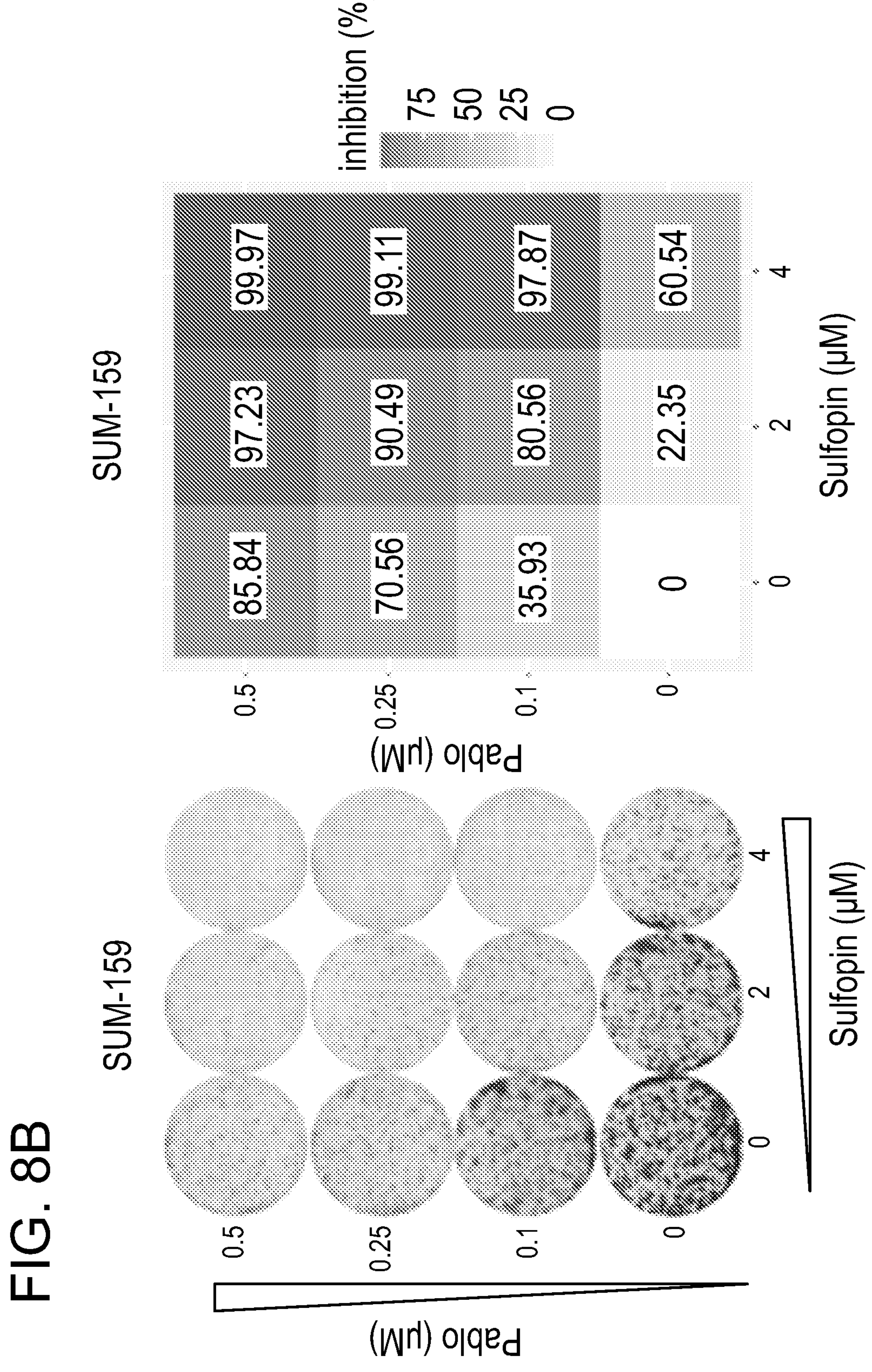
Figure 8D:
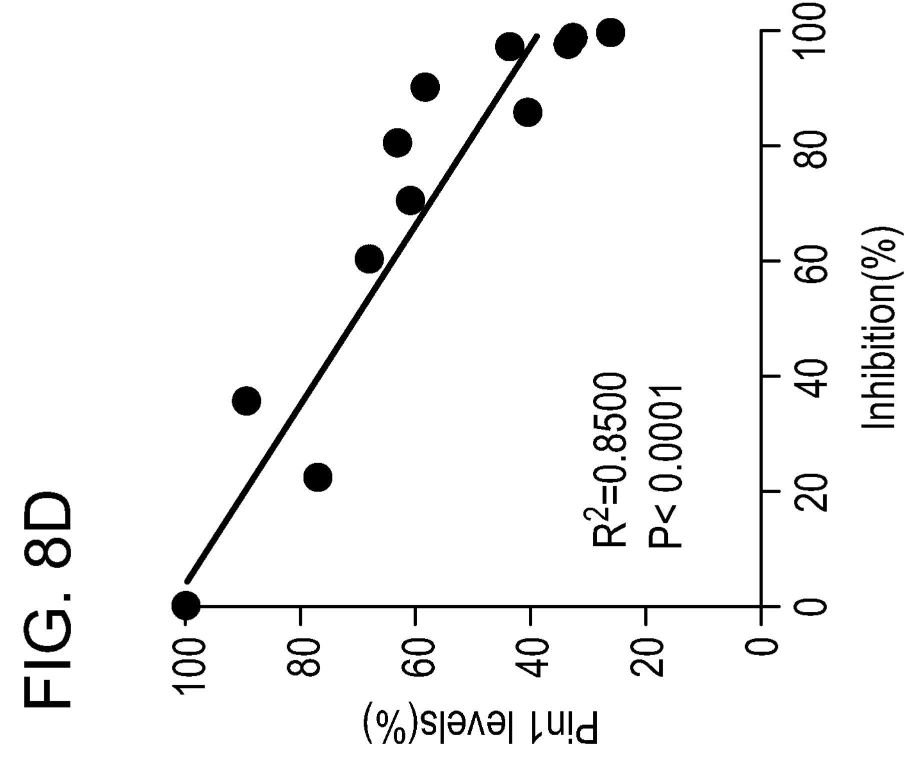
Figure 8C:
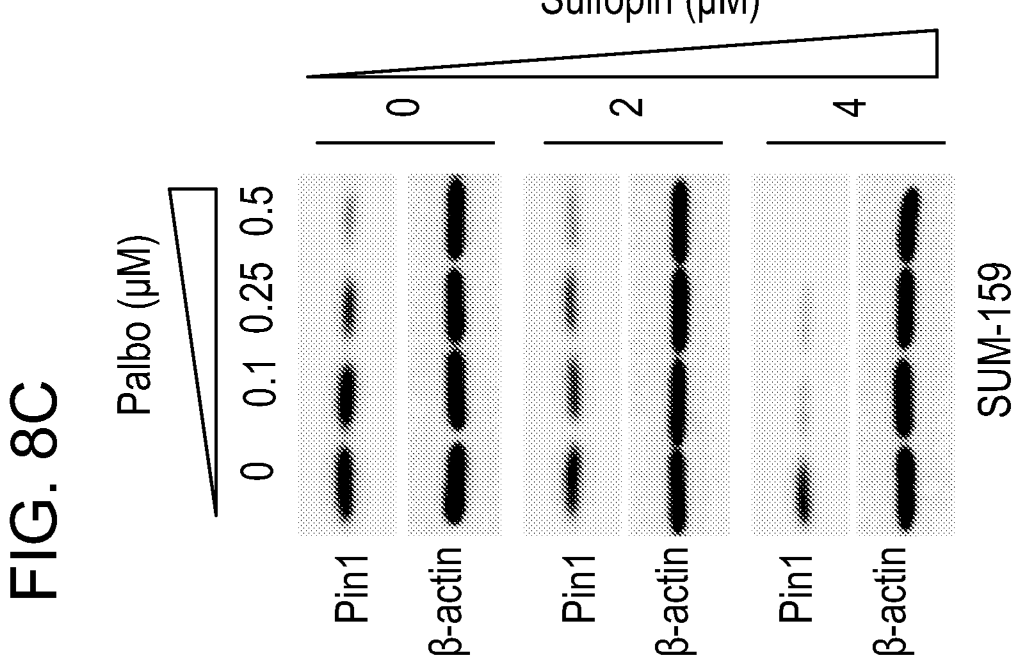
Figures 8E, 8F:
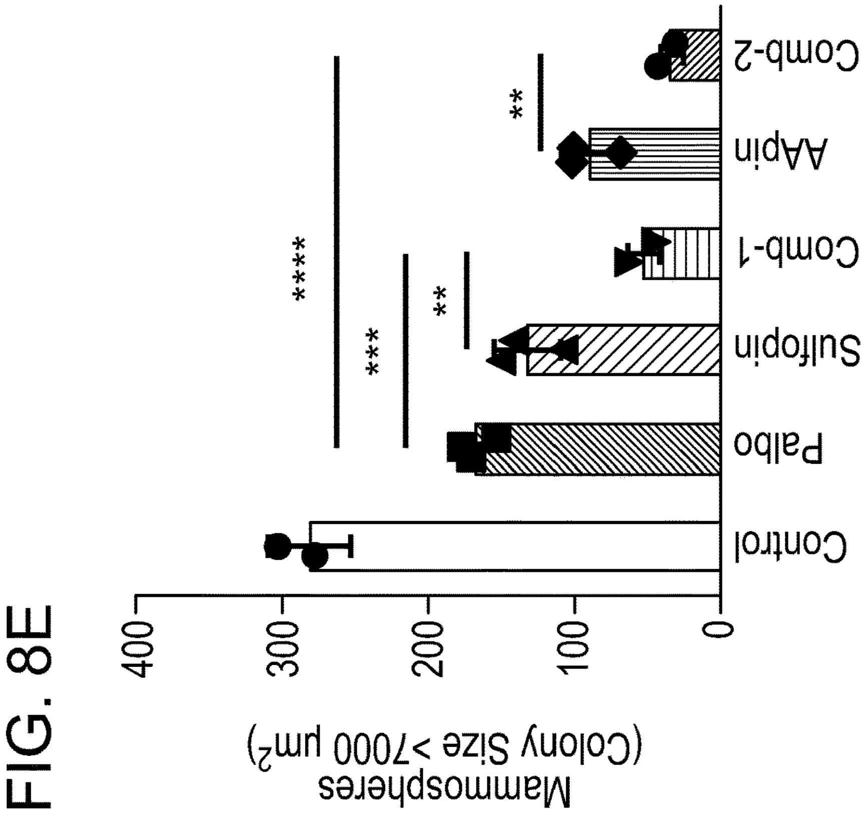
Figure 8H:
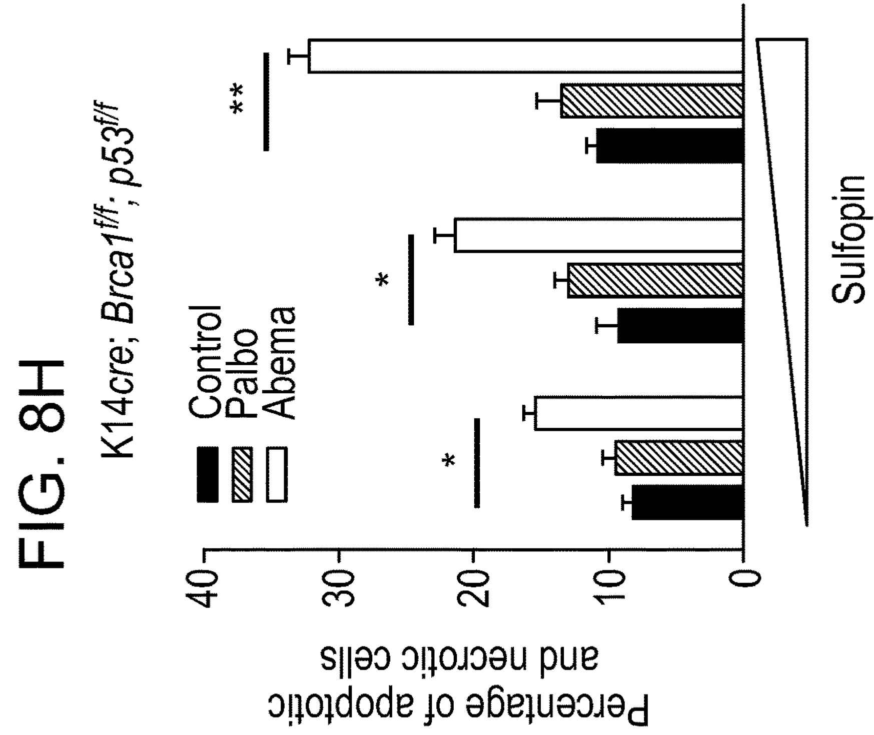
Figure 8G:
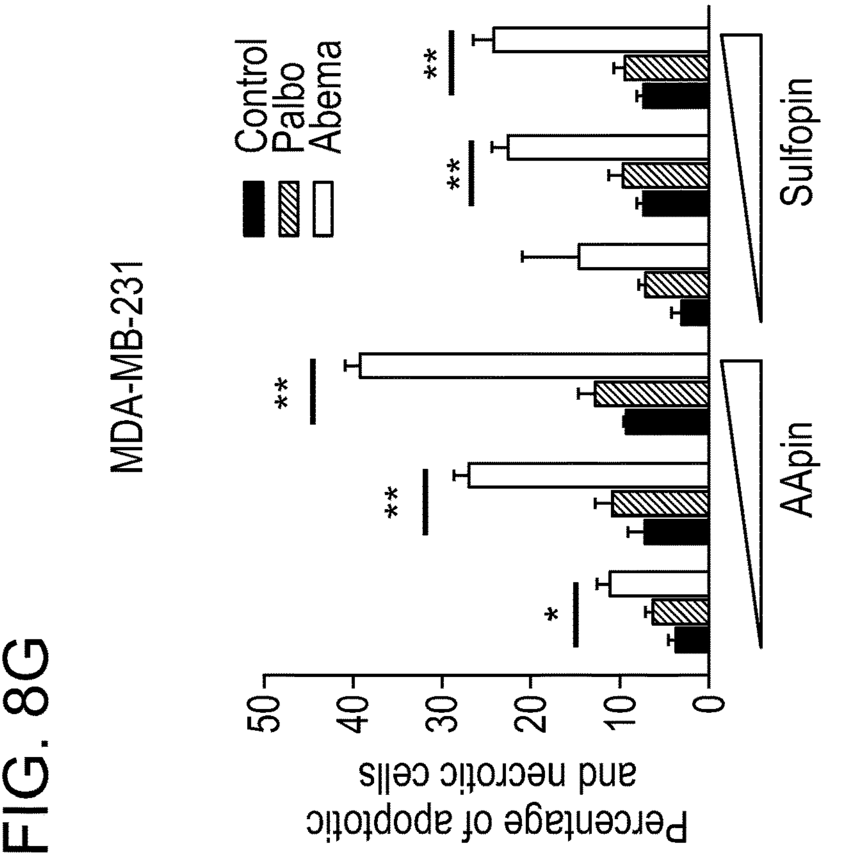

FIG. 8A-FIG. 8H is a set of growth matrices, immunoblots and graphs that show that Pin1 inhibitors synergize with CDK4/6 inhibitors against TNBC in cell models. FIG. 8A-FIG. 8H show the efficacy of Pin1 inhibition in combination with CDK4/6 inhibition. FIG. 8A is a set of colony formation and growth inhibition matrices of MDA-MB-231 cells treated with indicated concentrations of sulfopin and palbociclib for two weeks. FIG. 8B is a set of colony formation and growth inhibition matrices of SUM-159 cells treated with indicated concentrations of sulfopin and palbociclib for two weeks. The heatmaps show the inhibition rates of cells after treatment. FIG. 8C is an immunoblotting analysis (IB) of Pin1 in SUM-159 cells after 2 weeks treatment from FIG. 8B). FIG. 8D is a graph that shows the correlation of Pin1 abundance and cell growth inhibition in SUM-159 cells from (FIG. 8B and FIG. 8C). FIG. 8E is a graph that shows mammosphere formation assay of MDA-MB-231 cells treated with 1 μM palbociclib, 10 μM sulfopin, AApin (10 μM ATRA plus 1 μM ATO) or a combination of both drugs for two weeks. FIG. 8F is a graph that shows cell counts of MDA-MB-231 cells treated with 1 μM palbociclib, 10 μM sulfopin or a combination of both drugs for 4 days. FIG. 8G is a graph that shows MDA-MB-231 cells treated with increasing concentrations of indicated drugs for 3 days, followed by analyzing apoptotic and necrotic cells by Annexin V and PI. FIG. 8H is a graph that shows mouse TNBC cells treated with increasing concentrations of indicated drugs for 3 days, followed by analyzing apoptotic and necrotic cells by Annexin V and PI.

Figure 9A:
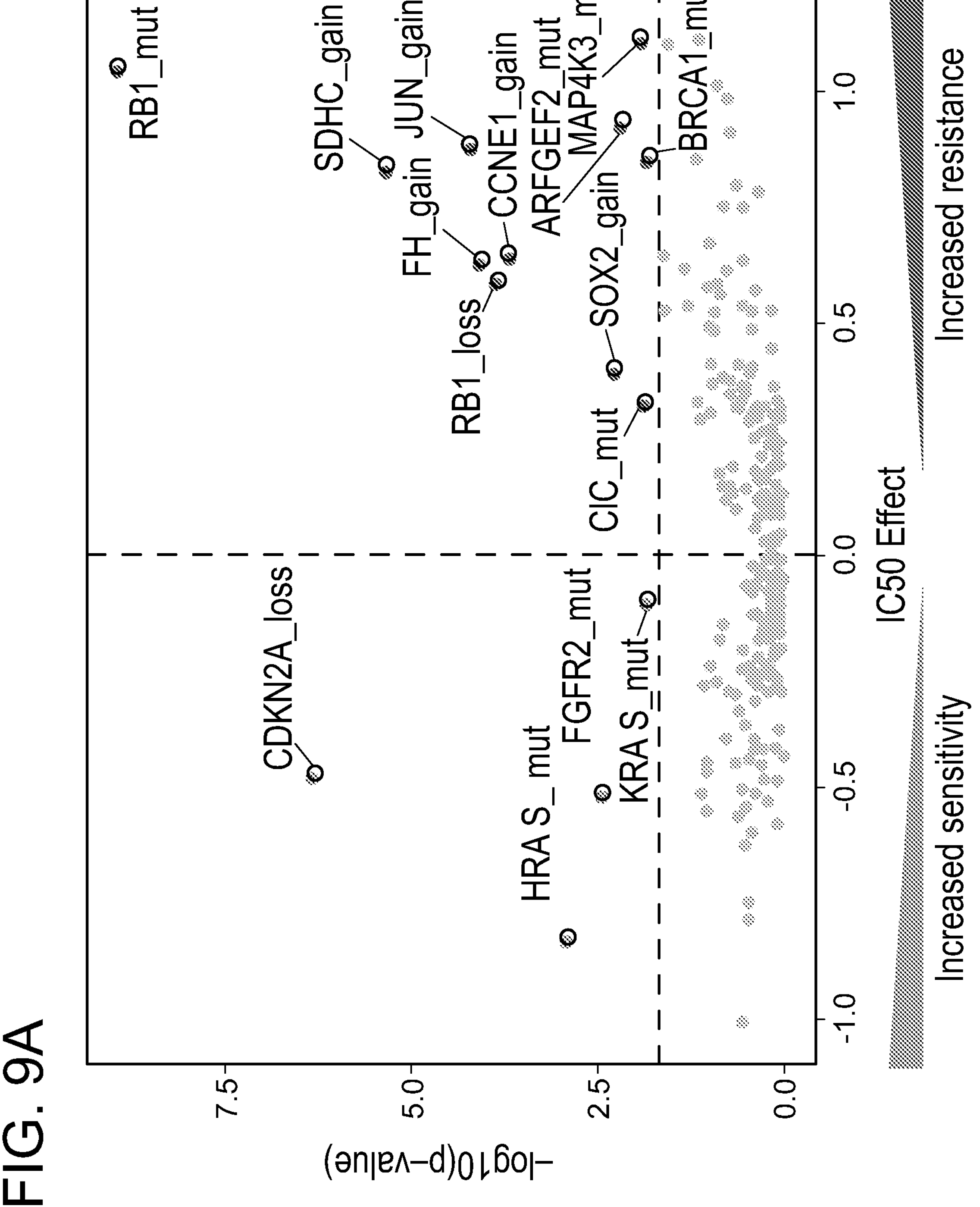
Figures 9B, 9C:
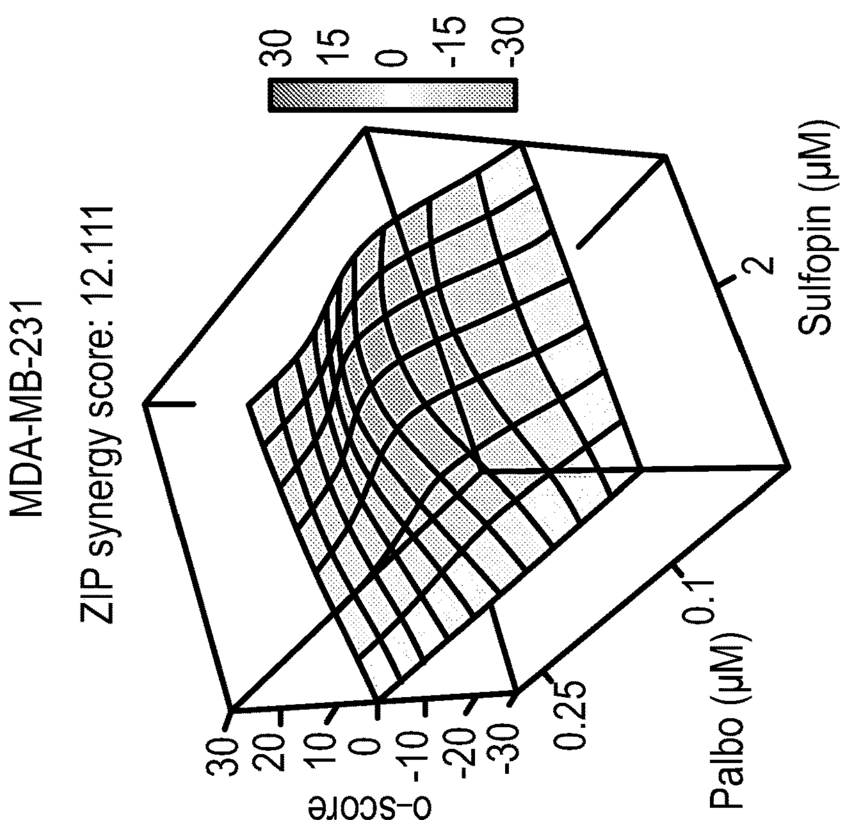
Figures 9D, 9E:
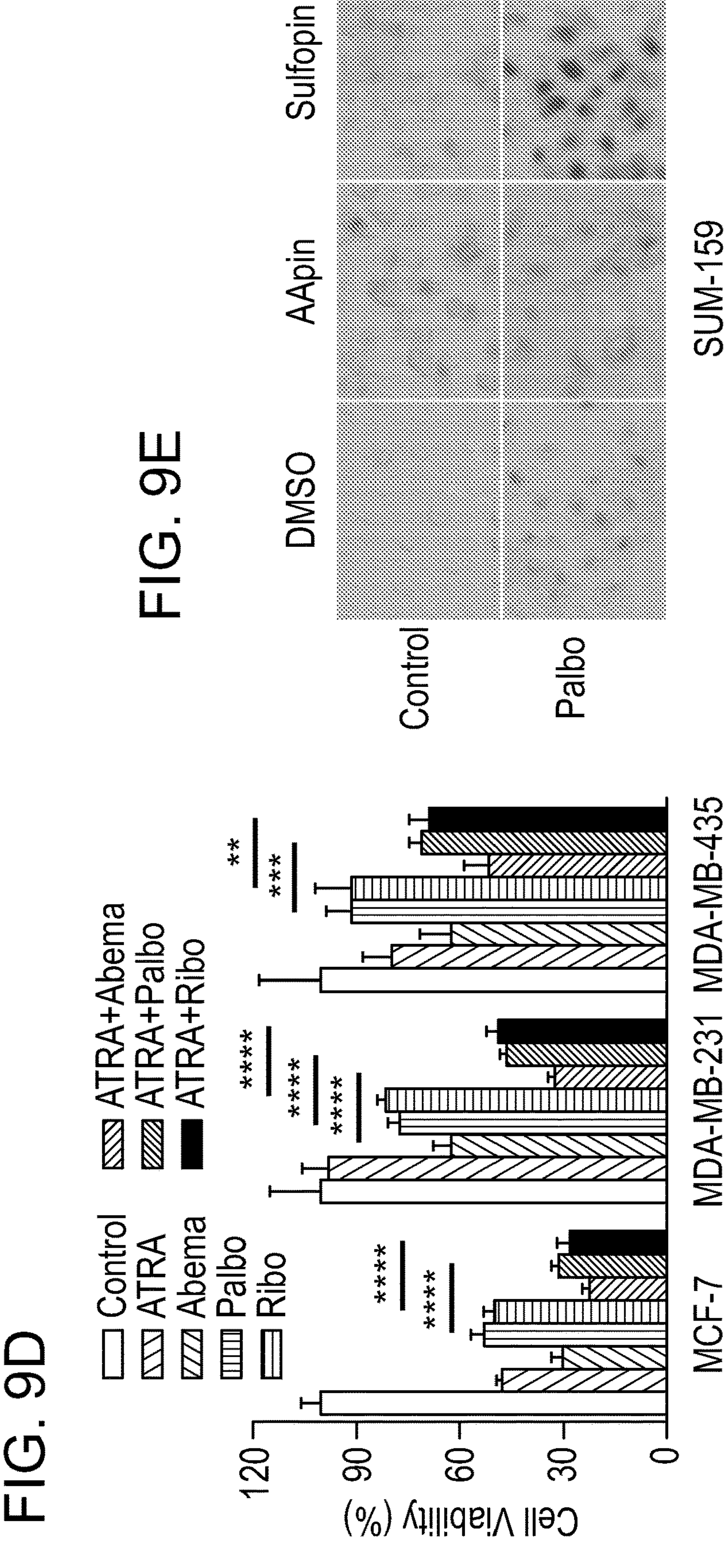
Figure 9F:
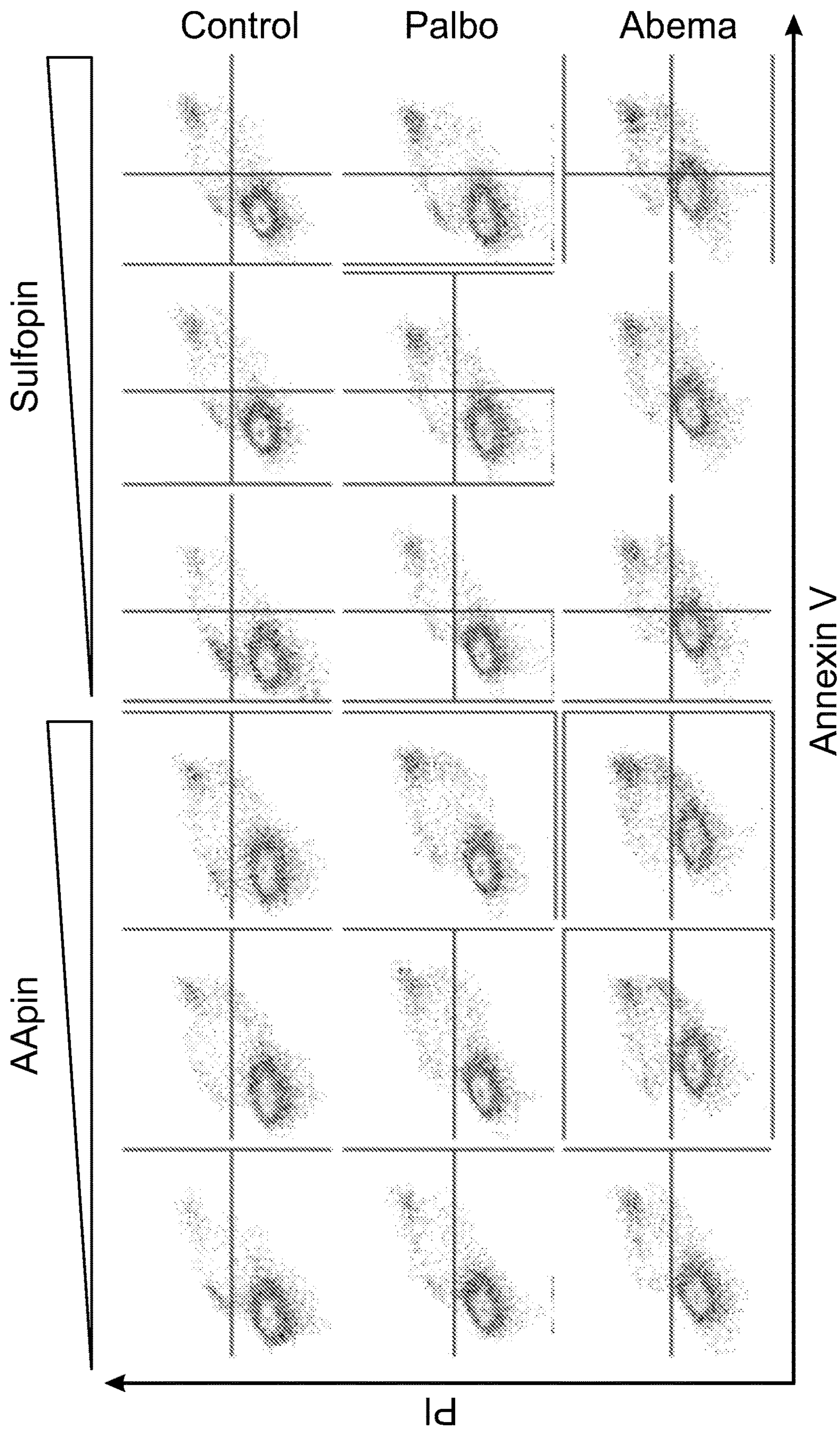
Figure 9G:
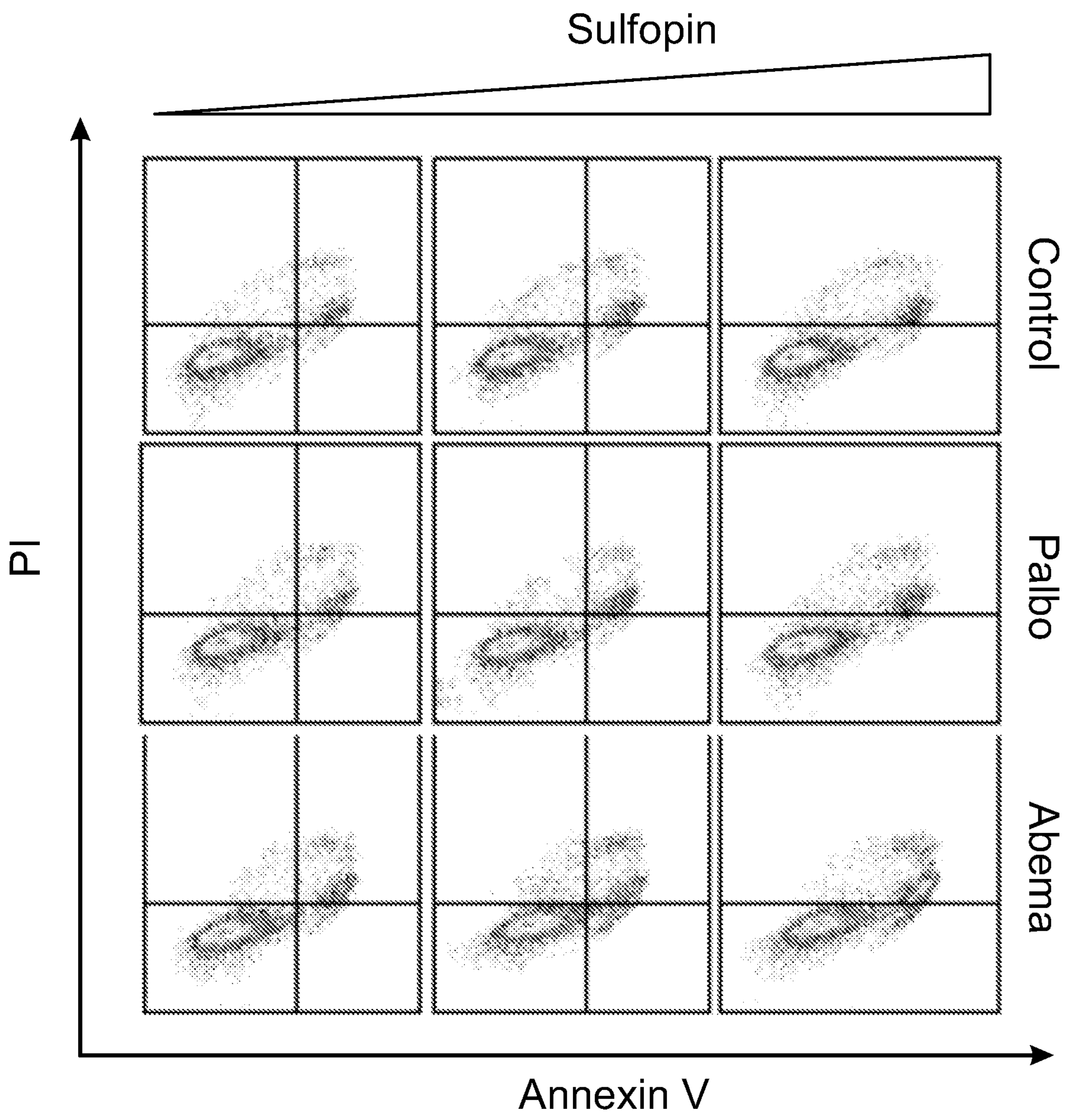

FIG. 9A-FIG. 9G is a set of volcano plots, graphs, images and dot plots that show that Pin1 inhibitors synergize with CDK4/6 inhibitors against TNBC in cell models. FIG. 9A is a volcano plot generated in VolcaNoseR that shows palbociclib sensitivity data from GDSC1 dataset. Each circle represented an association between genomic markers and palbociclib sensitivity analyzed using ANOVA. FIG. 9B is a graph that shows synergy scores for sulfopin combinations with palbociclib in MDA-MB-231 cells represented as 3D heat maps, with higher scores (darker red) denoting stronger synergy. FIG. 9C is a graph that shows synergy scores for sulfopin combinations with palbociclib in SUM-159 cells represented as 3D heat maps, with higher scores (darker red) denoting stronger synergy. FIG. 9D is a graph that shows ER+ (MCF-7) and ER-BC cells (MDA-MB-231 and MDA-MB-435) were treated with Pin1 inhibitors (30 μM ATRA) and 1 μM CDK4/6 inhibitors (palbociclib, ribociclib or abemaciclib) for 3 days and cell viability were assessed by CellTiter-Glo. FIG. 9E is a set of images that shows senescence was assessed by staining for SA-β-gal activity for SUM-159 cells treated with AApin (10 μM ATRA plus 1 μM ATO), 10 μM sulfopin, 1 μM palbociclib or combinations for 3 days. FIG. 9F is a set of dot plots of flow cytometry for MDA-MB-231 cells treated with increasing concentrations of indicated drugs for 3 days and apoptotic and necrotic cells were identified by Annexin V and PI. FIG. 9G shows a dot plot of flow cytometry for mouse TNBC cells treated with increasing concentrations of indicated drugs for 3 days and apoptotic and necrotic cells were identified by Annexin V and PI.

Figure 10C:
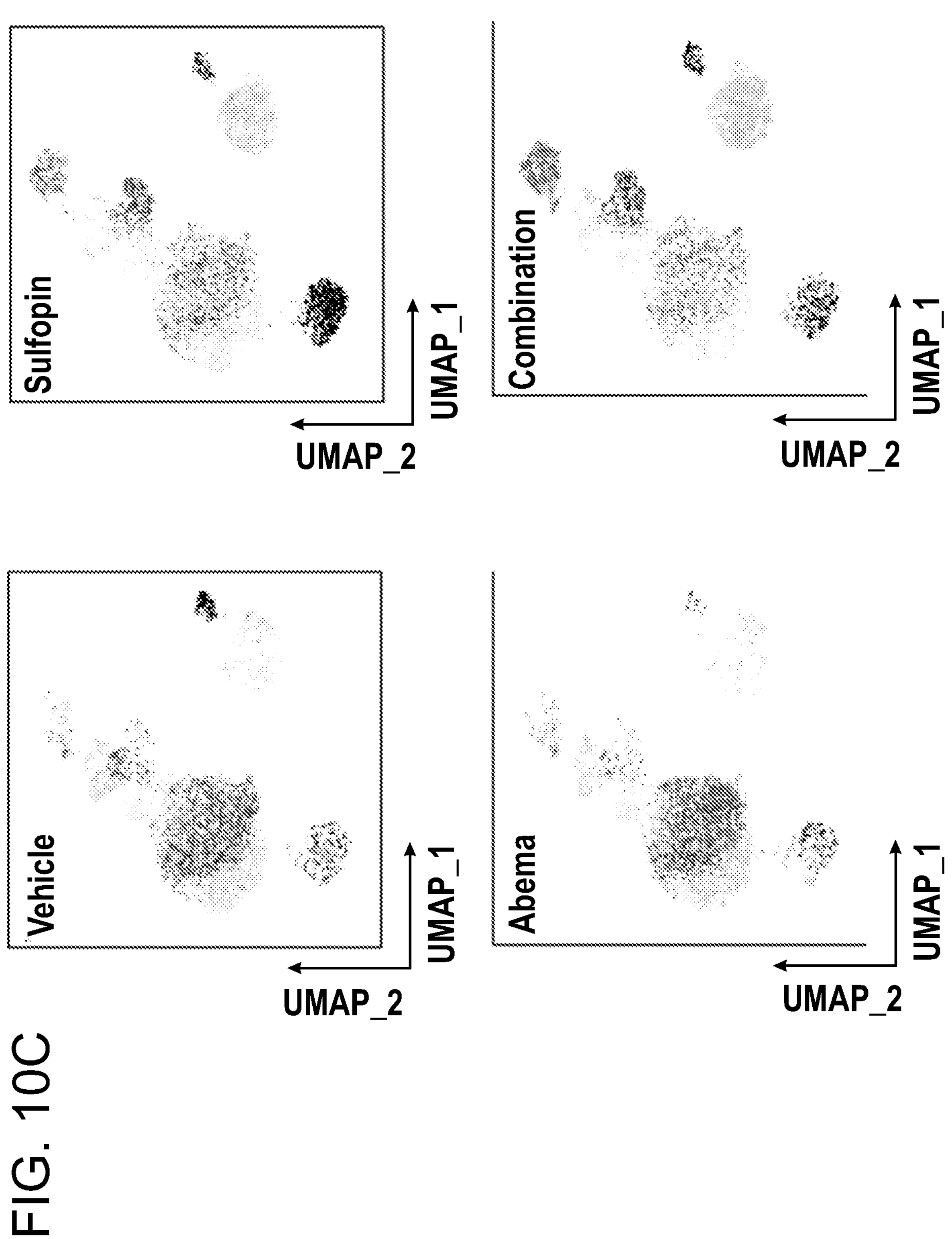
Figure 10D:
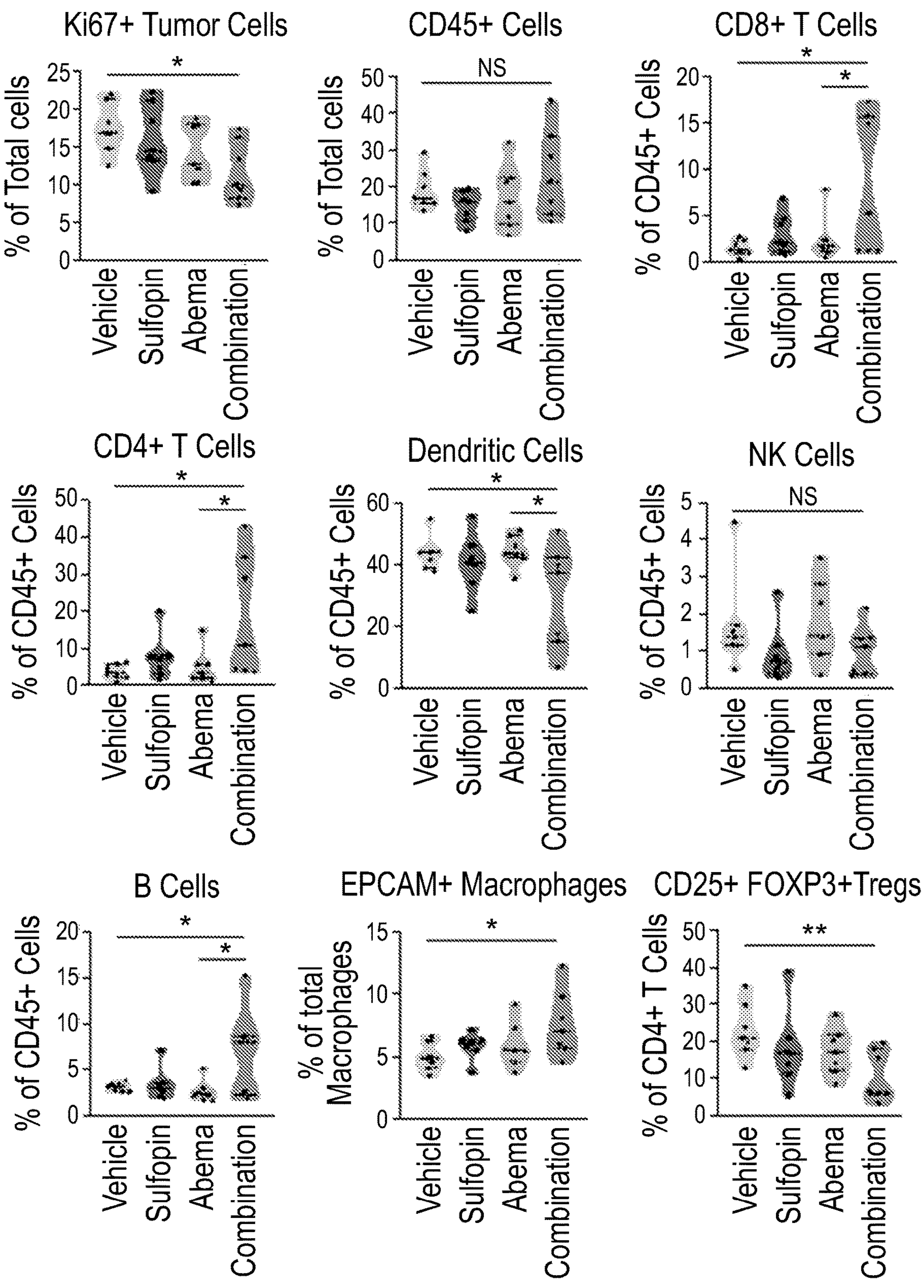
Figure 10E:
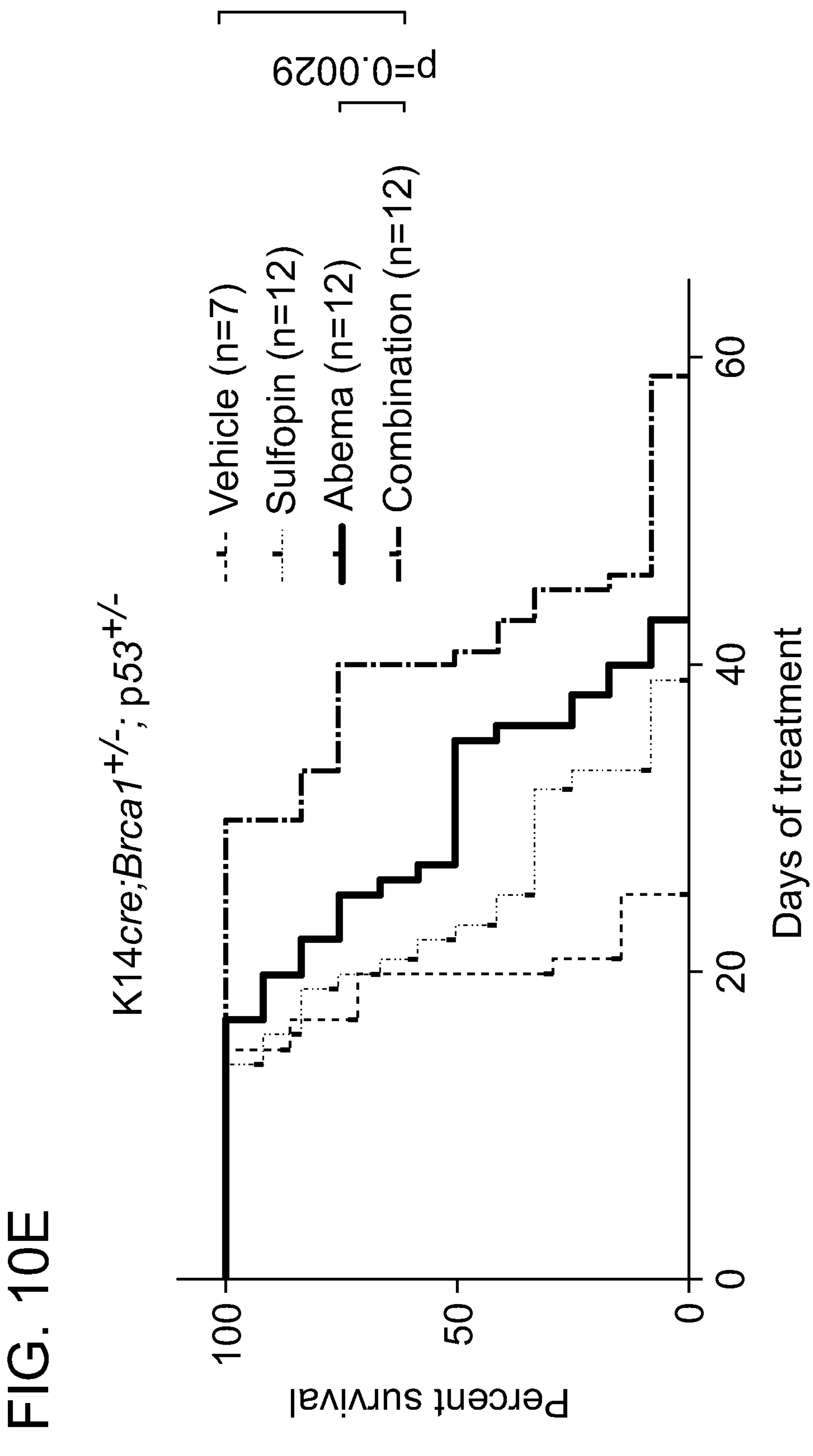
Figure 10F:
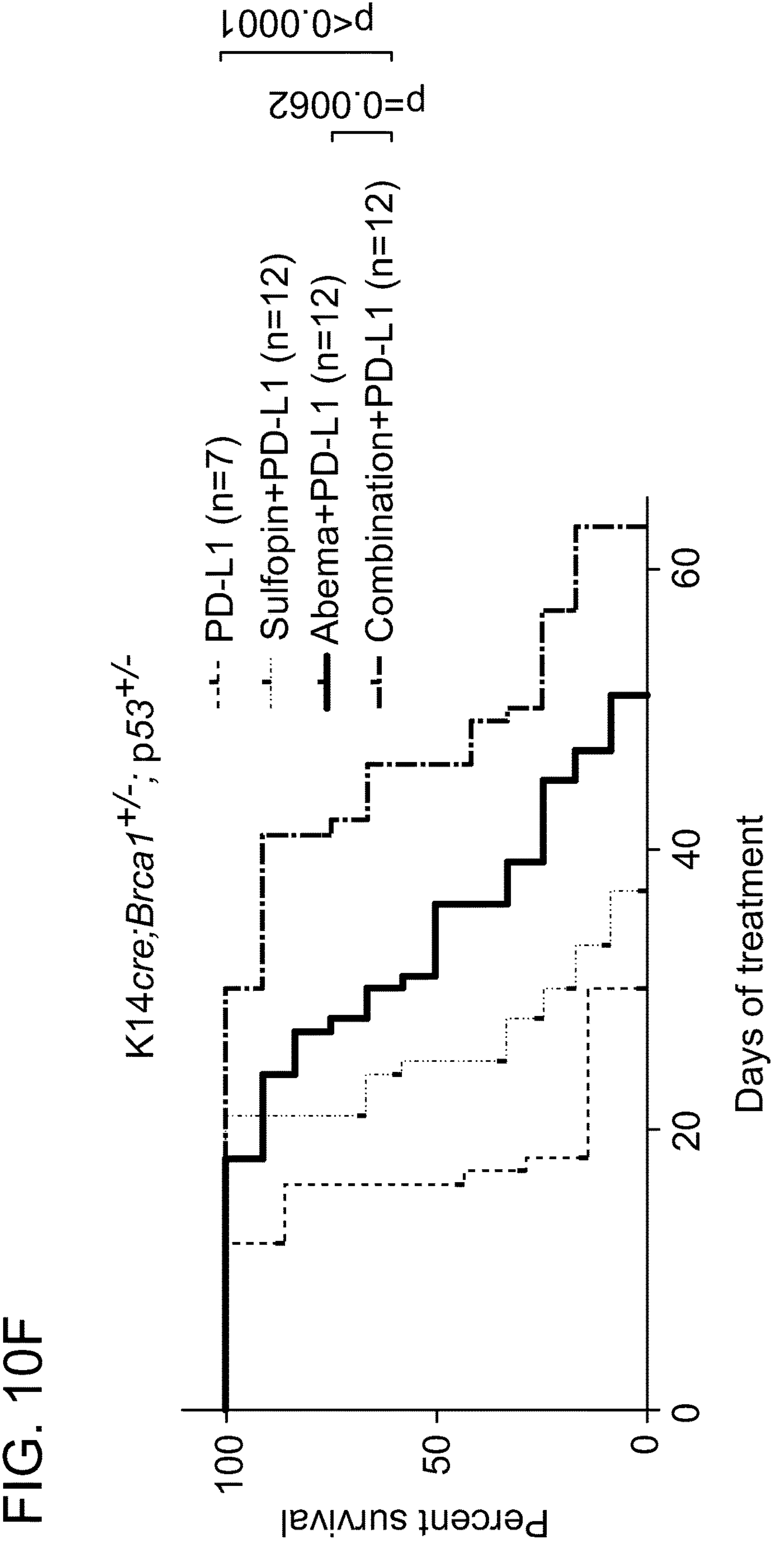

FIG. 10A-FIG. 10F is a set of graphs, images, and violin plots that show that pharmacologic inhibition of Pin1 and CDK4/6 boosts anti-tumor T cell activity and immune checkpoint inhibitor response in syngeneic TNBC mouse model. FIG. 10A is a graph that shows concatenated UMAP plots displaying 40,000 cells derived from K14cre; $Brca1^{+/-}$; $p53^{+/-}$ mouse tumors treated with sulfopin, abemaciclib or their combination for two weeks and colored by the main cell populations based on manual annotation of PhenoGraph clustering. FIG. 10B is a graph that shows concatenated UMAP plots displaying 24,000 CD45+ cells derived from K14cre; $Brca1^{+/-}$; $p53^{+/-}$ mouse tumors treated with sulfopin, abemaciclib or their combination for two weeks and colored by the main cell populations based on manual annotation of PhenoGraph clustering. FIG. 10C is a set of images that shows individual UMAP for CD45+ cells from different treatments. FIG. 10D is as set of violin plots generated by CyTOF data showing percentages of indicated cells from different treatments, including Ki67+ tumor cells, CD45+ cells, CD8+ cells, CD4+ T cells, dendritic cells, NK cells, B cells, EPCAM+ macrophages and CD25+ FOXP3+ Tregs. FIG. 10E is a graph that shows survival until mandatory euthanasia (tumor size 2 cm) for a cohort of mice bearing K14cre; $Brca1^{+/-}$; p53"-TNBC, treated with sulfopin, abemaciclib and the combination. FIG. 10F is a survival curve generated from the same cohort of mice bearing K14cre; $Brca1^{+/-}$; p53/TNBC, further treated with anti programmed death-ligand 1 (anti-PD-L1).

Figure 11A:
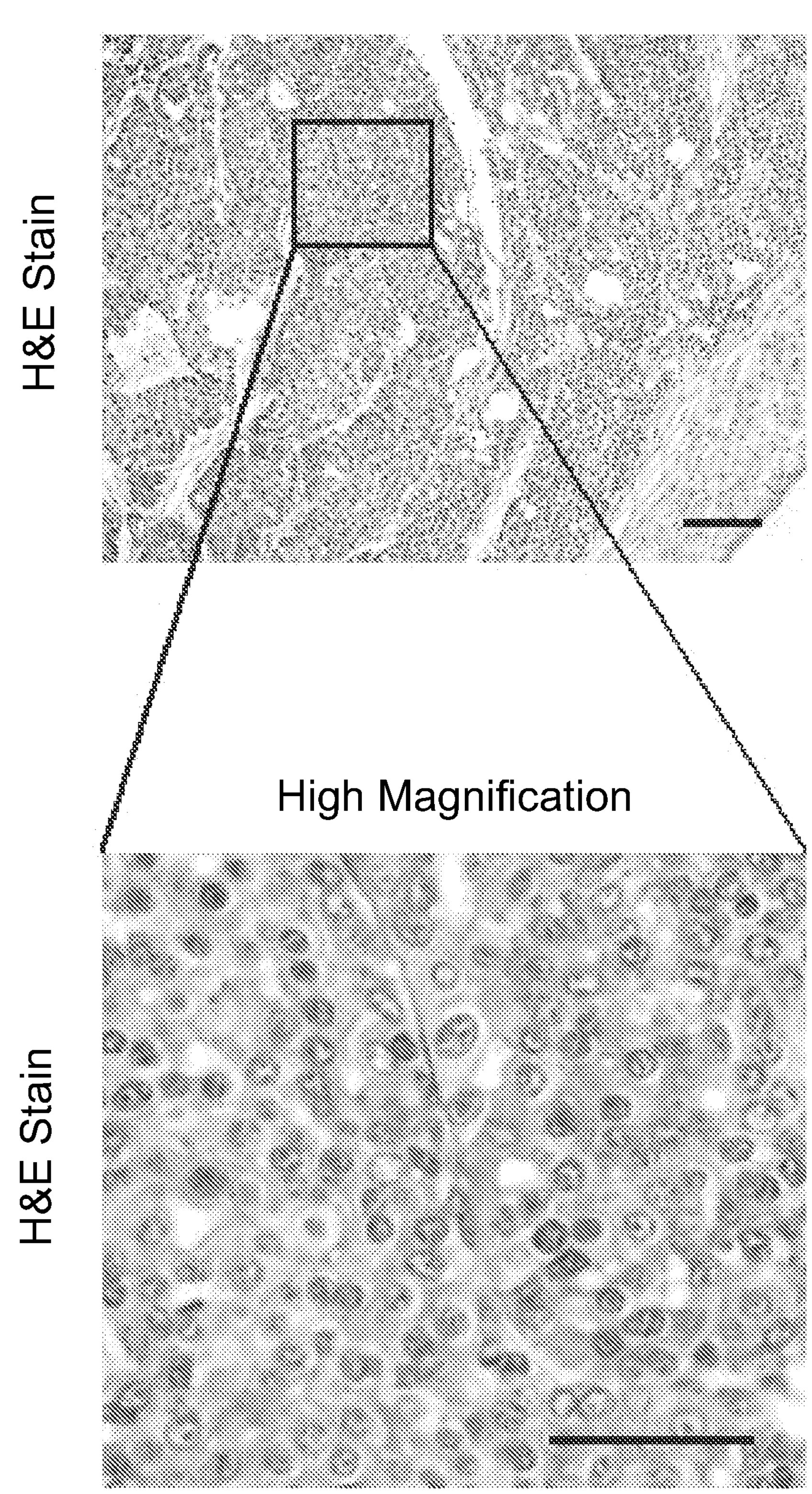
Figure 11B:
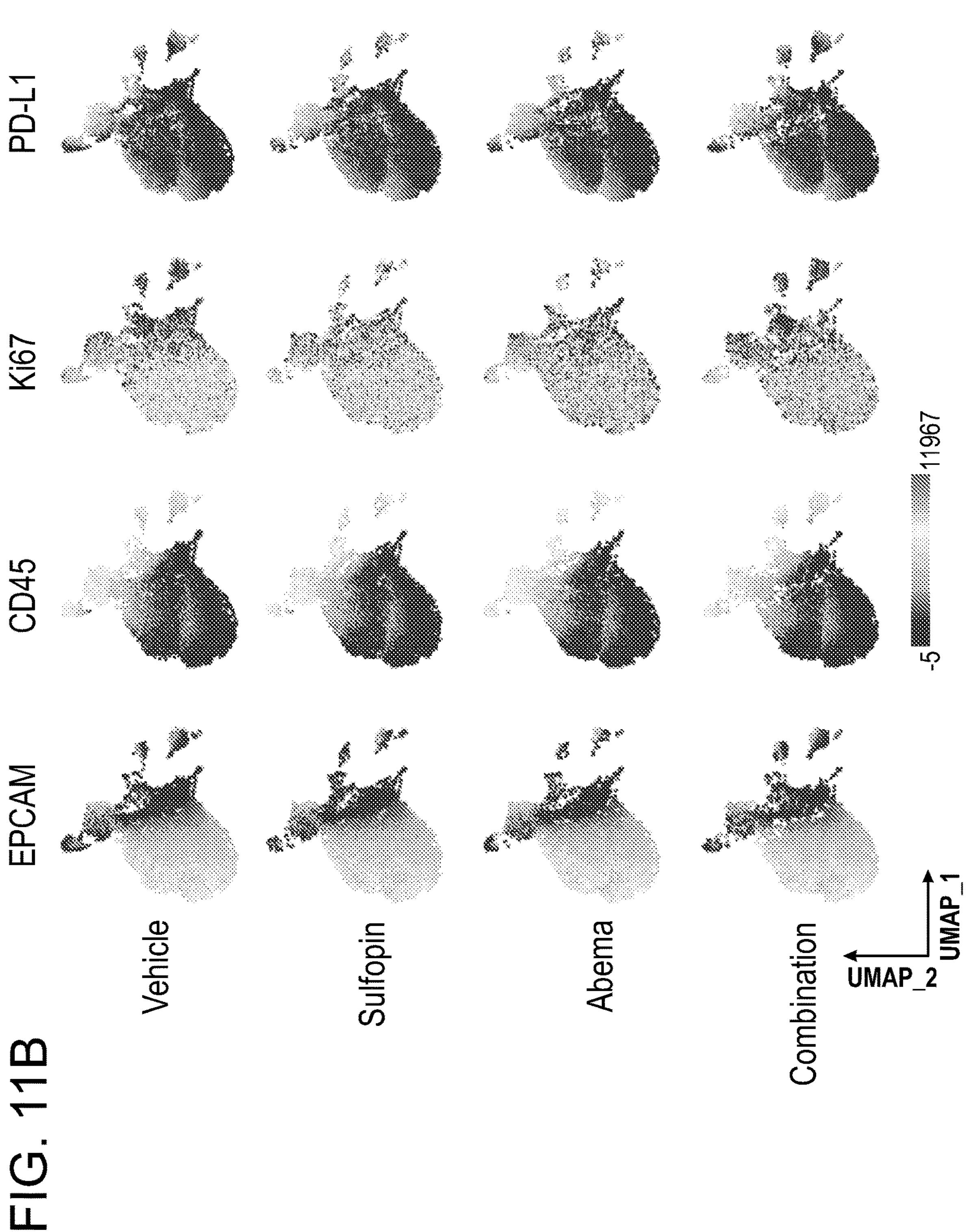

FIG. 11A-FIG. 11B is a set of images that show that pharmacologic inhibition of Pin1 and CDK4/6 boosts anti-tumor T cell activity and immune checkpoint inhibitor response in syngeneic TNBC mouse model. FIG. 11A is an image that shows microscopic tumors detected with H&E staining after autopsy. FIG. 11B is a set of images that shows UMAPs were color mapped by indicated markers on cells from different treatments.

Figure 12A:
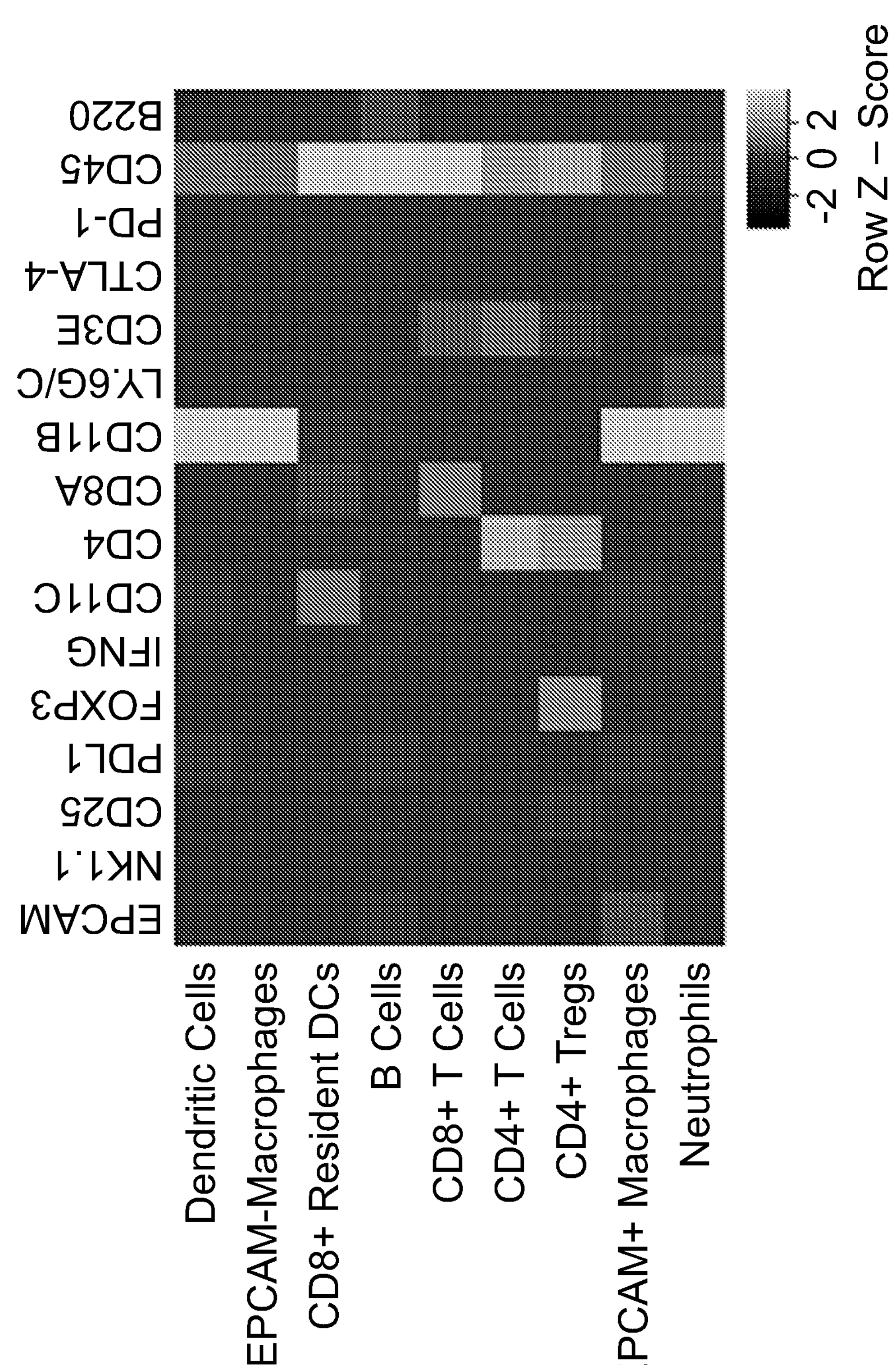
Figure 12B:
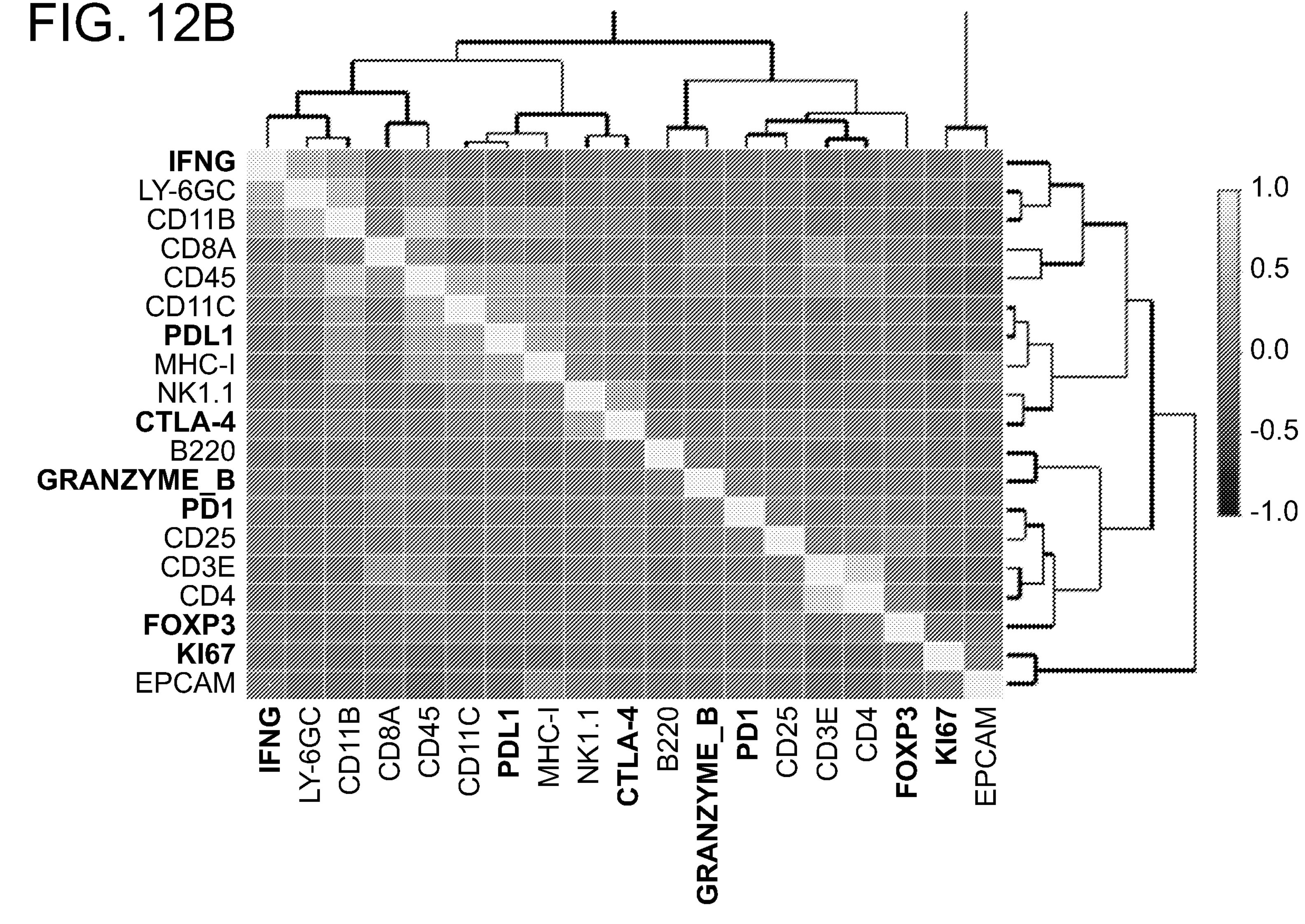
Figure 12C:
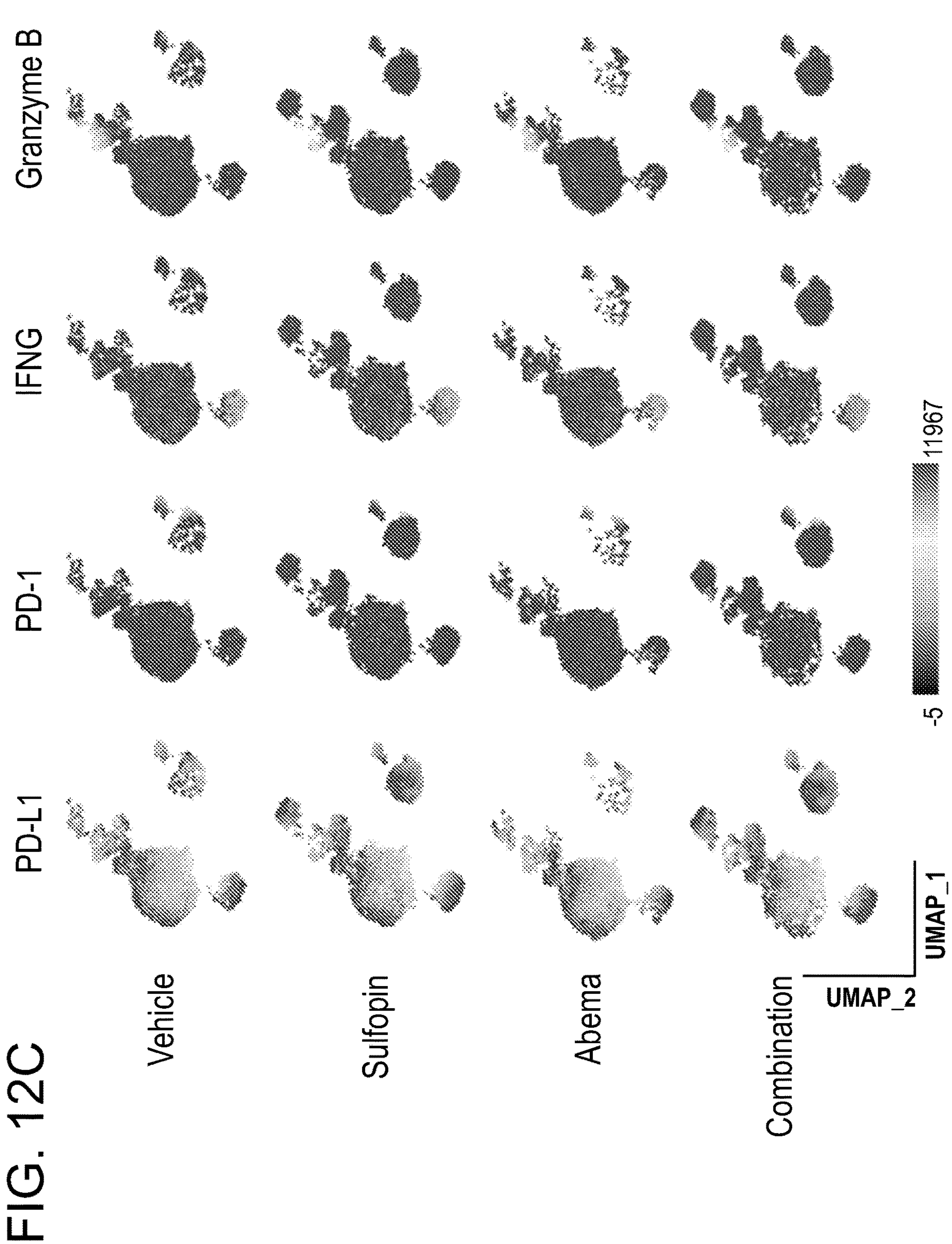
Figure 12D:
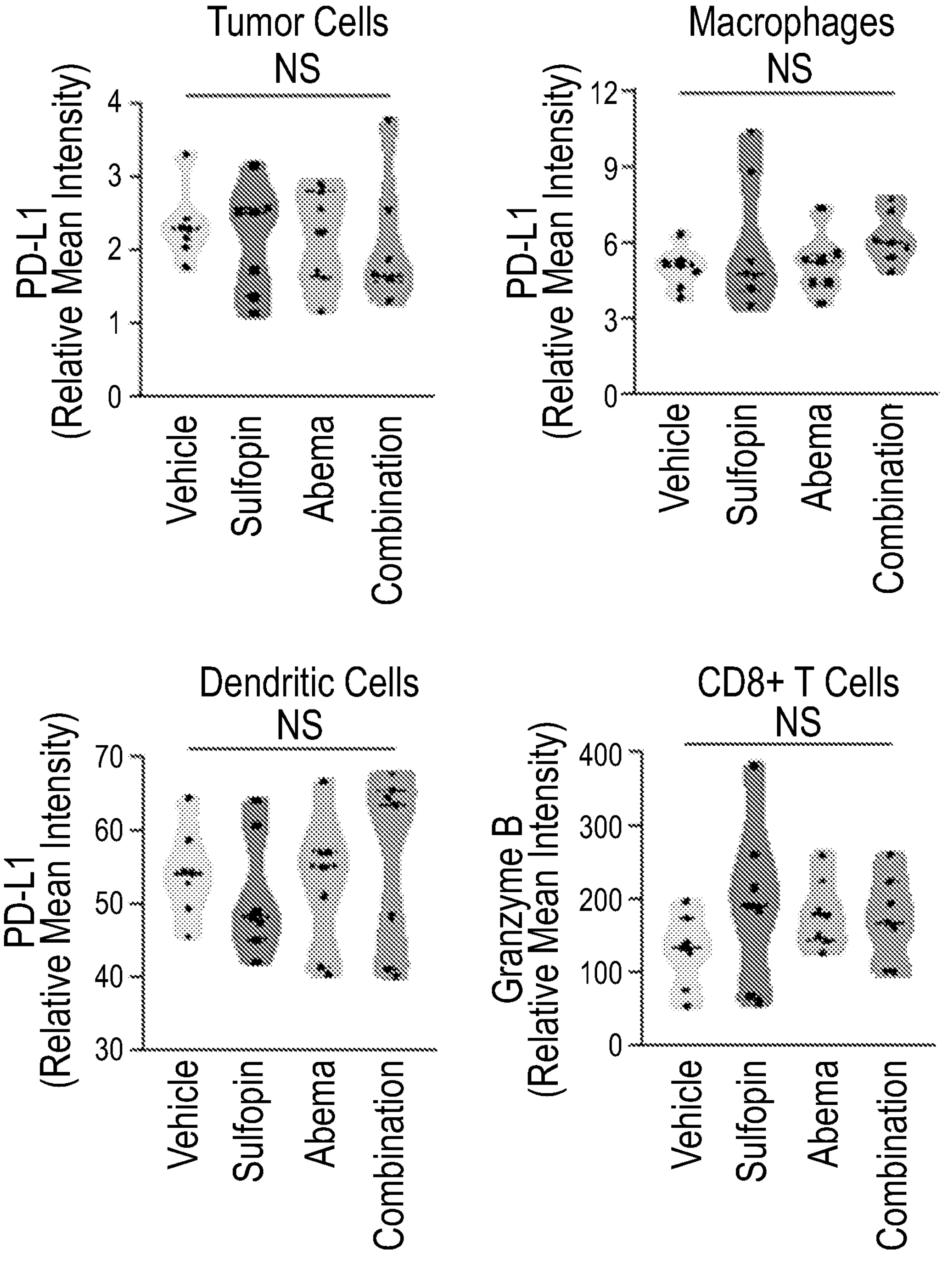

FIG. 12A-FIG. 12D is a set of heatmaps, matrices, images and violin plots that show that pharmacologic inhibition of Pin1 and CDK4/6 boosts anti-tumor T cell activity and immune checkpoint inhibitor response in syngeneic TNBC mouse model. FIG. 12A is a heatmap showing normalized expression of the indicated markers for PhenoGraph clusters which are grouped by expression profiles. FIG. 12B is a matrix that shows pairwise hierarchical clustering correlation matrix shown for the indicated parameters, with the Spearman's rank correlation coefficient displayed in the heatmap. FIG. 12C is a set of images that shows representative heatmaps of individual UMAP for CD45+ cells from different treatments, where the cells were colored by intensity of indicated markers. FIG. 12D is a set of violin plots generated by CyTOF data showing relative mean intensity for PD-L1 and Granzyme B in indicated cells from different treatments.

Figures 13A, 13B, 13C, 13D:
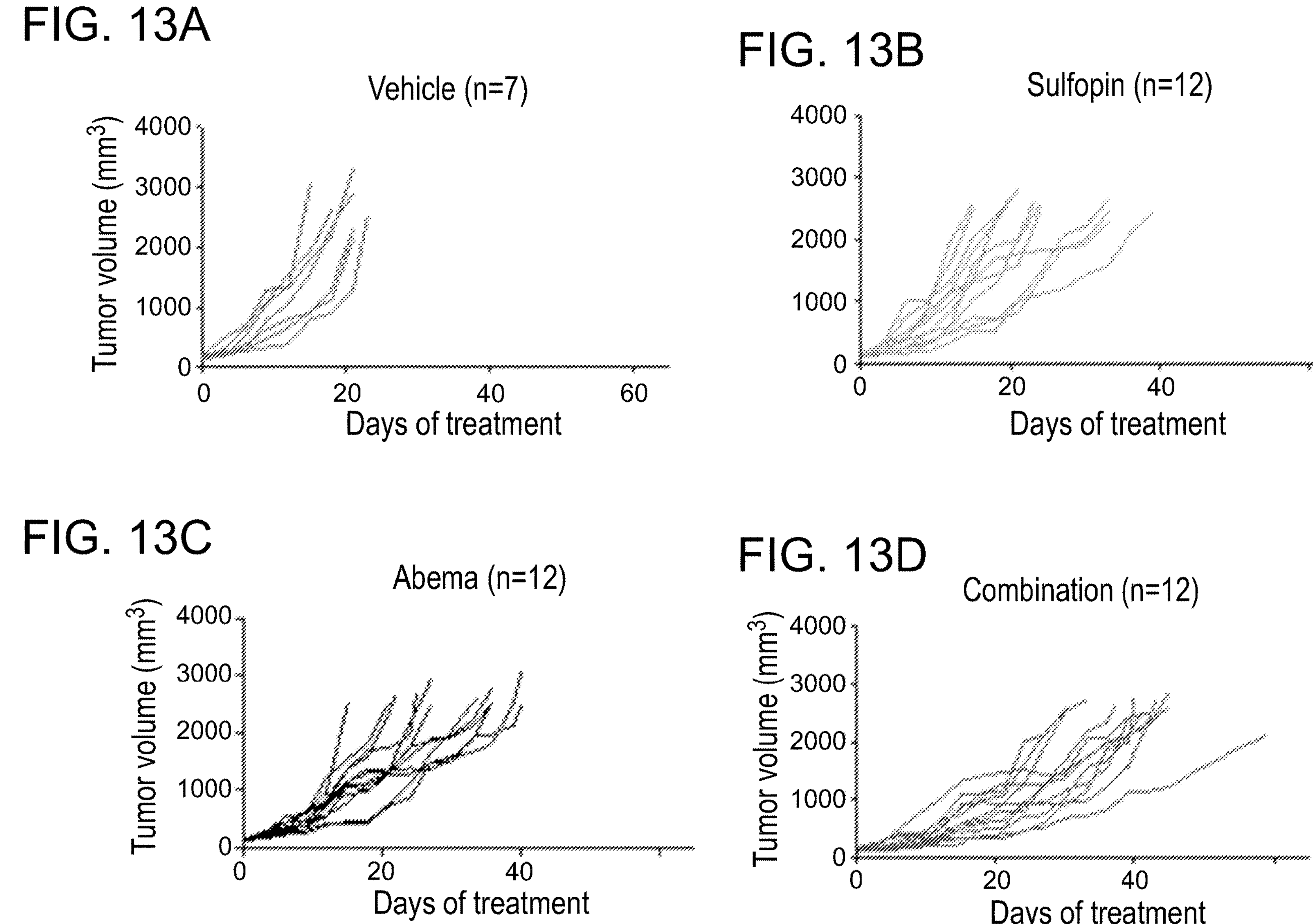
Figures 13E, 13F, 13G, 13H:
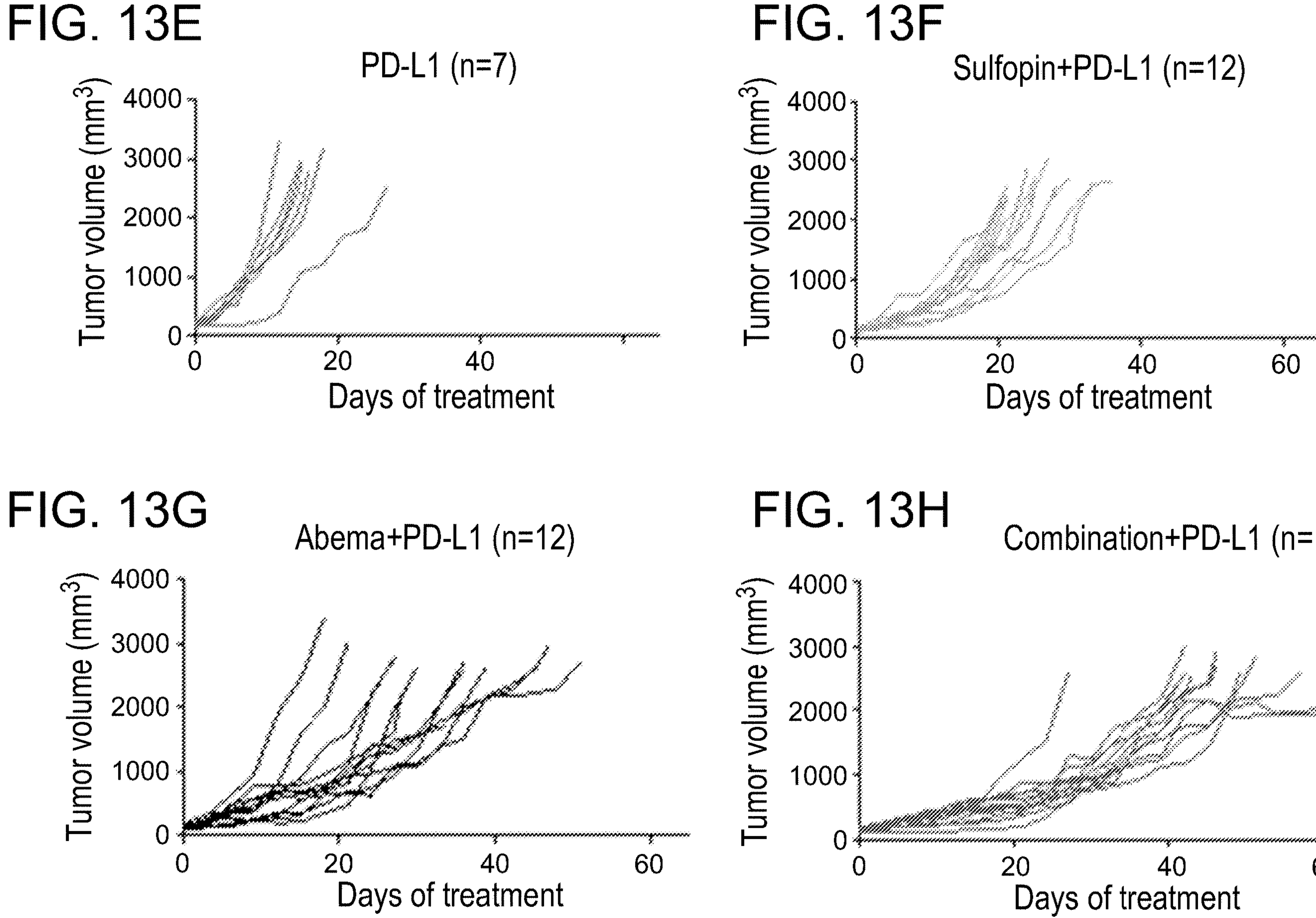

FIG. 13A-FIG. 13H is a set of plots that show that pharmacologic inhibition of Pin1 and CDK4/6 boosts anti-tumor T cell activity and immune checkpoint inhibitor response in syngeneic TNBC mouse model. FIG. 13A-FIG. 13D show the comparison of individual K14cre; $Brca1^{+/-}$; p537/tumor volume plots from mice in different treatment groups. FIG. 13A is a plot for vehicle. FIG. 13B is a plot for sulfopin treatment. FIG. 13C is a plot for abemaciclib treatment. FIG. 13D is a plot for combination sulfopin and abemaciclib treatment. FIG. 13E-FIG. 13H show the evaluation of the effects of the combination of anti-PD-L1 immune checkpoint inhibition with sulfopin, abemaciclib or sulfopin plus abemaciclib in the K14cre; $Brca1^{+/-}$; p53" mouse model of TNBC. FIG. 13E is a plot for PD-L1. FIG. 13F is a plot for sulfopin+PD-L1. FIG. 13G is a plot for abemaciclib+PD-L1. FIG. 13H is a plot for the sulfopin+abemaciclib combination+PD-L1.

Figure 14A:
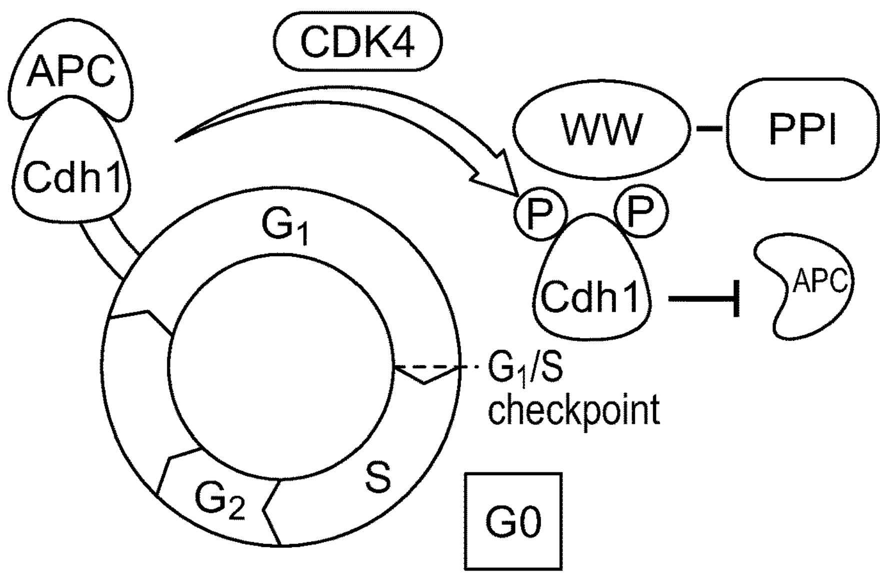
Figure 14B:
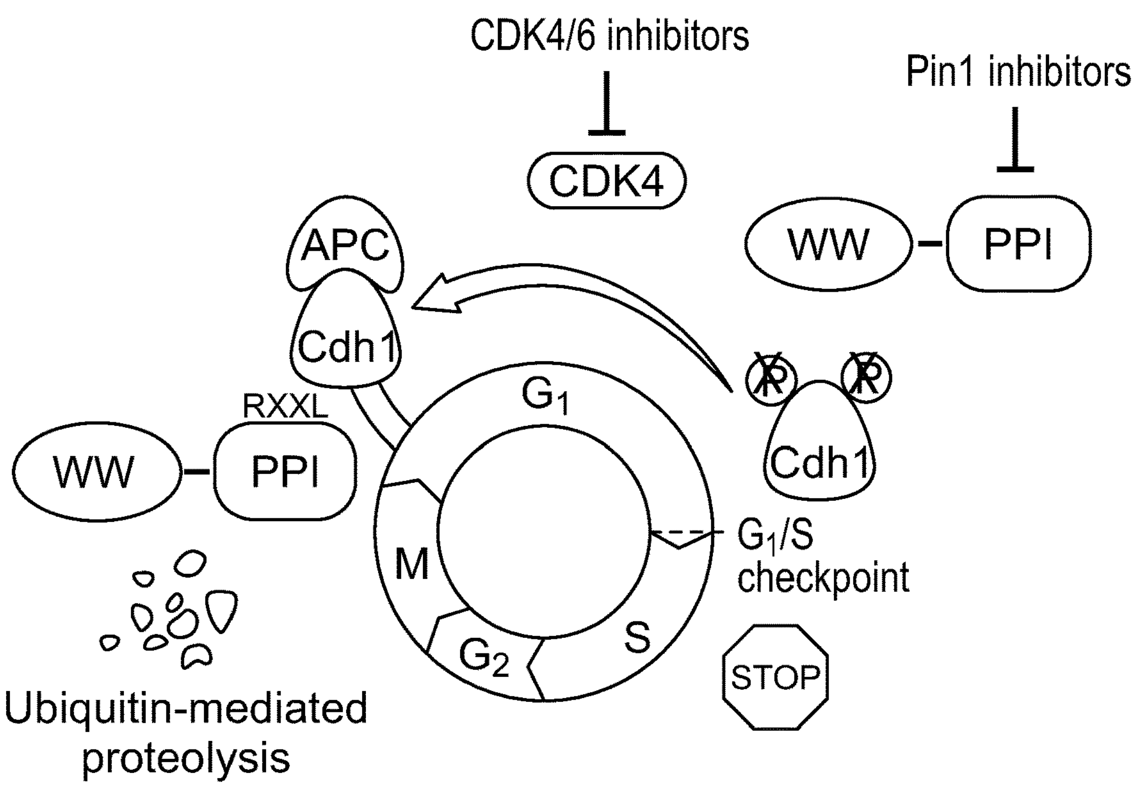
Figure 14C:
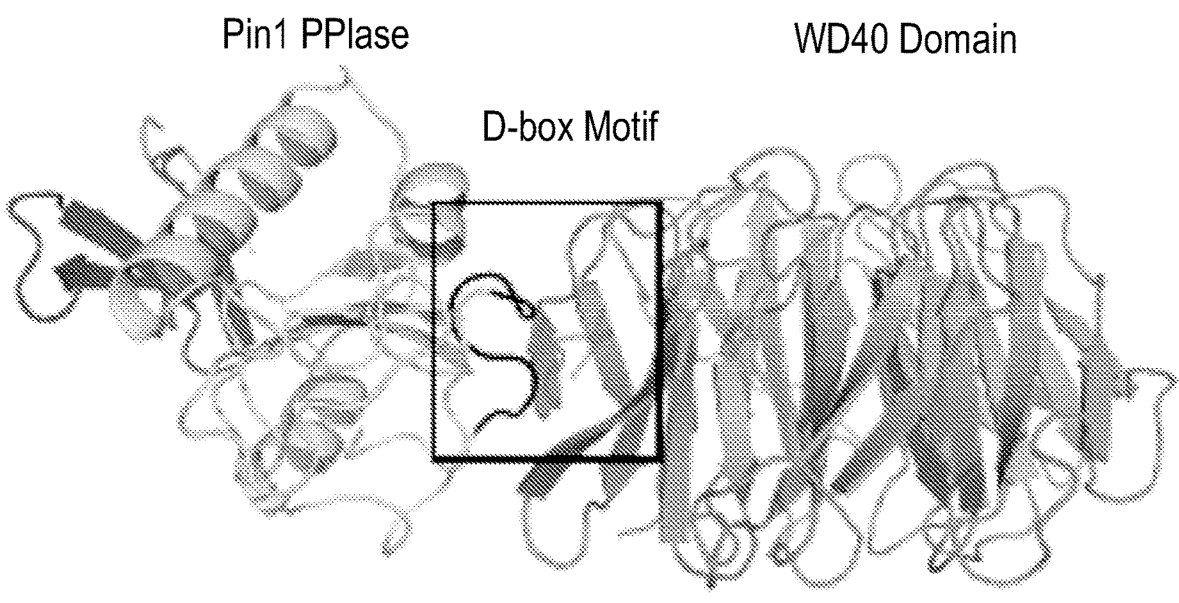
Figure 14D:
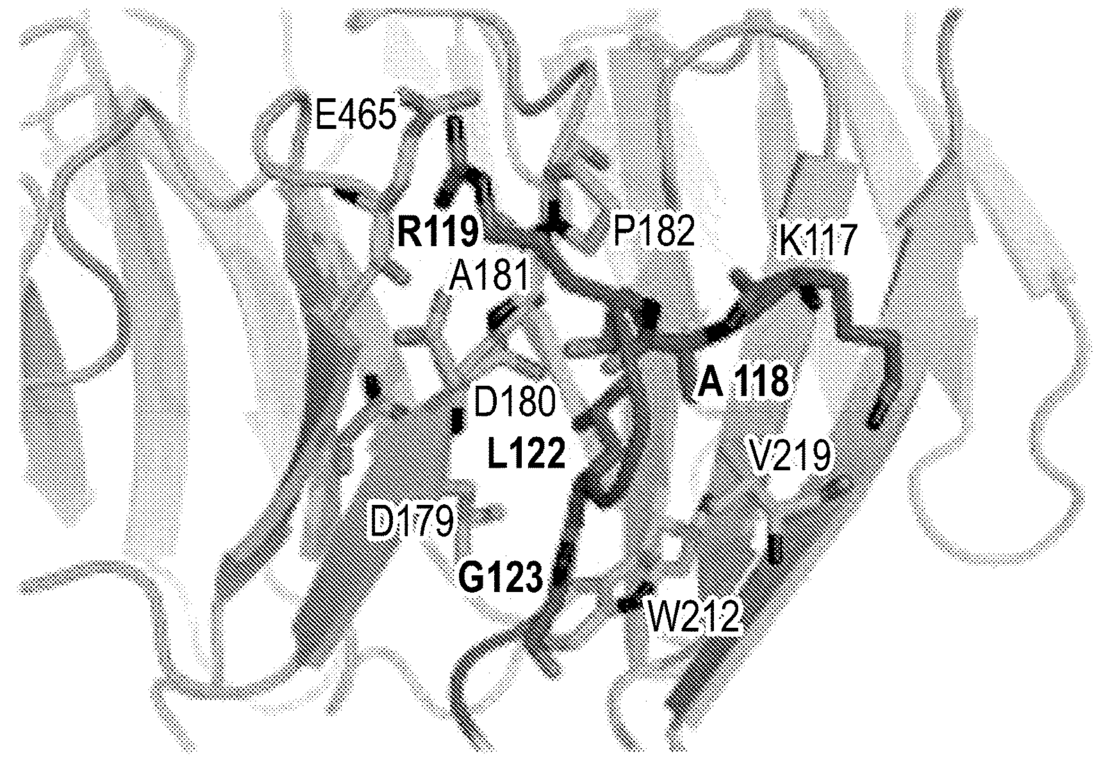
Figure 14E:
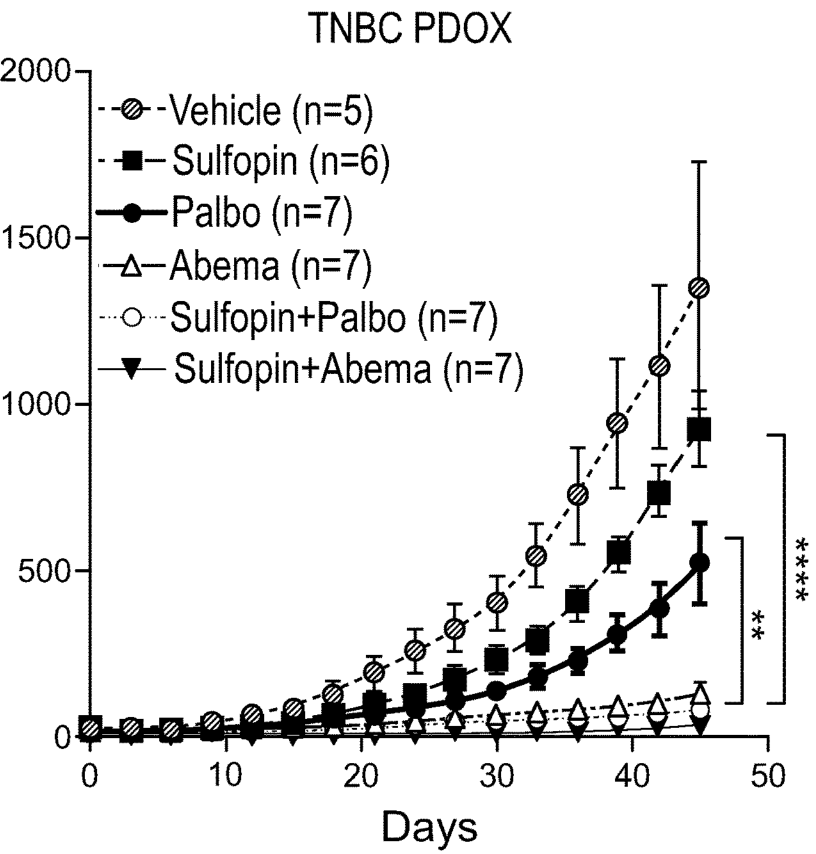
Figure 14F:
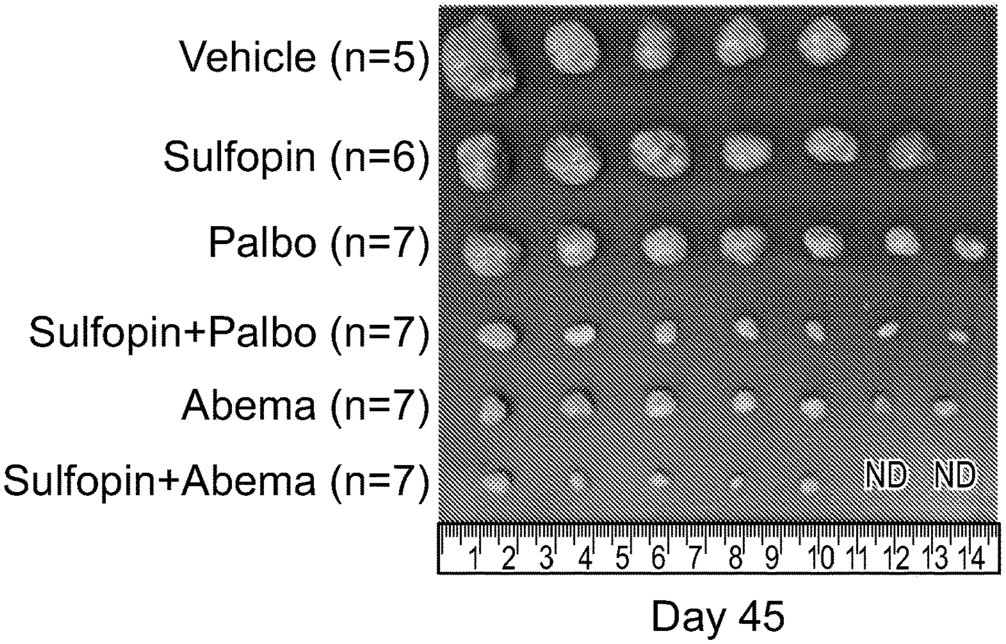
Figure 14G:
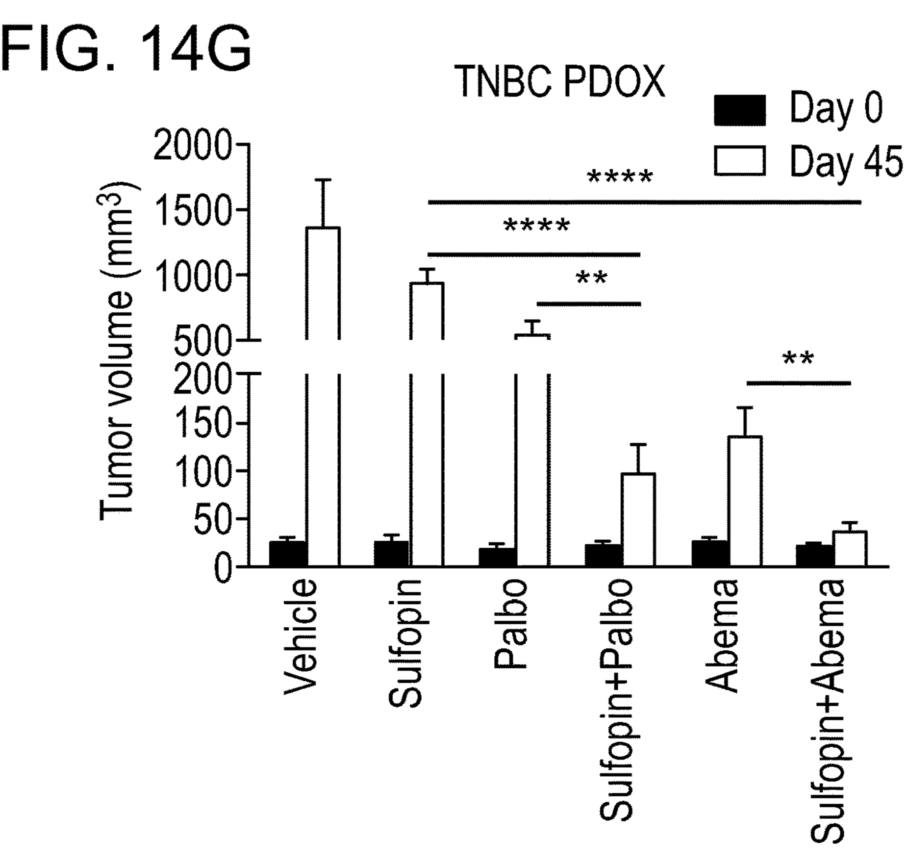
Figure 14H:
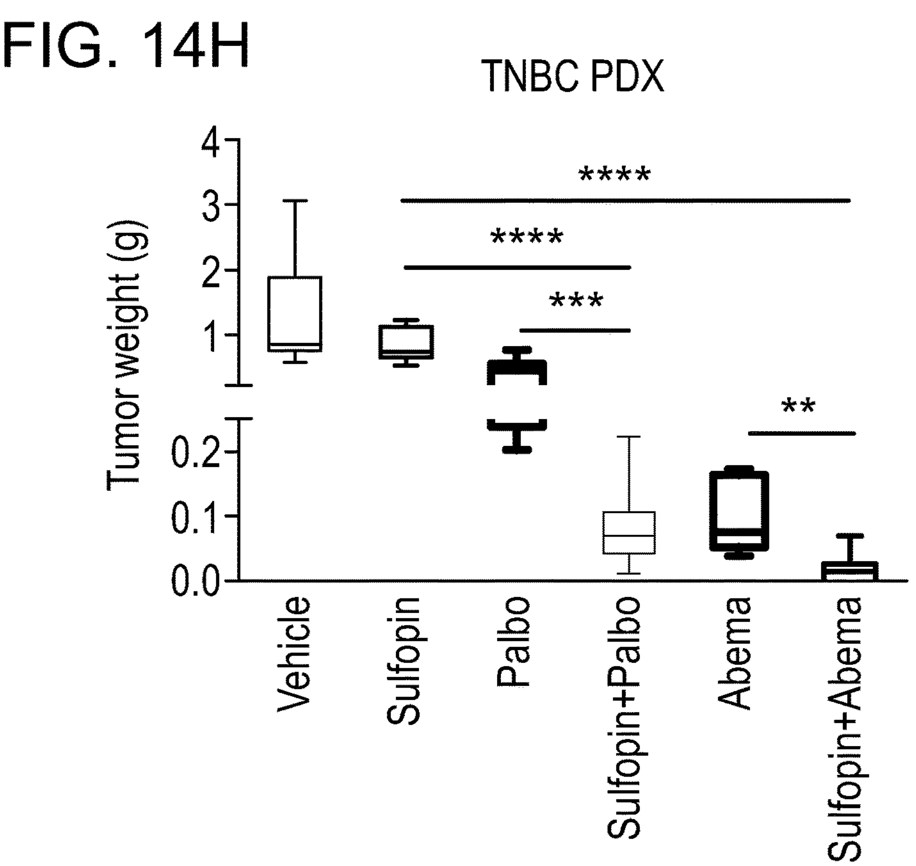

FIG. 14A-FIG. 14H is a set of representations, illustrations, graphs and images that show that Pin1 inhibitors synergize with CDK4/6 inhibitors against TNBC in PDOX models. FIG. 14A is a cartoon representation that shows that under physiologic conditions, an increase in CDK4/6 activity phosphorylates Cdh1, becoming a substate for Pin1, which in turn stabilizes phosphorylated Cdh1 by phosphorylation-dependent isomerization, thereby leading to inactivation of $APC/C^{Cdh1}$ and enforcing the G1/S checkpoint. FIG. 14B is a cartoon representation that shows that when CDK4/6 and Pin1 are inhibited, non-phosphorylated Cdh1 binds to the Pin1 PPIase domain likely via the D-box and renders it a substrate for $APC/C^{Cdh1}$ for ubiquitin-mediated degradation. FIG. 14C is a structural modeling illustration of docking the Pin1 PPIase domain (Cyan; PDB: 1PIN) to the Cdh1-WD40 domain (Chartreuse; PDB: 4UI9_R). FIG. 14D is a structural representation that shows that R119 of PPIase domain forms the electrostatic interaction with Cdh1 residues D180 and E465. FIG. 14E is a graph that shows tumor growth in mice with established TNBC patient-derived xenografts (TNBC PDOX) treated with sulfopin, CDK4/6 inhibitors or their combination. FIG. 14F is a set of images that show tumor sizes measured when mice were euthanized after 45 days. FIG. 14G is a graph of the corresponding tumor volumes. FIG. 14H is a graph of the corresponding tumor weights.

Figure 15A:
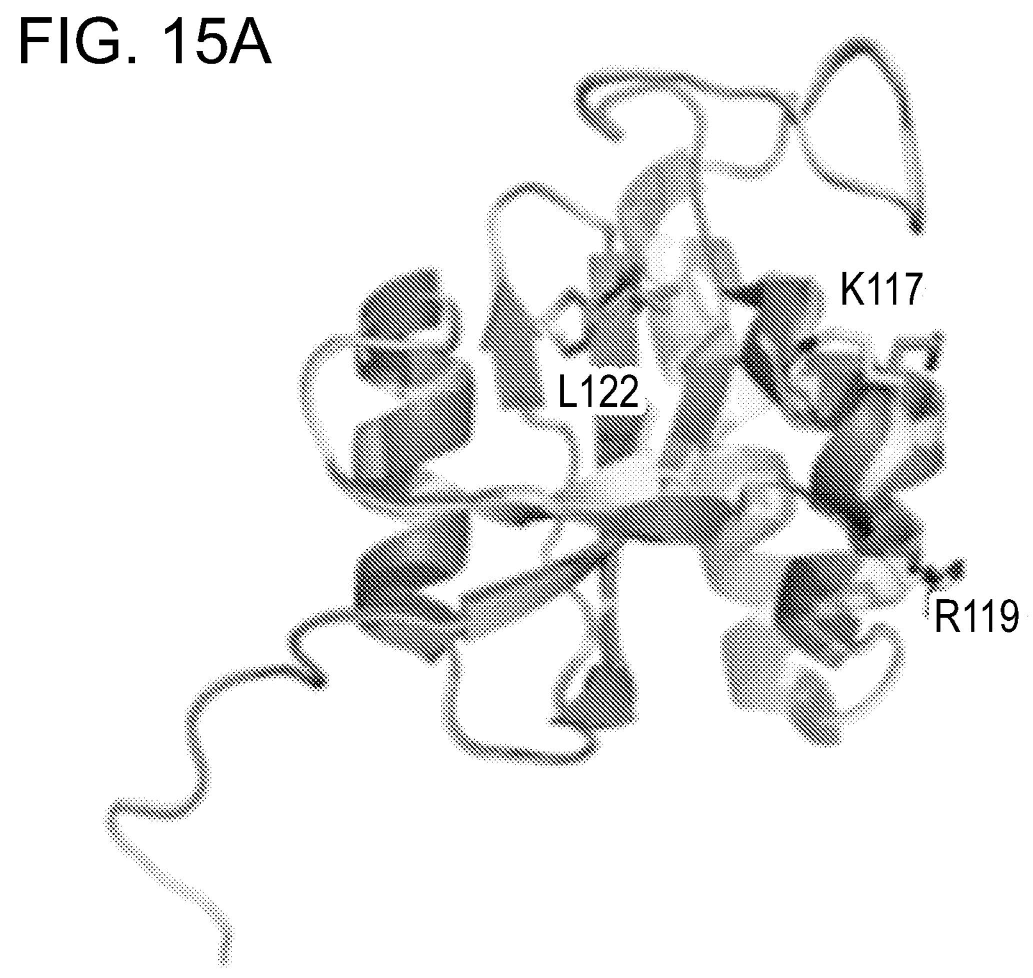
Figures 15B, 15C:
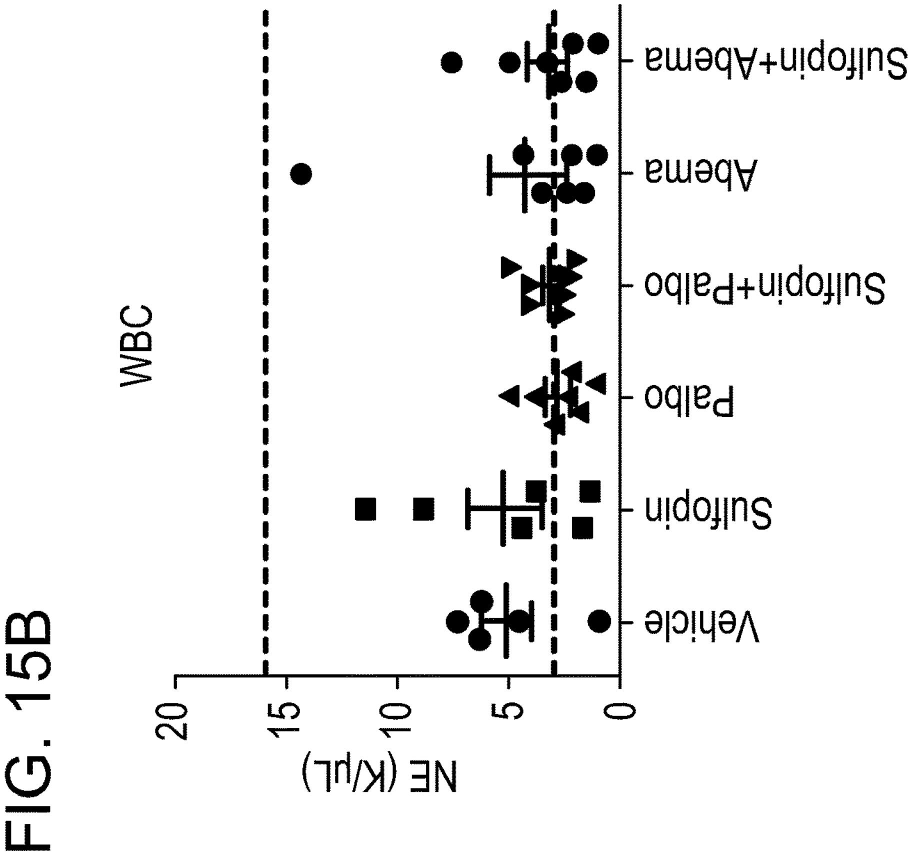
Figure 15E:
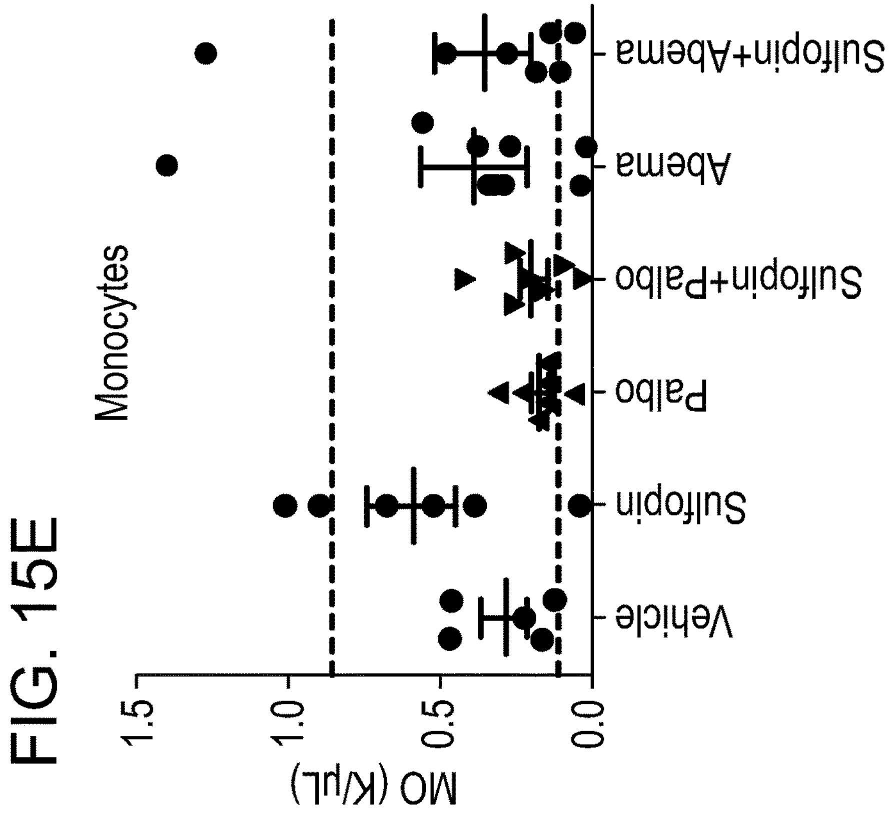
Figure 15D:
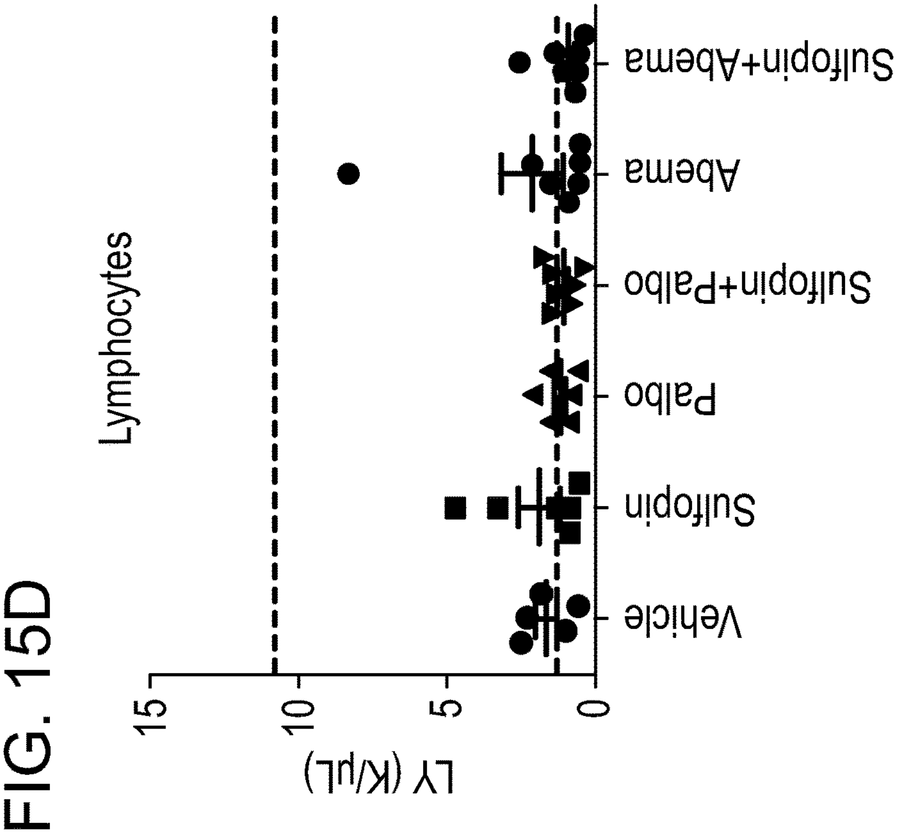
Figure 15G:
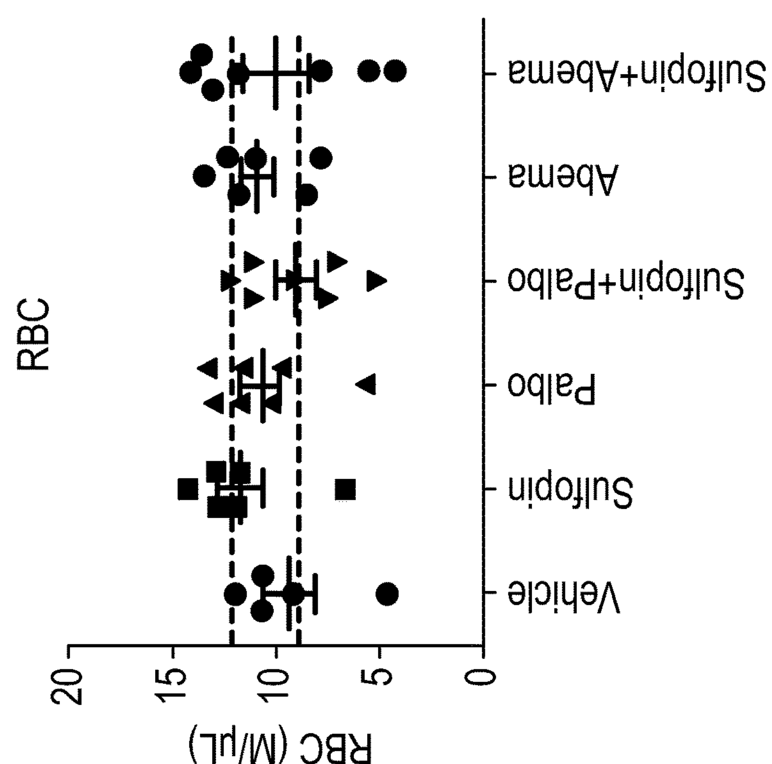
Figure 15F:
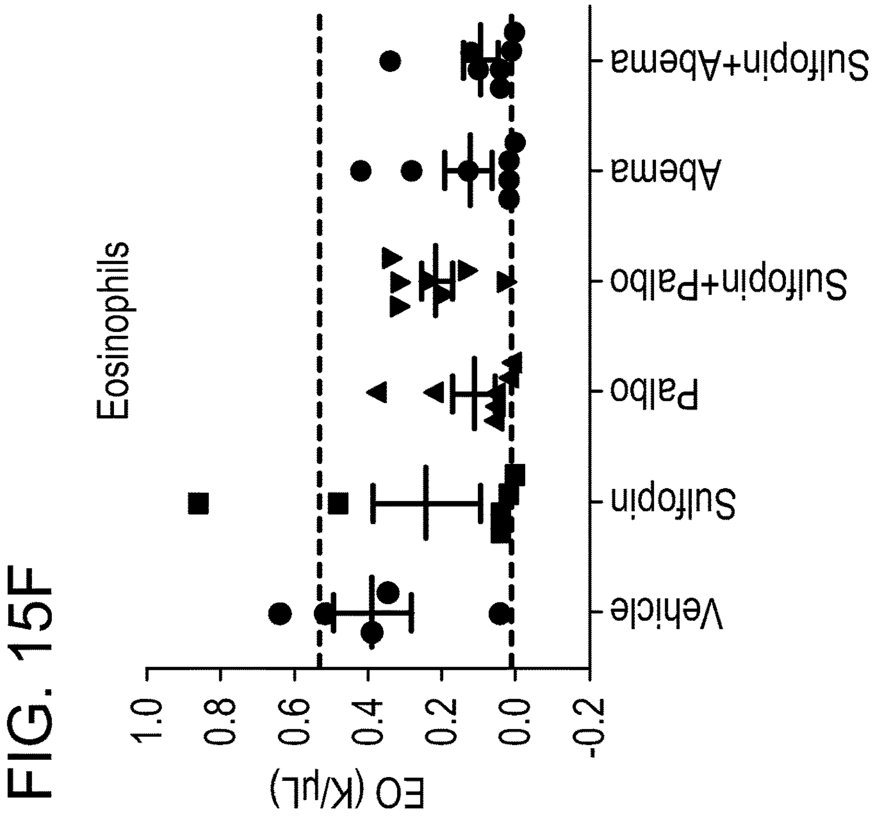
Figure 15I:
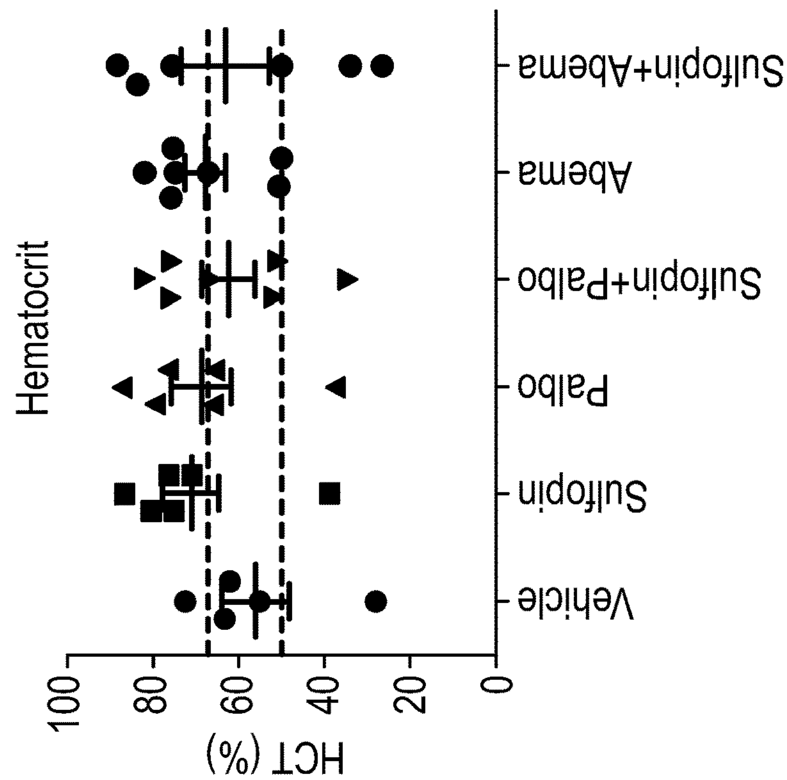
Figure 15H:
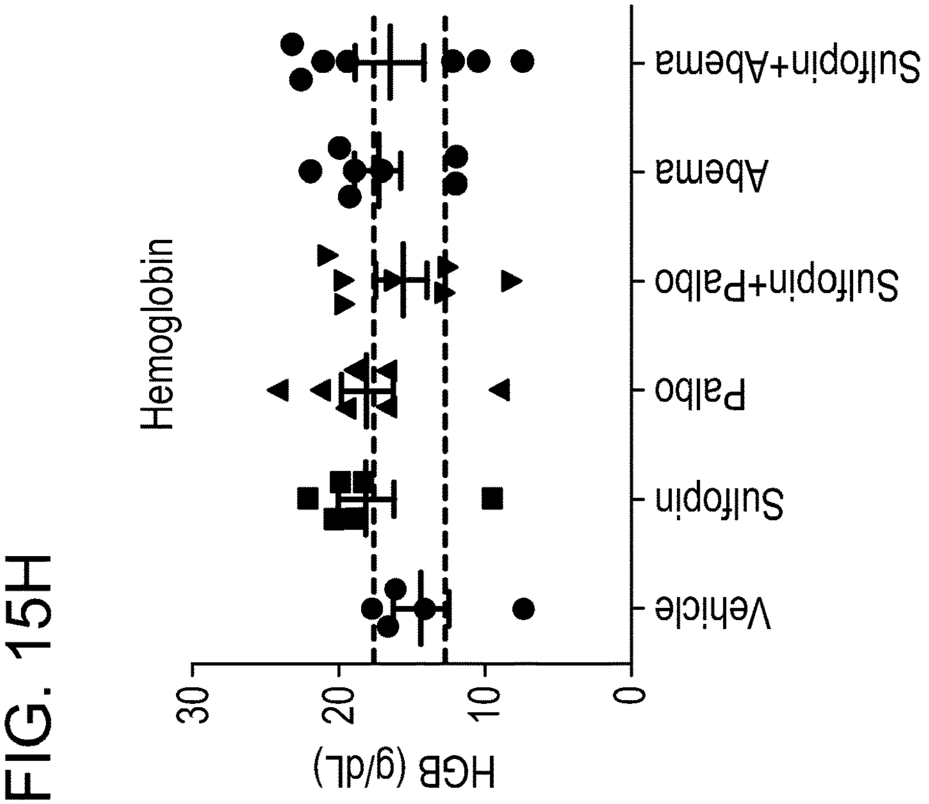
Figure 15J:
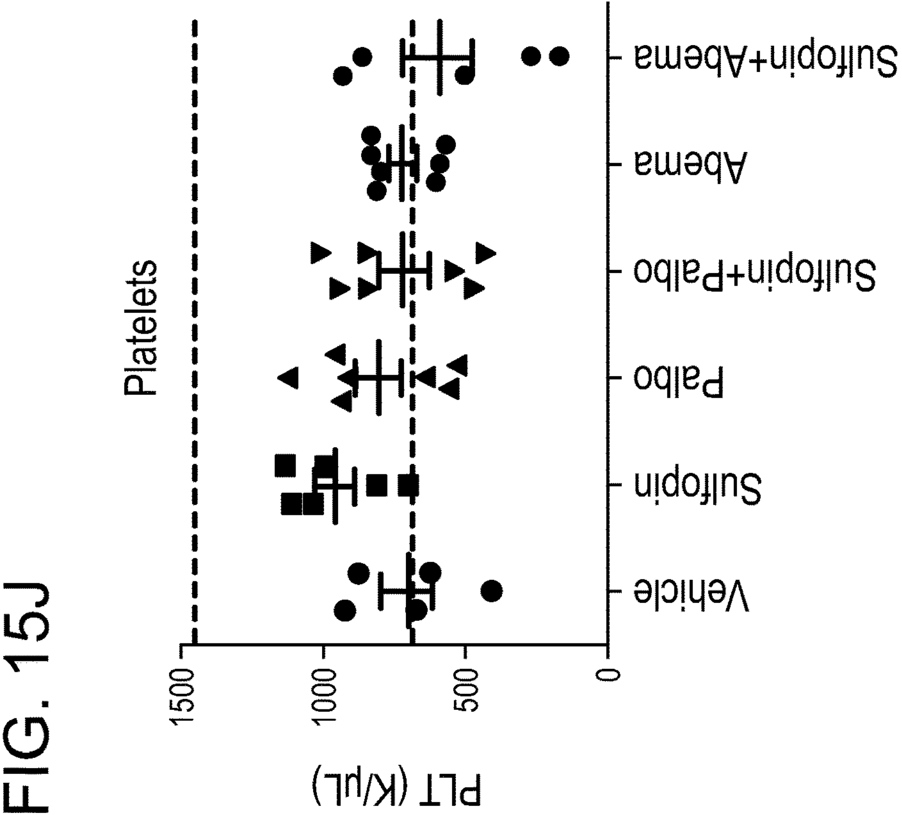
Figure 15K:
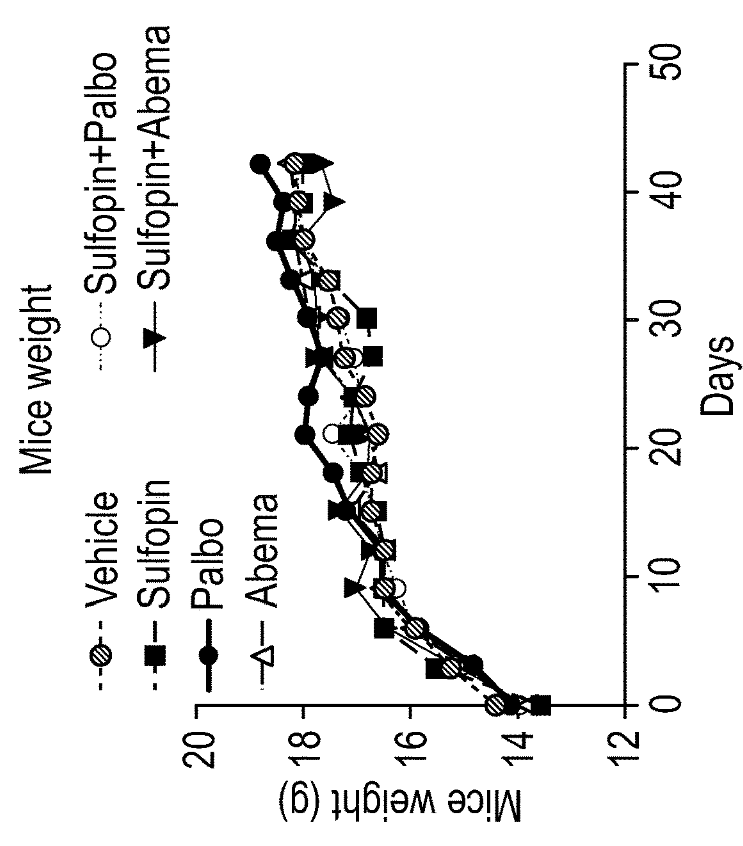

FIG. 15A-FIG. 15K is a set of representations and graphs that show that Pin1 inhibitors synergize with CDK4/6 inhibitors against TNBC in PDOX models. FIG. 15A is a structural representation that shows the superposition of free Pin1 (Green; PDB: 1PIN) and Pin1 in complex with Sulfopin (Cyan; PDB: 6VAJ). FIG. 15B-FIG. 15J show the hematological parameters that were analyzed in TNBC PDOX nude mice treated with indicated inhibitors for 45 days. FIG. 15B is a graph for WBC. FIG. 15C is a graph for neutrophils. FIG. 15D is a graph for lymphocytes. FIG. 15E is graph for monocytes. FIG. 15F is a graph for eosinophils. FIG. 15G is a graph for RBC. FIG. 15H is a graph for hemoglobin. FIG. 15I is a graph for hematocrit. FIG. 15J is a graph for platelets. FIG. 15K is a graph for mice weight. FIG. 15K is a graph that shows the body weights monitored in TNBC PDOX nude mice during the treatments.

Figure 16A:
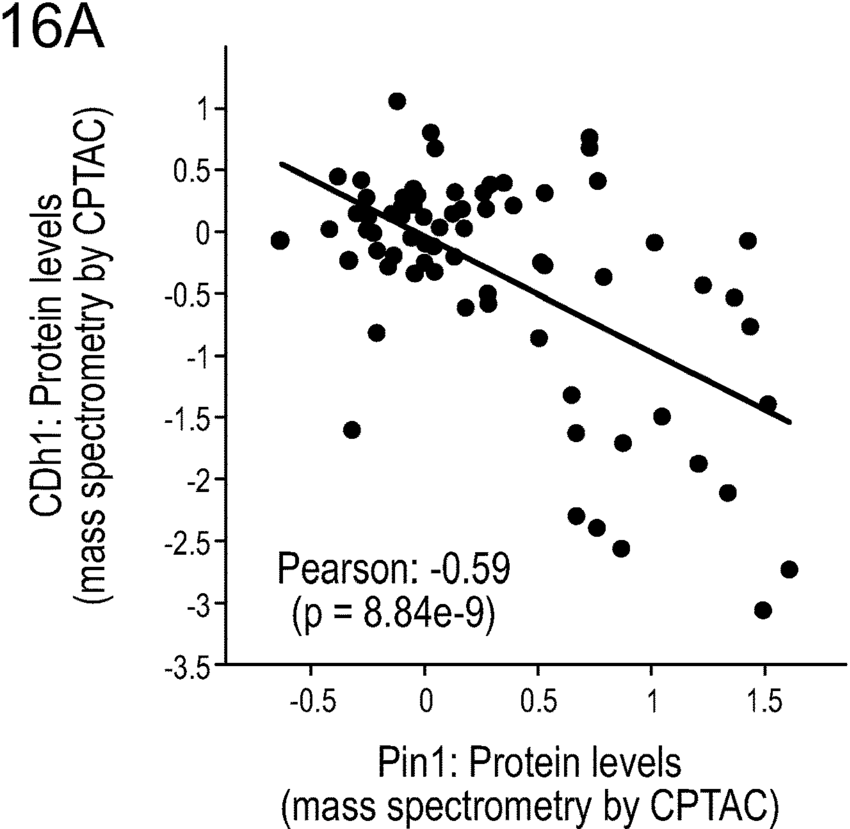
Figure 16B:
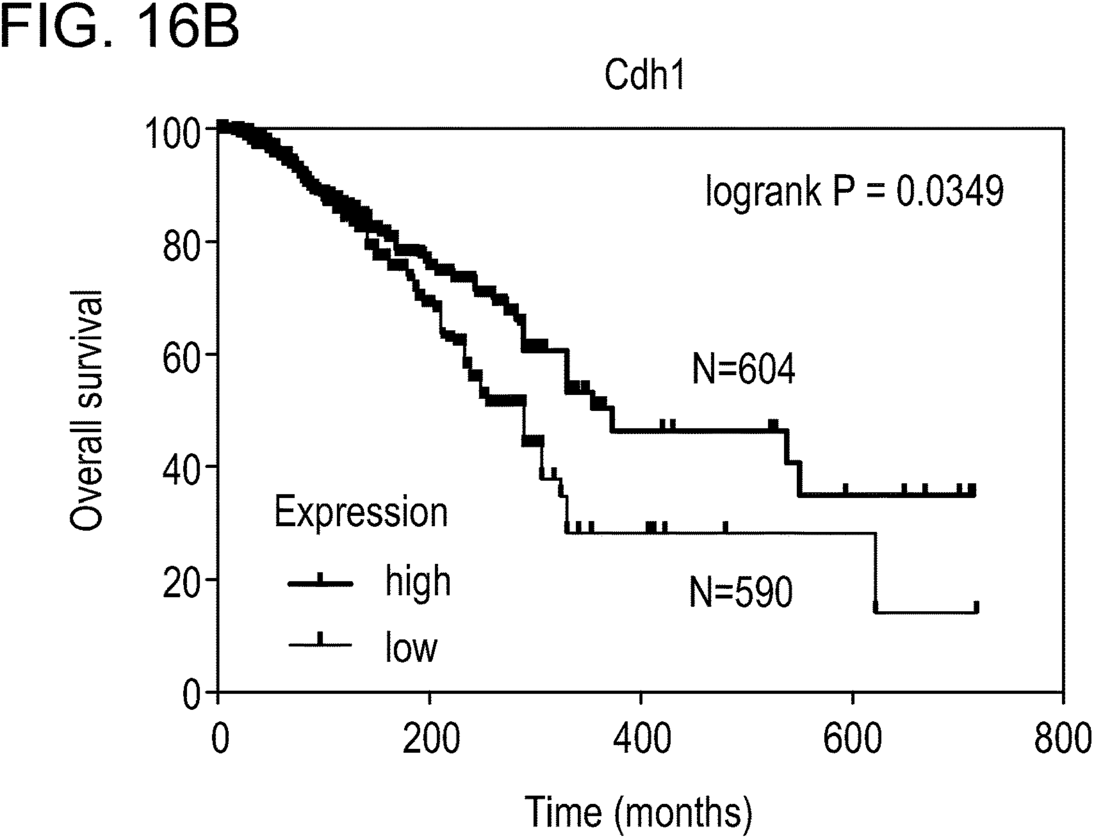

FIG. 16A is a graph showing the correlation between Pin1 protein levels and Cdh1 protein levels across 105 BRCA samples. FIG. 16B is a graph of overall survival versus time (months) for BRCA tumors in TCGA with low and high Cdh1 mRNA levels.

Figure 17A:
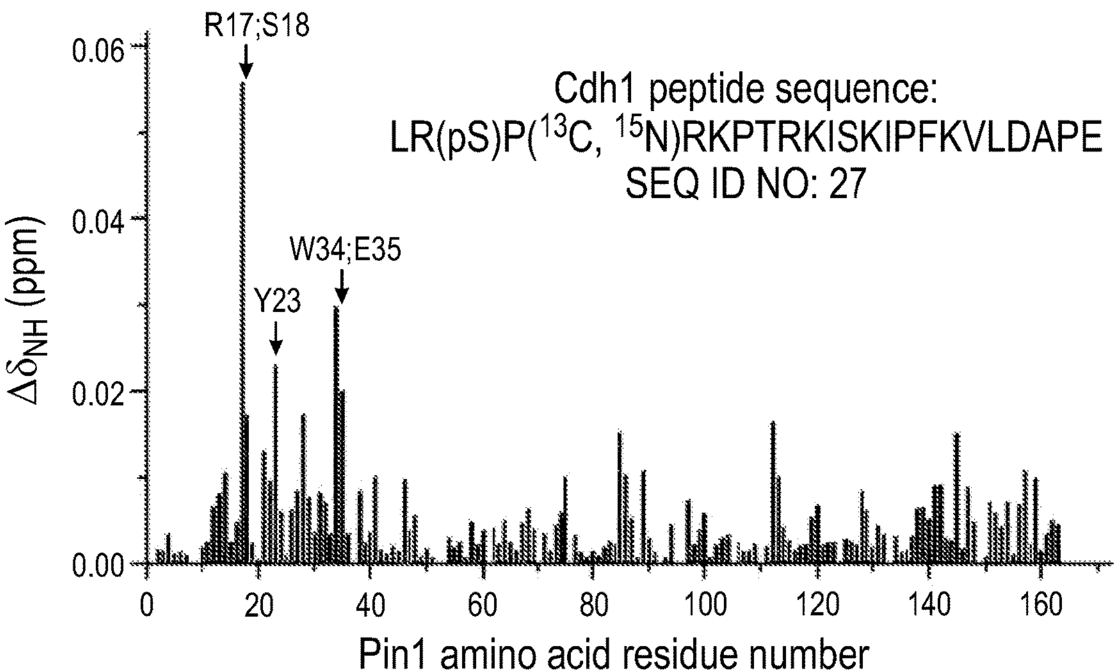
Figure 17B:
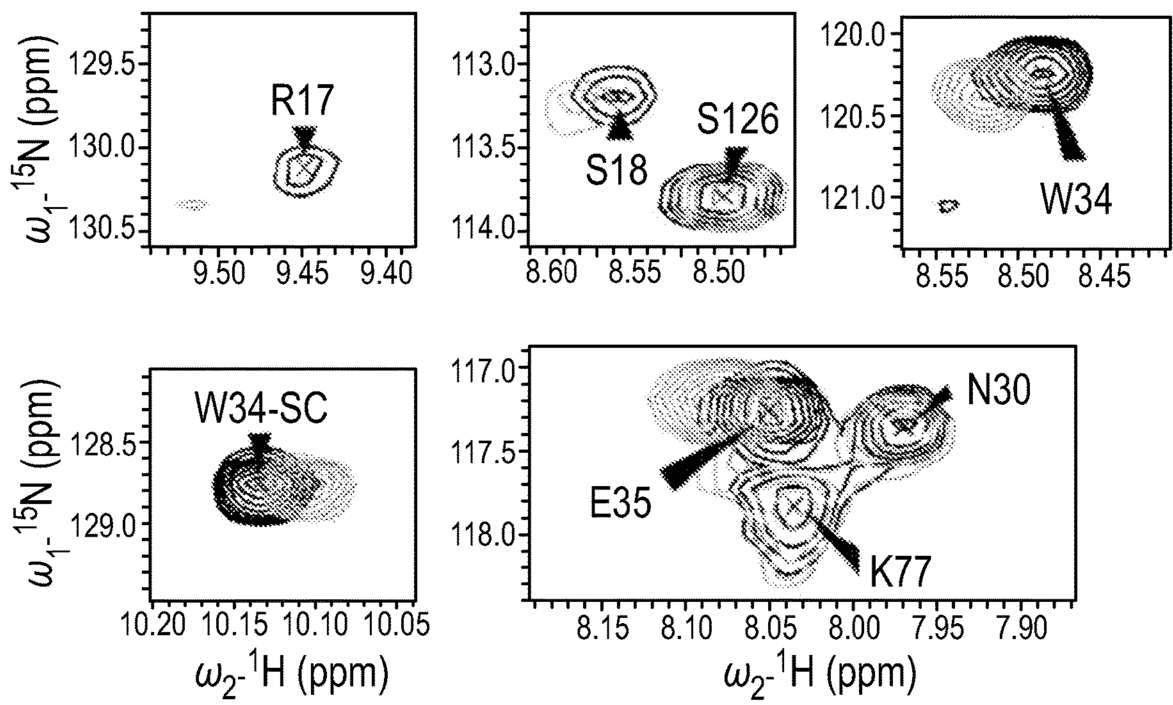
Figure 17C:
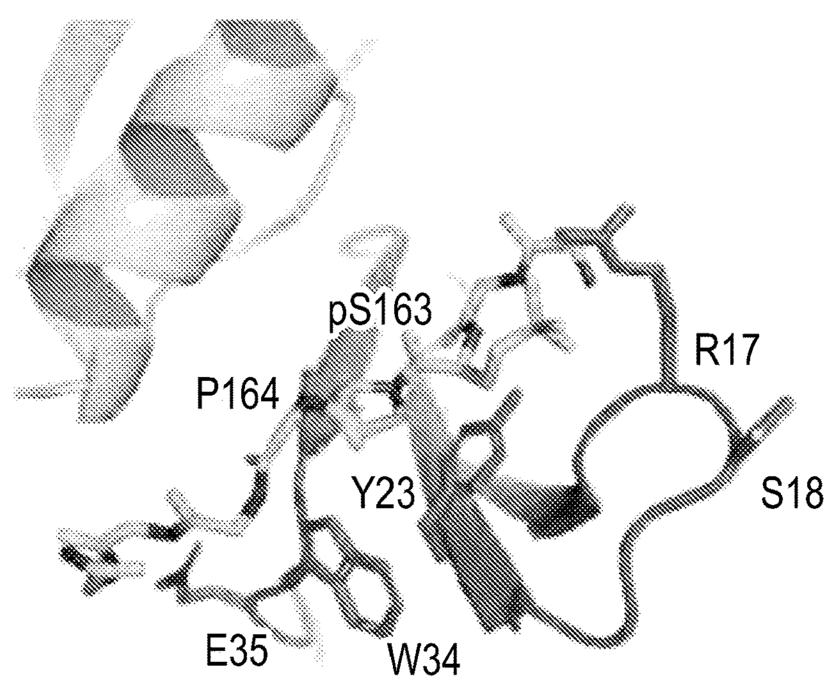
Figure 17D:
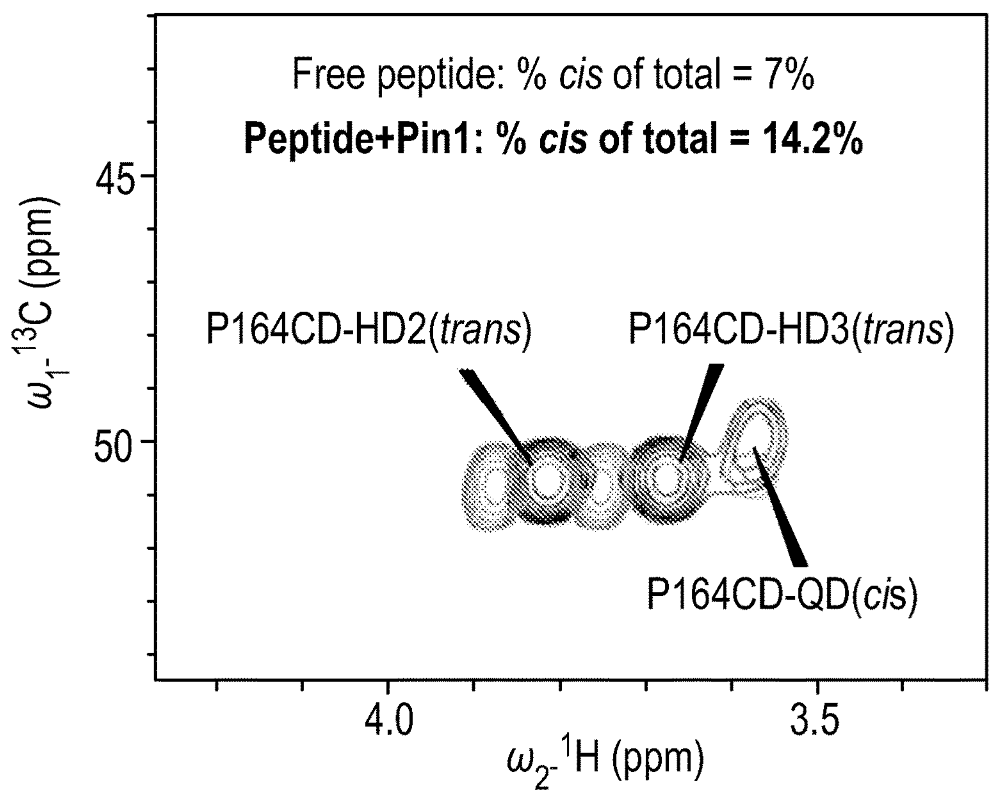

FIG. 17A is an NMR analysis of phosphorylated peptide bound to Pin1. FIG. 17B is a series of two dimensional (2D) 1H-15N Heteronuclear single quantum coherence (HSQC) spectrum of 15N-labeled Pin1 protein. FIG. 17C is a HADDOCK model demonstrating the putative interaction between the Cdh1 phosphopeptide shown as red sticks and Pin1 WW (magenta) and PPIase domain (cyan; PDB: 1PIN). FIG. 17D is an overlay of $^{13}C$-HSQC spectra acquired on 58 μM free peptide (red) and its 1:4 complex with Pin1 (green). The peak volumes were used to derive isomer population estimates.

Figure 18A:
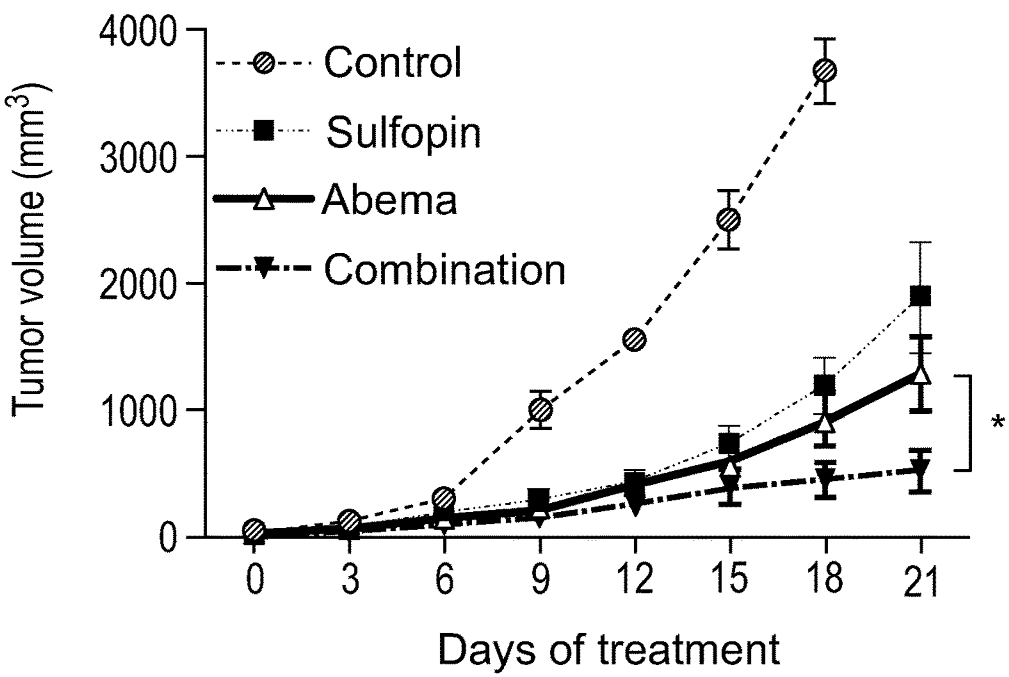
Figure 18B:
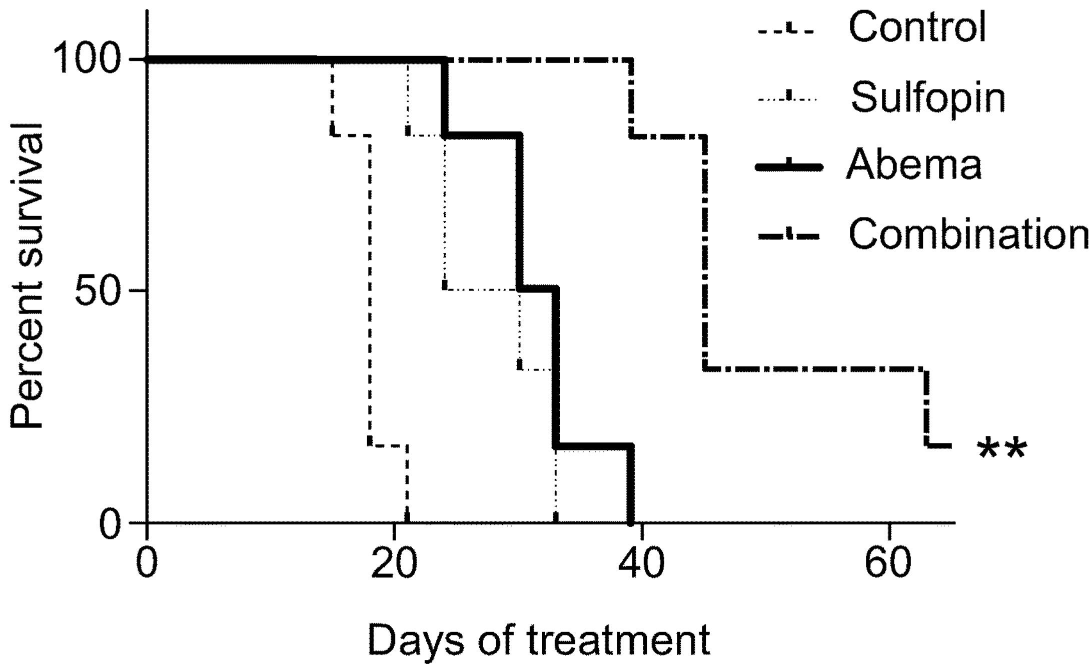
Figure 18C:
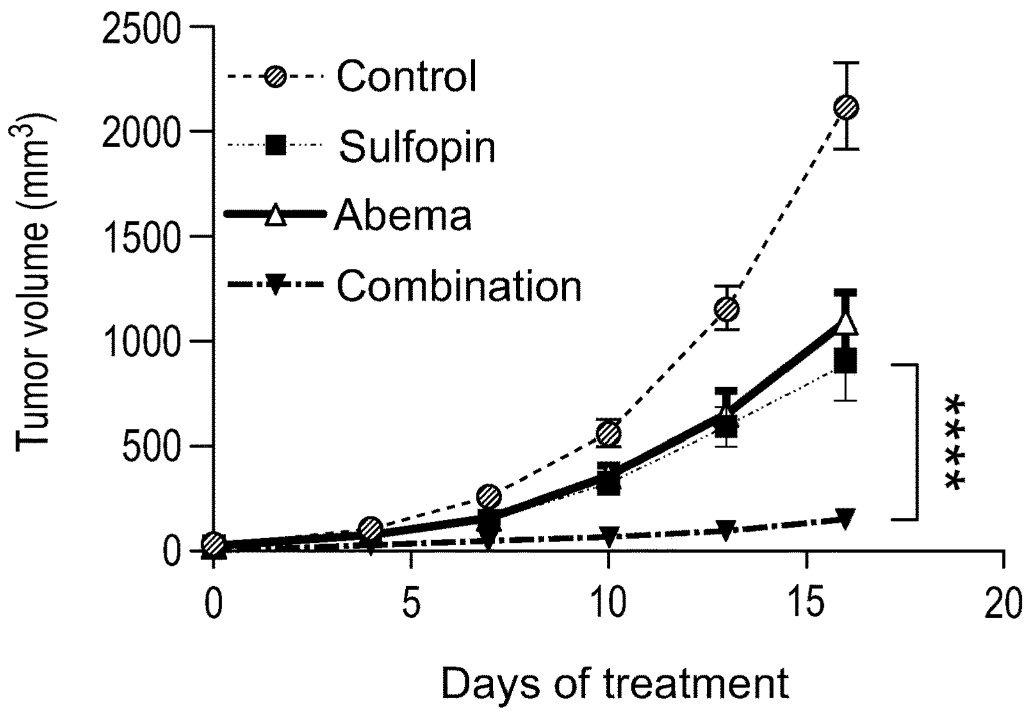
Figure 18D:
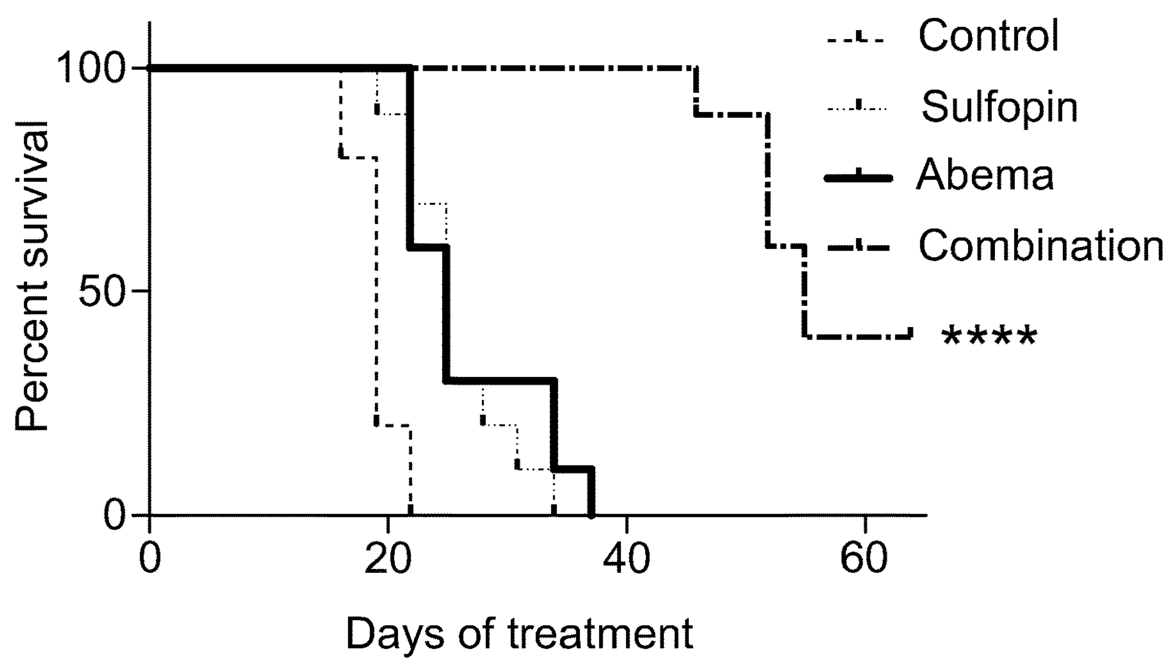

FIG. 18A is a growth curve generated from mice bearing K14cre; $p53^{f/f}$; $Brca1^{f/f}$ tumors treated with vehicle (n=6; median survival of 18 days), sulfopin (n=6; median survival of 27 days), abemaciclib (n=6; median survival of 31.5 days) or their combination (n=6; median survival of 45 days). FIG. 18B is a survival curve generated from mice bearing K14cre; $p53^{f/f}$; $Brca1^{f/f}$ tumors treated with vehicle (n=6; median survival of 18 days), sulfopin (n=6; median survival of 27 days), abemaciclib (n=6; median survival of 31.5 days) or their combination (n=6; median survival of 45 days). FIG. 18C is a growth curve generated from mice bearing K14cre;

p53"t/f, Brca1$^{wt/f}$ tumors treated with vehicle (n=10; median survival of 19 days), sulfopin (n=10; median survival of 25 days), abemaciclib (n=10; median survival of 25 days) or their combination (n=10; median survival of 55 days). FIG. 18D is a survival curve generated from mice bearing K14cre; p53$^{wt/f}$; Brca1$^{wt/f}$ tumors treated with vehicle (n=10; median survival of 19 days), sulfopin (n=10; median survival of 25 days), abemaciclib (n=10; median survival of 25 days) or their combination (n=10; median survival of 55 days).

Figures 19A, 19B:
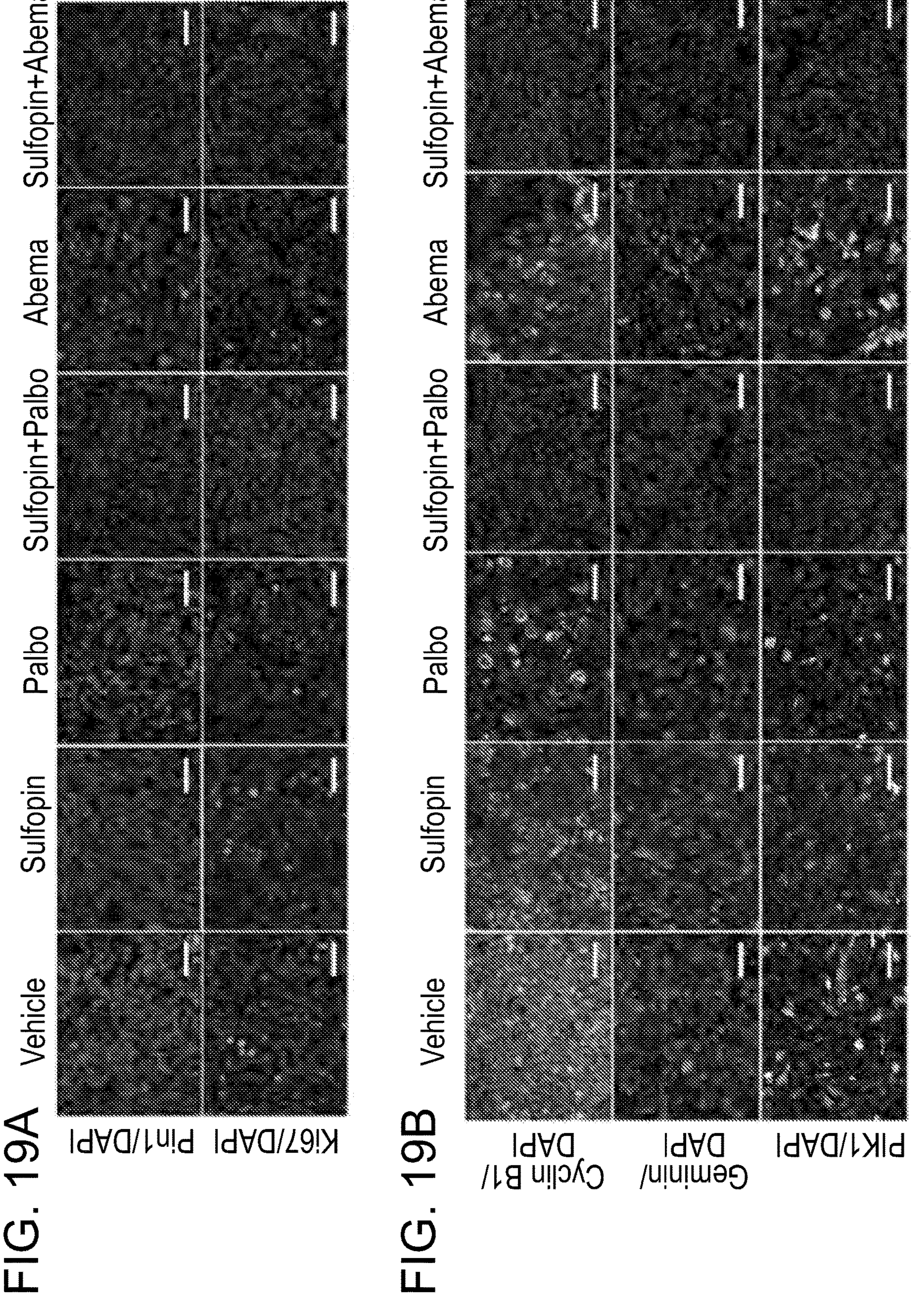

FIG. 19A is a set of representative immunofluorescence images for PDOX tumors stained with Pin1 (green) and Ki67 (red) for vehicle, sulfopin, palbociclib, sulfopin+palbociclib, abemaciclib, and sulfopin+abemaciclib (scale bars, 50 μm). FIG. 19B is a set of representative immunofluorescence images for PDOX tumors stained with Cyclin B1 (cyan), Geminin (purple) and Plk1 (yellow) for vehicle, sulfopin, palbociclib, sulfopin+palbociclib, abemaciclib, and sulfopin+abemaciclib (scale bars, 50 μm).

Figure 20A:
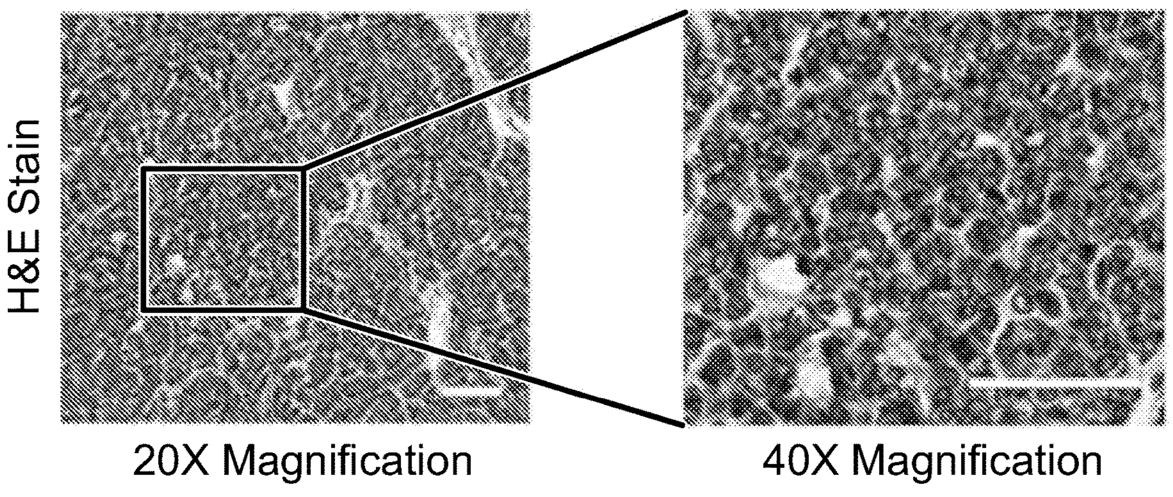
Figure 20B:
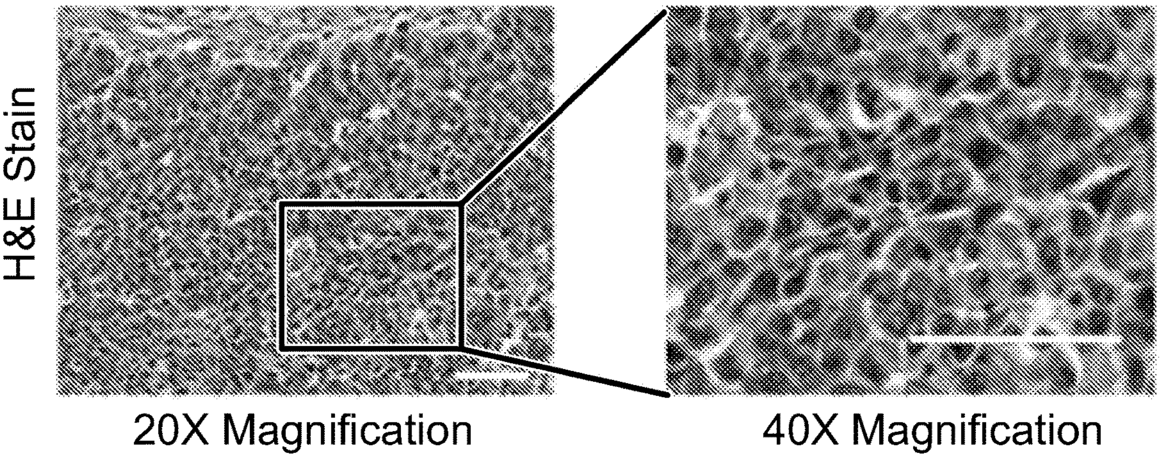

FIG. 20A is a set of representative images of H&E staining in K14cre; p53$^{wt/f}$; Brca1$^{wt/f}$ tumors at 20× and 40× magnification (scale bars, 50 μm). FIG. 20B is a set of representative images of H&E staining in K14cre; p53$^{f/f}$, Brca1$^{f/f}$ tumors at 20× and 40× magnification (scale bars, 50 μm.

Figure 21A:
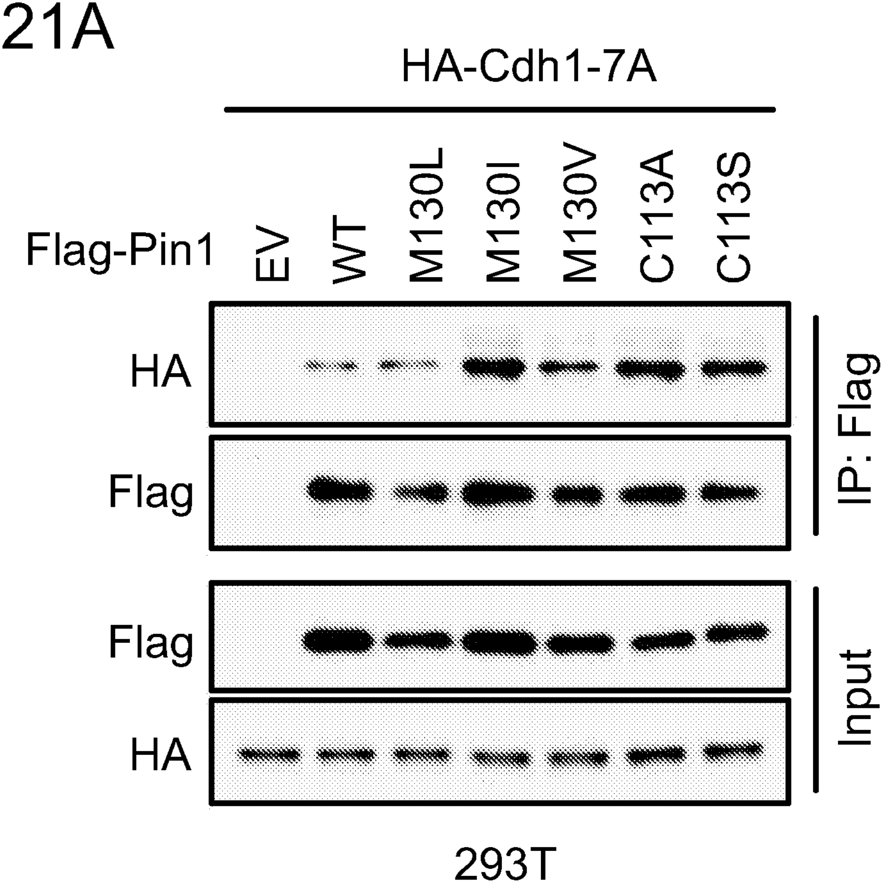

FIG. 21A is an immunoblot analysis of immunoprecipitates from 293T cells stably co-expressing Flag-Pin1-WT or disabling mutations and the phosphosite-deficient mutant Cdh1-7A treated with 10 μM MG132 for 12 hrs and pulled down using Flag-M2 beads.

Figure 21B:
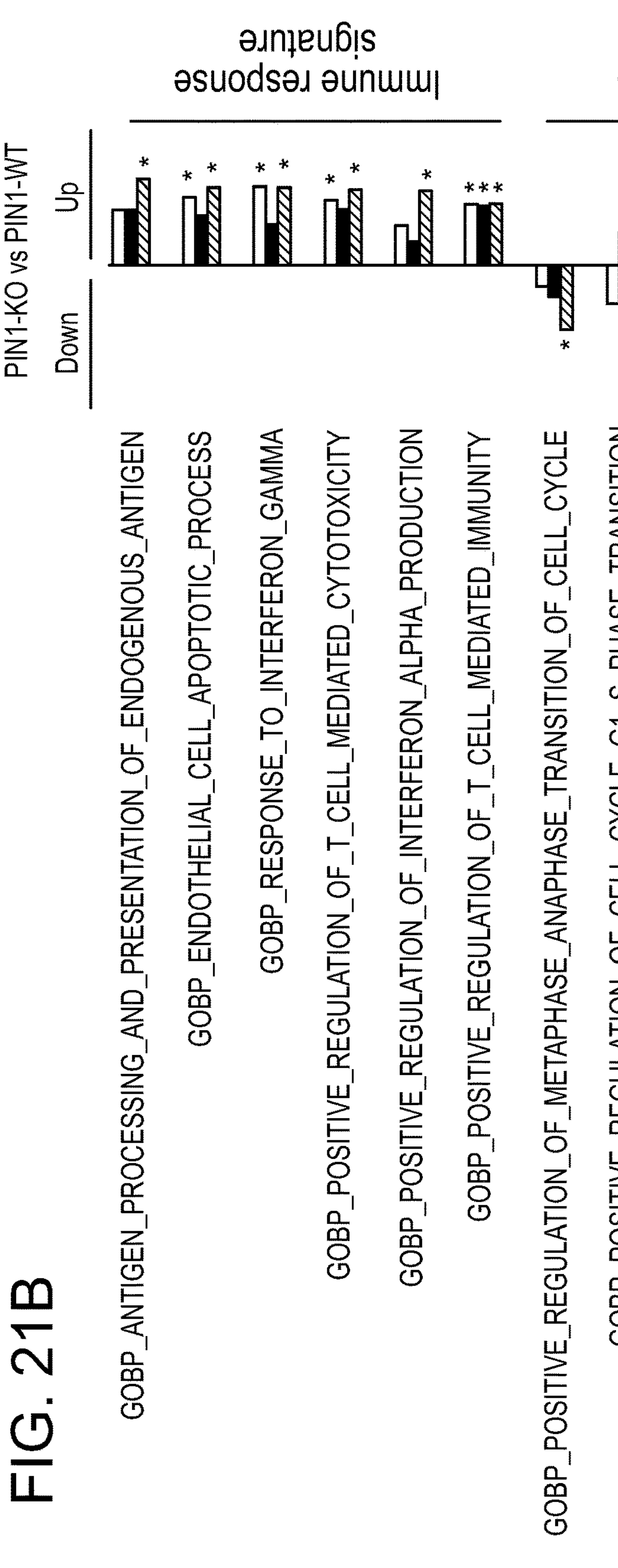

FIG. 21B is a bar graph that shows a visualization of the functional transcriptional outputs of the three cell lines. Normalized counts of Pin1 KO versus WT cells were used for GSEA analysis against the biological process related gene sets. Normalized enrichment scores (NES) were used to generate bar graphs.

Figure 21C:
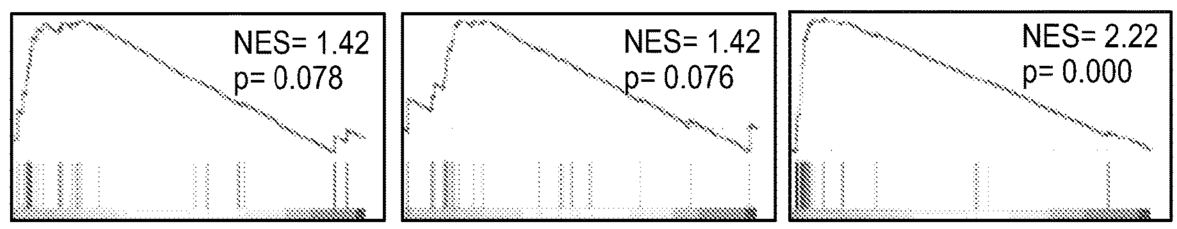
Figure 21C:
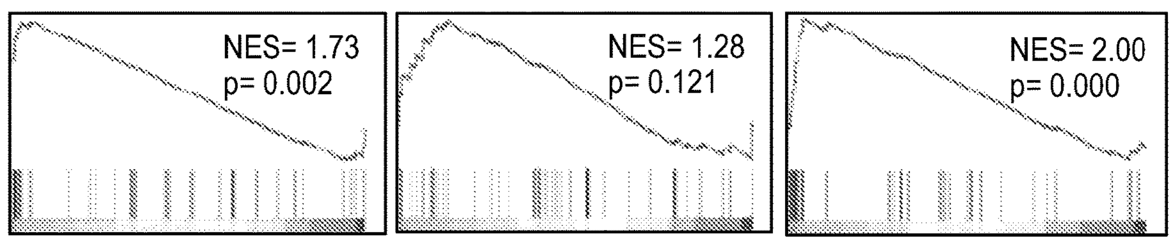
Figure 21C:
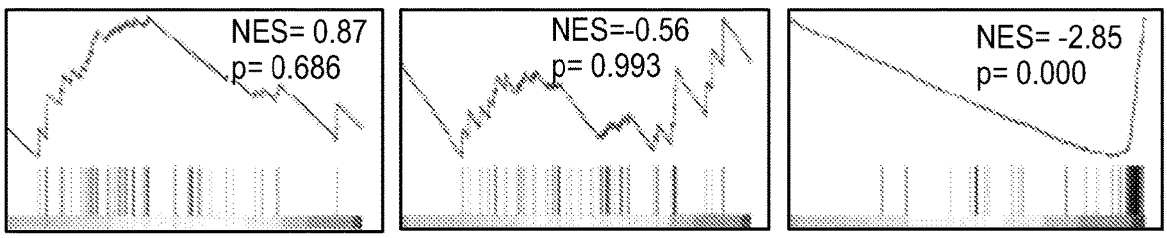
Figure 21C:
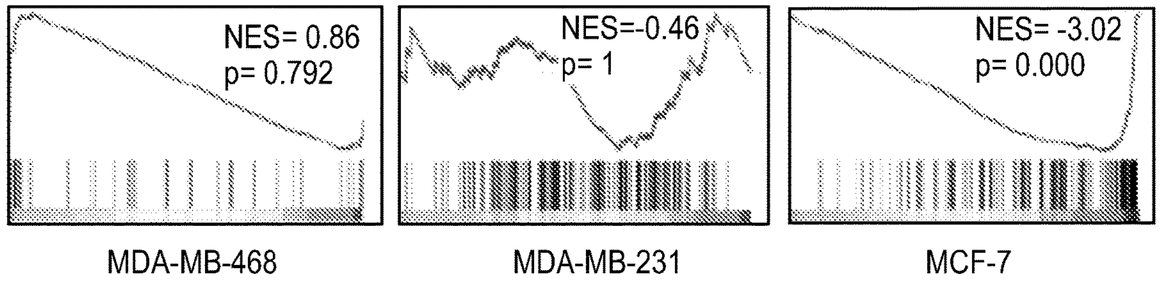

FIG. 21C is a set of enrichment plots for the indicated up-regulated and down-regulated gene sets analyzed by GSEA in Pin1 KO versus WT cells.

FIG. 21D is a graph of a Gene Ontology (GO) enrichment analysis applied to proteomics of Pin1 KO versus WT MDA-MB-231 cells. Color codes for p-value (darker shading is more significant) and symbol size codes for the ratio of proteins related to specific GO term/total number of proteins significantly altered.

Figure 22A:
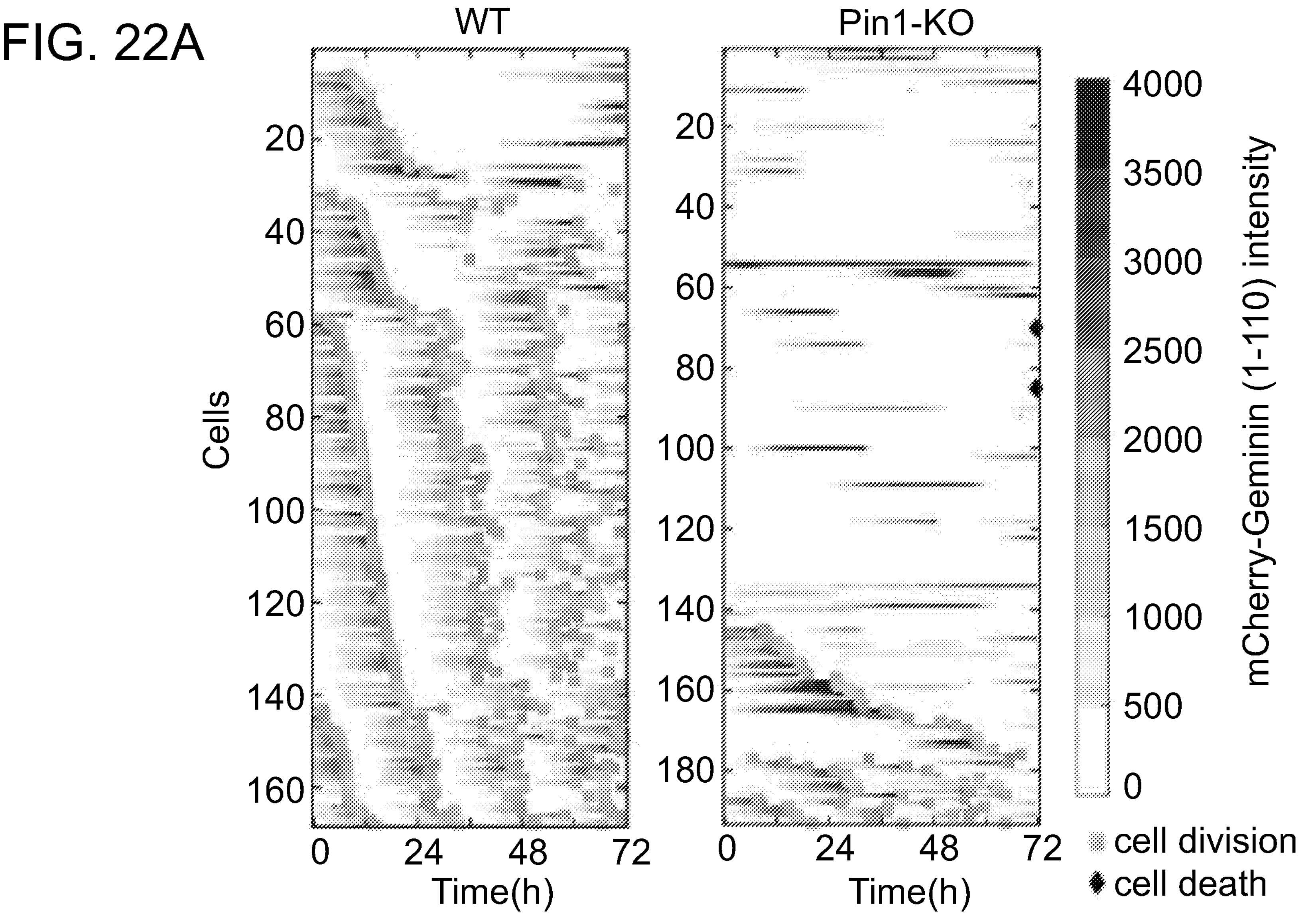

FIG. 22A is a set of images tracking cell division and cell death at the single cell level. Asynchronous cultures of MCF-7 WT and Pin1 KO cells expressing the APC-degron reporter were followed for 72 hours for single cell expression of mCherry-Geminin (shades of blue).

Figure 22B:
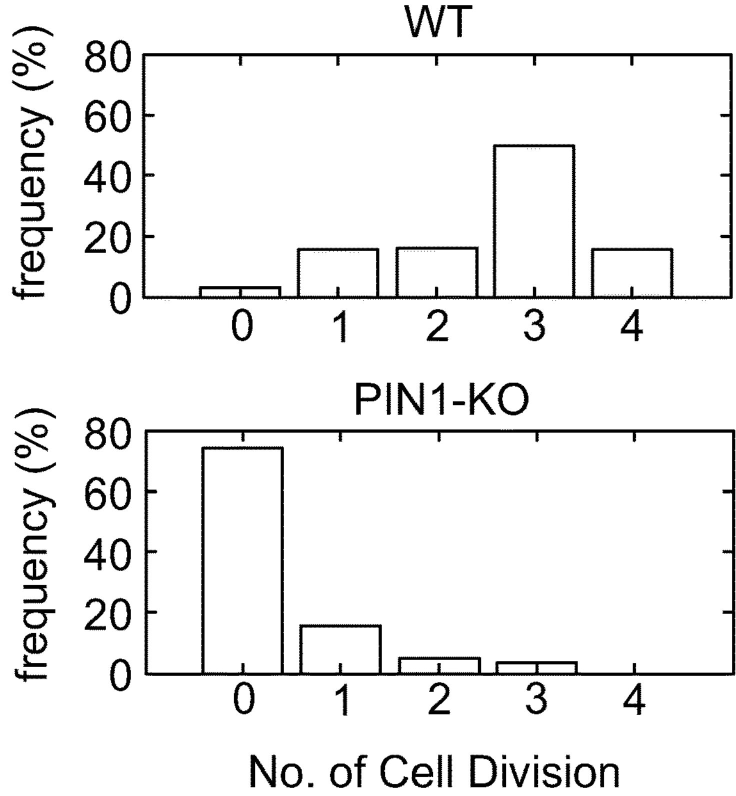

FIG. 22B is a graph of cell division frequency in WT and Pin1 KO MCF-7 cells stably expressing the APC-degron reporter from FIG. 22A.

Figure 22C:
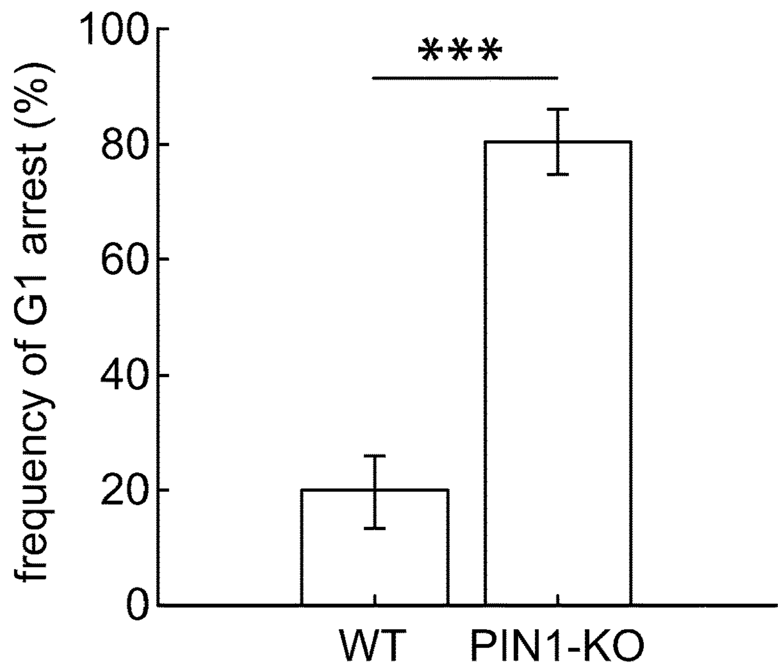

FIG. 22C is a bar graph showing the frequency of G1 arrest (ratio of G1 arrested cells to total cells).

Figure 22D:
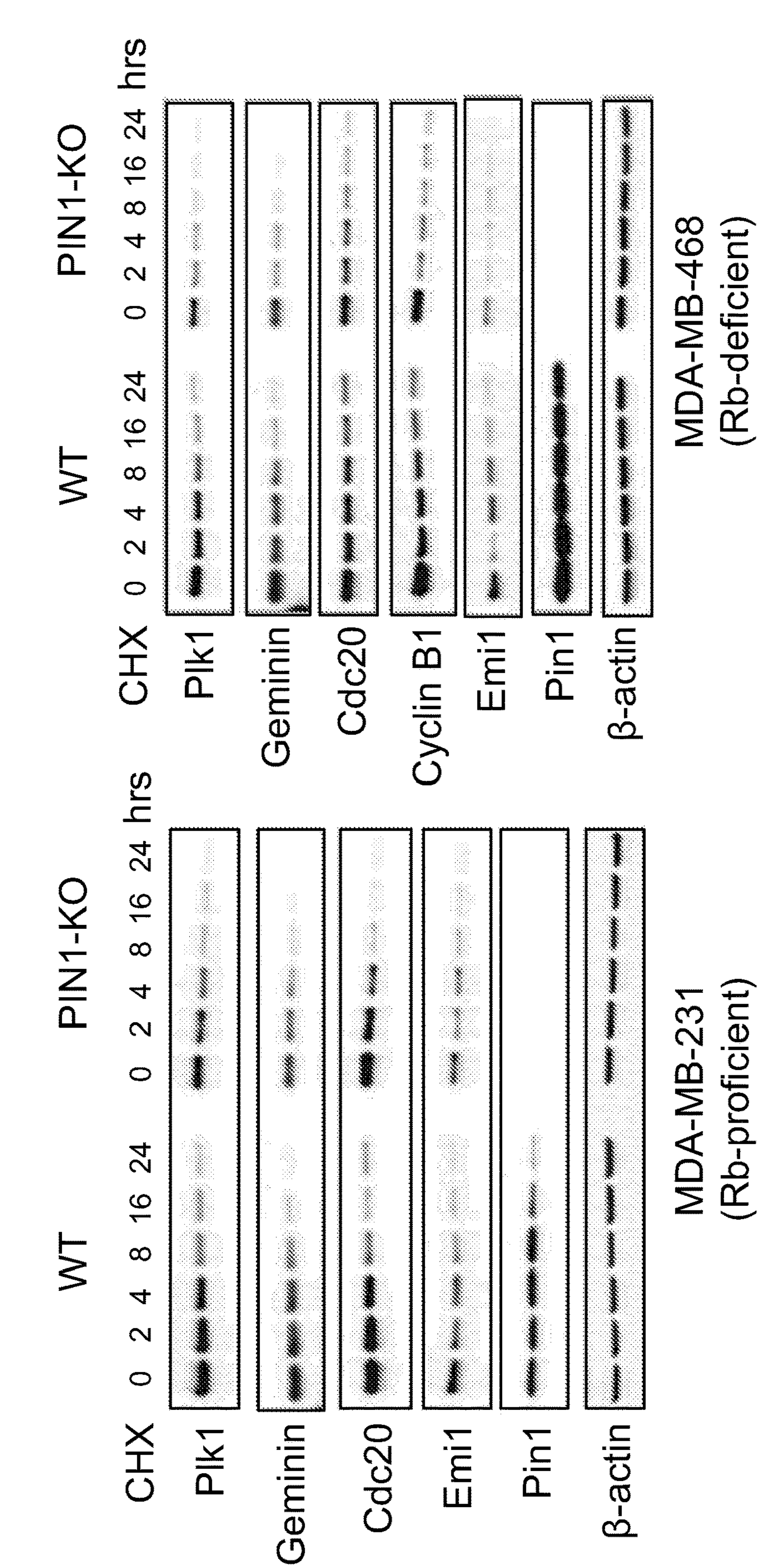

FIG. 22D is a set of immunoblots showing the results from the cycloheximide (CHX) chase assay for the indicated proteins derived from WT and Pin1 KO MDA-MB-231 cells (left) or WT and Pin1 KO MDA-MB-468 cells (right) treated with 50 μg/mL of CHX for the indicated time.

Figure 23A:
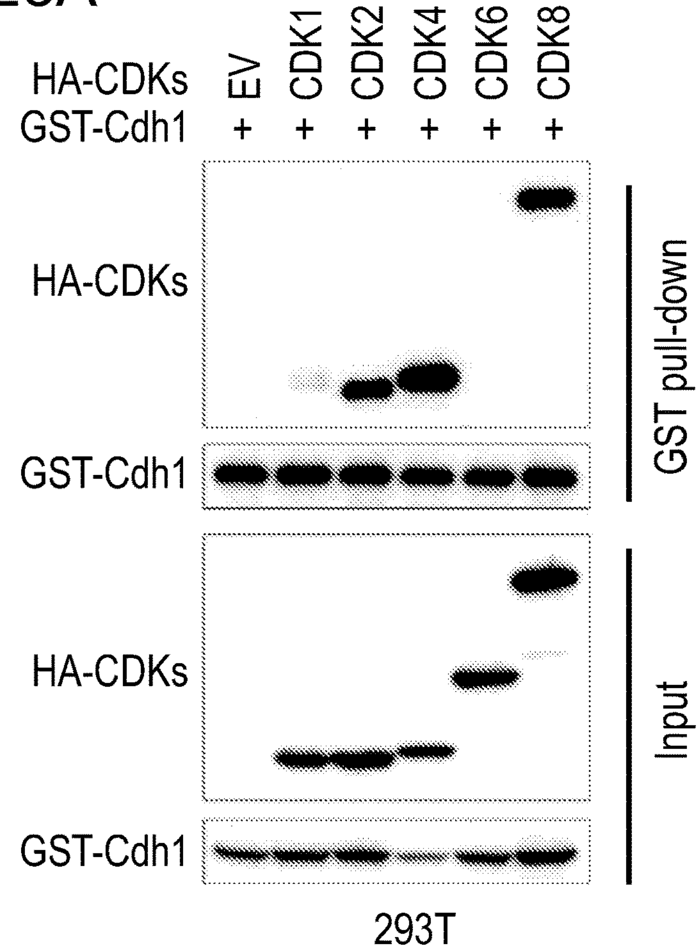

FIG. 23A is an immunoblot showing 293T cells transfected with the indicated constructs for 36 hrs. Input is 5% of the total lysates used in IP.

Figure 23B:
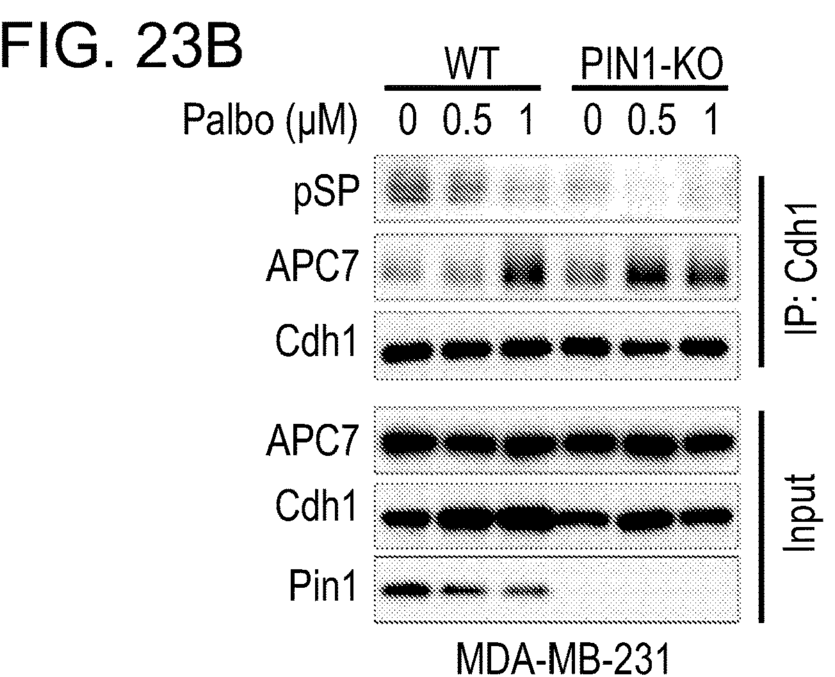

FIG. 23B is an immunoblot analysis of immunoprecipitates derived from WT and Pin1 KO MDA-MB-231 cells treated with palbociclib and pulled down by anti-Cdh1 antibody. Input is 5% of the total lysates used in IP.

Figure 24A:
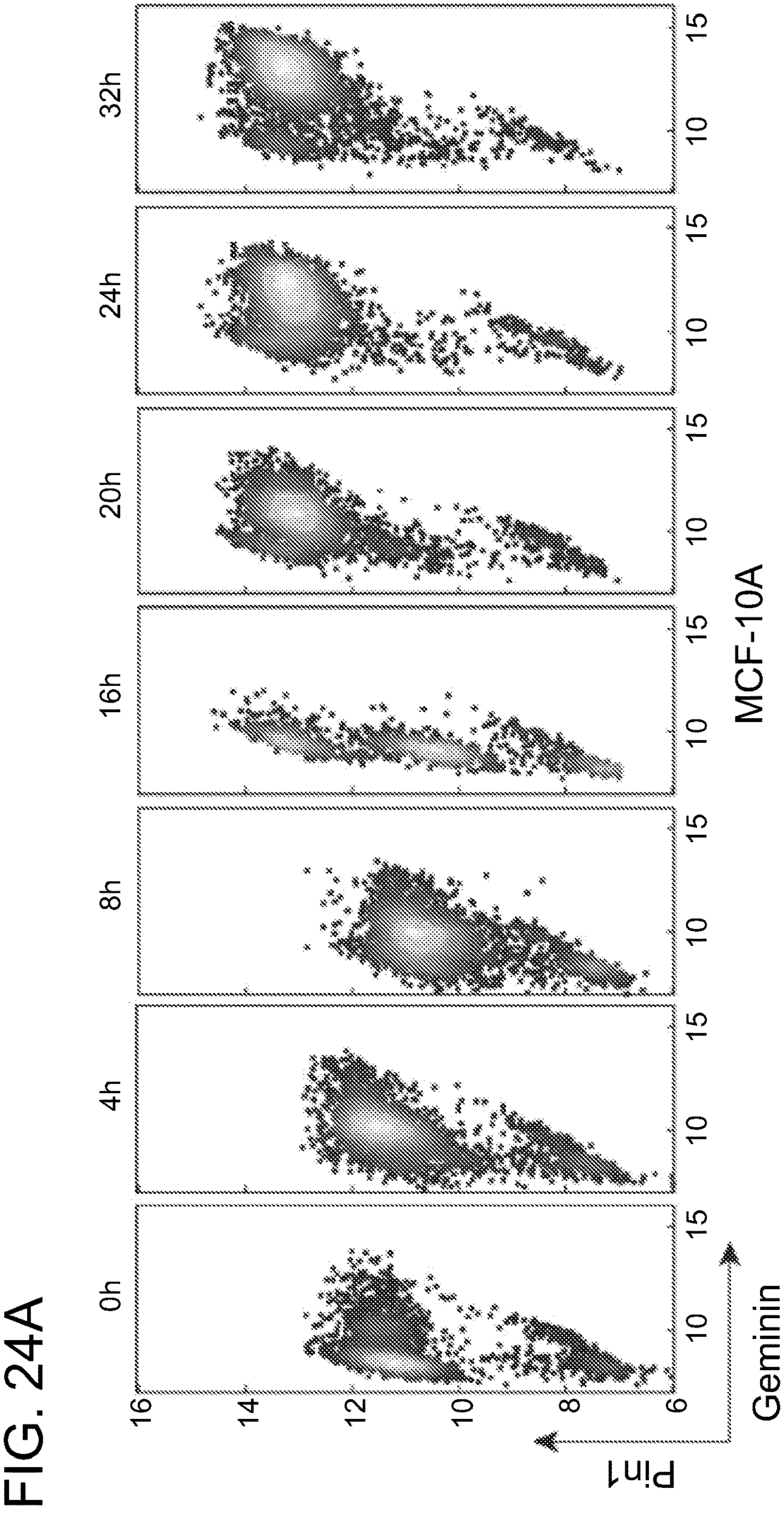

FIG. 24A is displays intensity plots of Pin1 and mCherry-Geminin (aa1-110) reporter in MCF-10A cells synchronized in the G1 phase, followed by release back into the cell cycle before fixing cells at indicated time points. Pin1 protein was stained with Cy5 (left panel). Fluorescent intensity of Pin1 and Geminin (aa1-110) were quantified and log 2 transformed across the time courses (right panel).

Figure 25A:
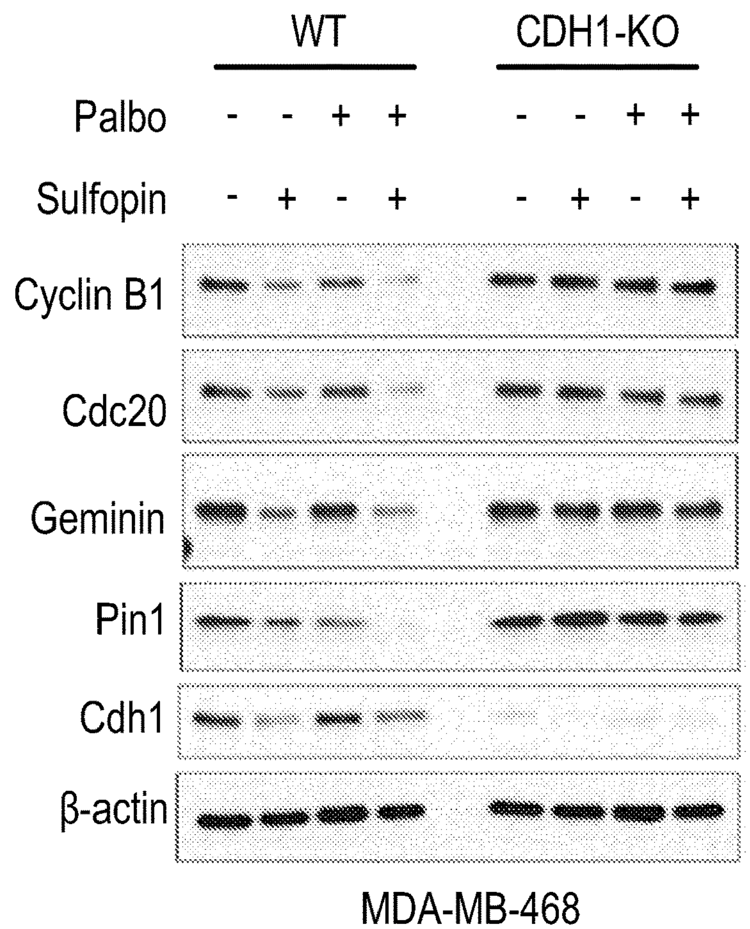

FIG. 25A is an immunoblot of WT and Cdh1 KO MEFs synchronized in the G1 phase by serum starvation, followed by releasing back into the cell cycle before harvesting cells at indicated time points.

Figure 25B:
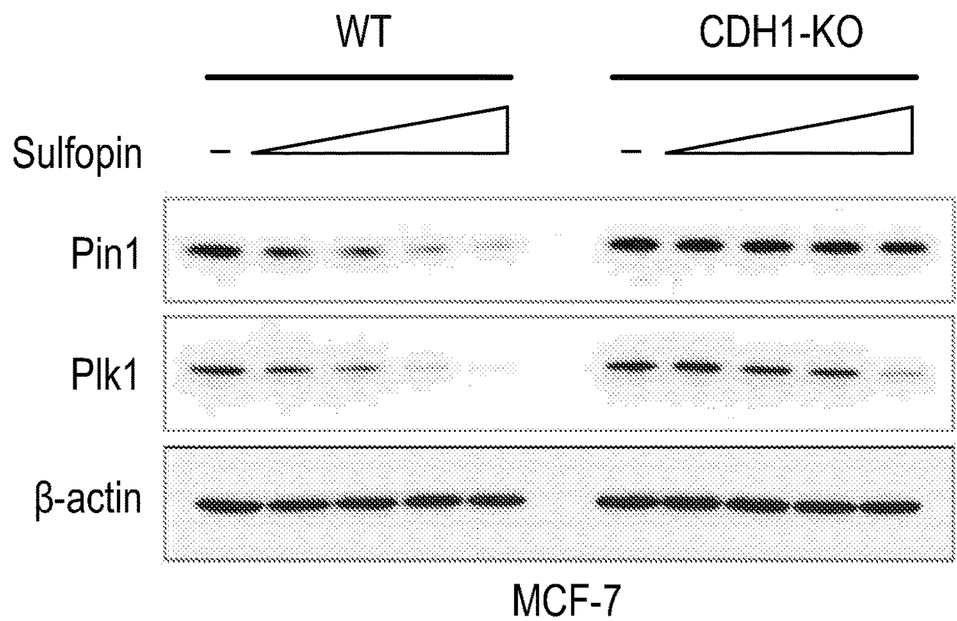

FIG. 25B is an immunoblot analysis for the indicated proteins derived from WT and Cdh1 KO MCF-7 cells treated with increasing concentrations of sulfopin (2, 4, 8, 10 μM) for 3 days.

Figure 25C:
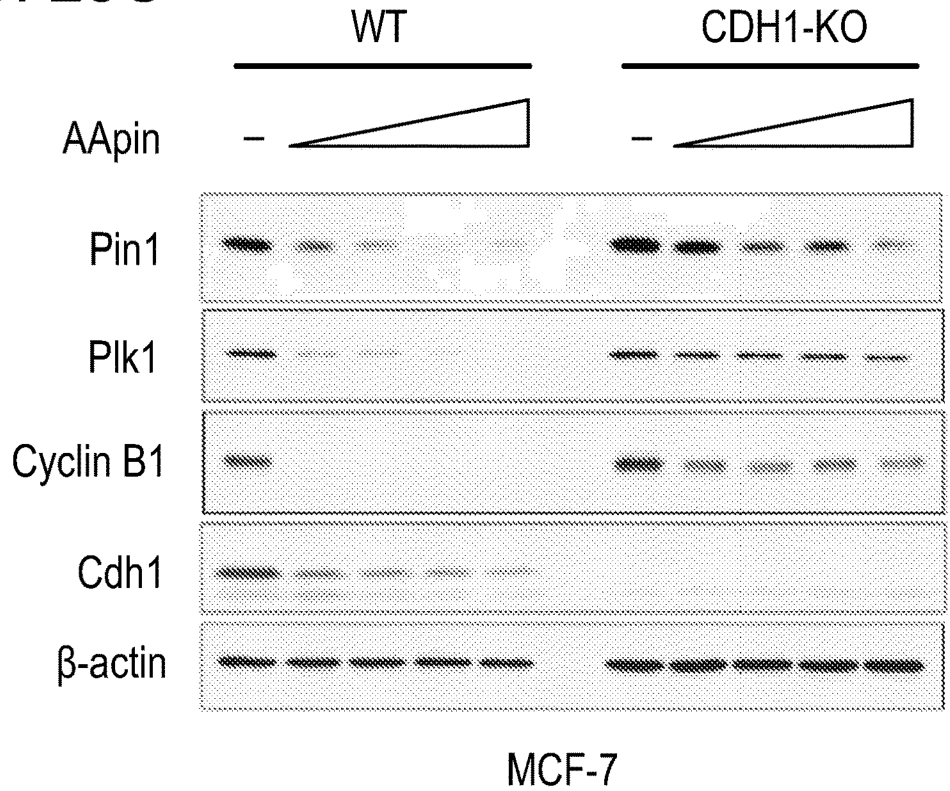

FIG. 25C is an immunoblot analysis for the indicated proteins derived from WT and Cdh1 KO MCF-7 cells treated with increasing concentrations of AApin (ATO (0.5, 1, 1.5, 2 μM) plus ATRA (5, 10, 15, 20 μM)) in 1:10 ratio for 3 days.

Figure 25D:
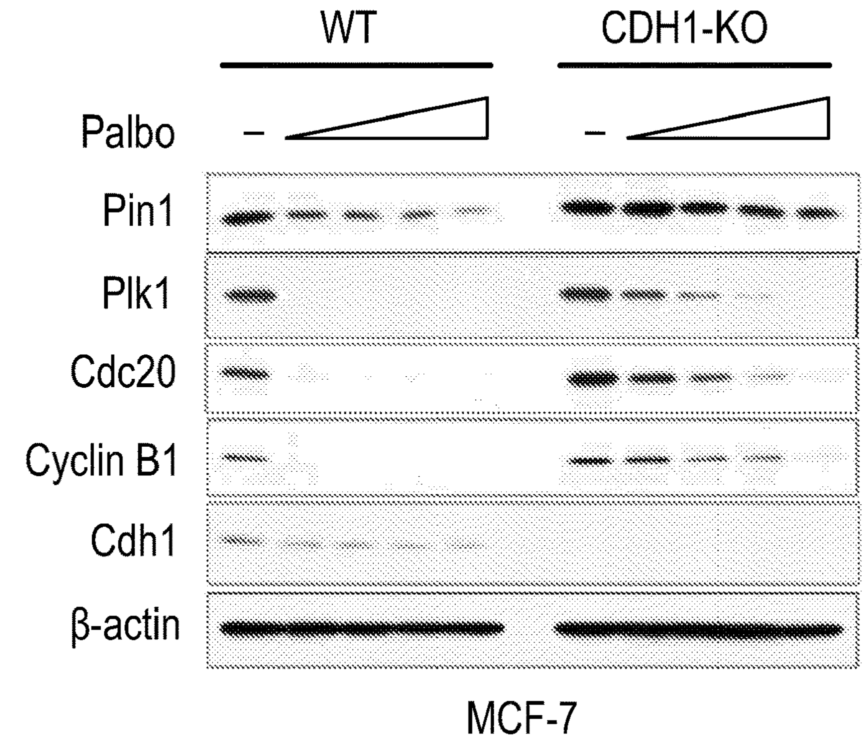

FIG. 25D is an immunoblot analysis for the indicated proteins derived from WT and Cdh1 KO MCF-7 cells treated with increasing concentrations of palbociclib (0.5, 1, 2, 4 μM) for 3 days.

Figure 25E:
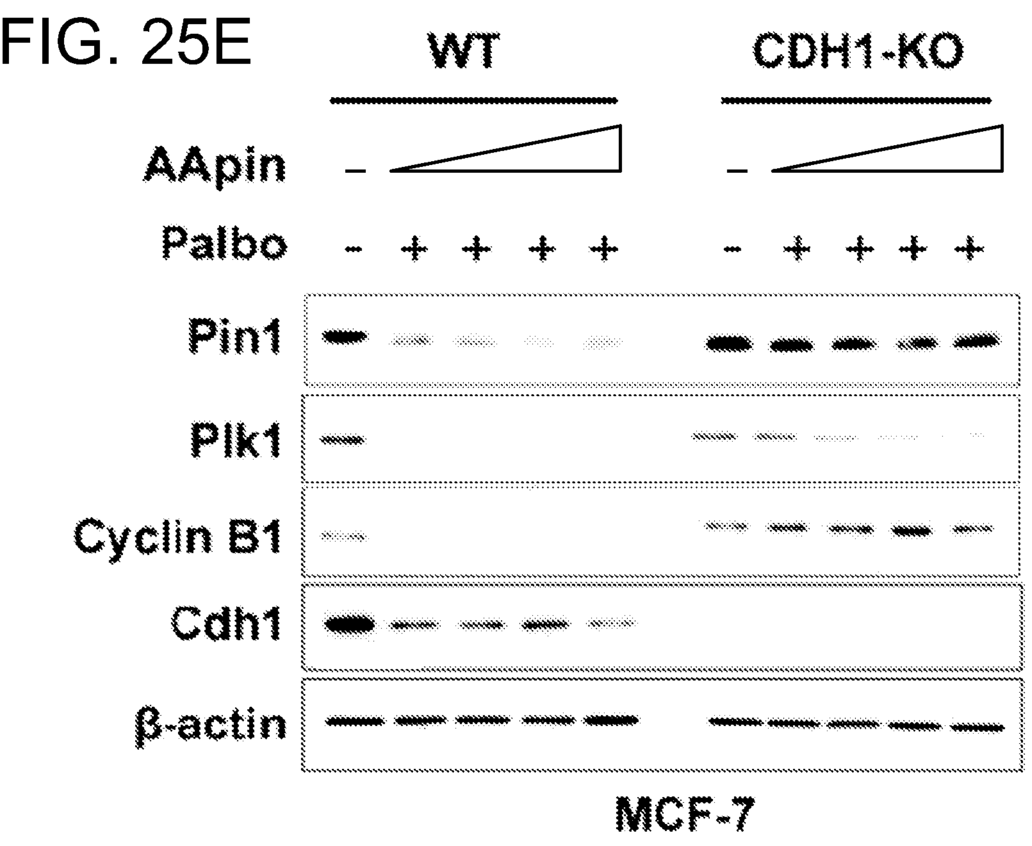

FIG. 25E is an immunoblot analysis for the indicated proteins derived from WT and Cdh1 KO MCF-7 cells treated with increasing concentrations of a combination of palbociclib and AApin for 3 days.

Figure 25F:
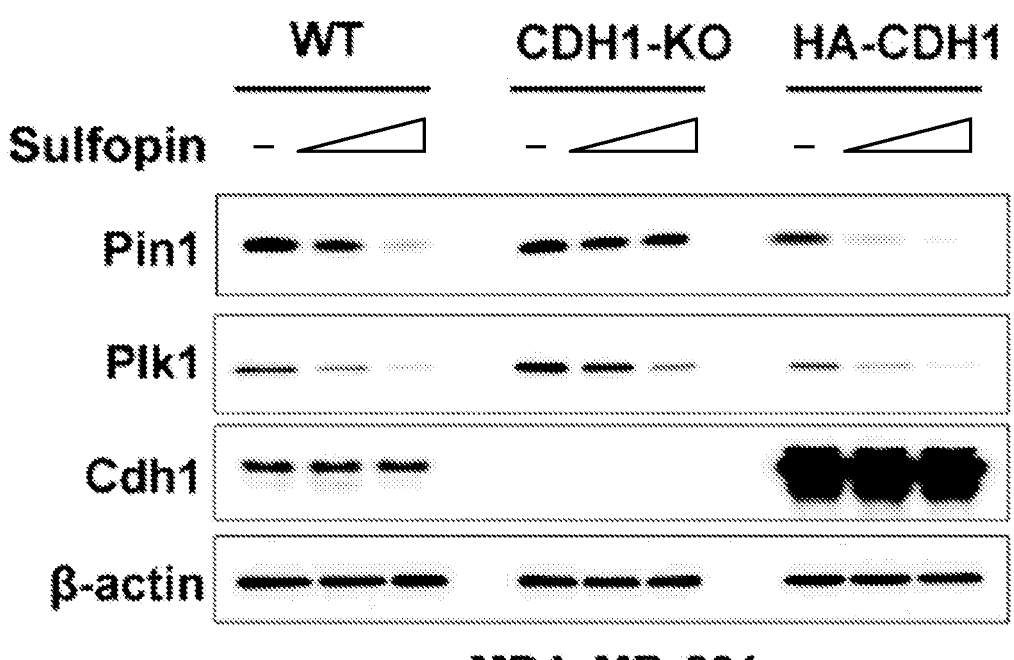

FIG. 25F is an immunoblot analysis for the indicated proteins derived from MDA-MB-231 cells stably expressing the indicated constructs and treated with increasing concentrations of sulfopin (5, 10 μM) for 3 days.

Figure 25G:
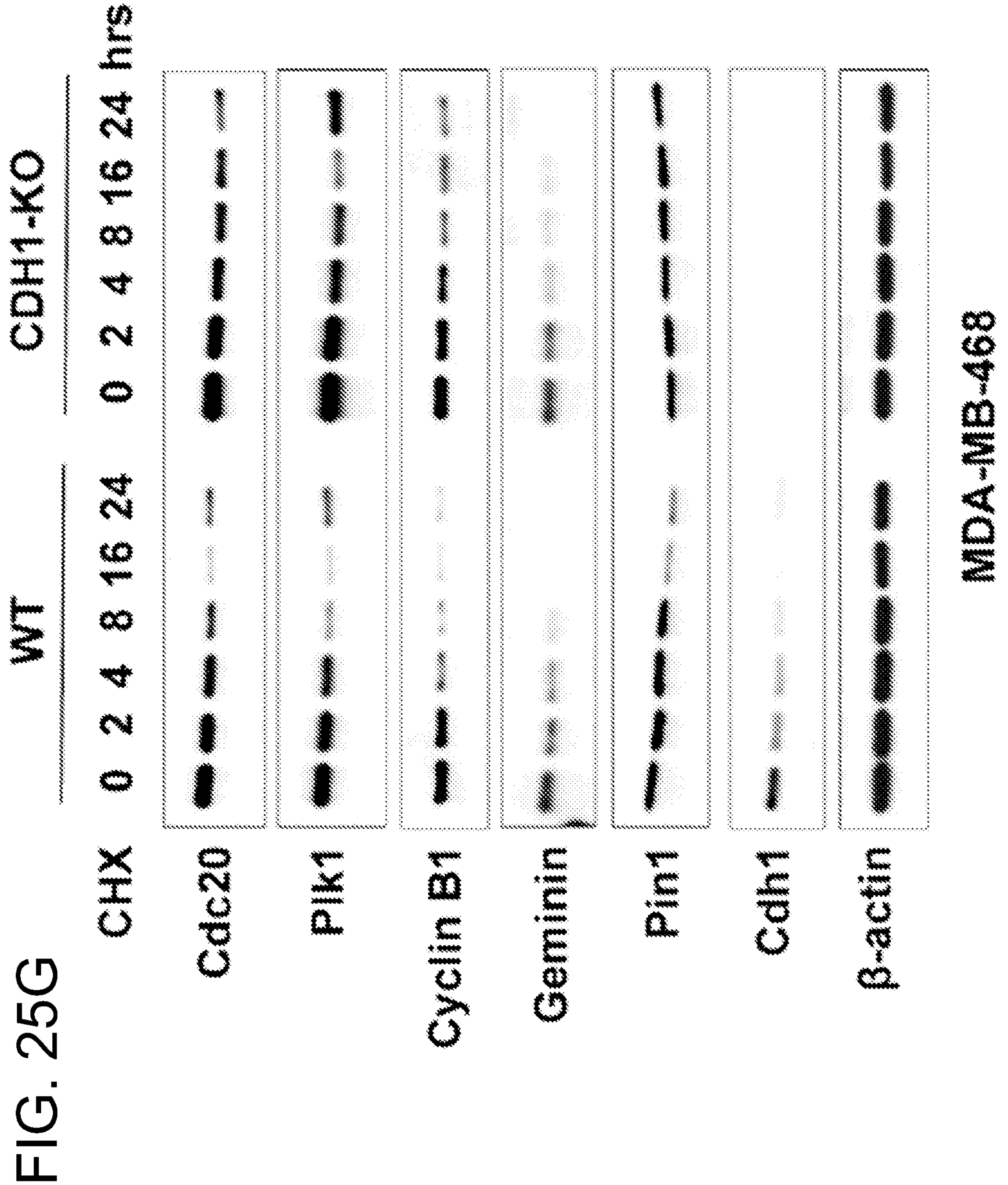

FIG. 25G is a set of immunoblots showing the results from the CHX chase assay for the indicated proteins derived from WT and Cdh1 KO MDA-MB-468 cells treated with 50 μg/mL CHX for the indicated time.

Figure 25H:
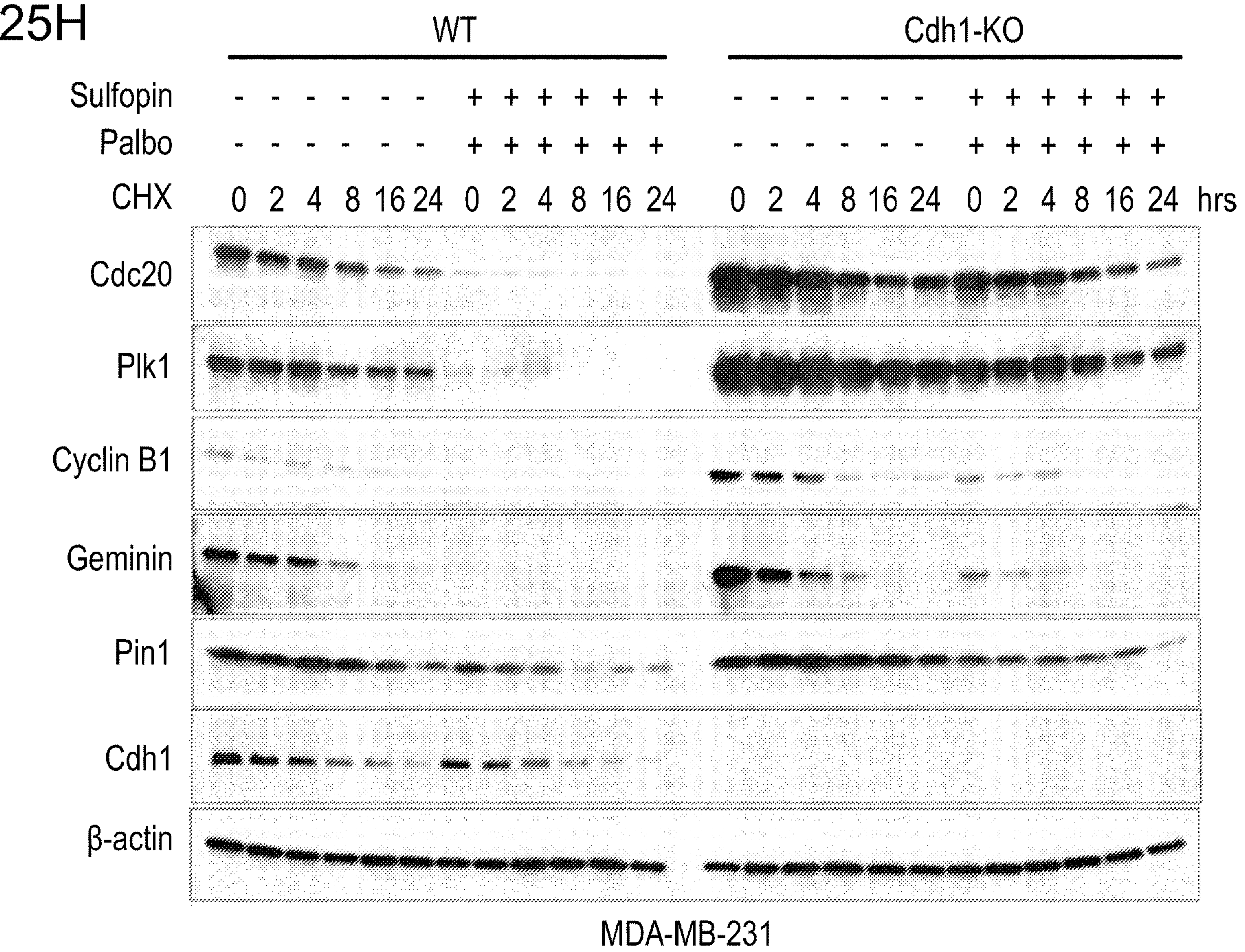

FIG. 25H is a set of immunoblots showing the results from the CHX chase assay for the indicated proteins derived from WT and Cdh1 KO MDA-MB-231 cells pre-treated with a combination of 10 μM sulfopin and 1 μM palbociclib for 36 hours followed by 50 μg/mL CHX treatment for the indicated time.

Figure 25I:
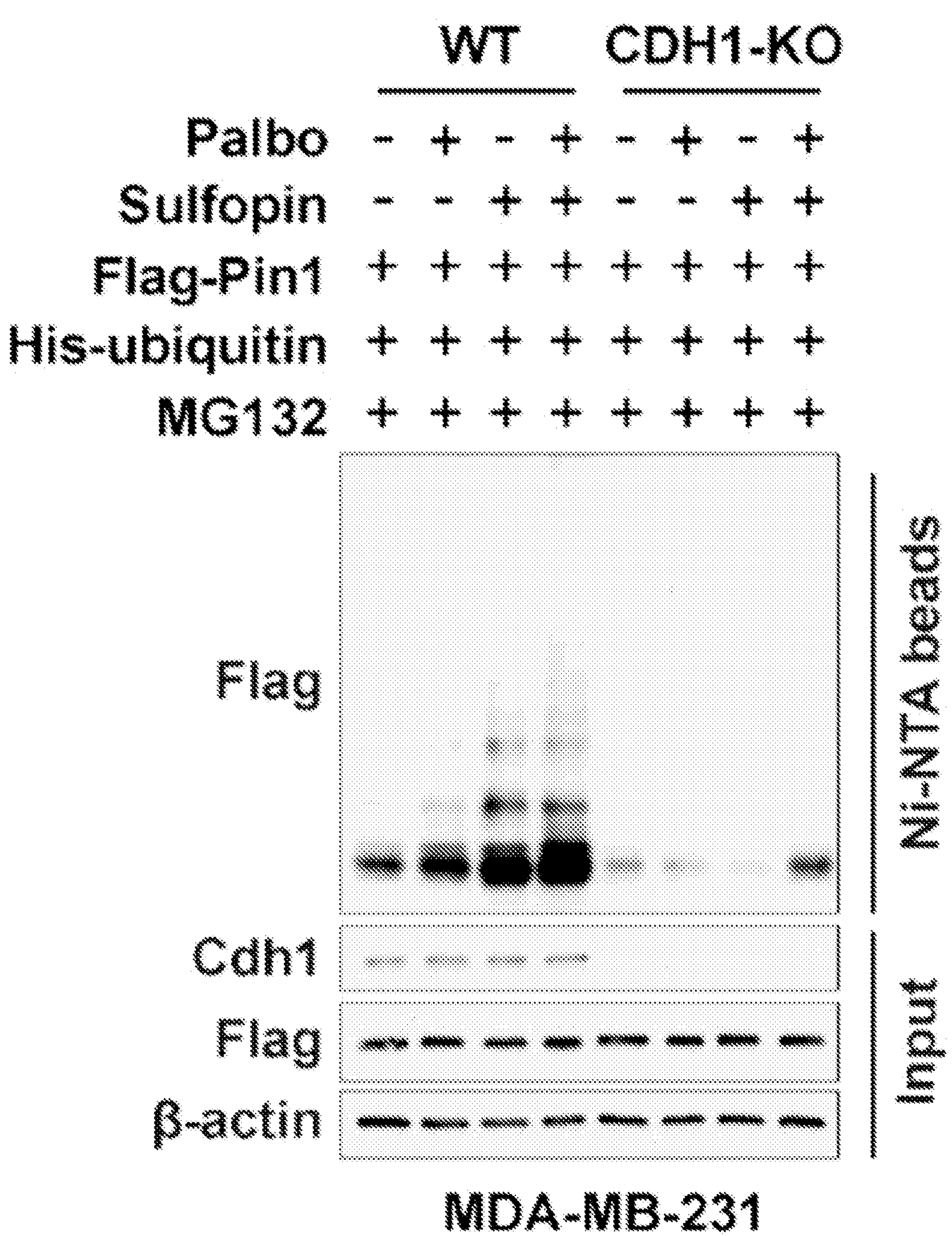

FIG. 25I is an immunoblot analysis of ubiquitinated proteins derived from WT and Cdh1 KO MDA-MB-231 cells transfected with the indicated constructs and treated with 1 MM palbociclib and 10 UM sulfopin for 3 days and 2 μM MG132 for the final 12 hrs and pulled down under denaturing conditions by nickel-nitrilotriacetic acid (Ni-NTA) agarose. The graphs were one representative experiment out of three independent experiments.

Figure 26A:
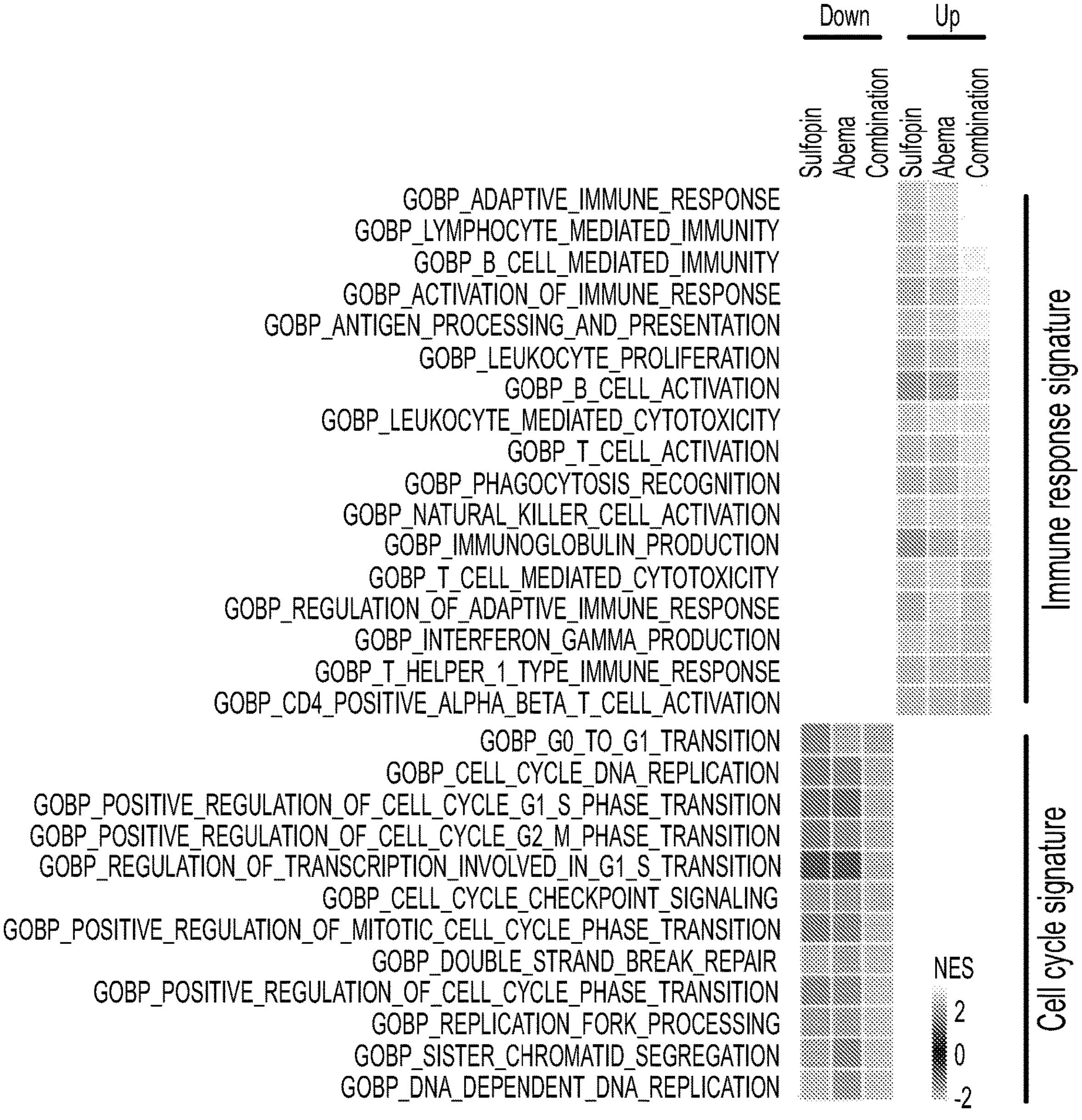

FIG. 26A is a set of heatmaps for visualization of the functional transcriptional outputs for each treatment. Normalized counts of each treatment versus vehicle were used for GSEA analysis against biological process related gene sets. Normalized enrichment scores (NES) were used to generate heatmaps.

Figure 26B:
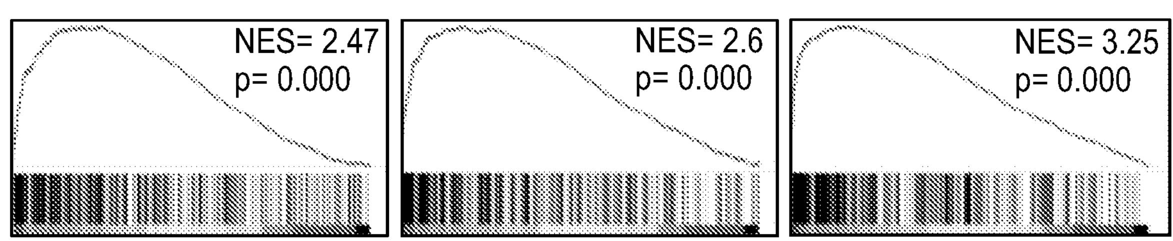
Figure 26B:
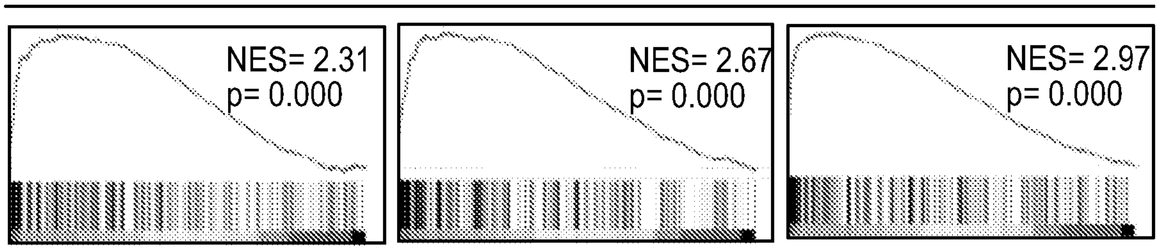
Figure 26B:
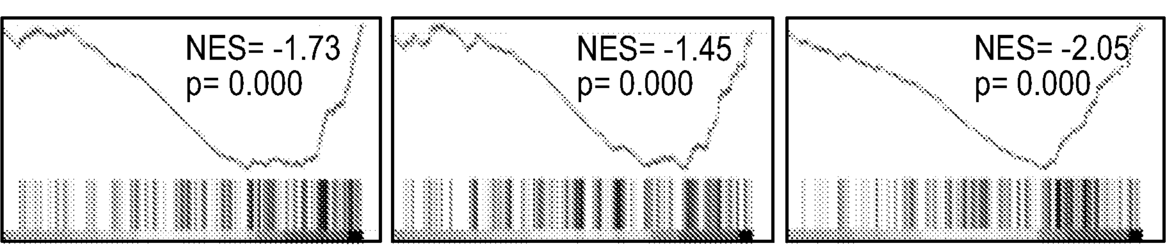
Figure 26B:
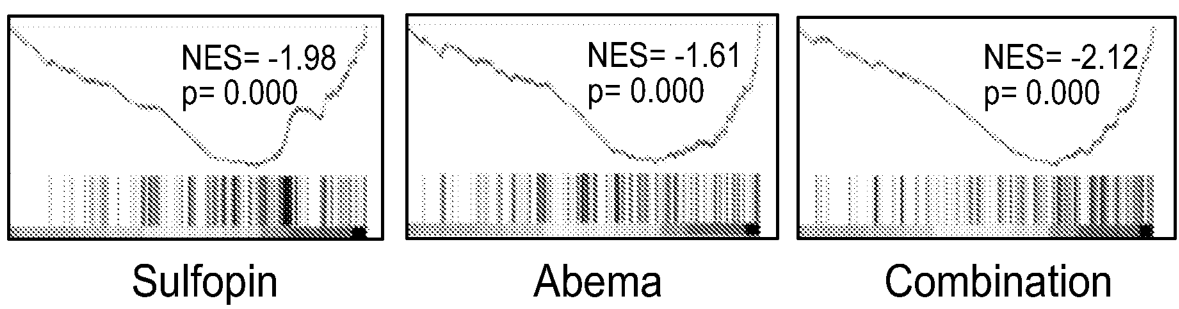

FIG. 26B is a set of enrichment plots for the indicated up-regulated and down-regulated gene sets analyzed by GSEA in each treatment versus vehicle.

Figure 27A:
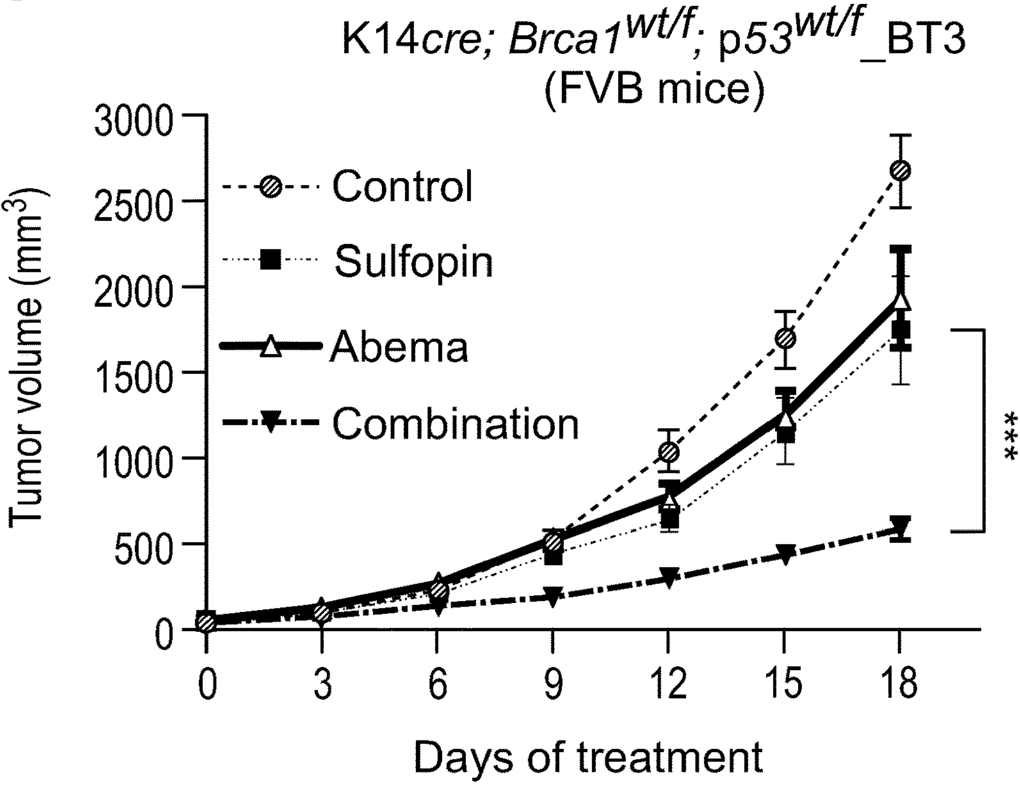

FIG. 27A is a growth curve generated from FVB mice bearing K14cre; p53$^{wt/f}$, Brca1$^{wt/f}$ BT3 tumors treated with vehicle (median survival of 18 days), sulfopin (median survival of 21 days), palbociclib (median survival of 21 days) or their combination (median survival of 34.5 days), n=10 mice per group.

Figure 27B:
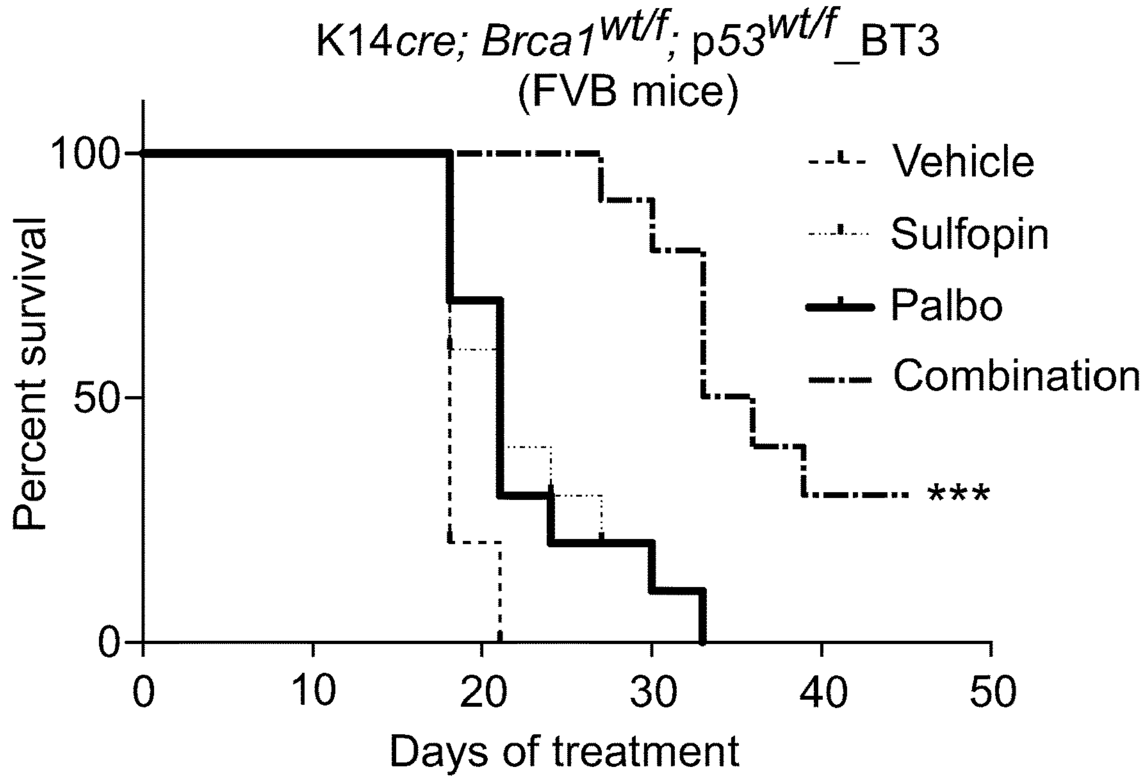

FIG. 27B is a survival curve generated from FVB mice bearing K14cre; p53$^{wt/f}$, Brca1$^{wt/f}$_BT3 tumors treated with vehicle (median survival of 18 days), sulfopin (median survival of 21 days), palbociclib (median survival of 21 days) or their combination (median survival of 34.5 days), n=10 mice per group.

Figure 27C:
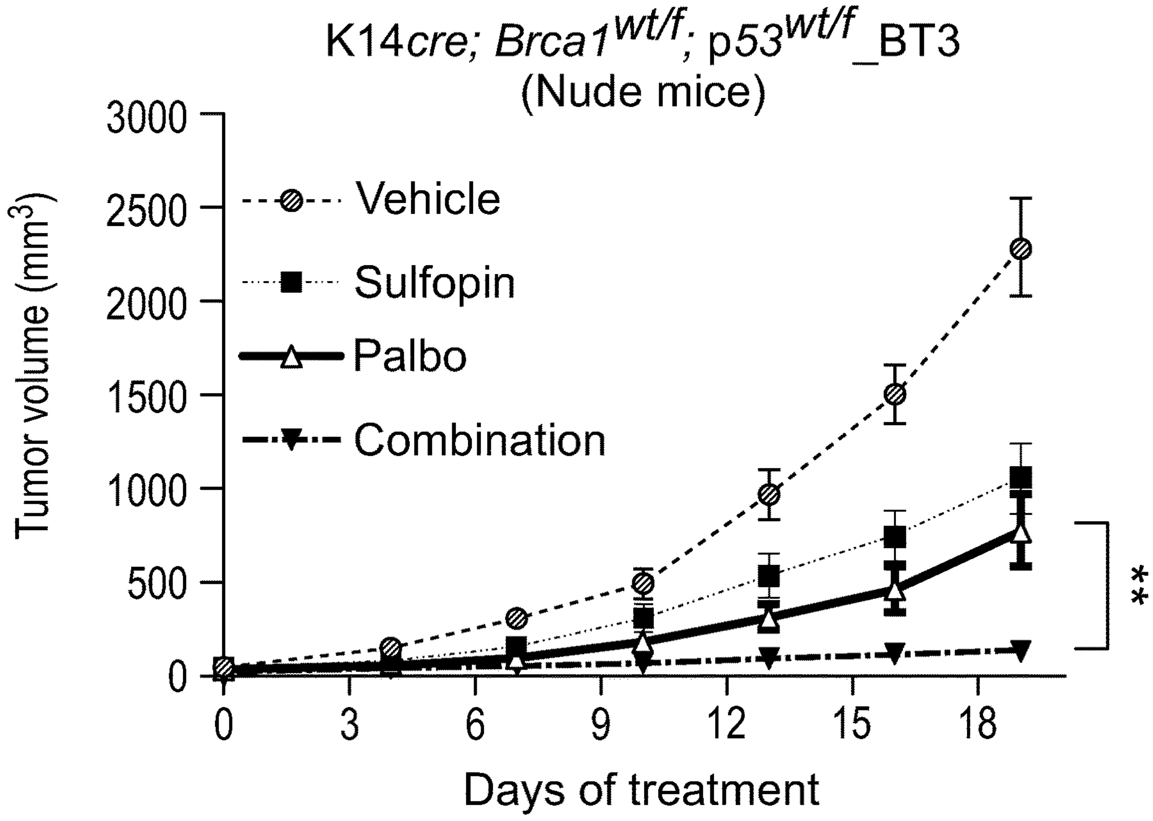

FIG. 27C is a growth curve generated from nude mice bearing K14cre; $p53^{wt/f}$; $Brca1^{wt/f}$ BT3 tumors treated with vehicle, sulfopin, palbociclib or their combination, n=6 mice per group. Data are mean±s.e.m. P values were determined by two-sided unpaired student's t-test or log-rank test.

Figure 27D:
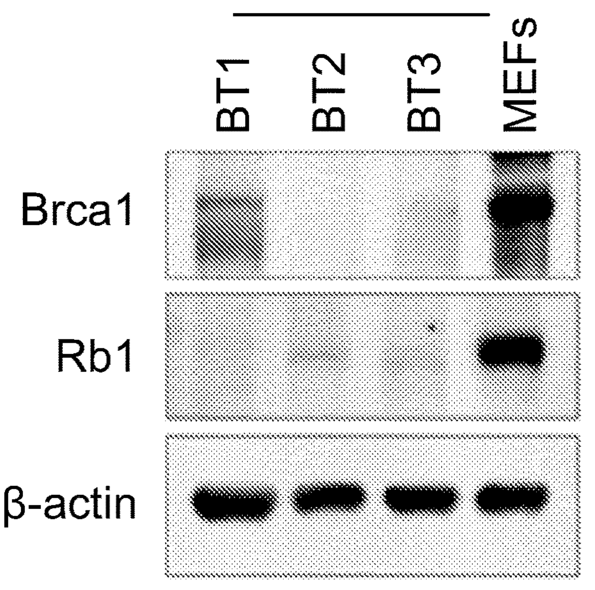

FIG. 27D is an immunoblot analysis for the indicated proteins derived from K14cre; $p53^{wt/f}$; $Brca1^{wt/f}$ tumors or MEFs.

Figure 27E:
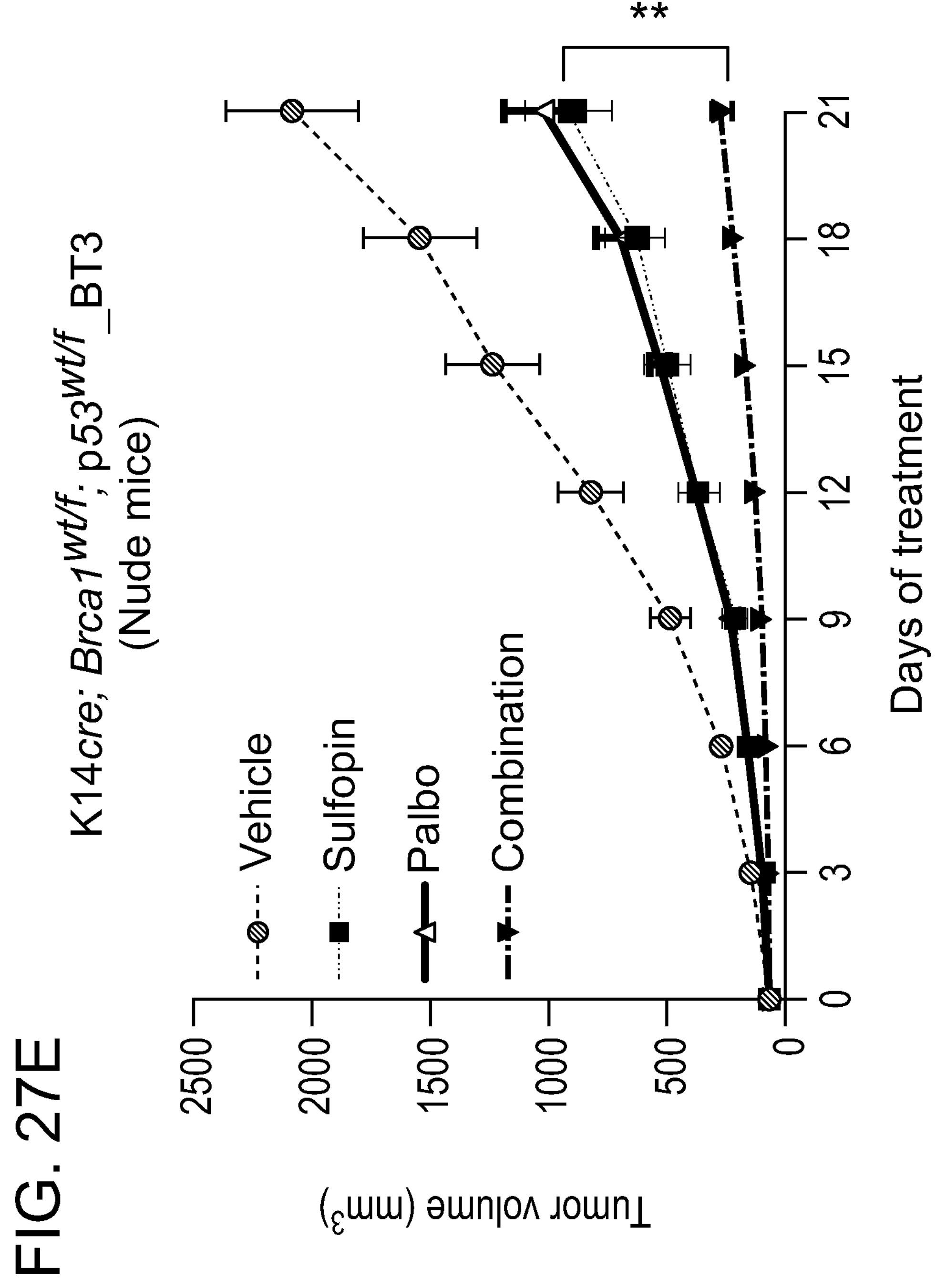

FIG. 27E is a growth curve generated from nude mice bearing K14cre; $p53^{wt/f}$, $Brca1^{wt/f}$_BT1 tumors treated with vehicle, sulfopin, palbociclib or their combination, n=5 mice per group. Data are mean±s.e.m. P values were determined by two-sided unpaired student's t-test or log-rank test.

DETAILED DESCRIPTION OF THE DISCLOSURE

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated to facilitate the understanding of the present disclosure.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed disclosure.

Identification of a Reciprocal Inhibitory Cell-Cycle Mechanism of Pin1-APC/$C^{Cdh1}$ as the Pin1 E3 Ligase Leading to Synergistic Antitumor Efficacy Disruption of cell cycle regulation leads to uncontrolled proliferation in cancer. The unique isomerase Pin1 orchestrates oncogenic signaling pathways and is a promising anticancer target, but its cell-cycle function and regulation are unclear. Here APC/$C^{Cdh1}$ is identified as the E3 ubiquitin ligase that targets Pin1 for degradation in G1. Surprisingly, APC/$C^{Cdh1}$ is also inactivated in a reciprocal inhibitory mechanism by Pin1-catalyzed isomerization of Cdh1 after CDK4-mediated phosphorylation for unchecked cell division in cancer. Consequently, Pin1 inhibitors irreversibly reactivate APC/$C^{Cdh1}$ E3 ligase by synergizing with CDK4/6 inhibitors to promote Pin1 degradation, thereby inducing insurmountable G1 arrest. Combined inhibition of Pin1 and CDK4/6 achieves synergistic anti-tumor effects and is not toxic to non-tumor cells but instead mobilizes immune surveillance. Combining Pin1- and CDK4/6-inhibitors with immunotherapy further improves survival of mice with triple-negative breast cancer. Herein is identified a reciprocal inhibitory cell-cycle mechanism of Pin1-APC/$C^{Cdh1}$ E3 ligase that is disrupted for uncontrolled proliferation in cancer, and then a strategy is developed to irreversibly reactivate APC/$C^{Cdh1}$ using clinically available Pin1 and CDK4/6 inhibitors to induce insurmountable G1 arrest, leading to synergistic antitumor efficacy and providing therapeutic opportunities for immunotherapies.

Role of Cdh1 in Cell Cycle Arrest

The sequential progression through the cell cycle is driven by a series of cyclin-dependent protein kinases (CDKs), proline-directed kinases that phosphorylate serine/threonine residues that precede proline (pSer/Thr-Pro) (Dephoure et al., Proc Natl Acad Sci USA 2008; 105:10762-7; Malumbres and Barbacid, Nat Rev Cancer 2009; 9:153-66; Olsen et al., Sci Signal 2010; 3: ra31-3). Progression through the G1 phase of the cell cycle requires CDK4/6, along with their partnering D-type cyclins (Choi and Anders, Oncogene 2014; 33:1890-903). Recent studies have identified AMBRA1 as an E3 ubiquitin ligase responsible for cyclin D1 degradation, playing a critical role in the control of cell cycle progression and the maintenance of genome stability (Maiani et al., Nature 2021; 592:799-803; Simoneschi et al., Nature 2021; 592:789-93: Chaikovsky et al., Nature 2021; 592:794-985). Two major downstream effectors of the activated cyclin D-CDK4/6 complex are the retinoblastoma (Rb) protein and the anaphase-promoting complex (APC/$C^{Cdh1}$), an E3 ubiquitin ligase that is activated by Cdh1 (encoded in humans by FZR1), whose activity is largely inhibited in cancer cells due to elevated CDK kinase activity (Harbour and Dean, Genes Dev 2000; 14:2393-409; Cappell et al., Cell 2016; 166:167-80). A functional collaboration between APC/$C^{Cdh1}$ and Rb effectively restrains cell cycle entry, as forced pRb-E2F expression alone is insufficient to drive cell cycle entry and an additional loss of APC/$C^{Cdh1}$ E3 ligase activity is required to trigger proliferation (Cappell et al., Cell 2016; 166:167-80). Cdh1 is required for Rb induced cell cycle arrest by triggering the degradation of the ubiquitin ligase for the CDK inhibitory protein p27, hence effectively stabilizing p27 (Binne et al., Nat Cell Biol 2007; 9:225-32). A recent study has shown that APC/$C^{Cdh1}$ inactivation, but not pRb-E2F activation, represents the true commitment point of no return for cell-cycle entry (Cappell et al., Cell 2016; 166:167-80).

High Pin1 Expression and Poor Prognosis in Cancer

Proline-directed phosphorylation also creates a substrate for a unique peptidyl-prolyl cis-trans isomerase, Pin1, that catalyzes cis-trans prolyl isomerization after phosphorylation. Indeed, Pin1 has been shown to turn on numerous oncoproteins and turn off many tumor suppressors after phosphorylation (Blume-Jensen and Hunter, Nature 2001; 411:355-65; Pawson and Scott, Trends Biochem Sci 2005; 30:286-90; Lu and Zhou, Nat Rev Mol Cell Biol 2007; 8:904-16; Mugoni et al., Cell Res 2019; 29:446-59). Thus, phosphorylation-targeted prolyl isomerization affords an additional, co-enzyme-free layer of regulation that promotes cell proliferation and transformation by coordinating numerous oncogenic signaling pathways (Zhou and Lu, Nat Rev Cancer 2016; 16:463-78; Pu et al., Front Cell Dev Biol 2020; 8:168). Moreover, Pin1 also drives the desmoplastic and immunosuppressive tumor microenvironment (TME) by acting on cancer associated fibroblasts (CAFs) to promote tumor malignancy and drug resistance (Koikawa et al., Cell 2021, 184, 1-19). Consequently, high Pin1 expression has been reported to correlate with poor prognosis in cancer including pancreatic, gastric, prostate and breast cancer (BC) (Zhou and Lu, Nat Rev Cancer 2016; Koikawa et al., Cell 2021, 184, 1-19; Daza-Martin et al., Nature 2019; 571:521-27; Hu et al., Oncogene 2017; 36:5177-88).

Pin1 Inhibition and Degradation

Pin1 has emerged as a unique drug target for overcoming drug resistance (Liu et al., Nat Cell Biol 2019; 21:203-13; Luo et al., Cancer Res 2020; 80:3033-45; Leung et al., Commun Biol 2021; 4:381). For example, Pin1 polymorphisms that reduce PIN1 expression are associated with reduced risk for multiple cancers in humans (Lu et al., Carcinogenesis 2009; 30:1717-21). Furthermore, $Pin1^{-/-}$ mice have no overt phenotype for half lifespan (Fujimori et al., Biochem Biophys Res Commun 1999; 265:658-63), but are resistant to cancer. Moreover, Pin1 inhibitors simultaneously block multiple oncogenic pathways and disrupt the desmoplastic and immunosuppressive TME, thereby synergizing with immunochemotherapy to eradicate aggressive cancer (Koikawa et al., Cell 2021, 184, 1-19; Wulf et al., EMBO J 2004; 23:3397-407; Liao et al., Mol Cell 2017; 68:1134-46 e6; Kozono et al., Nat Commun 2018; 9:3069). Notably, most of the Pin1 inhibitors identified so far not only inhibit Pin1 catalytic activity, but also induce Pin1 degradation at posttranslational levels (Koikawa et al., Cell 2021, 184, 1-19; Kozono et al., Nat Commun 2018; 9:3069; Wei et al., Nat Med 2015; 21:457-66; Dubiella et al., Nat Chem Biol 2021, 17, 954-63; Pinch et al., Nat Chem Biol 2020; 16:979-87; Campaner et al., Nat Commun 2017; 8:15772). However, little is known about the molecular mechanisms how these inhibitors induce Pin1 degradation.

Drug-induced degradation of driving oncoproteins provides an attractive anticancer strategy (Varshavsky, Trends Biochem Sci 2005; 30:283-6; Ablain et al., Cancer Discov 2011; 1:117-27). As inhibition of certain cellular pathways promotes feedback-mediated increased expression of the target protein, leading to pharmacological insufficiency (Duncan et al., Cell 2012; 149:307-21; Winter et al., Science 2015; 348:1376-81), induced protein degradation not only reduces the number of active proteins needed to be inhibited but also counteracts compensatory protein overexpression often observed upon loss of protein function. Furthermore, high systemic drug exposures may be needed to maintain sufficient target inhibition in vivo, increasing the risk of undesirable off-target effects (Lai et al., Nat Rev Drug Discov 2017; 16:101-14).

Notably, Pin1 was originally identified as a cell cycle regulator (Lu et al., Nature 1996; 380:544-7) and many cell-cycle checkpoint proteins (G1/S, M and checkpoint) were identified as Pin1 binding partners (Yeh and Means, Nat Rev Cancer 2007; 7:3818). However, it remains unclear whether Pin1 stability is regulated during cell cycle (Koikawa et al., Cell 2021, 184, 1-19; Kozono et al., Nat Commun 2018; 9:3069; Wei et al., Nat Med 2015; 21:457-66; Dubiella et al., Nat Chem Biol 2021, 17, 954-63; Pinch et al., Nat Chem Biol 2020; 16:979-87; Campaner et al., Nat Commun 2017; 8:15772). The identification of upstream regulators of Pin1 stability may offer new approaches to decrease Pin1 protein abundance, thereby providing therapeutic opportunities against cancer.

Pin1 substrates comprise proteins involved in signal transduction, including RAF1, HER2, eNOS, SMAD2/3, Notch1, Notch3, AKT, FAK, P70S6K, PTP-PEST, MEK1, GRK2, CDK10, FBXW7, PIP4Ks, PKM2 and JNK1; proteins involved in gene transcription including SIN3-RPD3, JUN, β-catenin, CF-2, hSPT5, MYC, NF-κB, FOS, RARa, SRC-3/AIB1, STAT3, MYB, SMRT, FOXO4, KSRP, SF-1, Nanog, PML, Mutant p53, ANp63, Oct4, ERa, PKM2, AR, SUV39H1, RUNX3, KLF10, Osterix and PML-RARα; proteins involved in cell cycle at the G1/S including Cyclin D1, KI67, Cyclin E, p27, LSF and RB1; proteins involved in cell cycle at the G2/M and M including NIMA, RAB4, CDC25, WEEI, PLK1, MYTI, CDC27, CENP-F, INCENP, RPB1, NHERF-1, KRMP1, CK2, TOPIIa, DAB2, p54NRB, SIL, EMII, CEP55, BORA, Survivin, SEPT9, SP1, SWI6, WHI5 and Separase; proteins involved in DNA damage/stress response and apoptosis including p53, BCL-2, p73, BIMEL, p66SHC, DAXX, MCL-1, NUR77, HIPK2, RBBP8, p63, HSF1, HIF-1α, CHE-1 and PGK1; proteins involved in immune response including NFAT, AUF1, IRF3, BTK, BAX, COX-2, p47PHOX, IRAK1, GR and FADD; proteins involved in viral or parasitic infection and transformation including HBX, A3G, v-Rel, Tax, Capsid protein, Integrase, BALF5, RTA, FBXW7 and ORF 1p; proteins involved in neuronal survival and degeneration including TAU, APP, Synphilin-1, Gephyrin, mGluR5, REST, GRO/TLEI and CRMP2A. (Zhou and Lu, Nature Reviews Cancer 16:463-478; Supplementary Information (2016)).

Pin1 Inhibitors Synergize with CDK4/6 Inhibitors

In this study, the active $APC/C^{Cdh1}$ E3 ubiquitin ligase responsible for a fundamental and evolutionary conserved regulation of Pin1 stability has been identified. Surprisingly, $APC/C^{Cdh1}$ E3 ligase activity is also inactivated in a reciprocal inhibitory mechanism by Pin1-catalyzed isomerization of Cdh1 after CDK4-mediated phosphorylation to promote cell-cycle progression in cancer. As a result, Pin1 inhibitors synergize with CDK4/6 inhibitors to eliminate triple-negative breast cancer (TNBC) by restoring $APC/C^{Cdh1}$ E3 ligase activity, which changes Pin1 from an inhibitor to a substrate of $APC/C^{Cdh1}$ for ubiquitination-mediated proteolysis. Collectively, a role of a reciprocal inhibitory cell-cycle mechanism of Pin1-$APC/C^{Cdh1}$ E3 ligase in cancer development is uncovered and a rationale is developed for combining Pin1 inhibitor(s) with CDK4/6 inhibitor(s) to synergistically eliminate breast cancer.

Identification of a Reciprocal Inhibitory Cell-Cycle Mechanism of Pin1-$APC/C^{Cdh1}$ This study conclusively identifies a reciprocal inhibitory cell-cycle mechanism between Pin1 and $APC/C^{Cdh1}$. Active unphosphorylated $APC/C^{Cdh1}$ acts as a tumor suppressor to target Pin1 for degradation. However, $APC/C^{Cdh1}$ E3 ligase activity is also inhibited by Pin1-catalyzed isomerization of Cdh1 after CDK4-mediated phosphorylation to promote cell-cycle progression in cancer (i.e., becomes inactive). In cancer, high levels of Pin1 and CDK4/6 activity tilt this balance in a positive feedback loop to promote unchecked cell proliferation and tumorigenesis. Moreover, combined inhibition of Pin1 and CDK4/6 is developed as a strategy to irreversibly reactivate the E3 ubiquitin ligase $APC/C^{Cdh1}$ to promote Pin1 degradation, inducing insurmountable G1 arrest, thereby displaying strong, synergistic anti-tumor effects. In this drug-induced proteolysis, restoration of protein function requires re-synthesis of the protein, providing a kinetic advantage, compared to the dissociation kinetics of an inhibitor from an active site (Ablain et al., Cancer Discov 2011; 1:117-27; Lai and Crews, Nat Rev Drug Discov 2017; 16:101-14). Thus, the reciprocal inhibition between Pin1 and $APC/C^{Cdh1}$ is a cell-cycle regulatory mechanism that is disrupted in breast cancer, but can be irreversibly reactivated using clinically available Pin1 and CDK4/6 inhibitors for synergistic anticancer therapy.

In some embodiments, the combination of one or more Pin1 inhibitors and one or more CDK4/6 inhibitors reactivates the E3 ubiquitin ligase $APC/C^{Cdh1}$ to promote Pin1 degradation. In some embodiments, the reactivation is irreversible. In some embodiments, the combination of one or more Pin1 inhibitors and one or more CDK4/6 inhibitors induces insurmountable G1 arrest. In some embodiments, the combination of one or more Pin1 inhibitors and one or more CDK4/6 inhibitors displays anti-tumor effects. In some embodiments, the anti-tumor effect is synergistic. In some embodiments, the combination of one or more Pin1 inhibitors and one or more CDK4/6 inhibitors eliminates triple-negative breast cancer (TNBC). In some embodiments, the elimination is synergistic.

Epithelial cells execute an active program to maintain interphase that relies on reducing the levels of continuously accumulating pro-mitogenic proteins including cyclins through ubiquitin-mediated degradation. A key ubiquitin ligase for the maintenance of interphase is $APC^{Cdh1}$ (Penas et al., Front Oncol 2011; 1:60), targeting a range of pro-mitogenic proteins. In cancer, Cdh1 is largely inactivated by N-terminal phosphorylation (Kramer et al., Mol Biol Cell 2000; 11:1555-69), in this study simulated by Cdh1-KO (FIG. 1E, FIG. 1F, FIG. 4A, and FIG. 6M-FIG. 6O), and activated by dephosphorylation, in this study simulated by mutation of all 7 S/T-P sites generating a phosphosite-deficient Cdh1, resulting in constitutively active $APC/C^{Cdh1}$ (FIG. 4C-FIG. 4L, FIG. 5D-FIG. 5F). As expected, $APC/C^{Cdh1}$ inactivation promoted mitotic progression, while enforced expression of constitutively active $APC/C^{Cdh1}$ blocked cell cycle progression.

Figure 4A:
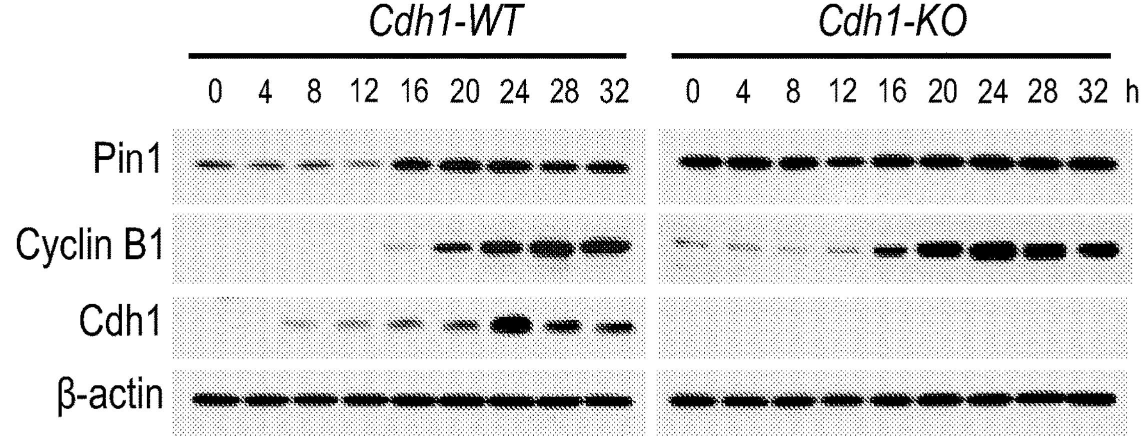
FIG. 4A-FIG. 4O is a set of immunoblots, representations and images that show that active APC/$C^{Cdh1}$ targets Pin1 for degradation and APC/$C^{Cdh1}$ E3 ligase activity is inhibited by CDK4-mediated Cdh1 phosphorylation.

Inactivation of Cdh1 in vivo is achieved through multi-site phosphorylation, which interestingly occurs on N-terminal serine or threonine residues that precede proline (pSer/Thr-Pro), a minimal consensus sequence for the phosphorylation-specific peptidyl-prolyl isomerase Pin1. Through the specificity for phosphorylated serine/threonine-proline motifs, Pin1 modulates the stability and activity of its targets with the net result of advancing a pro-mitotic progression (Theuerkorn et al., Curr Opin Pharmacol 2011; 11:281-7). Herein it is reported that the two opposing enzymes, $APC^{Cah1}$, which promotes maintenance of interphase, and Pin1, which promotes mitotic progression, directly interact with and negatively regulate each other. In its active, unphosphorylated form, Cdh1 binds the D-box of Pin1, which is buried within its PPIase domain and may be exposed by Pin1 inhibitors, and promotes the ubiquitin-dependent destruction of the pro-mitotic Pin1 (FIG. 4G-FIG. 4I, FIG. 5G). However, when CDK4/6 activity garners momentum at the end of G1, Cdh1 is successively phosphorylated and becomes a target for the Pin1-WW domain specifically at phospho-S163, which is the preferred high affinity interaction for the two proteins (FIG. 1K, FIG. 4M-FIG. 4O), leading to isomerization of the adjacent P164 and stabilization of phosphorylated, inactive Cdh1 and allowing for S-phase entry (FIG. 4A). Consequently, the outcome of the Pin1-Cdh1 interaction, decrease of Pin1 by active Cdh1 versus inactivation of Cdh1 through phosphorylation and phosphorylation-targeted prolyl-isomerization, depends on the activities of CDK4/6 and Pin1. These activities are strictly regulated in normal epithelial cells, but hyperactivated in epithelial cancers due to constitutive CDK activation and Pin1 overexpression (Zhou and Lu, Nat Rev Cancer 2016; 16:463-78; Yang et al., Oncogene 2017; 36:2255-64; VanArsdale et al., Clin Cancer Res 2015; 21:290510), leading to phosphorylation and isomerization of Cdh1 to irreversibly commit cells to overcoming the G1/S checkpoint and progress through the cell cycle.

Role of CDK4/6 and the Emergence of Resistance

In cancer, constitutive and deregulated CDK activation contributes not only to unscheduled proliferation but also to genomic and chromosomal instability. In turn, the resulting DNA damage and faltering mitotic checkpoints result in further increased CDK activity that drives tumor cell cycling (Malumbres and Barbacid, Nat Rev Cancer 2009; 9:153-66). Three inhibitors of CDK4/6 are currently approved for the treatment of metastatic breast cancer (BC). As single agents, neither palbociclib nor ribociclib has activity in TNBC (Matutino et al., Ther Adv Med Oncol 2018; 10:1758835918818346), while abemaciclib, with a somewhat broader target specificity (Hafner et al., Cell Chem Biol 2019; 26:1067-80 e8), is under investigation in this setting (NCT03130439). Despite an increased overall survival in Paloma-3 and Monaleesa-2 (Turner et al., N Engl J Med 2015; 373:209-19; Hortobagyi et al., N Engl J Med 2016; 375:1738-48), resistance to CDK4/6-inhibition inevitably emerges, and hence more effective combination therapies for ER+ tumors and development of combinations that are effective in TNBC are urgently needed. The data herein shows that combined inhibition of CDK4/6 and Pin1 permits deeper and longer-lasting remissions, even resulting in complete remission in some tumor mice.

Surprisingly, this regimen did not appear to affect hematopoiesis as blood counts remained normal and was overall associated with very little toxicity (FIG. 15). This is likely due to the fact that both Pin1 and CDKs are tightly regulated during the cell cycle in normal cells, suggesting that the mechanism uncovered is of specific importance for cancer cell proliferation when Pin1 is overexpressed and CDK4/6 activity is high. Targeting both Pin and CDK4/6 was surprisingly successful in treating a Rb-proficient human TNBC model, with 2/7 mice on sulfopin and abemaciclib achieving a complete remission and the remaining 5 with only minimal disease (FIG. 14F).

Pin1 Inhibition and PD-L1 Blockade

In a recent study on pancreatic cancer, Pin1 inhibition has been shown to increase PD-L1 expression (Koikawa et al., Cell 2021, 184, 1-19). While an apparent increase in PD-L1 expression was not observed in this immune-competent BC model (FIG. 12D), the combination of sulfopin and abemaciclib created an immune environment with increased cytotoxic CD8+ T cell infiltration while Tregs were decreased and also an increased phagocytic activity of tumor-associated macrophages (FIG. 10D), hence creating an immune environment conducive to the successful use of immunooncology agents. Interestingly, immune surveillance was only mobilized in combination treatment, which suggested two-drug regimen-induced robust Pin1 degradation may produce some covalent fragment peptides derived from Pin1 as a neo-antigen, which will get presented by MHC-I and be targeted by cytotoxic T cells, providing some evidence that covalent modified peptide can be antigenic (Canon et al., Nature 2019; 575:217-23). Whether this remodeling of the immune environment is a direct effect of Pin1 degradation induced by the sulfopin/abemaciclib combination on cancer cells or a consequence of tumor cell death requires further study. Syngeneic BC models are historically much harder to treat with chemotherapy or targeted agents than PDX models in immune-compromised hosts. Importantly, though, the combination of CDK4/6 inhibitors and sulfopin was also highly active in this hard-to-treat, highly undifferentiated and proliferative murine BC and, as expected based on immunophenotyping results (FIG. 10D) activity was augmented by PD-L1 blockade (FIG. 10F).

In some embodiments, the combination of one or more CDK4/6 inhibitors and one or more Pin1 inhibitors provides an immune environment with increased cytotoxic CD8+ T cell infiltration. In some embodiments, the combination of one or more CDK4/6 inhibitors and one or more Pin1 inhibitors provides decreased Tregs. In some embodiments, the combination of one or more CDK4/6 inhibitors and one or more Pin1 inhibitors provides increased phagocytic activity of tumor-associated macrophages. In some embodiments, the combination of one or more CDK4/6 inhibitors and one or more Pin1 inhibitors provides an immune environment conducive to the successful use of immunooncology agents. In some embodiments, the combination of one or more CDK4/6 inhibitors, one or more Pin1 inhibitors, and anti-PD-1 or anti-PD-L1 provides augmented activity.

The work herein reveals that Cdh1 acts as the downstream effector of CDK4 and is also a Pin1 E3 ligase, whose activity is inhibited by CDK4-mediated phosphorylation and Pin1-catalyzed isomerization in cancer. As such, pharmacological inhibition of Pin1 and CDK4/6 restores APC/$C^{Cdh1}$ E3 ligase activity by decreasing phosphorylation of Cdh1, which allows for targeting PPIase domain of Pin1 for ubiquitination-mediated proteolysis. This work highlights the reciprocal inhibitory mechanism between Pin1 and Cdh1 to regulate cell cycle progression at the G1/S checkpoint and provides a molecular rationale for combining Pin1 and CDK4/6 inhibitor treatment to synergistically induce tumor regression. Moreover, the combination of these two drugs triggered immune surveillance in tumors that can be harnessed using additional immune-checkpoint blockade, offering a well-tolerated combination regimen with high efficacy against TNBC.

In some embodiments, the combination of one or more CDK4/6 inhibitors and one or more Pin1 inhibitors restores APC/$C^{Cdh1}$ E3 ligase activity by decreasing phosphorylation of Cdh1. In some embodiments, the combination of one or more CDK4/6 inhibitors and one or more Pin1 inhibitors allows for targeting PPIase domain of Pin1 for ubiquitination-mediated proteolysis. In some embodiments, the combination of one or more CDK4/6 inhibitors and one or more Pin1 inhibitors synergistically induces tumor regression. In some embodiments, the combination of one or more CDK4/6 inhibitors and one or more Pin1 inhibitors, triggers immune surveillance in tumors. In some embodiments, the combination of one or more CDK4/6 inhibitors, one or more Pin1 inhibitors, and anti-PD-1 or anti-PD-L1 provides a well-tolerated combination regimen with high efficacy against TNBC.

Compounds of the present disclosure may be in the form of a free acid or free base, or a pharmaceutically acceptable salt. As used herein, the term "pharmaceutically acceptable" refers to a material, such as a carrier or diluent, which does not abrogate the biological activity or properties of the compound, and is relatively non-toxic, i.e., the material may be administered to a subject without causing undesirable biological effects (such as dizziness or gastric upset) or interacting in a deleterious manner with any of the components of the composition in which it is contained. The term "pharmaceutically acceptable salt" refers to a product obtained by reaction of the compound of the present disclosure with a suitable acid or a base. Examples of pharmaceutically acceptable salts of the compounds of this disclosure include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the disclosure can form pharmaceutically acceptable salts with various organic bases such as lysine, arginine, guanidine, diethanolamine or metformin.

In some embodiments, the compound of the present disclosure is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e., 2H, may afford certain therapeutic advantages resulting from greater metabolic stability, for example, increased in vivo half-life or reduced dosage requirements, and thus may be advantageous in some circumstances.

Compounds of the present disclosure may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present application may be made and used in the form of individual isomers and substantially free of other isomers, or in the form of a mixture of various isomers, e.g., racemic mixtures of stereoisomers.

In addition, the compounds of the present disclosure embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

In some embodiments, the compound of the present disclosure is a Pin1 inhibitor. In some embodiments, the Pin1 inhibitor comprises ATO. In some embodiments, the Pin1 inhibitor comprises ATRA. In some embodiments, the Pin1 inhibitor comprises the combination of ATO and ATRA. In some embodiments, the Pin1 inhibitor comprises sulfopin.

$As_2O_3$ arsenic trioxide (ATO)

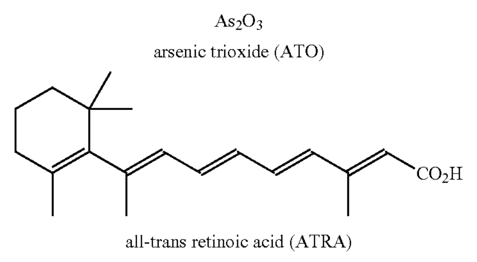

all-trans retinoic acid (ATRA)

-continued

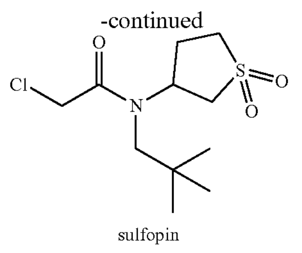

sulfopin

In some embodiments, the compound of the present disclosure is a CDK4/6 inhibitor. In some embodiments, the CDK4/6 inhibitor comprises palbociclib. In some embodiments, the CDK4/6 inhibitor comprises ribociclib. In some embodiments, the CDK4/6 inhibitor comprises abemaciclib.

In some embodiments, the present disclosure provides one or more immunotherapies. In some embodiments, the one or more immunotherapies comprises anti-PD-1 or anti-PD-L1. In some embodiments, the immunotherapy comprises anti-PD-1. In some embodiments, the immunotherapy comprises anti-PD-L1.

Methods of Synthesis

In another aspect, the present disclosure is directed to a method for making a compound of the disclosure, or a pharmaceutically acceptable salt thereof. Broadly, the compounds or pharmaceutically acceptable salts thereof may be prepared by any process known to be applicable to the preparation of chemically related compounds. In some embodiments, the compounds are prepared using chiral HPLC to separate enantiomers from a racemic mixture.

Pharmaceutical Compositions

Another aspect of the present disclosure is directed to a pharmaceutical composition that includes a therapeutically effective amount of the compounds of the disclosure (e.g., sulfopin, palbociclib, abemaciclib, ribociclib, etc.) or a pharmaceutically acceptable salt(s) thereof, and a pharmaceutically acceptable carrier. The term "pharmaceutically acceptable carrier," as known in the art, refers to a pharmaceutically acceptable material, composition, or vehicle, suitable for administering compounds of the present disclosure to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, compounds of the disclosure (e.g., sulfopin, ATRA, ATO, palbociclib, abemaciclib, ribociclib, etc.) may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compositions are formulated for oral or intravenous administration (e.g., systemic intravenous injection).

Accordingly, compounds of the present disclosure may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate, or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the disclosure may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups, and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished using a liquid suspension or crystalline or amorphous material with poor water solubility. Prolonged absorption of the compound from a parenterally administered formulation may also be accomplished by suspending the compound in an oily vehicle.

In certain embodiments, compounds of the disclosure may be administered in a local rather than systemic manner, for example, via injection of the conjugate directly into an organ, often in a depot preparation or sustained release formulation. In specific embodiments, long-acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The compounds may be formulated for buccal or sublingual administration, examples of which include tablets, lozenges, and gels.

The compounds may be formulated for administration by inhalation. Various forms suitable for administration by inhalation include aerosols, mists, or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds of the disclosure may be formulated for topical administration which as used herein, refers to administration intradermally by application of the formulation to the epidermis. These types of compositions are typically in the form of ointments, pastes, creams, lotions, gels, solutions, and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents can transport a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a compound of the disclosure or a pharmaceutically acceptable salt or a stereoisomer thereof; or a composition including the compounds of the disclosure or a pharmaceutically acceptable salt or a stereoisomer thereof, effective in producing the desired therapeutic response in a particular patient suffering from a Pin1-mediated disease or disorder. The term "therapeutically effective amount" includes the amount of the compound of the application or a pharmaceutically acceptable salt or a stereoisomer thereof, when administered, may induce a positive modification in the disease or disorder to be treated (e.g., remission), or is sufficient to prevent development or progression of the disease or disorder, or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed and the particular pharmaceutically acceptable carrier utilized.

The total daily dosage of the compounds and usage thereof may be decided in accordance with standard medical practice, e.g., by the attending physician using sound medical judgment. The specific therapeutically effective dose for any particular subject will depend upon a variety of factors including the disease or disorder being treated and the severity thereof (e.g., its present status); the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", 10th Edition, A. Gilman, J. Hardman and L. Limbird, eds., McGraw-Hill Press, 155-173, 2001).

Compounds of the present disclosure and their pharmaceutically acceptable salts may be effective over a wide dosage range. In some embodiments, the total daily dosage (e.g., for adult humans) may range from about 0.001 to about 1000 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosage may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present disclosure is directed to methods of treating diseases or disorders involving dysfunctional (e.g., dysregulated) CDK4/6 and/or Pin1 activity, that entails administration of a therapeutically effective amount of a compound or compounds of the disclosure or a pharmaceutically acceptable salt thereof, to a subject in need thereof.

The diseases or disorders may be said to be characterized or mediated by dysregulated or dysfunctional CDK4/6 and/or Pin1 activity (e.g., elevated levels of CDK4/6 and/or Pin1 relative to a non-pathological state). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health. In some embodiments, compounds of the application may be useful in the treatment of proliferative diseases and disorders (e.g., cancer or benign neoplasms). As used herein, the term "cell proliferative disease or disorder" refers to the conditions characterized by unregulated or abnormal cell growth, or both. Cell proliferative disorders include noncancerous conditions, precancerous conditions, and cancer.

Pin1-catalyzed prolyl isomerization regulates the functions of its substrates through multiple different mechanisms, including controlling catalytic activity, turnover, phosphorylation, interactions with DNA, RNA or other proteins, and subcellular localization and processing. Pin1 is tightly regulated normally and its deregulation can have a major impact on the development and treatment of cancer and neurodegenerative diseases.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present disclosure may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

In general, methods of using the compounds of the present disclosure include administering to a subject in need thereof a therapeutically effective amount of a compound of the present disclosure.

Exemplary types of non-cancerous diseases or disorders that may be amenable to treatment with the compounds of the present disclosure include inflammatory diseases and conditions, autoimmune diseases, neurodegenerative diseases, heart diseases, viral diseases, chronic and acute kidney diseases or injuries, obesity, metabolic diseases, allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ecodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus *foliaceus*, paraneoplastic pemphigus, myasthenia gravis, immunoglobulin A nephropathy, autoimmune thyroiditis or Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenia purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cerebral malaria, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, graft-versus-host reaction, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sudden infant death syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, cystic fibrosis, uveitis, polymyositis, proctitis, interstitial lung fibrosis, dermatomyositis, arteriosclerosis, amyotrophic lateral sclerosis, asocality, immune response, varicosis, vaginitis, including chronic recurrent yeast vaginitis, depression, and Sudden Infant Death Syndrome.

In some embodiments, the autoimmune disease that is treated is lupus, asthma or arthritis.

In some embodiments, the neurodegenerative disease is Alzheimer's disease or Parkinson's disease.

In other embodiments, the methods are directed to treating subjects having cancer. Broadly, the compounds of the present disclosure may be effective in the treatment of carcinomas (solid tumors including both primary and metastatic tumors), sarcomas, melanomas, and hematological cancers (cancers affecting blood including lymphocytes, bone marrow and/or lymph nodes) including leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., brain stem glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, acute promyelocytic leukemia, chronic lymphocytic leukemia, chronic myelogenous leukemia, chronic myeloproliferative disorders, anal cancer, colorectal cancer (e.g., colon cancer, rectal cancer), cutaneous T-cell lymphoma, lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), germ cell tumor, ovarian germ cell tumor, gestational trophoblastic tumor glioma, head and neck cancer, hepatocellular (liver) cancer, Hodgkin's lymphoma, non-Hodgkin's lymphoma, hypopharyngeal cancer, intraocular melanoma, ocular cancer, islet cell tumors (endocrine pancreas), renal cancer (e.g., Wilm's Tumor, clear cell renal cell carcinoma), laryngeal cancer, acute lymphoblastic leukemia, acute myeloid leukemia, hairy cell leukemia, lip and oral cavity cancer, liver cancer, lung cancer (e.g., non-small cell lung cancer and small cell lung cancer), primary central nervous system lymphoma, Waldenstrom's macroglobulinema, melanoma, intraocular (eye) melanoma, merkel cell carcinoma, mesothelioma malignant, mesothelioma, metastatic squamous neck cancer, multiple endocrine neoplasia syndrome, mycosis fungoids, myelodysplastic syndromes, myelodyplastic/myeloproliferative diseases, multiple myeloma, chromic myeproliferative disorders, nasopharyngeal cancer, neuroblastoma, oral cancer (e.g., mouth cancer, lip cancer, oral cavity cancer, tongue cancer, oropharyngeal cancer, throat cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), merkel cell skin carcinoma, squamous cell carcinoma, supratentorial primitive neuroectodermal tumors, testicular cancer, thymoma, thymoma and thymic carcinoma, thyroid cancer, transitional cell cancer of the renal pelvis and ureter and other urinary organs, urethral cancer, gestational trophoblastic tumor, vaginal cancer and vulvar cancer. In some embodiments, the cancer is triple-negative breast cancer or MYCN-driven neuroblastoma. In some embodiments, the cancer is endocrine resistant estrogen receptor positive (ER+) breast cancer, triple negative breast cancer, and either local, locally advanced, or metastatic.

Sarcomas that may be treatable with compounds of the present disclosure include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types).

In some embodiments, methods of the present disclosure entail treatment of subjects having cell proliferative diseases or disorders of the hematological system, liver (hepatocellular), brain, lung, colorectal (e.g., colon), pancreas, prostate, ovary, breast, or skin (e.g., melanoma).

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), acute myeloid leukemia (AML), acute promyelocytic leukemia (APL), mantle cell lymphoma (MCL) and ALK+ anaplastic large cell lymphoma) (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, refractory B-cell non-Hodgkin's lymphoma, and relapsed B-cell non-Hodgkin's lymphoma), childhood lymphomas, and lymphomas of lymphocytic and cutaneous origin, e.g., small lymphocytic lymphoma, primary CNS lymphoma (PCNSL), marginal zone lymphoma (MZL), leukemia, including chronic lymphocytic leukemia (CLL), childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver (hepatocellular)" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, a precancer or precancerous condition of the lung, benign growths or lesions of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer includes lung neoplasms having histologic and ultrastructural heterogeneity (e.g., mixed cell types).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer. Colon cancer includes malignant colon neoplasms, carcinoma in situ, typical carcinoid tumors, and atypical carcinoid tumors. Colon cancer includes adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polypopsis, Gardner's syndrome, Peutz-Jeghers syndrome, Turcot's syndrome and juvenile polyposis. Cell proliferative disorders of the colon can be characterized by hyperplasia, metaplasia, and dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, and dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the prostate.

The compounds of the present disclosure may be administered to a patient, e.g., a cancer patient, as a monotherapy or by way of combination therapy, and as a front-line therapy or a follow-on therapy for patients who are unresponsive to front line therapy. In some embodiments, the monotherapy comprises a CDK4/6 inhibitor. In some embodiments, the CDK4/6 inhibitor is palbociclib. In some embodiments, the CDK4/6 inhibitor is abemaciclib. In some embodiments, the CDK4/6 inhibitor is ribociclib. In some embodiments, the monotherapy comprises a Pin1 inhibitor. In some embodiments, the Pin1 inhibitor is ATRA plus ATO. In some embodiments, the Pin1 inhibitor is sulfopin. Therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received another therapy, such as chemotherapy, radioimmunotherapy, surgical therapy, immunotherapy, radiation therapy, targeted therapy or any combination thereof. In some embodiments, the immunotherapy is a checkpoint inhibitor (e.g., anti-PD-1, anti-PD-L1), a cell-cycle inhibitor (e.g., palbociclib, ribociclib, abemaciclib), or a targeted therapy (e.g., kinase inhibitor).

The methods of the present disclosure may entail administration of compounds of the disclosure or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5 or 6 weeks, and in other embodiments entails a 28-day cycle which includes daily administration for 3 weeks (21 days).

Combination Therapy

The compounds of the present disclosure (e.g., sulfopin, ATRA, ATO, palbociclib, abemaciclib, ribociclib, etc.) may be used in combination with at least one other active agent, e.g., anti-cancer agent or regimen, in treating diseases and disorders. The term "in combination" in this context means that the agents are co-administered, which includes substantially contemporaneous administration, by the same or separate dosage forms, or sequentially, e.g., as part of the same treatment regimen or by way of successive treatment regimens. Thus, if given sequentially, at the onset of administration of the second compound, the first of the two compounds is, in some cases, still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the one or more CDK4/6 inhibitors is palbociclib and the one or more Pin1 inhibitors is sulfopin. In some embodiments, the one or more CDK4/6 inhibitors is palbociclib and the one or more Pin1 inhibitors is ATRA and ATO. In some embodiments, the one or more CDK4/6 inhibitors is abemaciclib and the one or more Pin1 inhibitors is sulfopin. In some embodiments, the one or more CDK4/6 inhibitors is abemaciclib and the one or more Pin1 inhibitors is ATRA and ATO. In some embodiments, the one or more CDK4/6 inhibitors is ribociclib and the one or more Pin1 inhibitors is sulfopin. In some embodiments, the one or more CDK4/6 inhibitors is ribociclib and the one or more Pin1 inhibitors is ATRA and ATO. In some embodiments, the one or more CDK4/6 inhibitors is palbociclib, the one or more Pin1 inhibitors is sulfopin, and the immunotherapy is anti-PD-L1. In some embodiments, the one or more CDK4/6 inhibitors is abemaciclib, the one or more Pin1 inhibitors is sulfopin, and the immunotherapy is anti-PD-L1. In some embodiments, the one or more CDK4/6 inhibitors is ribociclib, the one or more Pin1 inhibitors is sulfopin, and the immunotherapy is anti-PD-L1. In some embodiments, the one or more CDK4/6 inhibitors is palbociclib, the one or more Pin1 inhibitors is ATRA and ATO, and the immunotherapy is anti-PD-L1. In some embodiments, the one or more CDK4/6 inhibitors is abemaciclib, the one or more Pin1 inhibitors is ATRA and ATO, and the immunotherapy is anti-PD-L1. In some embodiments, the one or more CDK4/6 inhibitors is ribociclib, the one or more Pin1 inhibitors is ATRA and ATO, and the immunotherapy is anti-PD-L1.

In some embodiments, is provided the combination of palbociclib plus sulfopin. In some embodiments, is provided the combination of palbociclib plus ATRA and ATO. In some embodiments, is provided the combination of abemaciclib plus sulfopin. In some embodiments, is provided the combination of abemaciclib plus ATRA and ATO. In some embodiments, is provided the combination of ribociclib plus sulfopin. In some embodiments, is provided the combination of ribociclib plus ATRA and ATO. In some embodiments, is provided the combination of palbociclib plus sulfopin plus anti-PD-1. In some embodiments, is provided the combination of palbociclib plus ATRA and ATO plus anti-PD-1. In some embodiments, is provided the combination of palbociclib plus sulfopin plus anti-PD-L1. In some embodiments, is provided the combination of palbociclib plus ATRA and ATO plus anti-PD-L1. In some embodiments, is provided the combination of abemaciclib plus sulfopin plus anti-PD-1. In some embodiments, is provided the combination of abemaciclib plus ATRA and ATO plus anti-PD-1. In some embodiments, is provided the combination of abemaciclib plus sulfopin plus anti-PD-L1. In some embodiments, is provided the combination of abemaciclib plus ATRA and ATO plus anti-PD-L1. In some embodiments, is provided the combination of ribociclib plus sulfopin plus anti-PD-1. In some embodiments, is provided the combination of ribociclib plus ATRA and ATO plus anti-PD-1. In some embodiments, is provided the combination of ribociclib plus sulfopin plus anti-PD-L1. In some embodiments, is provided the combination of ribociclib plus ATRA and ATO plus anti-PD-L1.

In some embodiments, the combinations are useful for treating cancer, e.g., endocrine resistant estrogen receptor positive (ER+) breast cancer, triple negative breast cancer, and either local, locally advanced, or metastatic. For example, the combinations are useful for treating endocrine resistant estrogen receptor positive (ER+) breast cancer or triple negative breast cancer. In some embodiments, the cancer is endocrine resistant estrogen receptor positive (ER+) breast cancer. In some embodiments, the cancer is triple negative breast cancer.

In some embodiments, is provided a method of treating cancer indicated by a greater therapeutic effect, wherein the subject is treated with a combination of one or more CDK4/6 inhibitors, and one or more Pin1 inhibitors. In some embodiments, is provided a method of treating cancer indicated by a greater therapeutic effect, wherein the subject is treated with a combination of one or more CDK4/6 inhibitors, one or more Pin1 inhibitors, and an immunotherapy. In some embodiments, the immunotherapy is anti-PD-1 or anti-PD-L1. In some embodiments, the greater therapeutic effect is indicated by a significant biomarker(s) level(s) change. In some embodiments, the greater therapeutic effect is indicated by a reduction in tumor size, e.g., a 5%, a 10%, a 25%, a 50%, or a 75% reduction in tumor size. In some embodiments, the greater therapeutic effect is indicated by complete or partial remission of disease, i.e., cancer. In some embodiments, the greater therapeutic effect is indicated by a reduction in the incidence of metastases by, e.g., 5%, 10%, 20%, 30% or more. In some embodiments, the greater therapeutic effect is indicated by preventing metastases. In some embodiments, the greater therapeutic effect is indicated by delayed tumor progression. In some embodiments, the greater therapeutic effect is indicated by suppressing tumor growth. In some embodiments, the greater therapeutic effect is indicated by an improvement in survival time. In some embodiments, the improvement in survival time is relative to treatment with one or more CDK4/6 inhibitors. In some embodiments, the improvement in survival time is relative to treatment with one or more Pin1 inhibitors. In some embodiments, the improvement in survival time with combination therapy is relative to treatment with one or more CDK4/6 inhibitors alone.

In some embodiments, is provided a method of treating cancer indicated by a synergistic therapeutic effect, wherein the subject is treated with a combination of one or more CDK4/6 inhibitors, and one or more Pin1 inhibitors. In some embodiments, is provided a method of treating cancer indicated by a synergistic therapeutic effect, wherein the subject is treated with a combination of one or more CDK4/6 inhibitors, one or more Pin1 inhibitors, and an immunotherapy. In some embodiments, the immunotherapy is anti-PD-1 or anti-PD-L1. In some embodiments, the synergistic therapeutic effect is indicated by a significant biomarker(s) level(s) change. In some embodiments, the synergistic therapeutic effect is indicated by a reduction in tumor size, e.g., a 5%, a 10%, a 25%, a 50%, or a 75% reduction in tumor size. In some embodiments, the synergistic therapeutic effect is indicated by complete or partial remission of disease, i.e., cancer. In some embodiments, the synergistic therapeutic effect is indicated by a reduction in the incidence of metastases by, e.g., 5%, 10%, 20%, 30% or more. In some embodiments, the synergistic therapeutic effect is indicated by preventing metastases. In some embodiments, the synergistic therapeutic effect is indicated by delayed tumor progression. In some embodiments, the synergistic therapeutic effect is indicated by suppressing tumor growth. In some embodiments, the synergistic therapeutic effect is indicated by an improvement in survival time. In some embodiments, the improvement in survival time is relative to treatment with one or more CDK4/6 inhibitors. In some embodiments, the improvement in survival time is relative to treatment with one or more Pin1 inhibitors. In some embodiments, the improvement in survival time with combination therapy is relative to treatment with one or more CDK4/6 inhibitors alone.

In some embodiments, the treatment regimen may include administration of the compounds of the disclosure, wherein the one or more CDK4/6 inhibitors and the one or more Pin1 inhibitors is each administered at an amount that is lower than the therapeutically effective amount administered when each of the one or more CDK4/6 inhibitors and the one or more Pin1 inhibitors is administered alone. In some embodiments, administration of the combination of the one or more CDK4/6 inhibitors and the one or more Pin1 inhibitors, each administered at a dose that is lower than the therapeutically effective amount, provides a therapeutic effect.

In some embodiments, the treatment regimen may include administration of the compounds of the disclosure in combination with one or more additional therapeutics. The dosage of the additional therapeutic may be the same or even lower than known or recommended doses. See, Hardman et al., eds., Goodman & Gilman's The Pharmacological Basis of Therapeutics, 10th ed., McGraw-Hill, New York, 2001; Physician's Desk Reference 60th ed., 2006. Anti-cancer agents that may be used in combination with the compounds are known in the art. See, e.g., U.S. Pat. No. 9,101,622 (Section 5.2 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy. In some embodiments, the treatment regimen may include immunotherapy, In some embodiments, the immunotherapy is a checkpoint inhibitor (e.g., anti-PD-1, anti-PD-L1), a cell-cycle inhibitor (e.g., palbociclib, ribociclib, abemaciclib), or a targeted therapy (e.g., kinase inhibitor).

In some embodiments, the compounds of the disclosure and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. The two or more anticancer therapeutics may be administered within the same patient visit.

In some embodiments, the compounds of the disclosure and the additional agent or therapeutic (e.g., an anti-cancer therapeutic) are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

The compounds of the disclosure may be administered to a patient suffering from a neurodegenerative disease or disorder in combination with another active agent. Representative examples of other active agents known to treat neurodegenerative diseases and disorders include dopaminergic treatments (e.g., Carbidopa-levodopa, pramipexole (Mirapex), ropinirole (Requip) and rotigotine (Neupro, given as a patch)). Apomorphine and monoamine oxidase B (MAO-B) inhibitors (e.g., selegiline (Eldepryl, Zelapar), rasagiline (Azilect) and safinamide (Xadago)) for Parkinson disease and movement disorders, cholinesterase inhibitors for cognitive disorders (e.g., benztropine (Cogentin) or trihexyphenidyl), antipsychotic drugs for behavioral and psychological symptoms of dementia, as well as agents aimed to slow the development of diseases, such as Riluzole for ALS, cerebellar ataxia and Huntington's disease, non-steroidal anti-inflammatory drugs for Alzheimer's disease, and caffeine A2A receptor antagonists and CERE-120 (adeno-associated virus serotype 2-neurturin) for the neuroprotection of Parkinson's disease.

The compounds of the disclosure may be administered to a patient suffering from an autoimmune disease or disorder in combination with another active agent. Representative examples of other active agents known to treat neurodegenerative diseases and disorders include corticosteroids (e.g., prednisone, hydrocortisone, and dexamethasone) immunosuppressant drugs, such as methotrexate, cyclophosphamide, and azathioprine. Other examples include immunosuppressive dugbelimumab (Benlysta®) for severe active lupus nephritis or severe active central nervous system lupus, asthma and arthritis, anti-malarial dugs (e.g., hydroxychloroquine (Plaquenil®) and chloroquine (Aralen®)) for lupus, combinations of corticosteroid and bronchodilator (e.g., fluticasone and salmeterol (Advair Diskus®), budesonide and formoterol (Symbicort®), and fluticasone and vilanterol (BREO)), and analgesics (e.g., acetaminophen), nonsteroidal anti-inflammation drugs (NSAIDs) (e.g., aspirin, ibuprofen, naproxen, indomethacin and celecoxib (Celebrex®)), traditional disease-modifying antirheumatic drugs (DMARDs) (e.g., tumor necrosis factor (TNF) inhibitors or TNF blockers (etanercept (Enbrel®) and adalimumab (Humira®)), Interleukin-6 (IL-6) inhibitors, Interleukin-1 (IL-1) receptor antagonists, B-cell inhibitors, Janus kinases (JAK) inhibitors, phosphodiesterase 4 (PDE 4) inhibitors and costimulation modulators) for treating rheumatoid arthritis (RA), ankylosing spondylitis, psoriatic arthritis, juvenile idiopathic arthritis and lupus.

Pharmaceutical Kits

The present compositions may be assembled into kits or pharmaceutical systems. Kits or pharmaceutical systems according to this aspect of the disclosure include a carrier or package such as a box, carton, tube or the like, having in close confinement therein one or more containers, such as vials, tubes, ampoules, or bottles, which contain the compound of the present application or a pharmaceutical composition. The kits or pharmaceutical systems of the disclosure may also include printed instructions for using the compounds and compositions.

These and other aspects of the present application will be further appreciated upon consideration of the following Examples, which are intended to illustrate certain particular embodiments of the application but are not intended to limit its scope, as defined by the claims.

EXAMPLES

Example 1: Methods

Cell Lines and Plasmids

The human breast cancer (BC) cell lines, MDA-MB-231, MDA-MB-468, BT-549, SUM159 MCF-7 and HEK293T were obtained from ATCC. Wild-type and Cdh1$^{-/-}$ MEFs were provided by Dr. Wenyi Wei. Among them, MDA-MB-231, MCF-7, HEK293T, MDA-MB-468, BT-549, MEFs and K14 cells were cultured in Dulbecco's modified Eagle's medium (DMEM) supplemented with 10% fetal bovine serum (FBS). SUM159 cells were cultured in RPMI-1640 medium with 10% FBS. MCF-10A cells were gifts from the S. D. Cappell group, and cultured in MEBMTM Basal Medium and Supplements (Lonza, CC-3150). All the cells used for the experiments tested negative for *mycoplasma* contamination.

pLenti-HA-Cdh1 was purchased from Applied Biological Materials Inc. pLKO-shRNF129, pLKO-shUBR5, pLKO-shRNF149, pLKO-shSMURF2, pLKO-shWWP2, pLKO-shUBE3A, pLKO-shUBE3B, pLKO-shNEDD4, pLKO-shKEAP1 and pLKO-shFBX07 were purchased from Sigma-Aldrich. pLenti-HA-Cdh1-6A, -7A, pLenti-3X Flag-Pin1, pLenti-3X Flag-Pin1-W34A, -W34A-RLAA, -RLAA, -M130L, -M130I, -C113A and -C113S were generated in the lab. His-ubiquitin constructs was provided by Dr. Yu-Ru Lee. The shRNA library for human E3 ubiquitin ligases (TRC library, RHS4896) was purchased from Thermo Scientific Open Biosystems.

Reagents and Antibodies

ATO (A1010), ATRA (R2625), MG132 (M7449), Thymidine (T1895), Nocodazole (M1404), Glutathione-Agarose (G4510), Carboxymethylcellulose sodium salt (CMC-Na, C4888) and Senescence Cells Histochemical Staining Kit (CS0030) were purchased from Sigma-Aldrich. palbociclib (PD0332991, S1116) and abemaciclib (S5716) from Selleckchem. Hoechst 33342 Solution and Dead Cell Apoptosis Kit with Annexin V FITC and PI from Thermo. Tumor Dissociation Kit (mouse) from Miltenyi Biotec. Sulfopin was provided by Dr. Nathanael Gray. Verzenio (abemaciclib tablets) was provided by Dr. Gerburg Wulf.

Anti-Pin1 mouse monoclonal antibody was provided by Dr. Xiao Zhen Zhou. Anti-Cdh1 (sc-56312) and anti-Cdc20 (sc-13162) antibodies were purchased from Santa Cruz. Anti-Pin1 rabbit monoclonal antibody (ab192036), anti-Apc7 (ab4171) and anti-Rb (ab181616) antibodies were purchased from Abcam. Monoclonal anti-Flag M2 antibody (F1804) from Sigma. Anti-HA-Tag rabbit mAb (3724), anti-HA-Tag mouse mAb (2367), anti-Cyclin B1 antibody (4138), anti-PLK1 rabbit mAb (4513) and anti-Geminin rabbit mAb (52508) antibodies were purchased from Cell Signaling Technology. Metal-conjugated antibodies used for CyTOF were purchased from Fluidigm.

In Vitro Treatment

Sulfopin and AApin (ATRA+ATO) treatment was described as previously (Kozono et al., Nat Commun 2018; 9:3069; Dubiella et al., Nat Chem Biol 2021, 17, 954-63, each of which is incorporated herein by reference in its entirety). Briefly, cells were seeded in 6-well plates and treated with increasing concentrations of AApin (ATO (0.5, 1, 1.5, 2 μM) plus ATRA (5, 10, 15, 20 μM) in 1:10 ratio) for 3 days. Cells were treated with increasing concentration of sulfopin (2, 4, 8, 10 μM) or palbociclib (0.5, 1, 2, 4 μM) for 3 days. Drugs were replenished in media every 24 hours to ensure that Pin1 and CDK4/6 inhibition was maintained for the duration of the experiment.

STED Imaging

Except where indicated otherwise the steps were performed at room temperature. Cells were rinsed with PBS twice and fixed with 2% PFA for 15 min. Fixative was removed by washing with PBS 3 times. Cells were then permeabilized with 0.1% Triton for 10 min. After removing Triton, cells were blocked with 5% BSA for 1 hour and then incubated with anti-Pin1 (Abcam) and anti-Cdh1 (Santa Cruz) antibodies overnight at 4° C. After three washes with PBS, the cells were then incubated with Alexa Fluor® 514 Goat Anti-Mouse (Invitrogen) and Alexa Fluor® 568 Goat Anti-Rabbit (Abcam) antibodies for 1 hour. Following the incubation, the cells were washed 3× with PBS and mounted for STED imaging. Colocalization rates were calculated using the LAS X software (Leica).

Real-Time RT-PCR

Total RNAs were extracted using the QIAGEN RNeasy mini kit. cDNA synthesis was performed using Maxima Universal First Strand cDNA Synthesis Kit from Thermo Scientific. qPCR reactions were performed with FastStart Universal SYBR Green Master (Rox) from Roche. The experiments were performed according to the manufacturer's instructions. The sequences of the primers used for qRT-PCR analyses were the following. RNF219_Forward: CAGACCGTGCAGAATGTTACA (SEQ ID NO: 1), RNF219_Reverse: TCCTGACCGTATGGCTTAGC (SEQ ID NO: 2); UBR5_Forward: GGATGATGAAGATGGAGATGATG (SEQ ID NO: 3), UBR5_Reverse: CGCAACAGCTCAGAGTCTCTC (SEQ ID NO: 4); RNF149_Forward: TTCCAGTAACGATGACCATAGG (SEQ ID NO: 5), RNF149_Reverse: CAGCATCAACATCAATTCCCT (SEQ ID NO: 6); WWP2_Forward: TTCGAGAGACTCCAGTGGAAC (SEQ ID NO: 7), WWP2_Reverse: GTTGTGGGTTCATCATTCACTG (SEQ ID NO: 8); FBXO7_Forward: TCATCCACAGATTCAGAGCATTC (SEQ ID NO: 9), FBXO7_Reverse: CAGAACAGTCAGCTGATTGATACA (SEQ ID NO: 10); UBE3A_Forward: GCTGCATGTTCTGCTGCTG (SEQ ID NO: 11), UBE3A_Reverse: ATACGTCAAGTCACATTCCACG (SEQ ID NO: 12); KEAP1_Forward: TACGACTGCGAACAGCGAC (SEQ ID NO: 13), KEAP1_Reverse: GCTGAGCGACTGTCGGAAG (SEQ ID NO: 14).

RNA Sequencing and Data Analysis

Total RNAs were extracted from the BC cell lines WT and Pin1 KO MDA-MB-231, MCF-7 and MDA-MB-468 respectively. RNA-sequencing samples were prepared as previously described (Allen et al., Nat Methods 2007; 4:511-6). Gene set enrichment analysis (GSEA) was performed using GSEA software (Broad). Normalized counts of Pin1 KO versus WT cells were used for GSEA analysis against the biological process related gene sets. Normalized enrichment scores (NES) were used to generate bar graphs for visualization of the functional transcriptional outputs of the three cell lines.

Drug Combination Test and Synergy Calculations

MDA-MB-231 and SUM-159 cells were seeded out in appropriate dilutions and treated with increasing concentrations of two drugs to form colonies in 1-3 weeks. Colonies are fixed with methanol (100% v/v), stained with crystal violet (0.5% w/v) and counted using Celigo Image Cytometer. The percentage of growth inhibition was calculated based on colony numbers and areas. The inhibition heatmaps and ZIP synergy scores were generated and calculated by SynergyFinder (Ianevski et al., Bioinformatics 2017; 33:2413-15).

Antibody Staining for Mass Cytometry

Except where indicated otherwise sample staining and acquisition were carried out at room temperature. Mouse tumor tissues were dissociated into single-cell suspension using the Tumor Dissociation Kit (Miltenyi Biotec) and the gentleMACS™ Octo Dissociator following manufacturer's instructions. Cells were stained with Cisplatin-195 Pt at a final concentration of 1 μM for 5 min. After viability staining, cells were incubated with Fc-Receptor blocking solution. Fifteen minutes later, the surface staining antibody cocktail was added into each cell suspensions and incubated for 30 min without washing out the Fc blocking. The cells were then washed with Maxpar Cell Staining Buffer (CSB) (Fluidigm) for a total of two wash. Then cells were incubated with Nuclear Antigen Staining Buffer (Fluidigm) with gentle vortex for 30 minutes. After two wash with Nuclear Antigen Staining Perm (Fluidigm), cells were stained with secreted and nuclear antigen antibody cocktail for 30 min. Following the staining, cells were washed twice with Nuclear Antigen Staining Perm and fixed by freshly made 1.6% paraformaldehyde for 10 min. Afterwards, cells were incubated with Cell-ID Intercalator-Ir (Fluidigm) overnight at 4° C. Cells were then washed in CSB buffer and with subsequent washes in Cell Acquisition Solution (CAS) (Fluidigm) to remove buffer salts and cell debris for total of two washes. Immediately prior to sample acquisition, cells were resuspended at $5\sim6\times10^5$ cells per mL in CAS containing EQ™ Four Element Calibration Beads (1:5) (Fluidigm) and filtered through a 40 μm cell strainer.

Mass Cytometry Acquisition Setting and Data Analysis

For quality control, the acquisition event rate was maintained under 500 events/s, and the EQ™ beads were confirmed to have clustered events >10,000 and median Eu151 and Eu153 intensity were over 1000 to ensure appropriate mass sensitivity. Original data acquired by CyTOF were randomized and normalized using the FSC processing function of the CyTOF software. The Gaussian Parameters were applied to gating the FSC processed files using FlowJo. Standard gating strategy were used for single cell analysis with multiple markers.

To visualize the high-dimensional data and identify clusters of cells with a similar expression of cell surface markers in CyTOF, the populations of interest were gated and UMAP algorithm was applied on data from a certain number of randomly selected cells from each sample. Clustering analysis was performed using the PhenoGraph implementation in the FlowJo plugins. The resulting PhenoGraph clusters were projected onto the UMAP. ClusterExplorer plugin in FlowJo was performed to define the cell clusters by typical marker expression. For hierarchical clustering, the distances between clusters were computed using Eucledian measurement method. Dendrograms were generated using average linkage. A normalized heatmap for each marker within all generated clusters was displayed. For pairwise correlation heatmap, the correlations between all pairs of parameters were calculated using the Spearman correlation and displayed in a heatmap. All cytometry data can be made available upon request.

Time-Lapse Live Imaging and Single-Cell Tracking

MCF-7 cells were stably expressed with mCherry-Geminin (1-110) and a histone H2B-Turquoise. Cells were then plated 24 hours before starting the microscope acquisition. Pin1 inhibitors or CDK4/6 inhibitors were added in the medium and imaged using a Nikon Eclipse TE-2000 inverted microscope with a 10× Plan Apo objective and a Hammamatsu Orca ER camera, equipped with environmental chamber controlling temperature, atmosphere (5% CO2) and humidity. Images were acquired every 30 min using the MetaMorph Software. For each condition filmed, 4 different fields were selected.

p53Cinema single cell analysis package was used for semiautomatic tracking of individual cells in live cell imaging datasets as described previously (Reyes et al., Mol Cell 2018; 71:581-91 e5). Tracking data were then used to quantify intensity of fluorescent reporters from background subtracted images by averaging 10 pixels within the cell nucleus. Cells were tracked using only information about a constitutively expressed nuclear marker, such as H2B-Turquoise, and were thus blind to the dynamics of molecular players of interest, such as mCherry-Geminin. Only cells that remained within the field of view throughout the entire duration of the experiment were considered for downstream analyses. The frequency of G1 arrest was defined as those cells that arrested in G1 phase for at least 20 hours after drugs were added. S/G2 durations were calculated by the time that cells spent in S/G2 phase after drugs were added.

Cell Synchronization and Cell Cycle Profiling

Cells synchronized by double thymidine block or nocodazole block as described previously (Wan et al., Dev Cell 2014; 29:377-91) were collected at the indicated time points and suspended in cell cycle kit (Beckman Coulter) according to the manufacturer's instructions. Stained cells were sorted with CytoFLEX LX1 Flow Cytometer. The results were analyzed by FSC Express software.

Annexin V-FITC-PI Double Staining

For detection of apoptosis, cells treated with indicated inhibitors were co-stained with Annexin V-FITC and PI (Dead Cell Apoptosis Kit, Invitrogen) according to the manufacturer's instructions. Stained cells were sorted with CytoFLEX LX1 Flow Cytometer.

Immunoblot (IB) and Immunoprecipitation (IP) Analyses

For IB analysis, cells were lysed in RIPA buffer (Thermo) supplemented with protease inhibitors (Sigma) and phosphatase inhibitors (Sigma). Protein concentrations were measured using Protein Assay Dye Reagent (Bio-Rad) and a Beckman Coulter. Equal amounts of protein were resolved by SDS-PAGE and probed with indicated antibodies. For immunoprecipitation analysis, cells were lysed in IP lysis buffer (Thermo) and pre-cleared by Mouse IgG-Agarose (Sigma) for 1 hour at 4° C. and then incubated with anti-Flag M2-Agarose (Sigma) for 2 hours at 4° C. The agaroses were washed four times with IP lysis buffer and boiled in standard Laemmli-Buffer with 5% final concentration of β-mercaptoethanol before being resolved by SDS-PAGE and immunoblotted with indicated antibodies.

In Gel Digestion, Mass Spectrometry and Data Procession

MDA-MB-231 cells stably expressing 3× Flag-Pin1 were immunoprecipitated with anti-Flag M2-Agarose. 3× Flag-Pin1 and Pin1-associated proteins were eluted by 3× Flag Peptide from the anti-Flag M2-Agarose and resolved by SDS-PAGE on 4-12% gradient gel (Invitrogen) for staining with Coomassie Brilliant Blue R350 (GE Healthcare). Specific bands were cut out from the gel and subjected to mass spectrometric peptide sequencing. The gel lanes stained with Coomassie blue were unevenly excised into 6 sections. Each section was cut into approximately 1-$mm^3$ pieces. The gel slices were first destained with the 30% acetonitrile in 100 mM $NH_4HCO_3$, dried by speedvac, and then incubated with 10 mM Dithiothreitol (DTT) for 1 h at 56° C. and then 20 mM iodoacetamide (IAA) in the dark for 45 min at room temperature. After reduction and alkylation, the samples were digested with trypsin (Promega) at 10 ng/μL overnight at 37° C. The supernatant was collected and then combined with peptides digested and extracted from the gel slices with 80% acetonitrile containing 0.1% TFA. Peptide purification was performed on a C18 column (MarocoSpin Columns, NEST Group INC) and 1 μg of the peptide was injected for mass spectrometry analysis.

The samples were measured by data-independent acquisition (DIA) mass spectrometry method as described previously (Hortobagyi et al., N Engl J Med 2016; 375:1738-48; Canon et al., Nature 2019; 575:217-23; Ianevski et al., Bioinformatics 2017; 33:2413-15). The Orbitrap Eclipse Tribrid mass spectrometer (Thermo Scientific) instrument coupled to a nanoelectrospray ion source (NanoFlex, Thermo Scientific) and EASY-nLC 1200 systems (Thermo Scientific, San Jose, CA). A 120-min gradient was used for the data acquisition at the flow rate at 300 nL/min with the temperature controlled at 60° C. using a column oven (PRSO-V1, Sonation GmbH, Biberach, Germany). All the DIA-MS methods consisted of one MS1 scan and 33 MS2 scans of variable isolated windows with 1 m/z overlapping between windows. The MS1 scan range is 350-1650 m/z and the MS1 resolution is 120,000 at m/z 200. The MS1 full scan AGC target value was set to be 500% and the maximum injection time was 100 ms. The MS2 resolution was set to 30,000 at m/z 200 with the MS2 scan range 200-1800 m/z and the normalized HCD collision energy was 28%. The MS2 AGC was set to be 4000% and the maximum injection time was 50 ms. The default peptide charge state was set to 2. Both MS1 and MS2 spectra were recorded in profile mode. DIA-MS data analysis was performed using Spectronaut v16 (Reyes et al., Mol Cell 2018; 71:581-91 e5; Wan et al., Dev Cell 2014; 29:377-91; Lee et al., Mol Cell 2011; 42:147-59) with directDIA algorithm by searching against the Uniprot (Zhang et al., Nature 2018; 553:91-95) downloaded human fasta file. The oxidation at methionine was set as variable modification, whereas carbamidomethylation at cysteine was set as fixed modification. Both peptide and protein FDR cutoffs (Qvalue) were controlled below 1% and the resulting quantitative data matrix were exported from Spectronaut. All the other settings in Spectronaut were kept as Default.

GST Pull-Down Assay

GST pull-down was performed as described previously (Lee et al., Mol Cell 2011; 42:147-59). Briefly, cells were stably expressing indicated proteins and lysed in pull-down buffer (20 mM Tris pH 8.0, 150 mM NaCl, 1 mM EDTA pH 8.0, 0.5% Nonidet-P40). The cell extracts were pre-cleared by glutathione agarose beads and incubated with 1 μM GST or GST fusion proteins overnight at 4° C. Protein complexes were recovered on glutathione agarose beads for 2 hours at 4° C., washed four to six times with pull-down buffer and eluted by boiling in SDS-containing sample buffer. Bound proteins were resolved by SDS-PAGE.

In Vivo Ubiquitination Assay

In Vivo Ubiquitination Assay was performed as described previously (Zhang et al., Nature 2018; 553:91-95). 293T cells were transfected with His-ubiquitin and the indicated constructs. Thirty-six hours after transfection, cells were treated with 2 μM MG132 for 12 hours and lysed in buffer A (6 M guanidine-HCl, 0.1 M $Na_2HPO_4$/$NaH_2PO_4$, and 10 mM imidazole pH 8.0). After sonication, the lysates were incubated with Ni-NTA beads (QIAGEN) for 3 h at 4° C. Subsequently, the His pull-down products were washed twice with buffer A, twice with buffer A/TI (1 volume buffer A and 3 volumes buffer TI), and once with buffer TI (25 mM Tris-HCl and 20 mM imidazole pH 6.8). The pull-down proteins were resolved by SDS-PAGE for immunoblotting.

In Vitro Kinase Assay

In vitro kinase assay was performed as previously described (Allen et al., Nat Methods 2007; 4:511-6). Briefly, HA-tagged Cdh1 WT and mutants were transfected into HEK293T cells, followed by being immunoprecipitated with monoclonal Anti-HA-Agarose antibody (Sigma A2095). The purified HA-Cdh1 proteins were then incubated with 500 μM of ATPγS (Abcam ab138911) and 0.5 μg of recombinant human cyclin D1+CDK4 proteins (Abcam ab55695) in the kinase reaction buffer (50 mM Tris-HCl, 10 mM $MgCl_2$, 0.1 mM EDTA, 2 mM DTT, 0.01% Brij 35, pH 7.5) for 30 min at room temperature. Then 2 mM of PNBM (Abcam ab138910) was added allowing the alkylating reaction to proceed for additional 2 h at room temperature. The reaction was then terminated by adding 5×SDS loading buffer and boiled for 10 min. Samples were then subjected to western analysis and immunoblotted with anti-Thiophosphate ester antibody (Abcam ab92570).

In Vivo Therapy for Patient-Derived Xenografts

All animal experiments were approved by the IACUC of the Beth Israel Deaconess Medical Center. Triple-negative BC patient-derived xenograft (TM00096) was purchased from Jackson Laboratories. Pieces from PDOX tumors were subcutaneously implanted into flank of 6-week-old BALB/c female nude mice. Tumor sizes were measured every three days by caliper after implantation and tumor volume was calculated by the modified ellipsoidal formula: tumor volume=½length×width$^2$. Treatments were started once the tumors reached 5 mm in diameter and continued until tumors reached 15 mm in any direction. Mice were randomly assigned to six groups with comparable average tumor size. Sulfopin treatment was given by intraperitoneal injection with a dosage of 40 mg/kg (dissolved solution: 5% DMSO in D5W, 7 days/week), palbociclib treatment was given by oral gavage with a dosage of 100 mg/kg (dissolved solution: saline, 5 days/week), abemaciclib treatment was given by oral gavage with a dosage of 100 mg/kg (dissolved solution: 0.5% CMC-Na, 5 days/week), or drug combinations in which each compound was administered at the same dose and scheduled as a single agent. The investigators were not blinded to allocation during experiments and outcome assessment.

In Vivo Therapy for Immunocompetent TNBC Mouse Models

All animal experiments were approved by the IACUC of the Beth Israel Deaconess Medical Center. Maximum permitted the longest dimension of tumors was 20 mm. Pieces from breast tumors generated in K14cre; $p53^{f/f}$; $Brca1^{f/f}$ or K14cre; $p53^{wt/f}$; $Brca1^{wt/f}$ female mice were transplanted into the mammary pad of 6-week-old FVB female mice. For survival studies, treatments were started once the tumors reached 3-5 mm in diameter and continued until mice were symptomatic or tumors reached 20 mm in any direction, at which point mice were euthanized. For time point analysis, mice were sacrificed two weeks post-treatment initiation. Control and anti-PD-L1 antibody (clone 29E.2A3) treatments were conducted by intraperitoneal injection with a dosage of 200 μg per mouse every three days. sulfopin treatment was given by intraperitoneal injection with a dosage of 60 mg/kg (7 days/week), abemaciclib treatment was given by oral gavage with a dosage of 100 mg/kg (7 days/week), or drug combinations in which each compound was administered at the same dose and scheduled as a single agent. Tumor sizes were measured every three days by caliper after implantation and tumor volume was calculated by the modified ellipsoidal formula: tumor volume=½length×width$^2$. The investigators were not blinded to allocation during experiments and outcome assessment.

Single Sample Gene Set Enrichment (ssGSEA) Analysis

Gene Ontology (GO) enrichment analysis for biological processes was performed in TCGA primary breast tumor samples using the ssGSEA module in GenePattern (Barbie et al., Nature 2009; 462:108-12; Reich et al. GenePattern 2.0. Nat Genet 2006; 38:500-1). Relative ssGSEA scores for biological processes across samples were displayed in heatmaps, with "Pin1 low" and "Pin1 high" being defined as having a Pin1 mRNA level outside one standard deviation of the mean. ssGSEA transforms a single sample's gene expression profile to a gene set enrichment profile. The enrichment scores and high vs. low expression of Pin1 phenotype were used to calculate the receiver operating characteristic (ROC), the area under the ROC curve (AUC), the Matthew's correlation coefficient (MCC) and two-sided Wilcox test for each GO gene set.

NMR Spectroscopy

All NMR experiments were acquired on Bruker NEO 600 MHz spectrometer equipped with a TCI cryoprobe at 25° C. 0.1 mM $^{13}C$, $^{15}N$-enriched Pin1 sample dissolved in pH 6.6 buffer made-up of 20 mM Potassium Phosphate, 100 mM $NaSO_4$ and 10% $D_2O$ was used to study peptide interaction. NMR assignments of Pin1 were taken from the BMRB database (accession number 27579) and confirmed using 3D-HNCA experiment. Synthetic peptides Cdh1-pS163 (comprised of Cdh1 residues 161-183 with phosphorylated Ser163 and isotope labeled Pro164, LR (pS)P($^{13}C$, $^{15}N$) RKPTRKISKIPFKVLDAPE) (SEQ ID NO: 27). were purchased from Pepmic. A systematic titration between Pin1 and phosphopeptide was performed by acquiring 2D-HSQC spectra. The absolute average chemical shift perturbation was calculated by using an equation, [(A8H2+ (A8N/5) 2)/2]½, available in software NMRFAM Sparky version 1.414.

Experiment-Guided Model

The chemical shift perturbation was interpreted as ambiguous iterative restraints used for docking a random conformation of the phosphopeptide on Pin1 (PDB: 1PIN) (Ranganathan et al., Cell 1997; 89:875-86) using HADDOCK2.2 webserver (van Zundert et al., J Mol Biol 2016; 428:720-25). The restraints were derived by marking two strongly perturbed Pin1 residues, R17 and W34 as active residues and three moderately perturbed residues S18, Y23 and E35 as passive residues. The peptide was assumed to be fully flexible with the phosphoserine, pS163, and its adjacent proline, P164, being the active residues that interact with Pin1. In subsequent runs, the model was refined using ambiguous distance restraints based on the interpretation of previously solved crystal structures of similar phosphopeptides bound to the WW domain of Pin1 (Verdecia et al., Nat Struct Biol 2000; 7:602-08).

Proline Isomerization Study

Commercially synthesized specific $^{13}C$, $^{15}N$-P164 labeled Cdh1 phosphopeptide was used to facilitate direct quantitative determination of the cis and trans proline populations. The strong $^{13}C$-HSQC peaks originating from Pro164 can be easily distinguished from the weak peaks due to ~1% natural abundance $^{13}C$ present in the rest of the peptide. Two isolated sets of peaks were observed for P164. Based on the interpretation of the chemical shifts, the major peaks were assigned as trans isomer and the minor peaks were assigned as cis isomer (Schubert et al. J Biomol NMR 24, 149-154 (2002)). The proline resonance assignments were further confirmed using a 2D-$^{13}C$-HSQCTOCSY experiment while no attempts were made to stereospecifically assign proton resonances, thus the assignment of HB2 and HB3, HG2 and HG3, and HD2 and HD3 are interchangeable. 58 μM free peptide and its complex with a 4-fold molar excess of Pin1, dissolved in the above-mentioned NMR buffer were used to estimate the cis and trans isomer populations at 25° C.

Docking Model

A docking model was built to explain the interaction between Pin1 (PDB: 1PIN) (Ranganathan et al., Cell 1997; 89:875-86) and the WD40 domain of Cdh1 (PDB: 4UI9_R) (Chang et al., Nature 2015; 522:450-54) using the HADDOCK2.2 webserver (van Zundert et al., J Mol Biol 2016; 428:720-25). The docking was performed using ambiguous iterative restraints between Pin1 residues K117 to G128 and FRZ1 residues on the D-box binding interface, as observed in the anaphase-promoting complex (PDB: 4UI9) (Chang et al., Nature 2015; 522:450-54). The model was refined using additional weak ambiguous distance restraints between the two canonical Pin1 residues, R119 and L122, and FRZ1 residues D180, P182, E465 and L467.

Immunofluorescence Analysis

PDOX tumor tissue sections were boiled in 10 mM sodium citrate (pH 6.0), for antigen retrieval after deparaffinization. The sections were permeabilized with PBS containing 0.1%-0.5% Triton X-100 and blocked with PBS containing 5% Goat serum for 30 min RT. The primary antibodies were diluted in PBS containing 1% Goat serum (1:200) and incubated in slides for overnight at 4° C. The slides were rinsed by PBS three times, each time for 5 min. Secondary antibodies were diluted in PBS (1:1000) and incubated for 20 min at room temperature. 20 mg/mL DAPI was used to label nuclear of cells. Slides were scanned at least three different representative areas at 20× magnification using BZ-X800 fluorescence microscope (KEYENCE).

Quantification and Statistical Analysis

GraphPad Prism 8, FlowJo v10.6.2, MATLAB 2019b, PyMOL 4.60 and RStudio 4.0.2 were used to generate most charts and statistical analyses. Image J was used to quantify the relative intensity of IBs. The Database for Annotation, Visualization and Integrated Discovery (DAVID) was used to Identify enriched biological themes, particularly GO terms. Data are typically mean±s.d. or mean±s.e.m. Data were analyzed by Unpaired two-sided t-test. Kaplan-Meier survival analysis was used for survival studies, and the groups were compared using the log-rank test. Differences of *P<0.05,  P<0.01, * P<0.001, and **** P<0.001 were considered statistically significant. Statistical details of experiments, including statistical tests and sample sizes used, can be found throughout. All experiments were performed on biological replicates unless otherwise specified.

Example 2: Cell Cycle Regulator APC/$C^{Cdh1}$ is a Physiological Upstream E3 Ubiquitin Ligase for Pin1

Figure 1A:
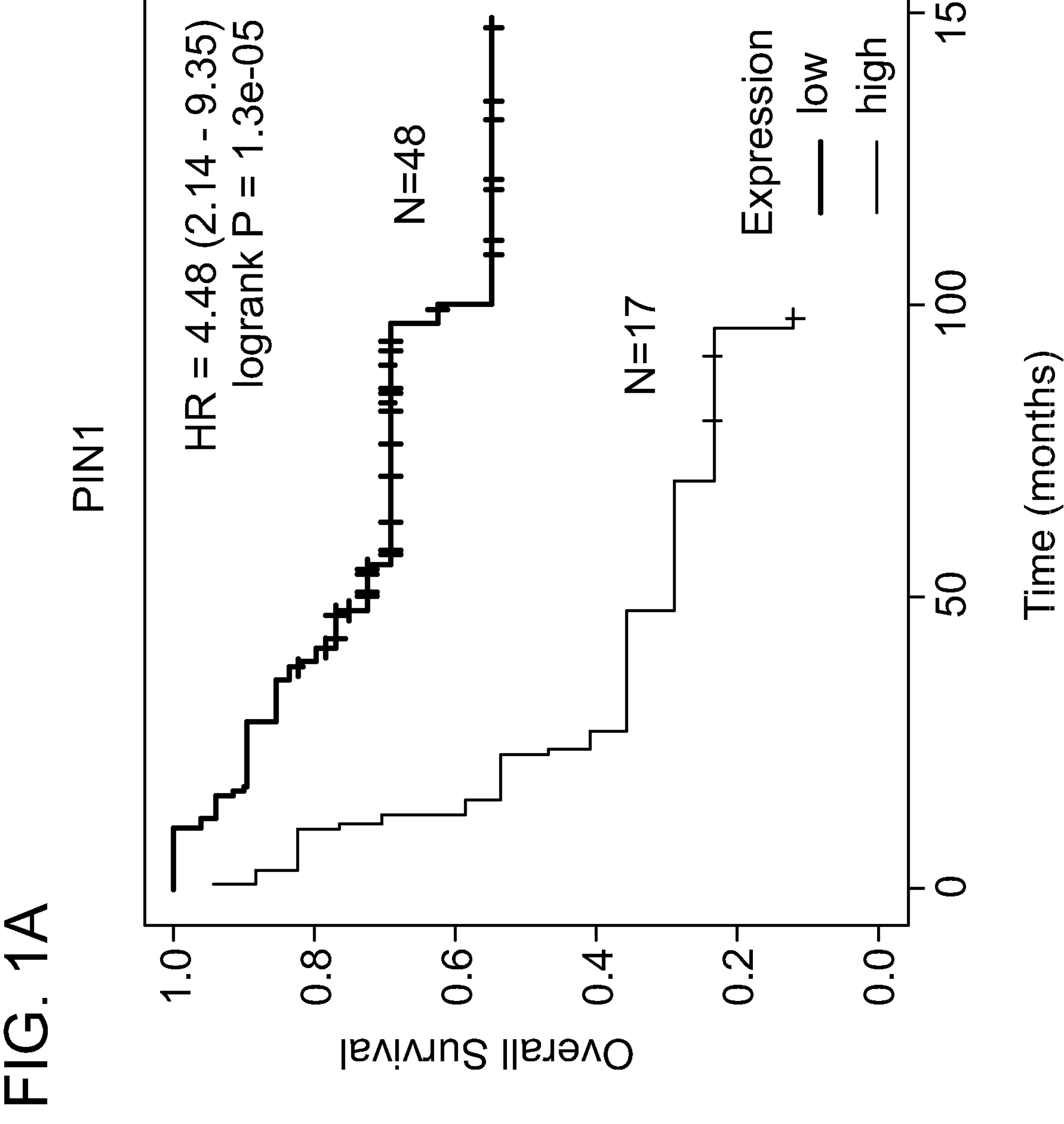
FIG. 1A-FIG. 1L is a set of graphs, images and immunoblots that show that the cell cycle regulator APC/$C^{Cdh1}$ is a physiological upstream E3 ubiquitin ligase for Pin1.
Figure 1B:
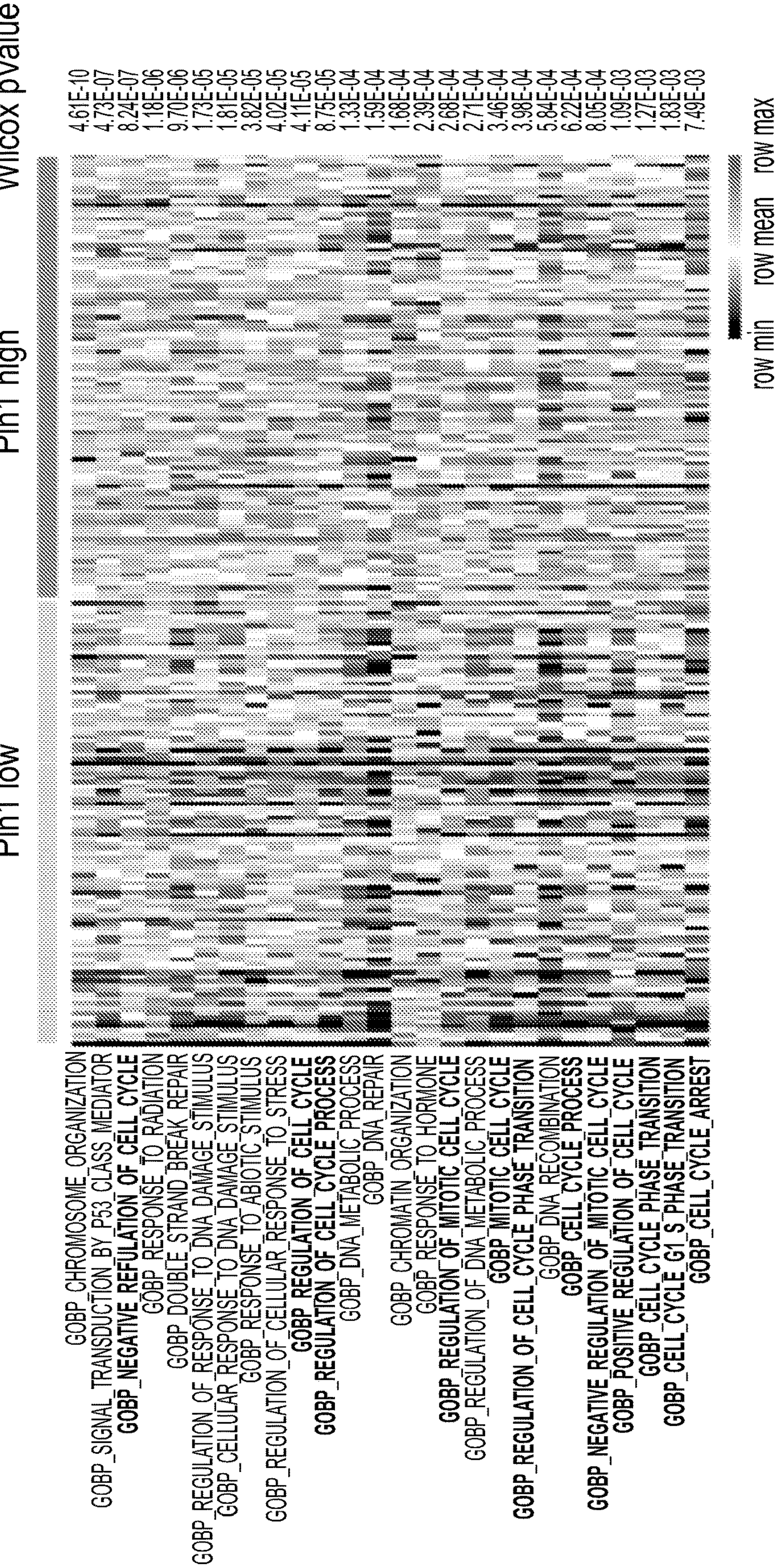
Figure 2A:
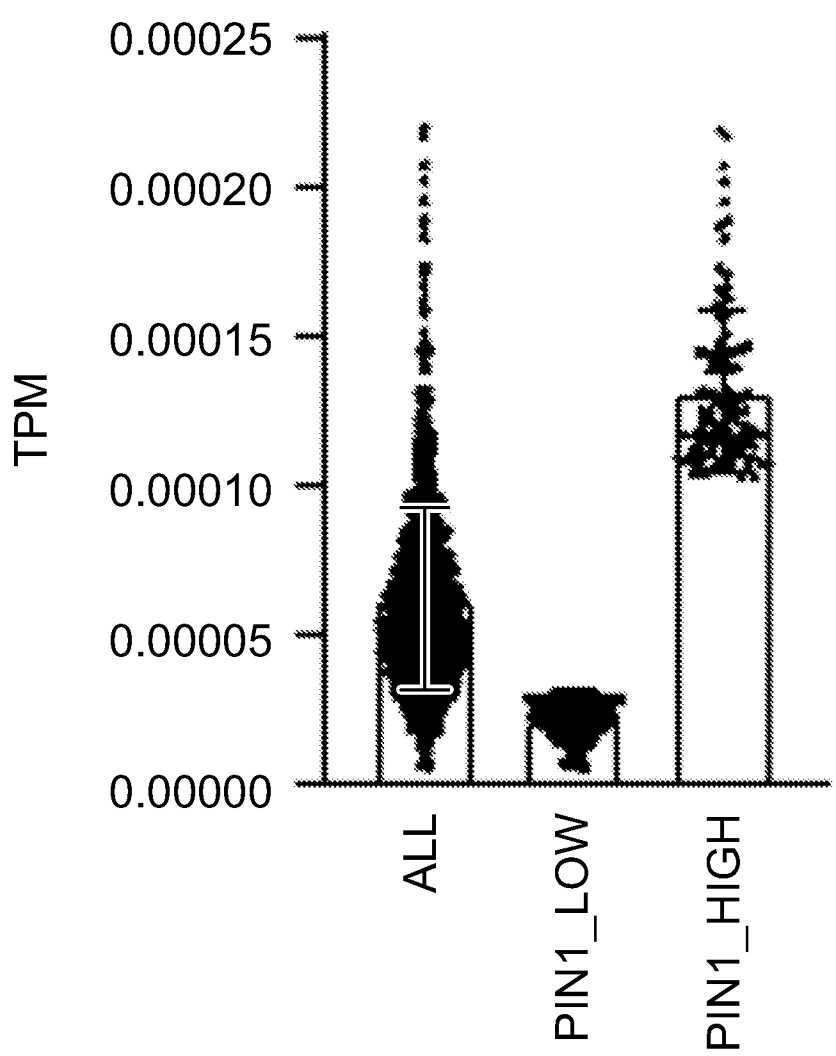
Figure 2C:
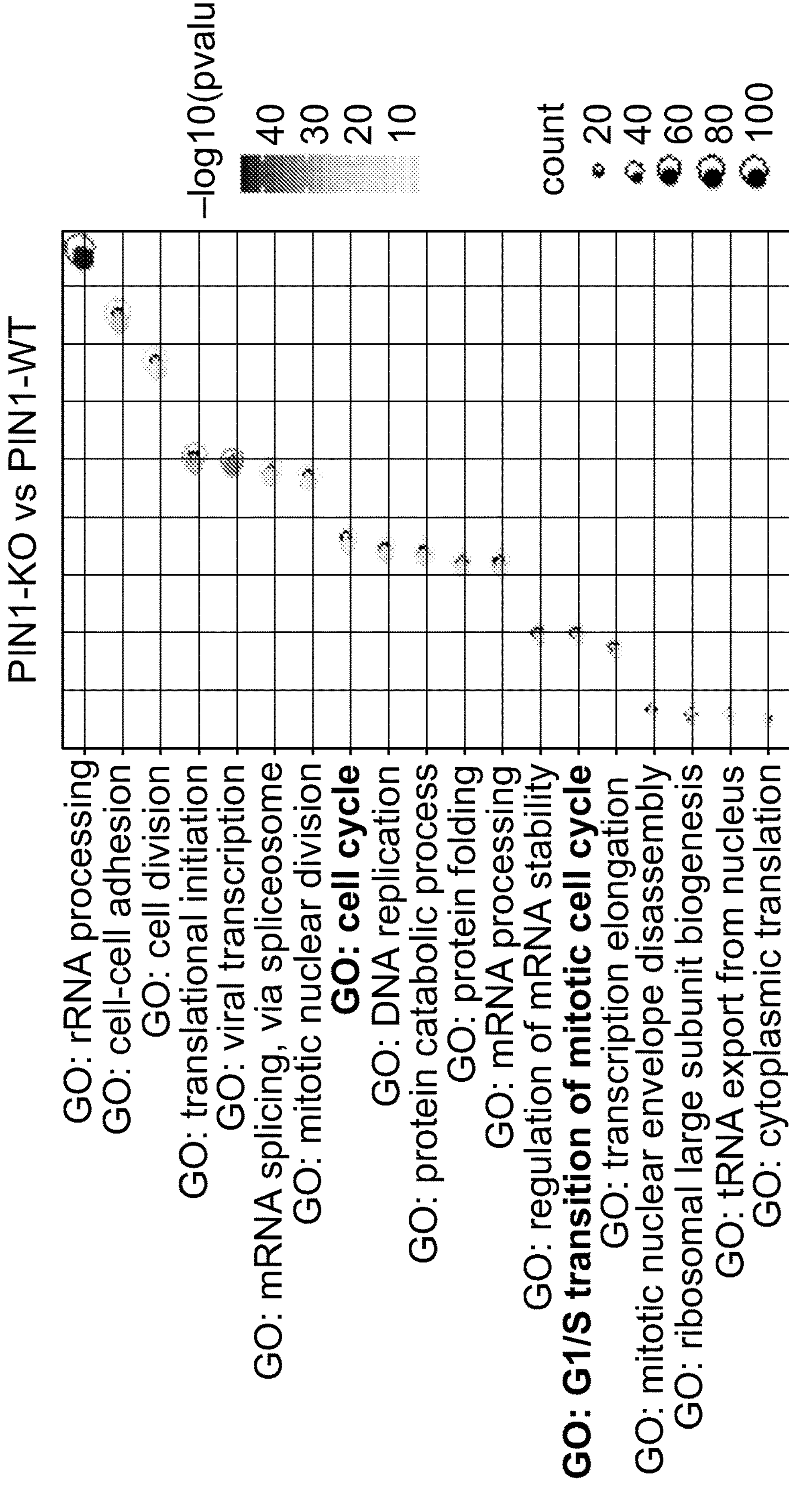

Pin1 is an established critical oncoprotein (Zhou and Lu, Nat Rev Cancer 2016; 16:463-78), whose expression strongly correlates with poor clinical prognosis in human BC tissues (FIG. 1A), as median survival was less than 2 years for the Pin1-high group, but over 10 years for the Pin1-low group (Nagy et al., Sci Rep 2021; 11:6047; Tang et al., Genome Med 2018; 10:94). To evaluate potential impact of Pin1 upregulation on biological processes in human BC tissues, RPPA data from TCGA was grouped by Pin1 low and Pin1 high transcriptional levels and the correlation of Pin1 levels with biological process signatures was tested using single-sample Gene Set Enrichment Analysis (ssGSEA), a computational method that determines whether an a priori defined set of genes shows statistically significant, concordant differences between two biological states (Barbie et al., Nature 2009; 462:108-12). Surprisingly, it was determined that in the Pin1 high group, cell cycle signatures were significantly higher expressed (FIG. 1B, FIG. 2A), and to a lesser extent cell cycle signatures were enriched in the transcriptome dataset. The heatmap in FIG. 1B shows the relative scores of ssGSEA analysis for RPPA data for tumors with Pin1 low versus Pin1 high, ranked by significance as determined by Wilcox test. The box plot in FIG. 2A shows the distribution of Pin1 mRNA levels across BC tumors (n=1211). Z-score >1 for Pin1 high group and Z-score <−1 for Pin1 low group. Moreover, expression of signatures associated with the adaptive immune system was significantly lower in the Pin1 high group, resulting in an inverse relationship of cell cycle progression and adaptive immune activation (FIG. 2B) (Heatmap shows relative scores of ssGSEA analysis for signatures). It was discovered that Pin1 KO in the TNBC cell line MDA-MB-231 perturbed key biological processes including cell cycle progression upon reanalysis of proteomic data obtained previously (FIG. 2C) (Kozono et al., Nat Commun 2018; 9:3069). In FIG. 2C, the codes for p-value (brighter purple is more significant) and symbol size codes for the ratio of proteins related to specific GO term/total number of proteins significantly altered are shown. Collectively, these data suggested that reducing Pin1 protein abundance may provide therapeutic opportunities against cancer.

Figure 2D:
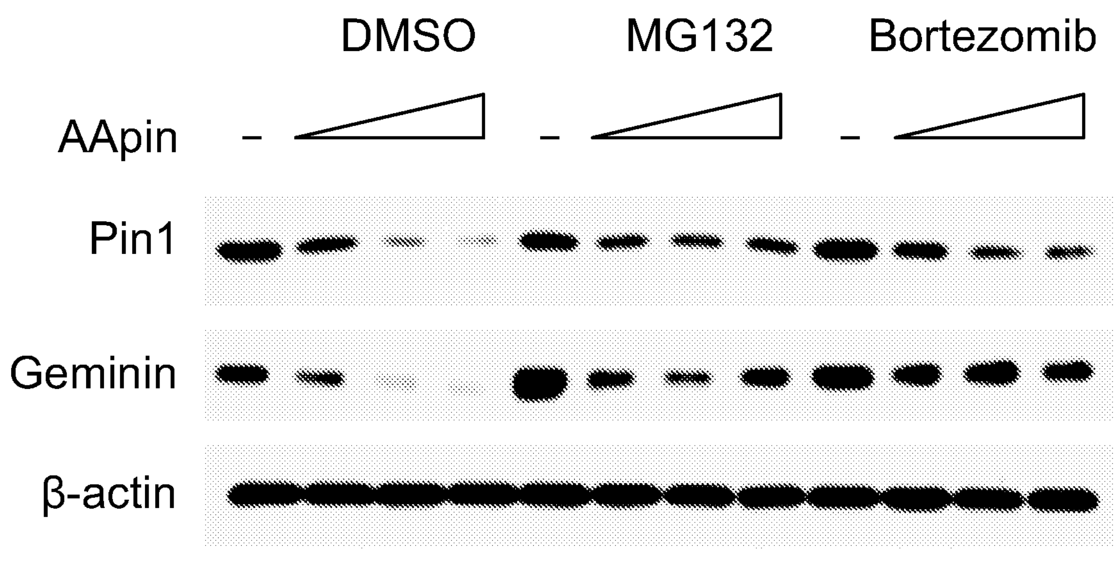
Figure 2D:
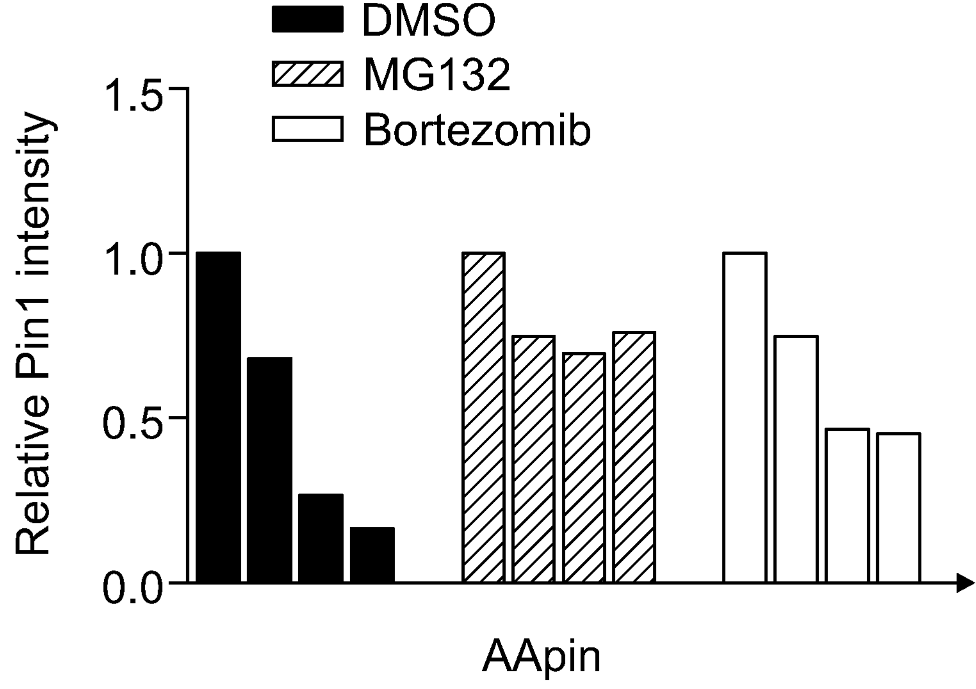

Exploration of the intrinsic upstream regulators that could affect Pin1 protein stability was then sought. Given that most of the Pin1 inhibitors identified so far, including the highly selective sulfopin and the approved drug combination of ATRA and ATO (AApin), not only inhibit Pin1 catalytic activity, but also induce Pin1 degradation at posttranslational levels (Kozono et al., Nat Commun 2018; 9:3069; Wei et al., Nat Med 2015; 21:457-66; Dubiella et al., Nat Chem Biol 2021, 17, 954-63; Pinch et al., Nat Chem Biol 2020; 16:979-87), the underpinning mechanism of Pin1 degradation was investigated. It was found that Pin1 inhibitor-induced Pin1 degradation was rescued by the proteasome inhibitors MG132 and bortezomib (FIG. 2D), indicating that Pin1 degradation is via the ubiquitin-proteasome pathway. FIG. 2D shows the IB analysis for indicated proteins derived from MDA-MB-231 cells treated with increasing concentrations of AApin (ATO (0.5, 1, 1.5, 2 μM) plus ATRA (5, 10, 15, 20 μM) in 1:10 ratio) for 3 days and 10 μM MG132 or 1 μM bortezomib for last 12 hrs before harvesting (top) and the corresponding quantification of Pin1 western blots (bottom).

Figure 1C:
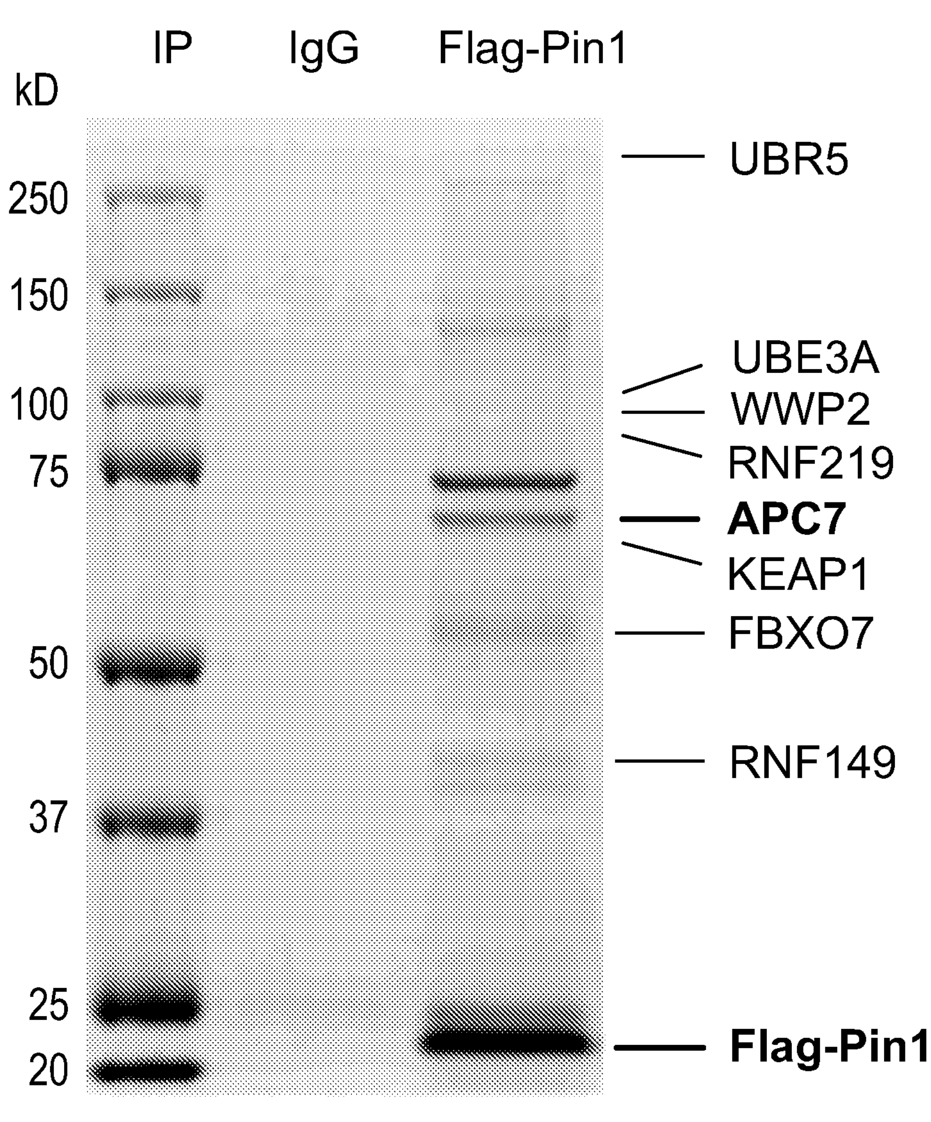
Figures 1D, 1E, 1F:
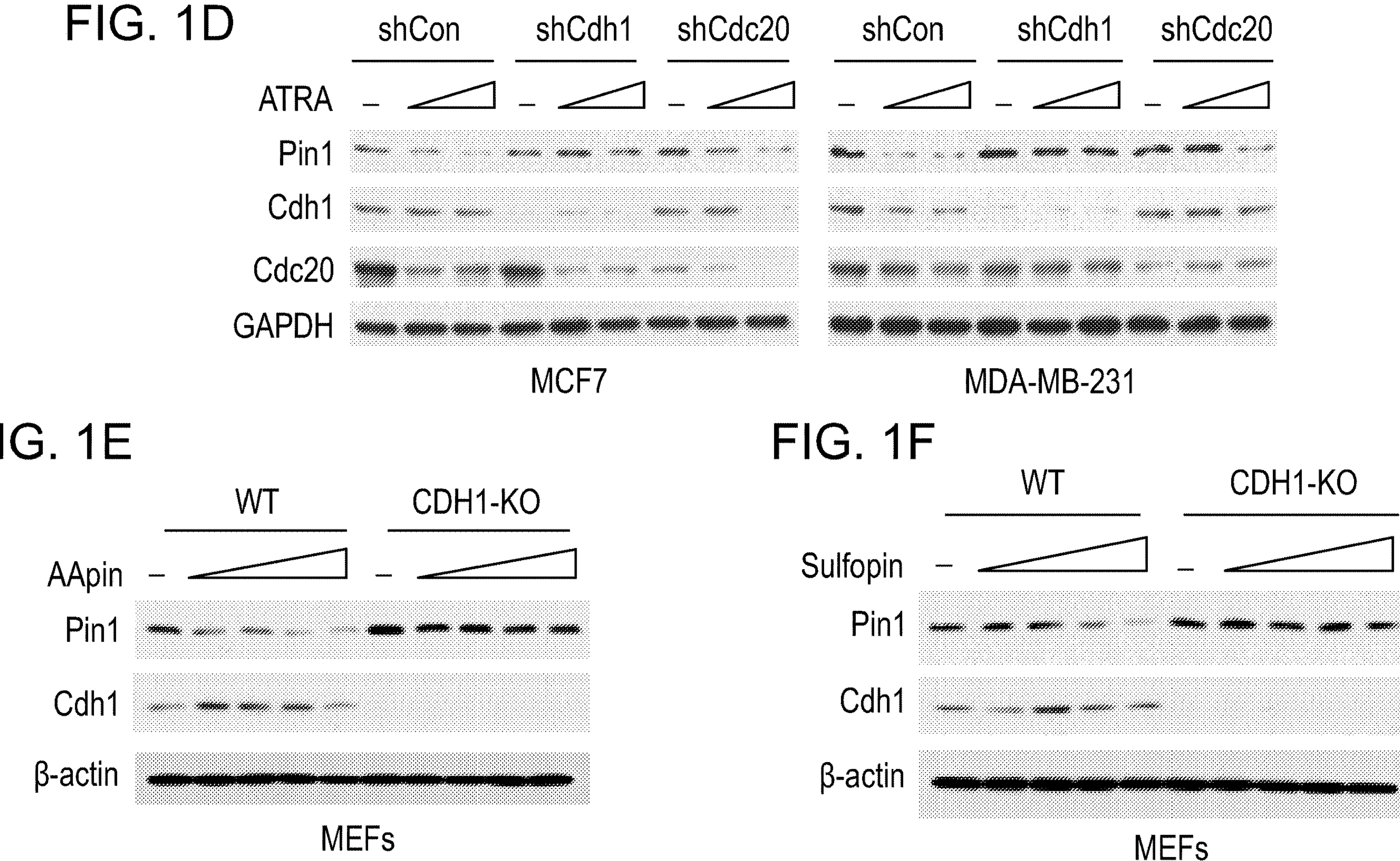
Figure 1H:
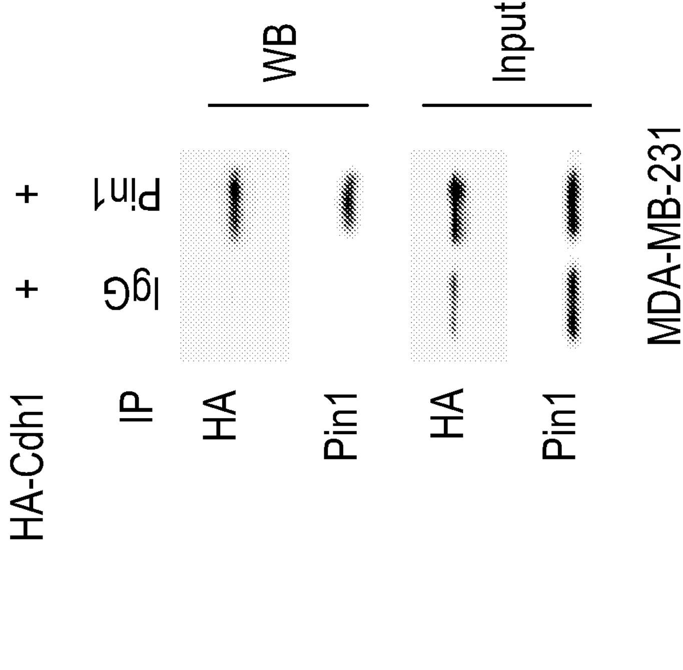
Figure 1G:
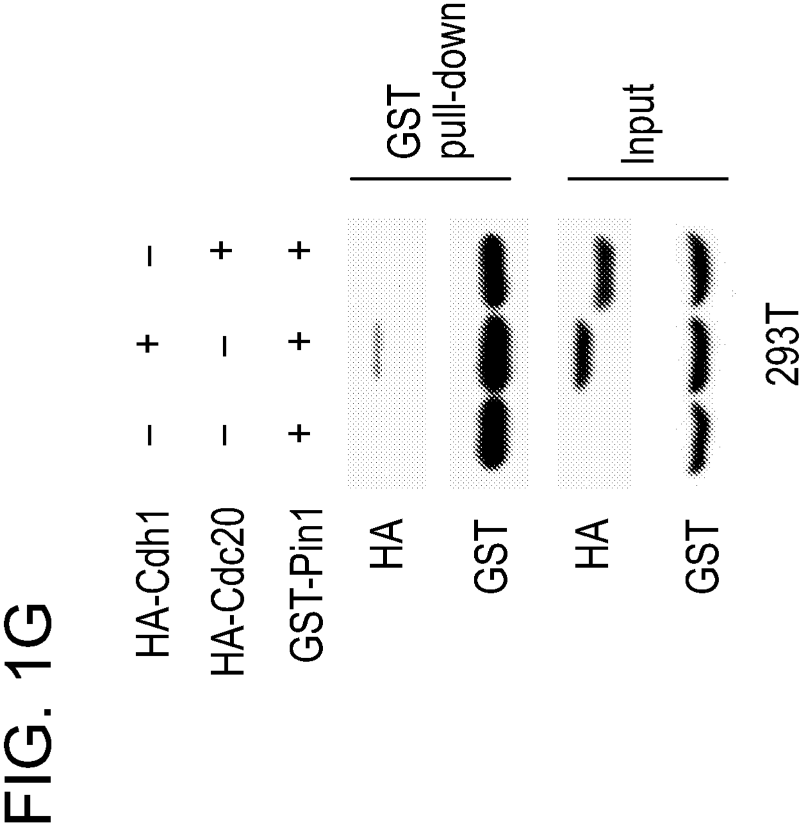
Figure 1I:
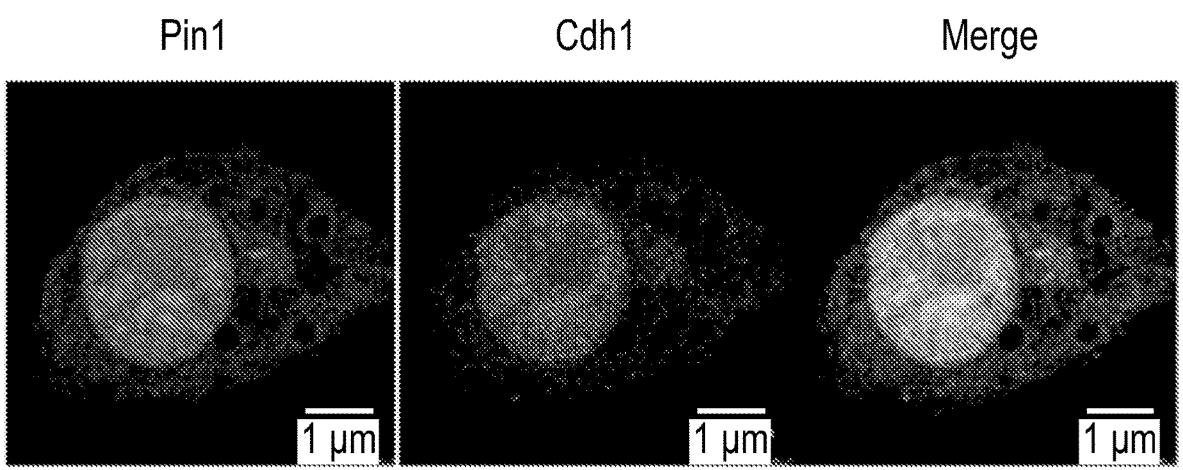

To identify the specific E3 ubiquitin ligase for Pin1, a selected library of lentiviral-based E3 ligase short hairpin RNAs (shRNAs) in MDA-MB-231 cells was screened, including E3 ligases functioning as tumor suppressors (BRCA1, BARD1, SIAH1, Fbw7, et al.) and E3 ligases acting in protein quality control (CHIP, UBR1, AMFR, RNF4, et al.). However, none of these E3 ligases was responsible for Pin1 inhibitor-induced degradation. Immunoprecipitation coupled with mass spectrometry (IP-MS) was performed and identified several Pin1-interacting E3 ligases or E3 ligase-related proteins in MDA-MB-231 cells (FIG. 1C). Proteins were identified by mass spectrometric peptide sequencing. MDA-MB-231 cells were transfected with 3XFlag-Pin1 and treated with 10 μM MG132 for 12 hrs. Lysates were immunoprecipitated with M2 (anti-Flag) or control (IgG) beads. Among them, APC7 is a tetratricopeptide repeat (TPR)-containing subunit of the APC/C E3 ligase complex that controls mitotic progression and serves to recruit Cdh1 and Cdc20 to the APC/C core complex (Han et al., J Biol Chem 2009; 284:15137-46; Vodermaier et al., Curr Biol 2003; 13:1459-68). Functioning as APC/C activators, Cdc20 and Cdh1 (encoded in humans by the FZR1 gene) regulate the activity and substrate specificity of the E3 ligase complex (Li and Zhang, Cell Div 2009; 4:2). Here, Pin1 inhibitor-induced Pin1 degradation was rescued by knockdown of endogenous Cdh1, but not its close homologue, Cdc20 (FIG. 1D) (MCF-7 and MDA-MB-231 cells stably expressing shCdh1 or shCdc20 were treated with increasing concentrations of ATRA (5 μM, 20 μM) for 3 days, followed by immunoblotting of cell lysates) or other candidate E3 ubiquitin ligases (FIG. 3A-FIG. 3G) (IB of Pin1 from MDA-MB-231 cells stably expressing indicated shRNAs and treated with AApin (1.5 UM ATO plus 15 μM ATRA) for 3 days). The knockdown efficiency of the respective shRNA plasmids was validated by RT-PCR), which was further confirmed in Cdh1-KO mouse embryonic fibroblasts (MEFs) (FIG. 1E, FIG. 1F). These results suggest that Cdh1 is the prime candidate to mediate Pin1 inhibitor-induced Pin1 degradation, which was further substantiated by the findings that Pin1 specifically interacted with Cdh1, but not Cdc20, as shown by the GST-Pin1 pull-down assay (FIG. 1G) and co-immunoprecipitation and co-localization of endogenous Pin1 and Cdh1 in MDA-MB-231 cells (FIG. 1H, FIG. 1I). MDA-MB-231 cells stably expressing HA-Cdh1 were treated with 10 μM MG132 for 12 hrs and precipitated with IgG or anti-Pin1 antibodies. Input is 5% of the total lysates used in IP (FIG. 1H). Colocalization rates were calculated by LAS X software. Scale bars, 5 μm (FIG. 1I).

Figure 1J:
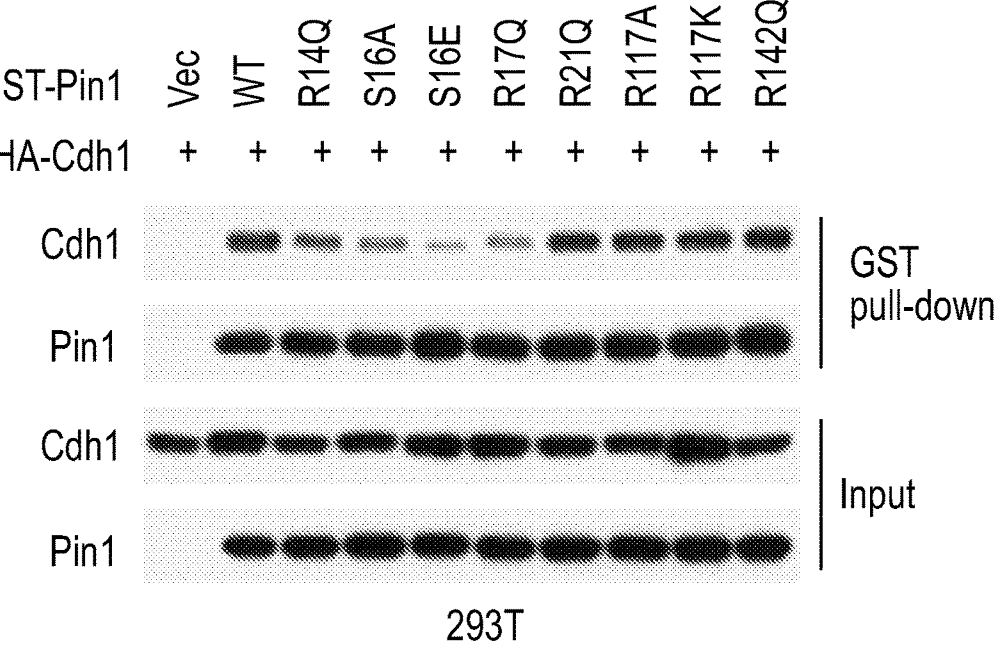
Figures 1K, 1L:
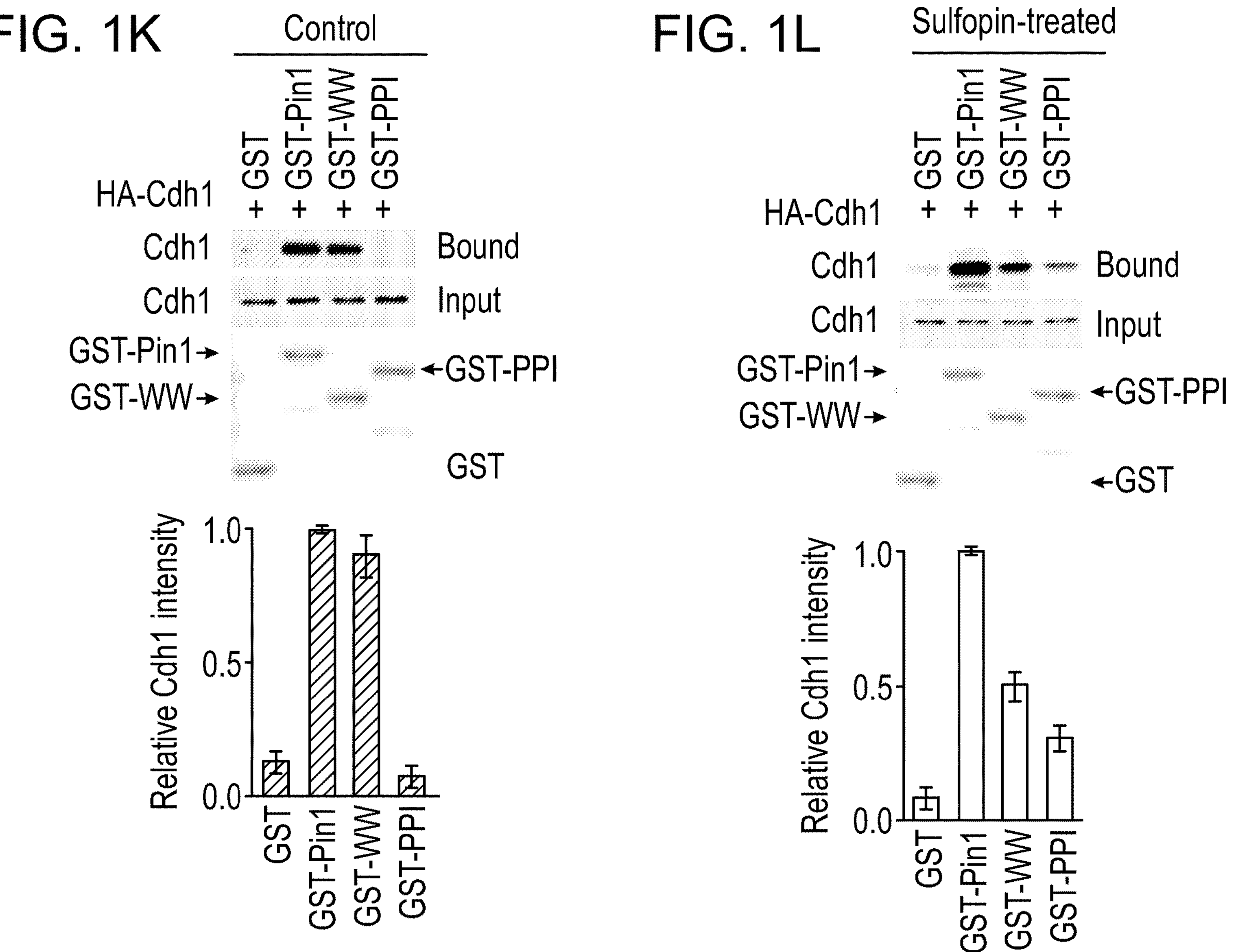
Figure 3A:
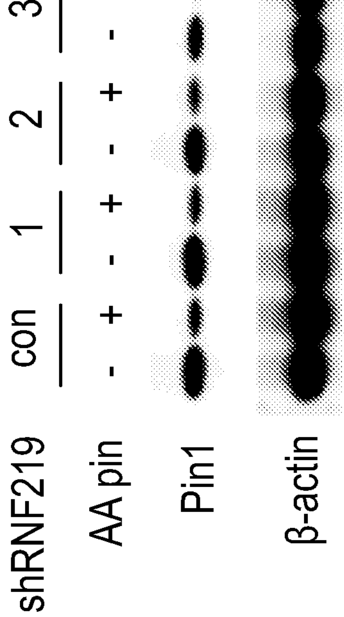
Figure 3B:
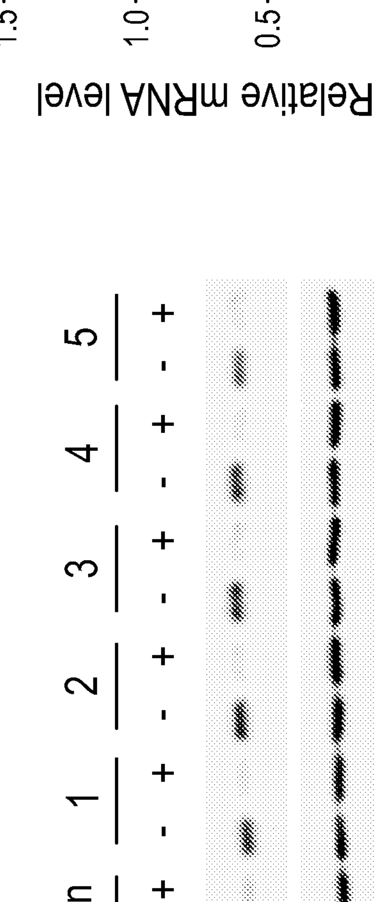
Figure 3B:
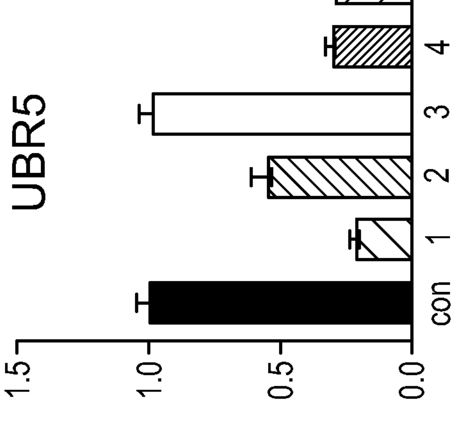
Figure 3C:
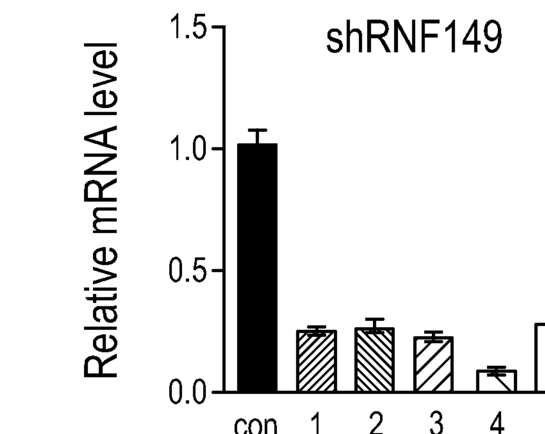
Figure 3D:
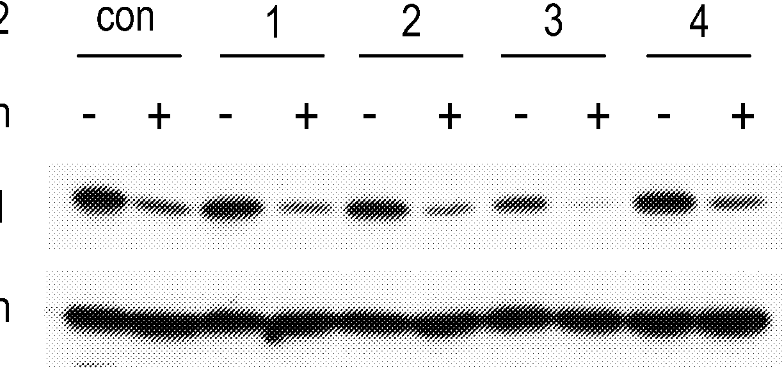
Figure 3D:
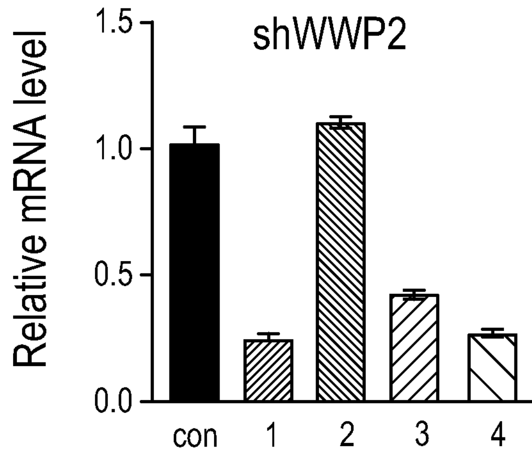
Figure 3E:
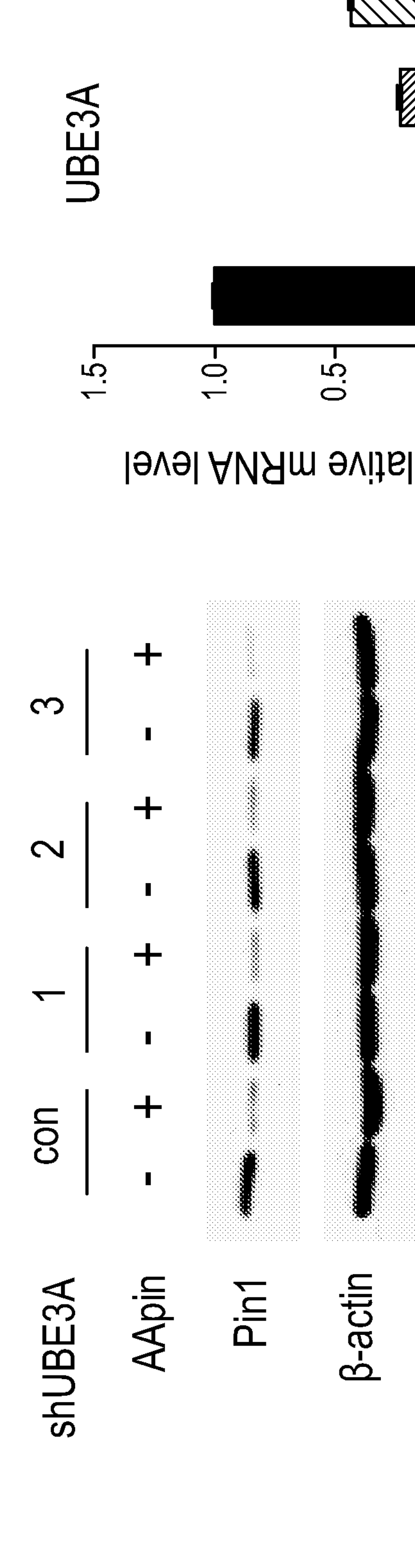
Figure 3F:
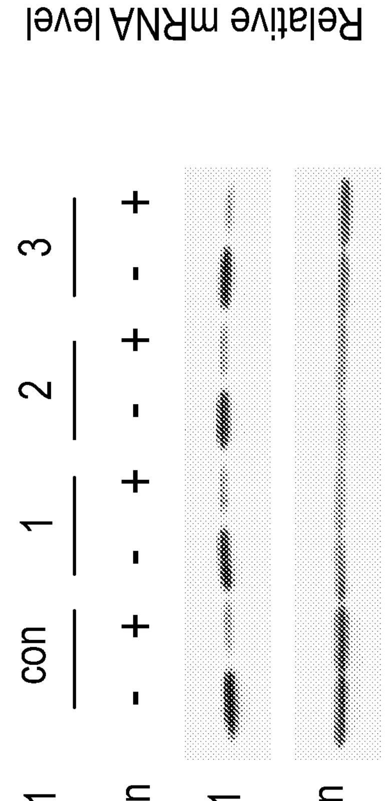
Figure 3H:
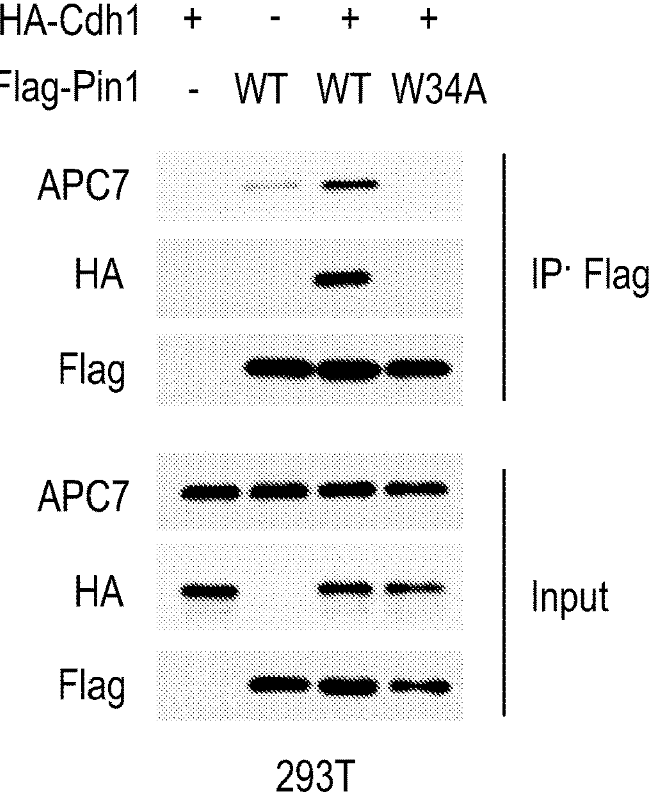
Figure 3I:
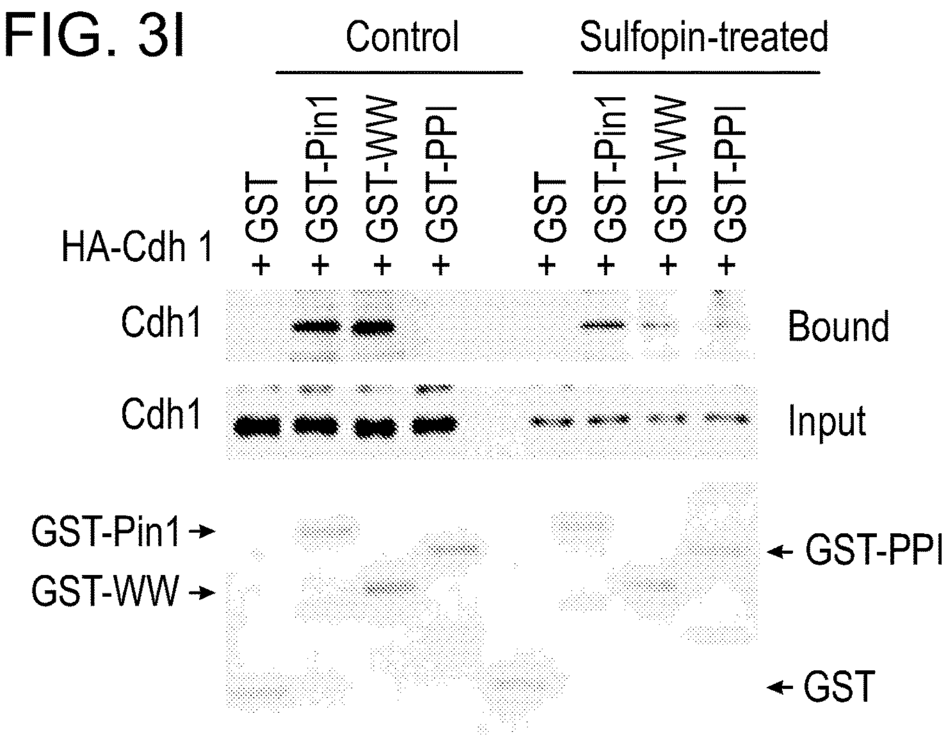

To further define the molecular mechanism of Cdh1-mediated Pin1 degradation, the interaction of Pin1 and Cdh1 was examined using GST pull-down assays using GST-Pin1 point mutations. IB analysis of GST pull-down precipitates derived from 293T cells transfected with HA-Cdh1 and GST-Pin1 mutants as indicated for 36 hrs. The graphs were one representative experiment out of three independent experiments. It was found that the residues S16, R17 and W34 at the core of the Pin1 WW domain were required for interaction with phosphorylated Cdh1 (FIG. 1J, FIG. 3I), showing that the Pin1 WW domain acts as the predominant pSer/Thr-Pro substrate binding module, with a binding affinity ten times higher than that of the PPIase domain that catalyzes the isomerization of pSer/Thr-Pro motifs (Verdecia et al., Nat Struct Biol 2000; 7:639-43; Lu et al., Science 1999; 283:1325-8). However, surprisingly, treatment with the Pin1 covalent inhibitor, sulfopin, changed the binding mode of Cdh1 to Pin1 with a shift from binding to the WW domain to the PPIase domain (FIG. 1K, FIG. 1L). FIG. 1K and FIG. 1L show the shift of Cdh1 binding from the WW− to the PPIase domain of Pin1 upon inhibition of PPIase activity. Immunoblot (IB) analysis of indicated GST pull-down precipitates (full-length Pin1 and isolated WW− and PPIase fragments) derived from MCF-7 cells stably expressing HA-Cdh1 and treated with vehicle or sulfopin for 3 days and 10 μM MG132 for last 12 hrs before harvesting. Bottom graphs quantification of IB analysis for bound HA-Cdh1. The graphs were one representative experiment out of two or three independent experiments. This unexpected finding prompted an investigation into the possibility that Cdh1 can target Pin1 for proteasomal degradation. To this end, whether Pin1 contains a destruction box (D-box) motif was examined, since most APC/$C^{Cdh1}$ substrates contain a D-box motif with the conserved consensus RXXL sequence (X presents any amino acid) (Davey and Morgan, Mol Cell 2016; 64:12-23). Indeed, Pin1 has a putative D-box within its PPIase domain (FIG. 3J) and the mutation of this D-box abolished the ability of Cdh1 to degrade Pin1 (FIG. 4H, FIG. 4I), as described below. Note the sequence homology of destruction box (D-box) motifs (RXXL) in human and mouse. Bottom graphs showing preference of the D box-binding pocket. Residues in red are the consensus residues of the degron; "Ψ" signifies a leucine, isoleucine, or valine residue; "x" signifies any residue but with preferences for particular residues. The graphs were one representative experiment out of three independent experiments. These results consistently indicate that APC/$C^{Cdh1}$ likely is a physiological upstream E3 ubiquitin ligase for Pin1.

Figure 4B:
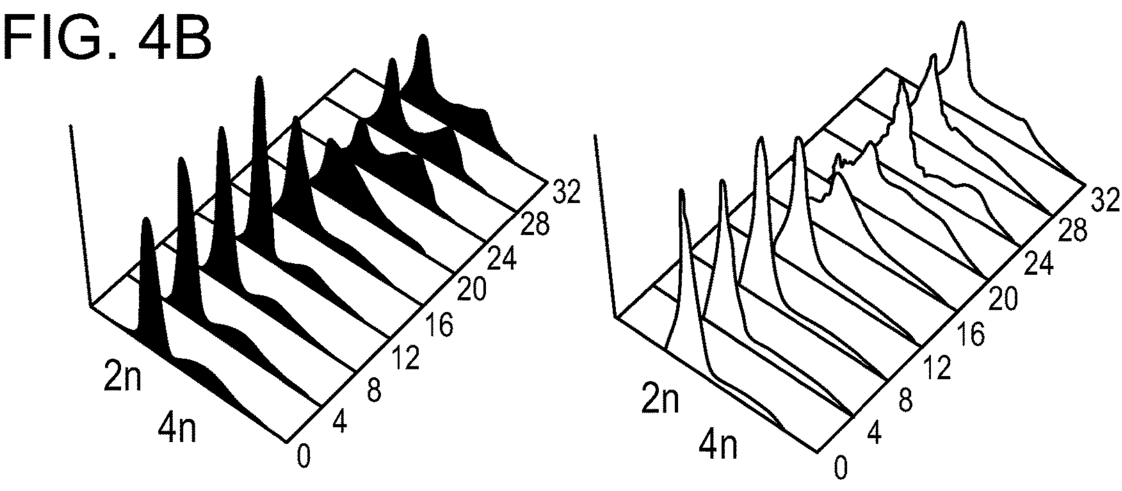
Figure 4C:
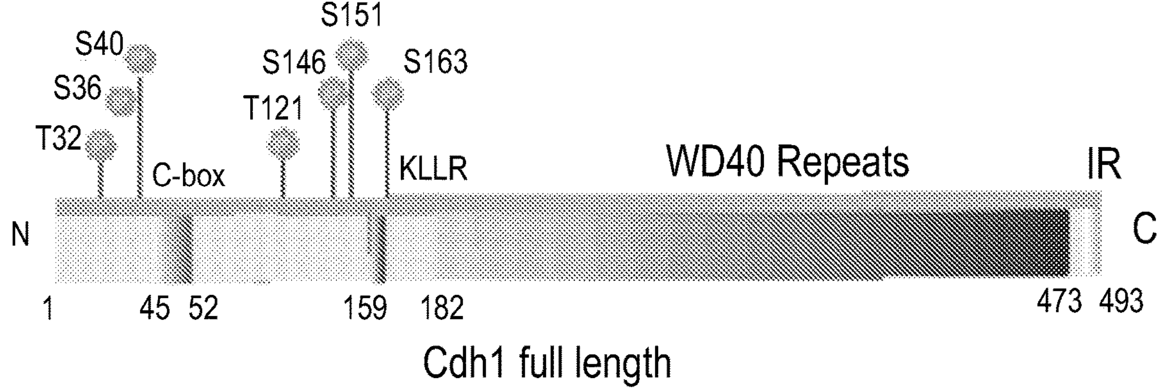
FIG. 4C is a cartoon representation that shows that the domain architecture of Cdh1 contains previously identified serine/threonine sites in the N-terminus that are potential phosphorylation sites for CDKs.
Figure 4D:
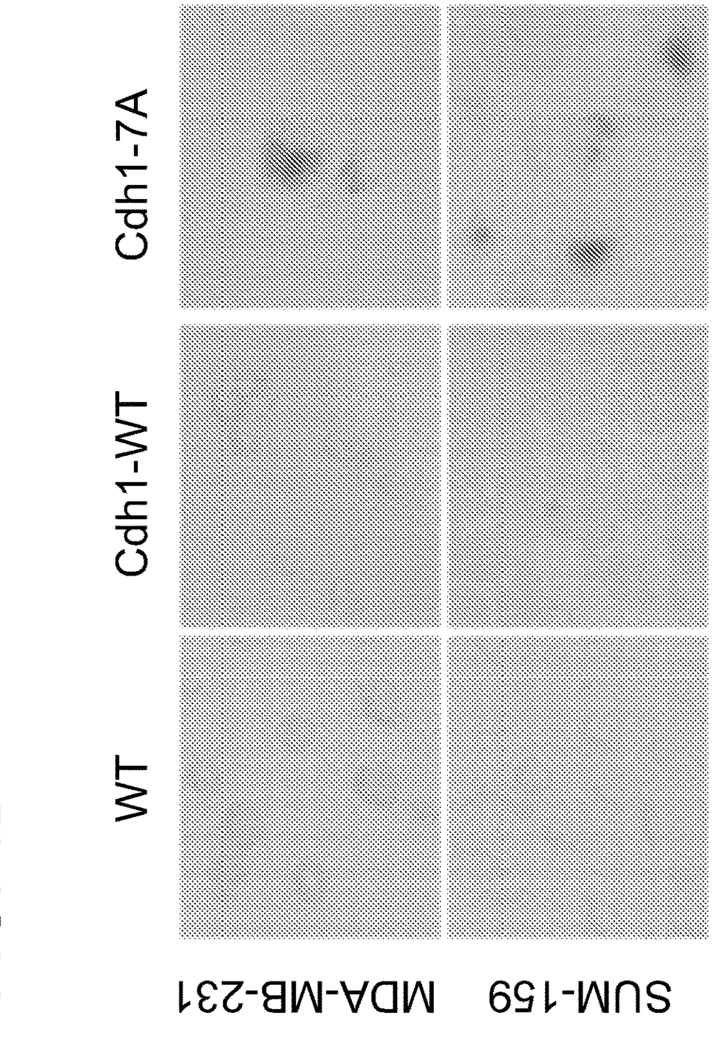
Figure 4D:
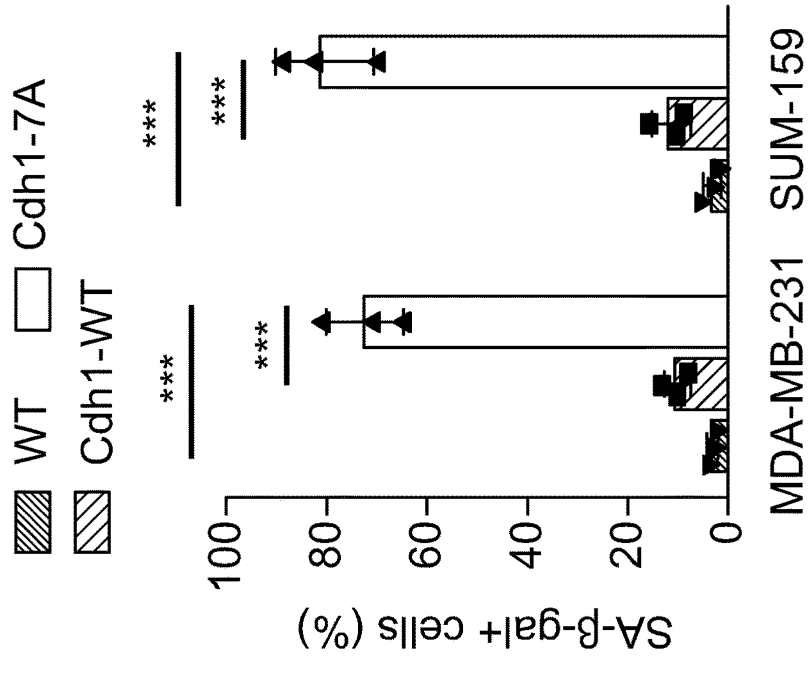
Figure 4E:
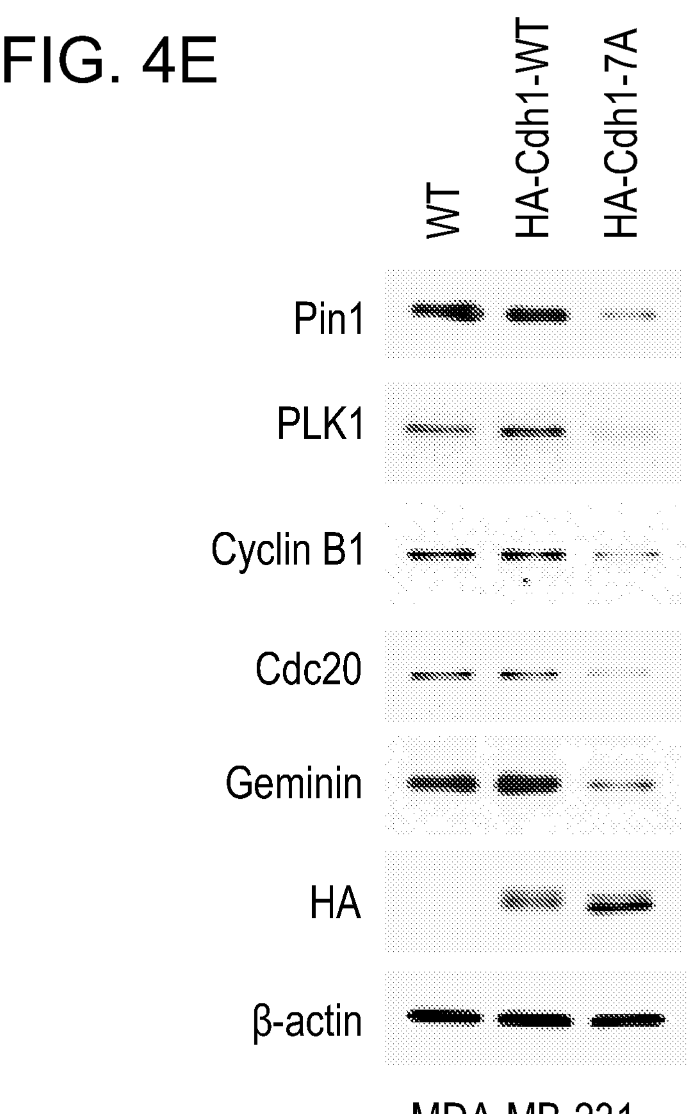
Figures 5A, 5B:
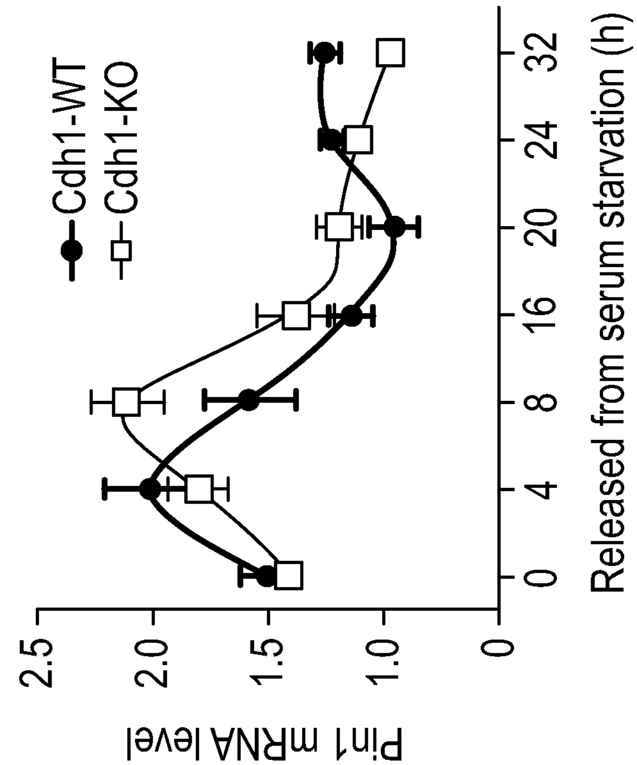
FIG. 5A-FIG. 5M is a set of graphs, images, immunoblots and heat maps that shows that active APC/$C^{Cdh1}$ targets Pin1 for degradation and APC/$C^{Cdh1}$ E3 ligase activity is inhibited by CDK4-mediated Cdh1 phosphorylation.
Figure 5C:
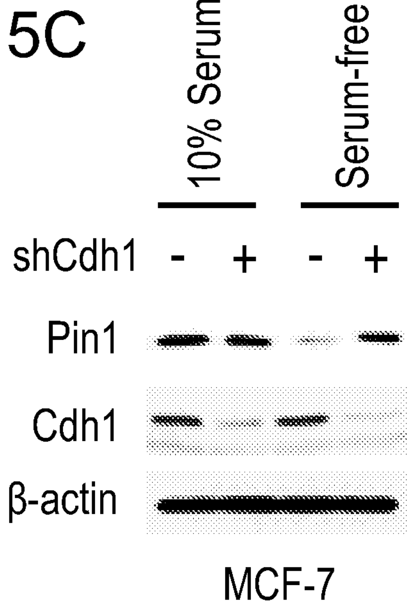
Figure 5C:
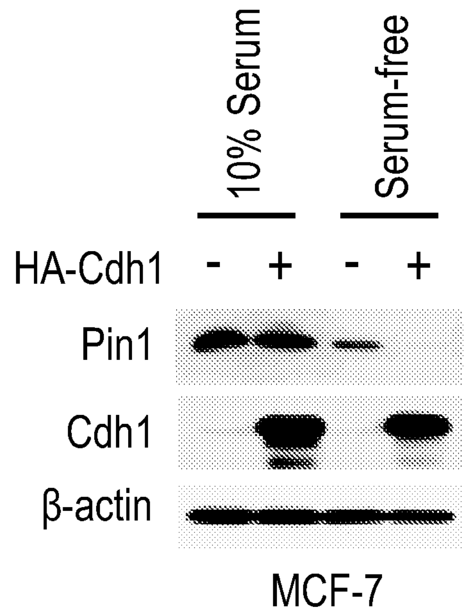
Figure 5D:
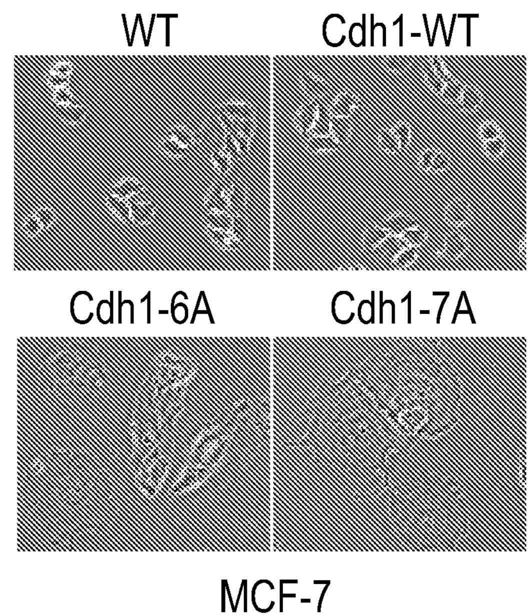
Figure 5D:
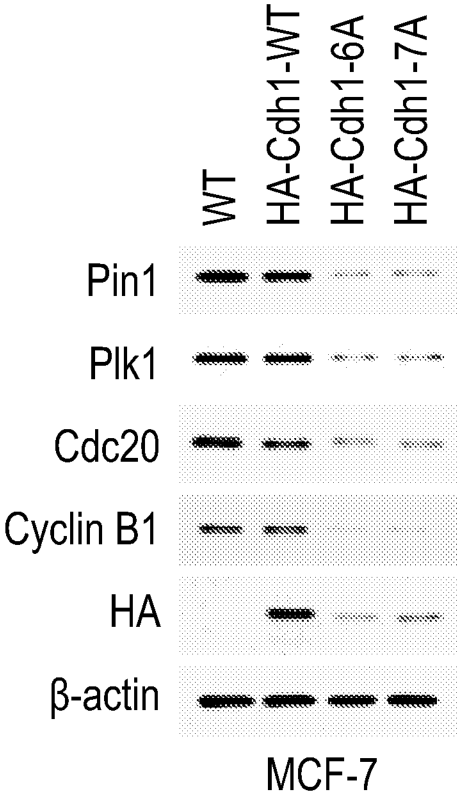
Figure 5F:
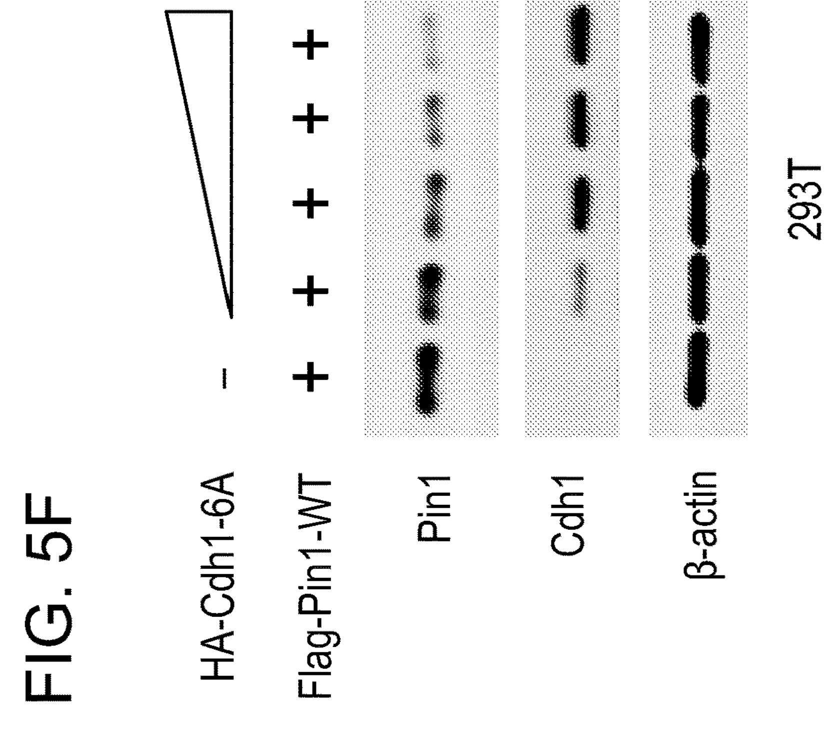
Figure 5E:
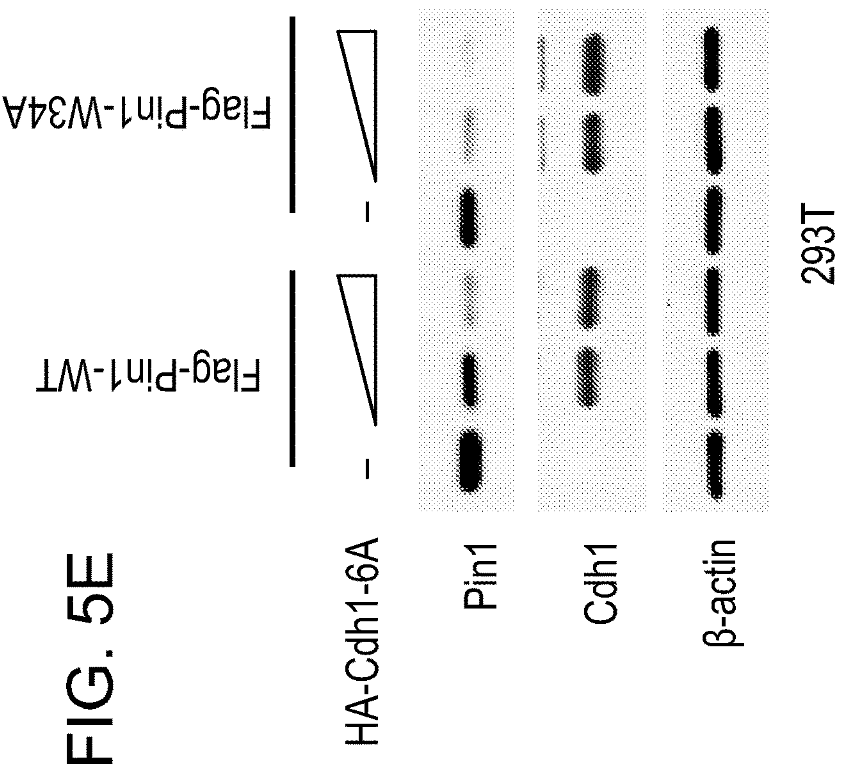
Figure 5G:
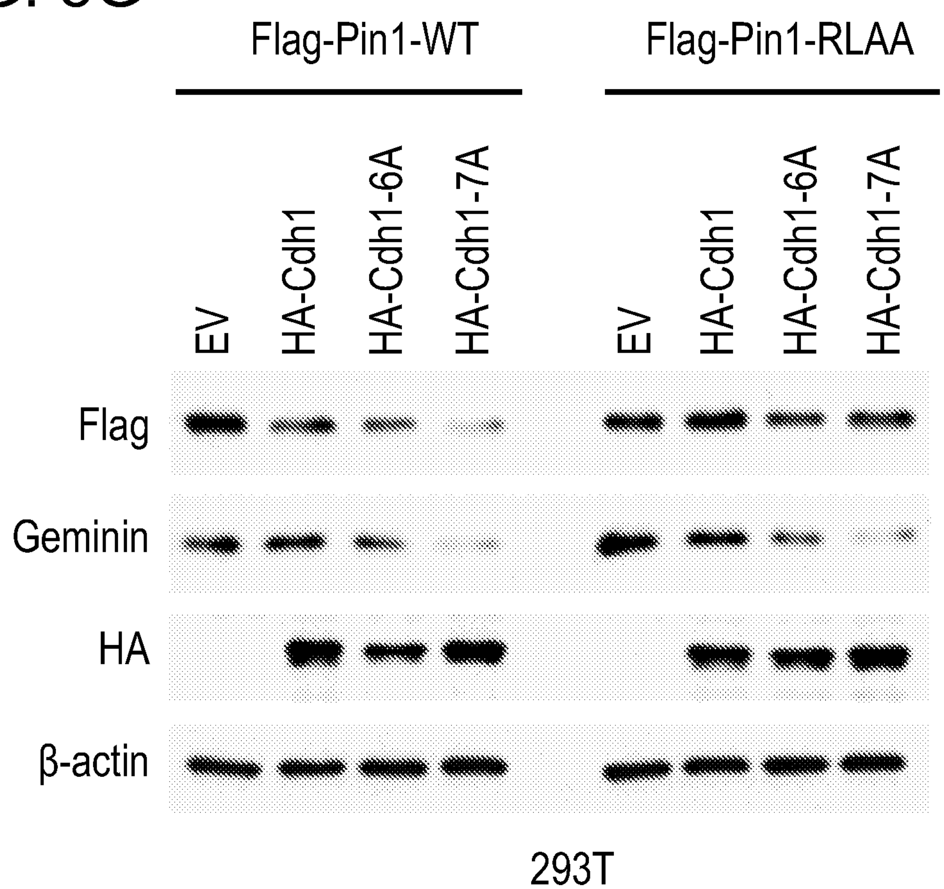

Example 3: Active APC/$C^{Cdh1}$ Targets Pin1 for Degradation and APC/$C^{Cdh1}$ E3 Ligase Activity is Inhibited by CDK4-Mediated Cdh1 Phosphorylation The above findings suggest that APC/$C^{Cdh1}$ is an E3 ubiquitin ligase for Pin1 and when Pin1 PPIase activity is inhibited, Cdh1 switching from interacting with the WW domain to the PPIase domain raised the possibility that Pin1 might change from an upstream regulator to a downstream substrate of APC/$C^{Cdh1}$ for degradation upon Pin1 catalytic inhibition. To understand this potential switch in more mechanistic details, the dynamics of APC/$C^{Cdh1}$ and Pin1 protein levels during the cell cycle were examined. From late mitosis throughout G1 phase, CDK inactivation maintains Cdh1 in a dephosphorylated state and hence APC/$C^{Cdh1}$ is active, preventing premature entry into S phase (Sivakumar and Gorbsky, Nat Rev Mol Cell Biol 2015; 16:82-94). Pin1 expression, on the other hand, was relatively low in G1 phase and started to accumulate at about 16 hours after release from serum starvation, coincident with the onset of S phase and the inactivation of APC/$C^{Cdh1}$ (FIG. 4A and FIG. 4B, left panel), allowing for the possibility that Pin1 was targeted by active APC/$C^{Cdh1}$ for destruction during G0/G1. Comparing Pin1 protein levels during the cell cycle in Cdh1 wild-type (WT) and knockout (KO) MEFs revealed that Cdh1 KO in MEFs resulted in stabilization of cyclin B1 and premature S-phase entry, as well as stabilization of Pin1 across the cell cycle, consistent with the notion that Pin1 is degraded by APC/$C^{Cdh1}$ (FIG. 4A, FIG. 4B, and FIG. 5A). Interestingly, while Pin1 protein levels were stabilized (FIG. 4A), Pin1 mRNA levels were not significantly different between Cdh1-WT and Cdh1-KO MEFs, strongly supporting a post-translational mechanism for Pin1 stabilization (FIG. 5B). Similarly, knocking down endogenous Cdh1 in MCF-7 cells stabilized Pin1 (FIG. 5C, left). Conversely, Pin1 levels were decreased by Cdh1 ectopic expression (FIG. 5C, right). Further, Cdh1 protein levels (protein level z-scores were measured with mass spectrometry by the Clinical Proteomic Tumor Analysis Consortium (CPTAC)) were negatively correlated with Pin1 protein levels and high levels of Cdh1 were associated with poor prognosis on BRCA tumors in TCGA (FIG. 16A, FIG. 16B). Altogether, these results suggest that Cdh1 is likely the prime candidate to mediate Pin1 degradation. Thus, Pin1 is likely a ubiquitin substrate of APC/$C^{Cdh1}$ in G1 phase.

Figure 4H:
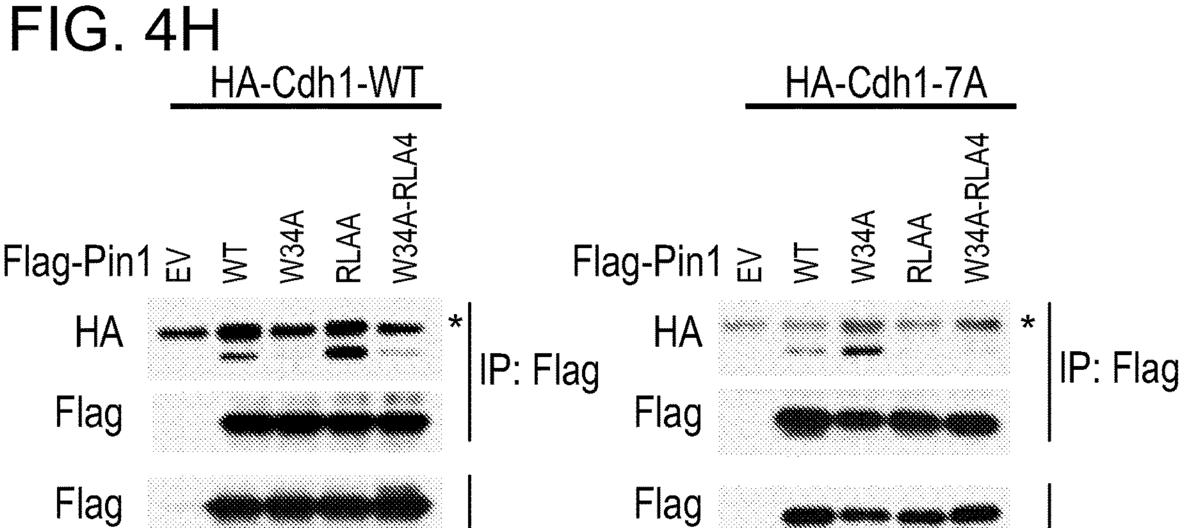
Figure 4I:
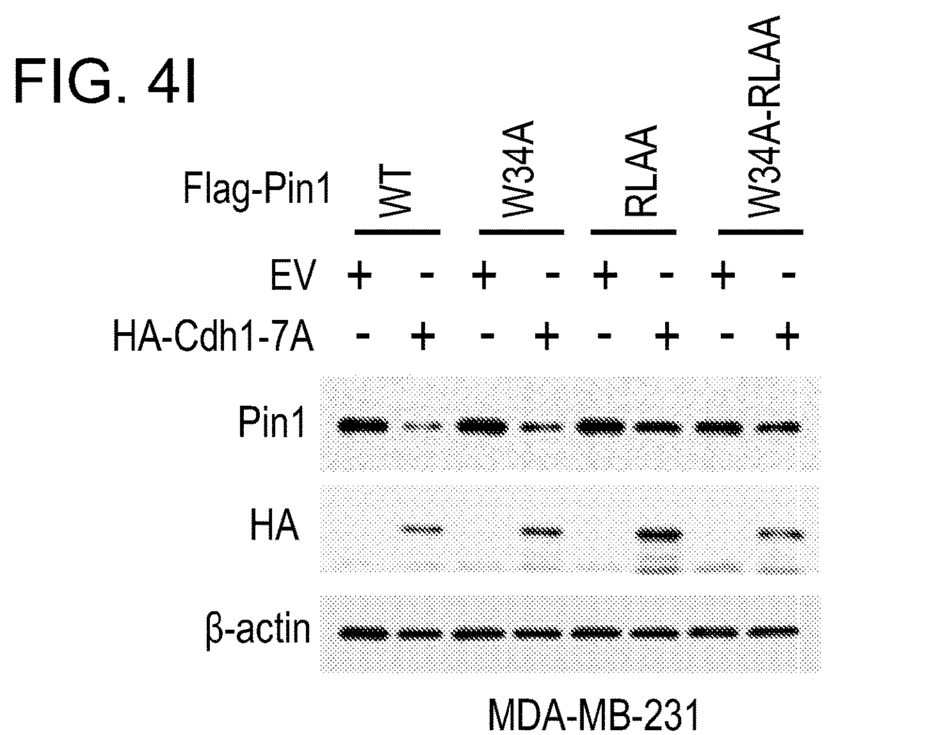
Figure 4J:
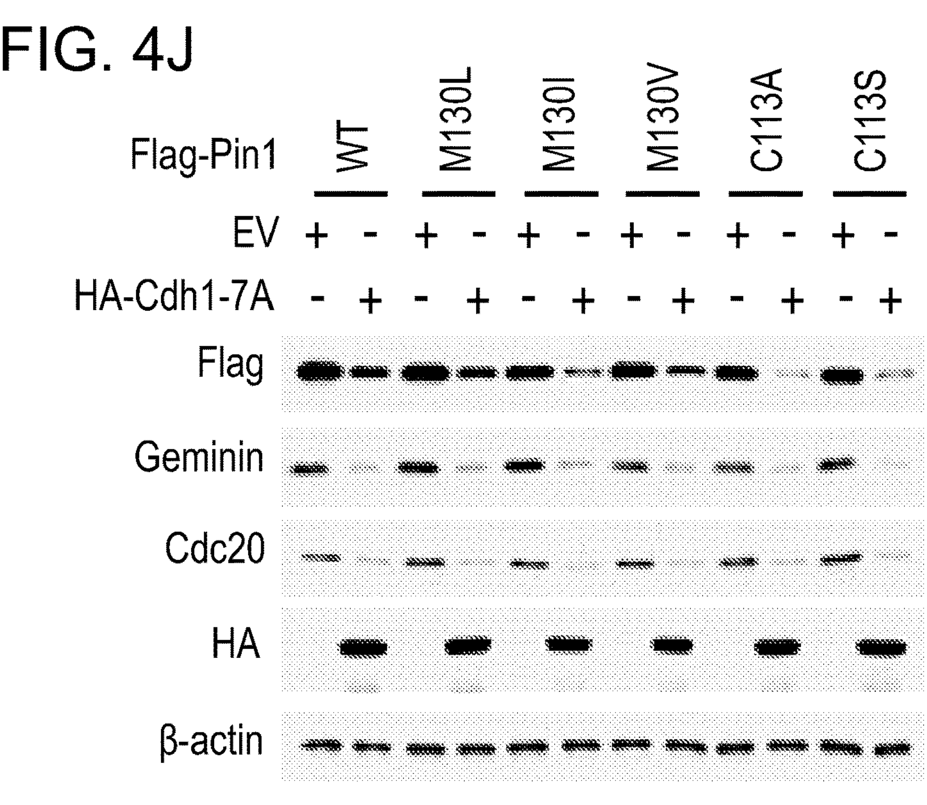
Figure 4K:
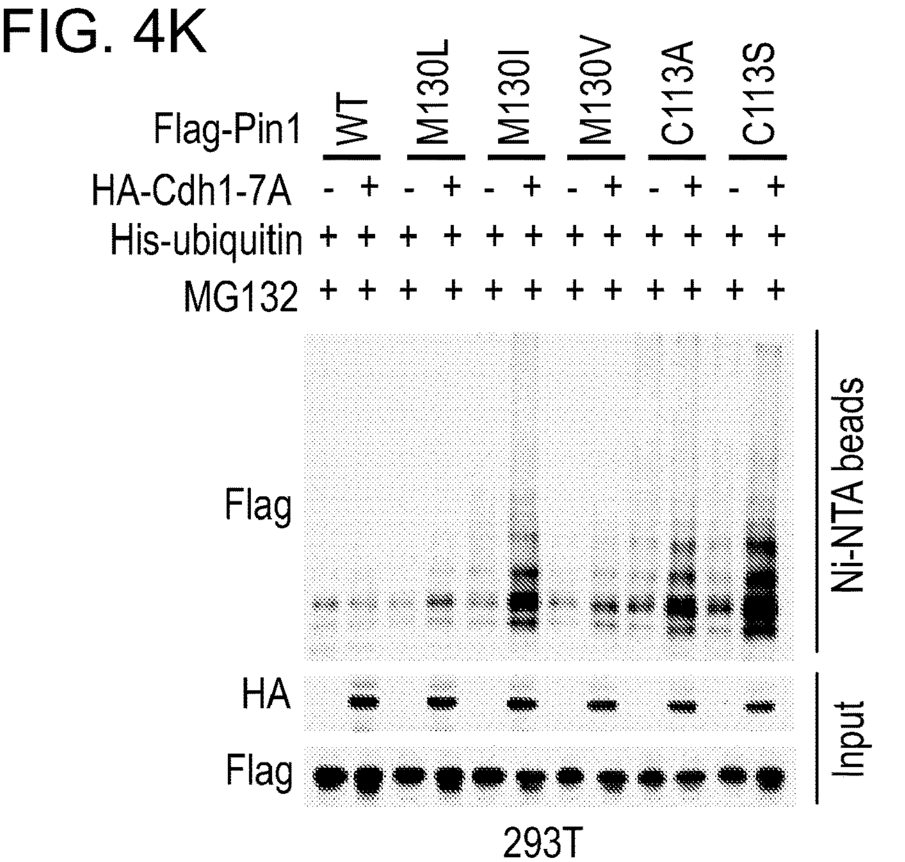
FIG. 4K-FIG. 4M is a set of immunoblots that show accelerated degradation of Pin1 with M130 or C113 mutations.
Figures 4L, 4M:
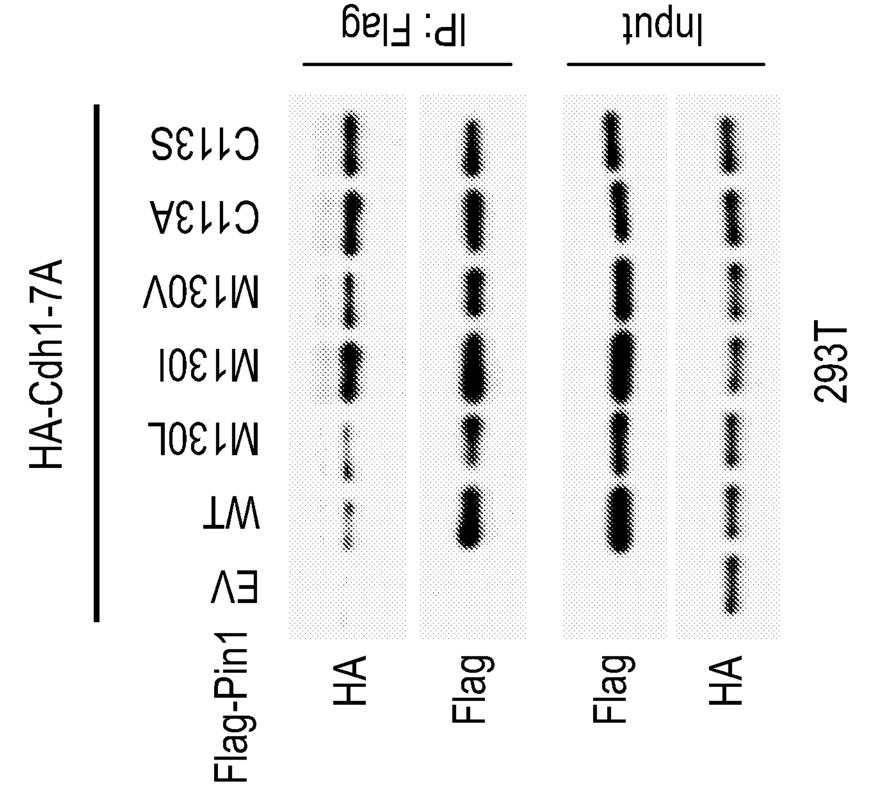

APC/$C^{Cdh1}$ E3 ubiquitin ligase activity is inhibited in cancer cells, likely due to hyperphosphorylation of Cdh1 induced by increased CDK kinase activity, subsequently resulting in decreased binding to the APC complex (Tamamori et al., Am J Physiol 1998; 275:H2036-40; Wan et al., Cancer Discov 2017; 7:42441; Kramer et al., Mol Biol Cell 2000; 11:1555-69). To examine the critical role of Cdh1 phosphorylation in APC activity, potential CDK phosphorylation sites that are also potential sites for prolyl isomerization, all of which are located at the N-terminus of Cdh1 flanking the C-box (FIG. 4C), were mutated. The C-box and KLLR (SEQ ID NO: 30) motifs are critical for Cdh1 association with the APC core complex. The C-terminal IR motif of Cdh1 mediates interaction with the TPR subunits APC7 and APC3. Ectopic expression of the phosphosite-deficient Cdh1-6A or -7A mutants which are able to bind the APC core and are constitutively active (Kramer et al., Mol Biol Cell 2000; 11:1555-69), but not Cdh1-WT, induced a senescence-like state in MDA-MB-231 (FIG. 4D) (Quantification of SA-β-gal positive cells (percent of total). Data in graphs are mean±s.d. analyzed by Unpaired two-sided t-test. * $P<0.001$) or MCF-7 cells (FIG. 5D) and a decrease of Pin1 protein abundance together with a noticeable decrease of other APC/$C^{Cdh1}$ substrates such as Plk1, Cdc20, Cyclin B1 in TNBC cell lines (FIG. 4E, FIG. 4F) (Data in graphs are mean #s.d. of 3 independent experiments, analyzed by Paired two-sided t-test.  $P<0.01$), and FIG. 5D-FIG. 5F), and Geminin, which could be blocked by proteasome inhibitor. Cdh1-7A mutants only had limited impacts on transcriptional levels of its substrates, but dramatically shortened the protein half-lives (data not shown). In agreement with the observation that Pin1 inhibitors induce Pin1 degradation, mutations of the Pin1 active site enhanced the interaction between Cdh1-7A and Pin1 and promoted Cdh1-7A-mediated Pin1 degradation and ubiquitination (FIG. 16A, FIG. 4K, FIG. 4L). These results reveal that APC/$C^{Cdh1}$ is likely the physiological E3 ubiquitin ligase for Pin1, and its activity is largely inhibited by phosphorylation of Cdh1 in tumor cells for uncontrolled proliferation.

Since Pin1 protein levels and APC/$C^{Cdh1}$ were negatively correlated, PIN1 was then knocked out to examine whether Pin1 not only is degraded by APC/$C^{Cdh1}$, but also whether it may inhibit APC/$C^{Cdh1}$ activity. Several Pin1 KO BC cell lines were established and it was found that Pin1 KO dramatically reduced cell viability in long-term clonogenic assays in both Rb-proficient and Rb-deficient BC cell lines (FIG. 21A). To further study the effects of Pin1 KO in cancer cells, RNA sequencing of three Pin1 KO BC cell lines was performed. Gene set enrichment analysis of biological process gene sets revealed a significant positive enrichment of immune response signature across all three Pin1 KO cell lines, and a significant decreased cell cycle signature in MCF-7 Pin1 KO cell line, but not the other two cell lines (FIG. 21B ((*$P<0.001$)), FIG. 21C). Global proteomic analysis of Pin1 KO in MDA-MB-231 cell line showed that Pin1 KO had noticeable effects on cell cycle progression (Kozono et al., Nat Commun 2018; 9:3069) (FIG. 21D). These data indicate Pin1 may affect cell cycle progression at both transcriptional and post-translational levels.

It was then discovered that Pin1 KO resulted in prolonged G1 phase and de-stabilization of APC/$C^{Cdh1}$ substrates across the cell cycle (FIG. 6A, FIG. 6B, FIG. 7D, FIG. 7E). To measure the effects of Pin1 KO more precisely on APC/$C^{Cdh1}$ activation kinetics in single cells, changes of the reporter levels during the cell cycle were analyzed by tracking MCF-7 wild-type or Pin1 KO single cells over 72 hours, reporter intensity in asynchronous cultures increased as a result of decreasing APC/$C^{Cdh1}$ activity (FIG. 22A left panel, blue) throughout S phase, leading right up to cell division (green). Pin1 KO led to reactivation of APC/$C^{Cdh1}$ along with G1 arrest reflected by starkly decreasing reporter intensity and cell division, or alternatively prolonged S/G2 phases in some cells, as expected because Pin1 has other substrates in the cell cycle (Zhou and Lu, Nat Rev Cancer 2016; 16:463-78) (FIG. 22A right panel, FIG. 22B, FIG. 22C (The error bar indicates 95% confidence interval determined by bootstrapping. Data in graphs are mean #s.d., analyzed by unpaired two-sided t-test. * P<0.001.)). To separate transcriptional regulation from post-translational to further confirm whether Pin1 regulated APC/$C^{Cdh1}$ E3 ligase activity directly, the protein stability of APC/$C^{Cdh1}$ substrates was detected and it was found that Pin1 KO pronouncedly decrease the half-lives of APC/$C^{Cdh1}$ substrates in both Rb-proficient and Rb-deficient cell lines (FIG. 22**D), thus Pin1 regulated APC/$C^{Cdh1}$ E3 ligase activity to control cell cycle progression. The graphs were one representative experiment out of three independent experiments.

To examine the underlying mechanisms of the reciprocal relationship between Cdh1 and Pin1, in vitro GST pull-down assays of either WT or phosphorylation-deficient Cdh1 were performed with full-length GST-Pin1, the isolated GST-WW and GST-PPIase domains. While Cdh1-WT bound Pin1 via the WW-domain, the phosphorylation-deficient Cdh1-7A bound to the Pin1 PPIase domain (FIG. 4G). To define the residues important for their interactions, co-IPs using a point mutation W34A in the Pin1 WW domain and a D-box motif mutation RLAA in the Pin1 PPIase domain as well as a dual mutation were performed. Consistent with GST pulldown assays, the W34A mutation prevented the Pin1 interaction with Cdh1-WT, as expected for all phosphorylation-dependent Pin1 substrate interactions (Zhou and Lu, Nat Rev Cancer 2016; 16:463-78), whereas the RLAA mutation within the PPIase domain did not interfere with the interaction with Cdh1-WT (FIG. 4H, left). However, Pin1-W34A still interacted with Cdh1-7A, indicative of a phosphorylation-independent interaction. Only mutations in the D-box motif in the Pin1 PPIase domain (RLAA) prevented the Pin1 interaction with Cdh1-7A, demonstrating that active Cdh1 interacts with the Pin1 D-box within the PPIase domain (FIG. 4H, right). In keeping with these findings, the RLAA mutation in Pin1, but not the W34 mutation, conferred resistance to Cdh1-7A-mediated Pin1 degradation (FIG. 4I (Non-specific bands for IgGH marked with asterisks (*)) and FIG. 3G), suggesting that activated Cdh1 can induce Pin1 degradation, likely through the RXXL motif (i.e., the D-box motif) in the Pin1 PPIase domain. To further support this model, M130A or C113A in the Pin1 PPIase domain, which are critical for the binding to the Pin1 inhibitors (Kozono et al., Nat Commun 2018; 9:3069; Dubiella et al., Nat Chem Biol 2021, 17, 954-63), were specifically mutated and found that these mutations enhanced the interaction between Cdh1-7A and Pin1 and promoted Cdh1-7A-mediated Pin1 degradation and ubiquitination (FIG. 4J-FIG. 4L). FIG. 4J shows the IB analysis for indicated proteins derived from MDA-MB-231 cells stably co-expressing phosphosite-deficient Cdh1 (Cdh1-7A) or empty vector (EV) in the presence of Flag-Pin1 and its mutants.

Figure 3J:
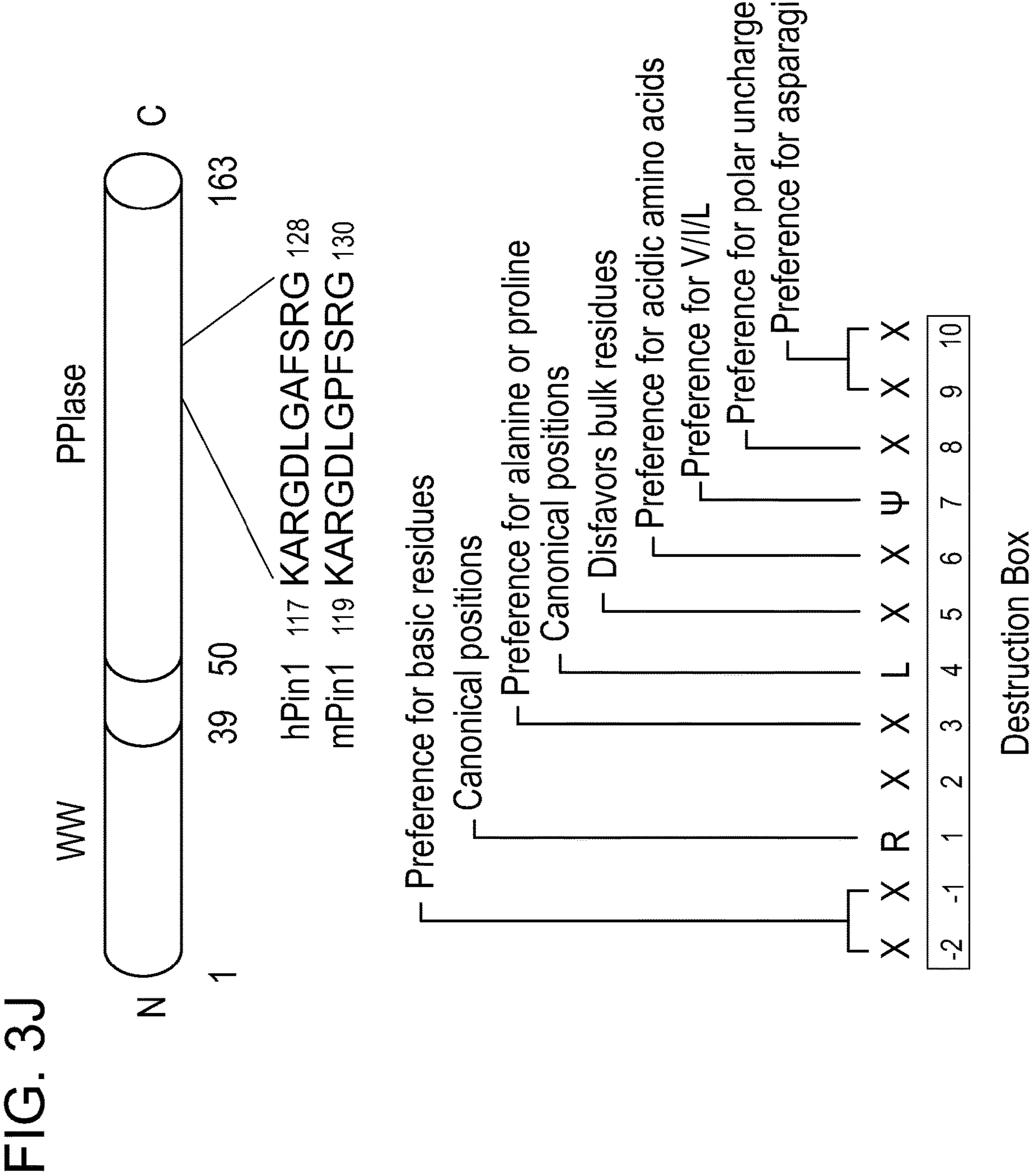
Figure 5H:
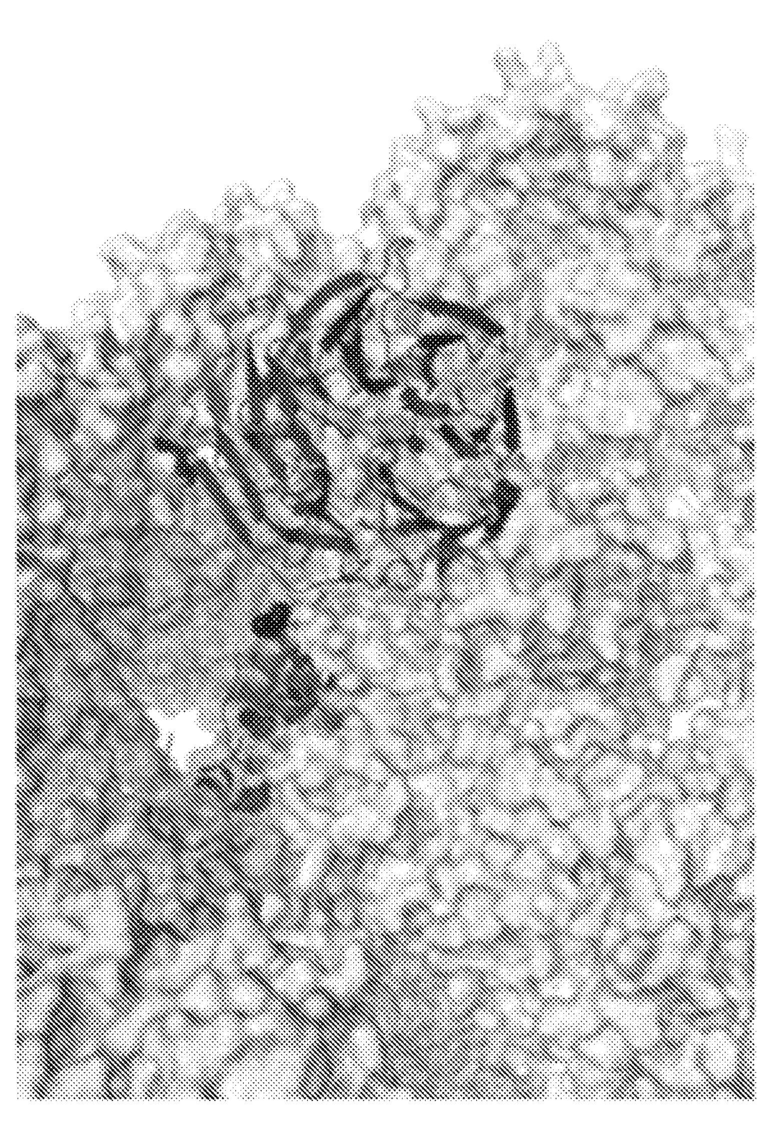
Figure 5J:
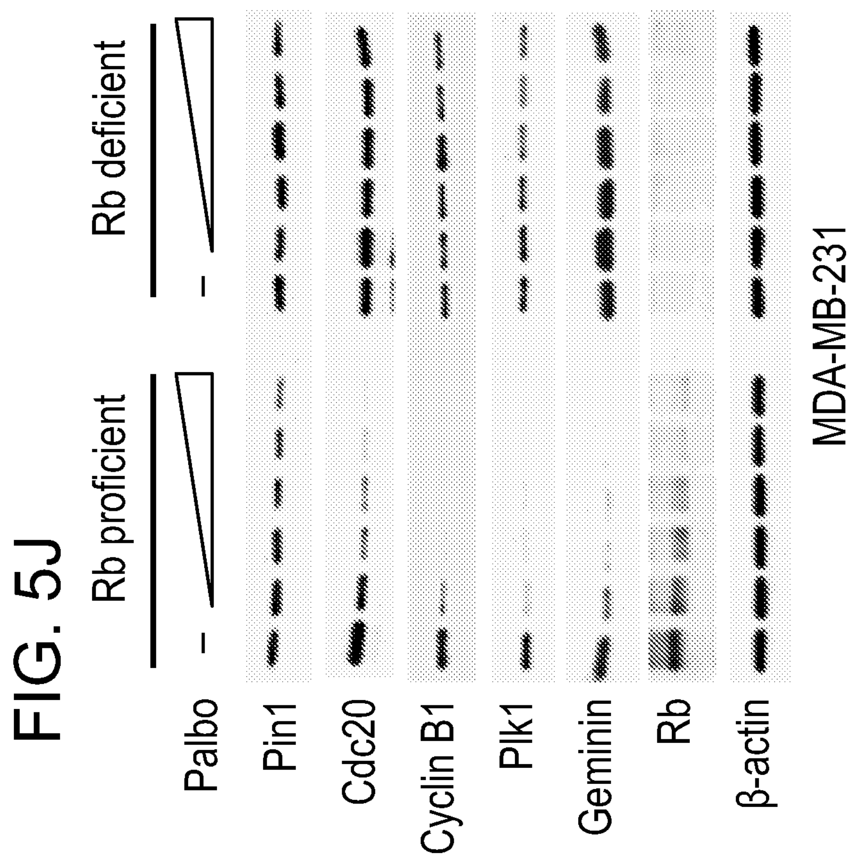

The above data suggest that the Pin1-Cdh1 interaction has two different functions. On the one hand, when phosphorylated in tumor cells, Cdh1 binds to the WW domain of Pin1, which in turn catalyzes prolyl isomerization to stabilize phosphorylated Cdh1 and promote its dissociation from the APC core (FIG. 5H), thereby rendering APC/$C^{Cdh1}$ inactive. On the other hand, when unphosphorylated and active, Cdh1 binds to the PPIase domain of Pin1 and targets Pin1 for degradation via its D-box motif. (FIG. 3J). Notably, this later interaction may be pharmacologically enhanced by Pin1 inhibitor engagement, which might be harnessed for developing a new strategy against cancer. Cdh1 shown in cartoon is composed of N-terminal domain $Cdh1^{NTD}$ and WD40 domain. $Cdh1^{NTD}$ (α-helix) interacts with APC core. Phosphorylation sites for Ser146, Ser151 and Ser163 are shown in blue spheres.

Figures 4N, 4O:
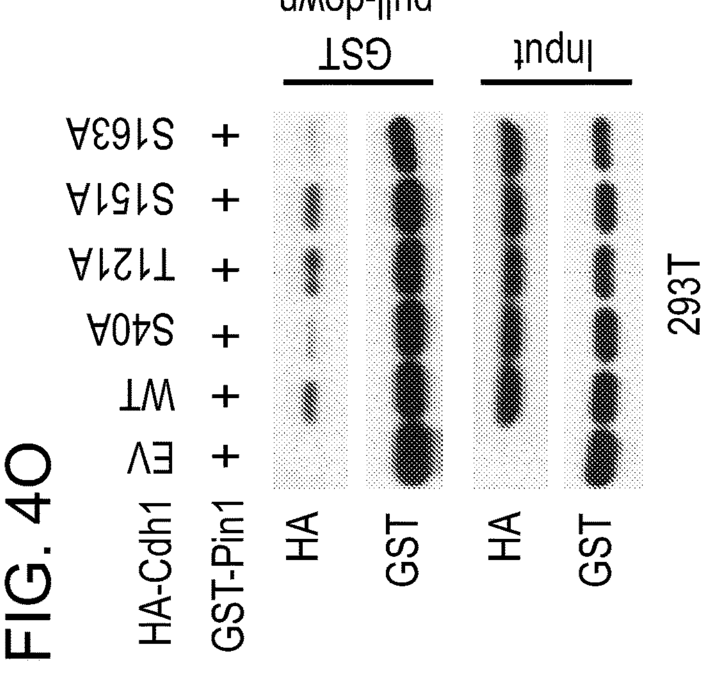
FIG. 4N is an immunoblot that shows that CDK4 physically interacts with Cdh1.
Figure 5I:
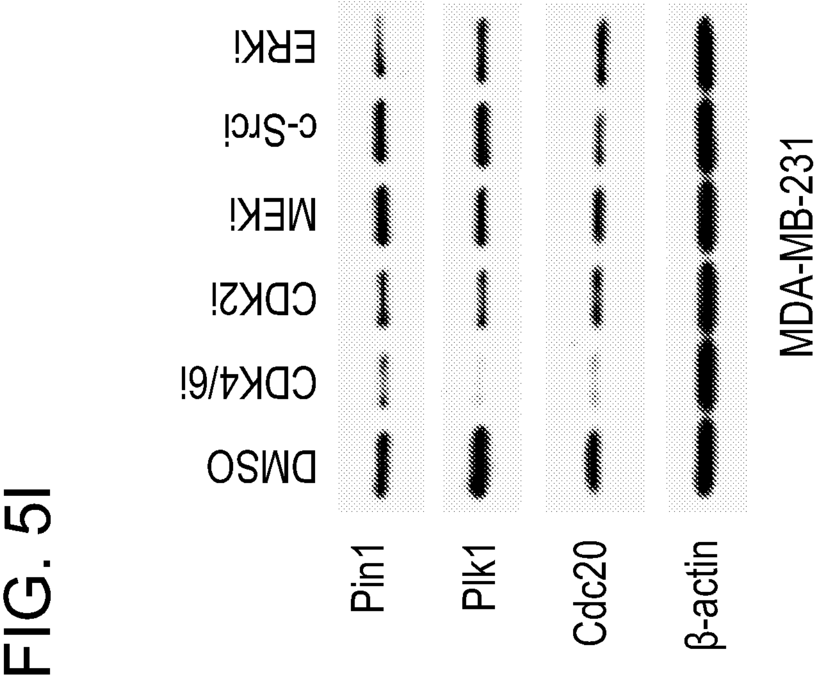

In the APC/$C^{Cdh1}$ complex, Cdh1 can be directly phosphorylated and inactivated by Cyclin A2/CDK2, Cyclin D1/CDK4/6 and ERK, resulting in its dissociation from the APC core complex (Cappell et al., Cell 2016; 166:167-80; Wan et al., Cancer Discov 2017; 7:42441). It was found that CDK2, CDK4 and CDK8, but not CDK6, strongly interacted with Cdh1 (FIG. 4M, FIG. 23A) and that CDK4 specifically phosphorylates Cdh1 at S163 (FIG. 4N), as a S→A mutation of S163 prevented Pin1 pulldown, presumably due to extinction of the Ser-Pro site at this location (FIG. 4N (293T cells were transfected with indicated constructs for 36 hrs. Input is 5% of the total lysates used in IP), FIG. 4O (The graphs were one representative experiment out of three independent experiments)). Among inhibitory candidate kinases for Cdh1 that can control APC/$C^{Cdh1}$ activity, inhibition of CDK4/6 with palbociclib significantly decreased the levels of both APC/$C^{Cdh1}$ known substrates and Pin1 (FIG. 5I). These results supported CDK4 as the predominant Cdh1 upstream kinase to inhibit APC/$C^{Cdh1}$ E3 ligase activity (FIG. 4M-FIG. 4O). Rb1-deficient cells, which upregulate the endogenous CDK4/6 inhibitor p16, were found to be resistant to palbociclib and resulted in compromised synergistic anti-proliferative effect (FIG. 5J-FIG. 5M) (Zhang et al., Nature 2018; 553:91-95). The graphs were one representative experiment out of three independent experiments. Collectively, these data demonstrate that active APC/$C^{Cdh1}$ targets Pin1 for degradation via interacting with the D-box motif in the Pin1 PPIase domain, but APC/$C^{Cdh1}$ E3 ligase activity is inhibited by CDK4-mediated phosphorylation of Cdh1 in tumor cells, thus APC/$C^{Cdh1}$ may function as a haploinsufficient tumor suppressor (Garcia-Higuera et al., Nat Cell Biol 2008; 10:802-11; Song et al., Cell 2011; 144:187-99).

To directly visualize Pin1 binding and isomerization of phosphorylated Cdh1, a Cdh1-pS163 peptide was synthesized and the interaction with Pin1 was mapped using nuclear magnetic resonance (NMR). FIG. 17A shows the average chemical shift perturbation in the Pin1 backbone amide resonances on the binding of the Cdh1 phosphopeptide. Data was acquired at pH 6.6 and 25° C. with 1:13 molar excess of the Cdh1 phosphorylated peptide shown. The perturbation data indicated that the Cdh1-pS163 peptide binds to the WW domain with moderately strong affinity (FIG. 17A). Pin1 residue R17 showed the strongest perturbation, and along with residues S18, Y23, W34 and E35 formed a continuous patch that interacts with phosphoserine, pS163, and the adjoining proline, P164. The experiment-guided model suggests that the phosphate group from pS163 has a charge: charge interaction with R17 while P164 stacks in the pocket formed by Y23 and W34 (FIG. 17B, FIG. 17C), as the phosphopeptide binding appears fast on the NMR timescale as seen by the movement of representative 15N-HSQC peaks from the backbone of R17, S18, W34, and E35, and the sidechain of W34. This was confirmed by GST pull-down assays using Pin1 point mutations (FIG. 1J). Interestingly, weak perturbation was observed in the PPIase domain active site, which may mediate Pin1-catalyzed isomerization of Cdh1-pS163 peptide. Specific $^{13}C$ enrichment of the P164 was used for direct quantitative measurement of the P164 isomerization states using a 2D-$^{13}C$ HSQC spectrum. The results showed that 7% cis-P164 isomer was present in the free peptide, but Pin1-catalyzed isomerization doubled this population to 14.2% (FIG. 17D). These results suggest that Pin1 binds to and catalyzes the cis trans prolyl-isomerization of the Cdh1-pS163-P motif, which may stabilize phosphorylated Cdh1 and render APC/$C^{Cdh1}$ inactive, as Cdh1 specific phosphatase would not engage with cis proline.

Example 4: Pharmacologic Inhibition of Pin1 and CDK4/6 Restores APC/$C^{Cdh1}$ E3 Ligase Activity As Pin1 recognizes and interacts with phosphorylated Cdh1 through the WW domain, the effects of Pin1 on the fate of phosphorylated Cdh1 and its effects by pharmacologic manipulations were examined. First, whether Cdh1's ability to prevent S-phase entry is regulated by Pin1-catalyzed isomerization was tested. Pin1 KO resulted in destabilization of APC/$C^{Cdh1}$ substrates across the cell cycle and prolonged G1 phase (FIG. 6A, FIG. 6B, and FIG. 7A-FIG. 7C). DNA contents were measured by FACS in Pin1+/+ and Pin1−/− MDA-MB-231 cells synchronized at the G1/S boundary by double thymidine block and then released back into the cell cycle for 4 hours.

To determine whether Pin1 not only is degraded by active APC/$C^{Cdh1}$, but also whether it may inhibit APC/$C^{Cdh1}$ activity in a reciprocal mechanism, the effects of Pin1 KO on the fate of phosphorylated Cdh1 were examined. It was found that Pin1 KO dramatically reduced Cdh1 phosphorylation, but promoted the binding of Cdh1 to APC complex, which was enhanced by palbociclib (FIG. 23B). It was found that Pin1 inhibition, that is, the prevention of prolyl-isomerization, led to dephosphorylation of Cdh1, which reduced binding to the Pin1 WW domain, but increased binding to the Pin1 PPIase domain (FIG. 6K, FIG. 1K, FIG. 1L, FIG. 3I). The change of binding modes suggests Pin1 switches from being an upstream regulator to a downstream substrate of Cdh1. Through this mechanism, treatment with inhibitors of Pin1 or CDK4/6 reactivated APC/$C^{Cdh1}$ as assessed by the decrease of surrogate markers Plk1 and Cyclin B1 as well as Pin1 in MDA-MB-231 and MCF-7 cells, which was largely rescued by Cdh1 KO (FIG. 6O, FIG. 7I, FIG. 7J, FIG. 6N). Moreover, combining the Pin1 inhibitor with the CDK4/6 inhibitor caused a more pronounced activation of APC/$C^{Cdh1}$ and Pin1 poly-ubiquitination (FIG. 6M, FIG. 6L).

To assess the impact of Pin1- and CDK4/6-inhibition on APC/$C^{Cdh1}$ activity in individual BC cells, MCF-7 stably expressing the Fucci reporter system was used with mCherry-conjugated to a Geminin fragment containing the APC/$C^{Cdh1}$ degron motif (RXXL) (FIG. 7D) (Cappell et al., Cell 2016; 166:167-80). In this experimental model, changes of the reporter signal directly reflect APC/$C^{Cdh1}$ E3 ligase activity, allowing for a real-time tracking of the activity of APC/$C^{Cdh1}$ at the single cell level (Cappell et al., Cell 2016; 166:167-80). MCF-10A cells were synchronized in G1 followed by releasing back into the cell cycle. Pin1 levels were strongly correlated with APC-degron reporter levels across the cell cycle (FIG. 24A). That overexpression of Pin1 potently inhibited APC/$C^{Cdh1}$ activity, was confirmed, as determined by the levels of APC degron and other $APC^{Cdh1}$ substrates in the absence or presence of the CDK4/6 inhibitor (FIG. 6C (IB analysis for indicated proteins from MCF-7 cells stably co-expressing the APC-degron reporter (mCherry-Geminin (1-110)) and empty vector (EV) or Flag-Pin1 and treated with increasing concentrations of palbociclib (0.5, 1, 2 μM) for 48 hours), FIG. 6D). Furthermore, when cells were treated with the CDK4/6 and Pin1 inhibitors and changes of the reporter levels were analyzed during the cell cycle by tracking single living cells over 72 hours, reporter intensity in asynchronous cultures increased as a result of decreasing APC/$C^{Cdh1}$ activity (FIG. 6E, left panel, intensity in blue) throughout S phase, leading right up to cell division (green). CDK4/6 inhibition caused activation of APC/$C^{Cdh1}$ as evidenced by starkly decreased reporter intensity and cell cycle arrest (FIG. 6E, middle panel). A few cells, presumably those that had already passed the G1/S checkpoint at the time when palbociclib was administered, proceeded to complete another cell division after addition of the CDK4/6 inhibitor, and none had multiple divisions. Hence, CDK4/6 inhibition caused an immediate reactivation of APC/$C^{Cdh1}$ reflected by decreasing reporter intensity along with G1 arrest, rather than cell death. Asynchronous cultures of MCF7 cells expressing the APC-degron reporter were followed for 4 days (96 hours) for single cell expression of mCherry-Geminin (shades of blue), mitosis (green), cell death (dark rhomboid).

In contrast, both Pin1 inhibitors (sulfopin and AApin) led to strikingly prolonged S/G2 phases (FIG. 6E, FIG. 6F), ending in cell death (FIG. 6E, right panel, black rhomboid) in some cells, or alternatively, a reactivation of APC/$C^{Cdh1}$ to induce G1 arrest (FIG. 6G (The error bar indicates 95% confidence interval determined by bootstrapping. Data in graphs are mean±s.d., analyzed by Unpaired two-sided t-test.  $P<0.01$, * $P<0.001$), FIG. 7E), indicating that Pin1 inhibition, different from CDK4/6 inhibition, has broad activity to arrest cells both in G1 and during mitosis.

To further confirm that Pin1 and CDK4/6 inhibitors directly reactivated APC/$C^{Cdh1}$, CDH1 was knocked out in both Rb-proficient and Rb-deficient BC cell lines. As expected, Pin1 and CDK4/6 inhibitors consistently decreased the protein levels of surrogate markers such as Cyclin B1 and Geminin as well as Pin1 in multiple cell lines, which were largely rescued by Cdh1 KO (FIG. 25A-FIG. 25F). Pin1 and CDK4/6 inhibitors also affected transcriptional levels in MDA-MB-231 cells, but not in MDA-MB-468 cells (FIG. 25B-FIG. 25F). To separate transcriptional regulation from post-translational one, we detected protein stability by cycloheximide chase assays. Cdh1 KO significantly prolonged the protein half-lives of Pin1 and APC/$C^{Cdh1}$ substrates with or without Pin1 and CDK4/6 inhibitors treatment (FIG. 25G, FIG. 25H (The graphs were one representative experiment out of three independent experiments.)). Moreover, combining the Pin1 inhibitor with the CDK4/6 inhibitor caused a more pronounced Pin1 poly-ubiquitination, which was diminished by Cdh1 KO (FIG. 25I).

Strikingly, the combination of the CDK4/6 inhibitor and Pin1 inhibitor caused a more pronounced activation of APC/$C^{Cdh1}$ and G1 arrest (FIG. 7F). To confirm these findings, the relationship of Pin1 and APC-degron reporter levels and cell cycle were analyzed by flow cytometry and treatment with Pin1 inhibitors was found to show a significant decrease of Pin1 and Geminin levels, corresponding to an increase of G1 arrested cells (FIG. 6H (DNA were labeled with Hoechst live cell dye. Y-axis, mCherry-Geminin; X-axis, DNA; color code of dots, Pin1 levels, FIG. 6I (Data in graphs are mean±s.d., analyzed by Unpaired two-sided t-test. * $P<0.05$,  $P<0.01$, * $P<0.001$)). Consistently, the Pin1 inhibitor induced Pin1 degradation together with other APC/$C^{Cdh1}$ substrates and G1 arrest (FIG. 6J, FIG. 7G, FIG. 7H). To investigate the mechanism of APC/$C^{Cdh1}$ activation by Pin1 inhibition, phosphorylation of Cdh1 was examined and Pin1 inhibitors were found to significantly decrease phosphorylation of Cdh1, resulting in reduced interaction with Pin1-WW domain and initiating the switch mechanism in which Cdh1 transited from a downstream substrate of Pin1 to an upstream degrader of Pin1 (FIG. 6K (HA-Cdh1-

7A expressed MDA-MB-231 cells were used along with a control), FIG. 1K, FIG. 1L). Moreover, treatment of Pin1 inhibitors induced Pin1 degradation through Cdh1-mediated poly-ubiquitination as with other APC/$C^{Cdh1}$ substrates (FIG. 6L). Cdh1 KO largely rescued the effects of Pin1 inhibitors to control levels and strongly reduced the efficacy of Pin1 and CDK4/6 inhibition as assessed by the stability of surrogate markers Plk1 and Cyclin B1 (FIG. 6M-FIG. 6O (IB analysis for indicated proteins derived from Cdh1+/+ and Cdh1−/− MCF-7 cells treated with increasing concentrations of palbociclib (0.5, 1, 2, 4 μM) (FIG. 6N) or AApin (ATO (0.5, 1, 1.5, 2 μM) plus ATRA (5, 10, 15, 20 μM) in 1:10 ratio) (FIG. 6M) or a combination of palbociclib and AApin (FIG. 6O) for 3 days. The graphs were one representative experiment out of three independent experiments) and FIG. 7I-FIG. 7L (Cells were treated with indicated drugs for 3 days and cell viability were assessed by CellTiter-Glo. Data in graphs are mean±s.d., analyzed by Unpaired two-sided t-test. *** P<0.001, ns, not significant. The graphs were one representative experiment out of three independent experiments)). Thus, these results indicate that APC/$C^{Cdh1}$ likely acts as a tumor suppressor, whose E3 ligase activity is inhibited by Pin1-catalyzed isomerization of Cdh1 after CDK4-mediated phosphorylation for unchecked cell-cycle progression. So, inhibition of both Pin1 and CDK4/6 restores APC/$C^{Cdh1}$ E3 ligase activity, which in turn degrades Pin1, creating a negative feedback loop between Pin1 and APC/$C^{Cdh1}$ and inducing insurmountable G1 arrest.

Example 5: Pin1 Inhibitors Synergize with CDK4/6 Inhibitors Against TNBC in Cell Models Selective CDK4/6 inhibitors have emerged as effective BC treatment (Sherr et al., Cancer Discov 2016; 6:353-67; O'Leary et al., Nat Rev Clin Oncol 2016; 13:417-30). However, most patients will achieve only partial remissions and eventually experience progression of the disease, indicative of primary and secondary resistance mechanisms (Knudsen and Witkiewicz, Trends Cancer 2017; 3:39-55; Pernas et al., Ther Adv Med Oncol 2018; 10:1758835918786451; Alvarez-Fernandez and Malumbres, Cancer Cell 2020; 37:514-29). To examine the factors contributing to sensitivity or resistance to CDK4/6 inhibitors, data from the Genomics of Drug Sensitivity in Cancer (GDSC) database (Yang et al., Nucleic Acids Res 2013; 41: D955-61) was analyzed. It was found that cancer cell lines harboring certain mutations or copy number alterations such as loss or inactivating mutations in RB1, amplification of CCNE1 or deleterious BRCA1 mutations were relatively more resistant to palbociclib. In contrast, cancer cell lines with mutations leading to the activation of RAS signaling or loss of CDKN2A were more sensitive to palbociclib (FIG. 9A). FIG. 9A is a volcano plot generated in VolcaNoseR that shows palbociclib sensitivity data from GDSC1 dataset. Each circle represented an association between genomic markers and palbociclib sensitivity analyzed using ANOVA. The limitation of CDK4/6 inhibitors underscores the urgent need to develop strategies to treat breast cancer.

These findings pinpointed CDK4 as Cdh1 upstream kinase to inhibit APC/$C^{Cdh1}$ E3 ligase activity and revealed the reciprocal inhibitory mechanism of Pin1-Cdh1. Thus, investigating the therapeutic advance of combination of Pin1 inhibitors and CDK4/6 inhibitors was initiated. To assess the synergistic effects, in vitro combination experiments were conducted in TNBC cell lines MDA-MB-231 and SUM-159 with matrices of palbociclib (CDK4/6 inhibitor) and sulfopin (highly selective Pin1 inhibitor). The combination of palbociclib and sulfopin resulted in a synergistic anti-proliferative effect in both cell lines (FIG. 8A, FIG. 8B, FIG. 9B, FIG. 9C). Then, the endogenous Pin1 protein levels corresponding to the drug matrices were examined. As expected, palbociclib and sulfopin cooperatively ablated Pin1 protein abundance, which correlated with the anti-proliferative effect in this combination (FIG. 8C, FIG. 8D). Similarly, the combination of palbociclib and sulfopin or AApin synergistically decreased TNBC cell viability in 3D-spheroids (FIG. 8E). Consistently, the anti-proliferative effects of Pin1- and CDK4/6-inhibitors were associated with a substantial induction of senescence and apoptosis, as well as a decrease in cell viability in TNBC and ER+ cell lines (FIG. 8F-FIG. 8H and FIG. 9D-FIG. 9G). Thus, Pin1 inhibitors synergized with CDK4/6 inhibitors resulting in effective response in TNBC.

Example 6: Pharmacologic Inhibition of Pin1 and CDK4/6 Boosts Anti-Tumor T Cell Activity and Immune Checkpoint Inhibitor Response in Syngeneic TNBC Mouse Models Both CDK4/6 and Pin1 are ubiquitously expressed enzymes, including in the tumor microenvironment (TME) (Goel et al., Nature 2017; 548:471-75; Choi et al., Biochem Biophys Res Commun 2020; 533:995-1003). Given the findings of immune activation in Pin1-low tumors (FIG. 2B), its efficacy in an immune competent host was explored. Hence, a mouse model of immune-competent aggressive TNBC derived from a mouse model of BRCA1-related cancer (Liu et al., Proc Natl Acad Sci USA 2007; 104:12111-6) through back breeding onto the FVB/N background was chosen. This model is heterozygous for p53 and BRCA1 (Table 1), hence resembling aggressive human triple-negative breast cancer with growth of highly proliferative and poorly differentiated mammary carcinomas in syngeneic FVB/N mice (FIG. 11A (Scale bars, 100 (top) and 50 μm (bottom)). Hence, two cohorts of immune-competent genetically engineered TNBC mouse models were generated: Brca1-deficient cohort, K14cre; $p53^{f/f}$; Brca1f/f, and Brca1-proficient cohort, K14cre; $p53^{wt/f}$; $Brca1^{wt/f}$ (Table 1). These mouse models resembled aggressive human TNBC with growth of highly proliferative and poorly differentiated mammary carcinomas in syngeneic immune-competent recipients (FIG. 20A and FIG. 20B). To ascertain the suitability of the model for this approach, its immune landscape was analyzed using cytometry by time-of-flight (CyTOF).

TABLE 1

| Genotyping results for CRE BRCA1 P53 transgenic mice | | |
|---|---|---|
| Primer and Probe sequences | | |
| BRCA Flox F | GGGATCCACTAGTTCTAGTTAGAGCGG | SEQ ID NO: 15 |
| BRCA Flox R | CCAGGGCTCTTAATCCAATCATTCTCCA | SEQ ID NO: 16 |

TABLE 1-continued

| Genotyping results for CRE BRCA1 P53 transgenic mice | | | | | |
|---|---|---|---|---|---|
| BRCA Flox probe | CAGAGAGCCTGTCTCAA | | | | SEQ ID NO: 17 |
| BRCA WTF | TGGGCTTGCTGACTAGTTATTACAG | | | | SEQ ID NO: 18 |
| BRCA WTR | GCTCTTAATCCAATCATTCTCCACCTTATTT | | | | SEQ ID NO: 19 |
| BRCA WT probe | CAAGCCCCGGGTGCAG | | | | SEQ ID NO: 20 |
| P53 Flox F | CGTATAATGTATGCTATACGAAGTTATCTGCAGCCCG | | | | SEQ ID NO: 21 |
| P53 Flox R | GGCACCTTTGATCCCAGCACA | | | | SEQ ID NO: 22 |
| P53 Flox Probe | TCCAACTGTCTCTGCCTC | | | | SEQ ID NO: 23 |
| P53 Wt F | CAGCAGTAACCTCCTGGGAATACTTCA | | | | SEQ ID NO: 24 |
| P53 Wt R | CTCAGGAAAACAAATTATGATTCGAAC | | | | SEQ ID NO: 25 |
| P53 WT Probe | CAGTCAGTCGCCCTTTC | | | | SEQ ID NO: 26 |
| Translated Result | CRE | BRCA1_FLOX | BRCA1_WT | P53_FLOX | P53_WT |
| cross-breed | + | + | + | + | + |

A 19-marker panel was designed to identify tumor cells and the major tumor infiltrating immune cell subtypes (Table 2).

TABLE 2

Panel Markers for CyTOF

| Reactivity (target species) | Mass cytometer instrument | Channel_min (lowest detection range) | Channel_max (highest detection range) | Product_id | Label (metal channel) | Signal value from the TDS for Ab | Target/ marker of the Ab) | Ab Clone | Updated at | Catalog (FDM = Fluidigm) | Tolerance values from the TDS for Ab |
|---|---|---|---|---|---|---|---|---|---|---|---|
| Mouse | Helios | 75 | 209 | 3151007B | 151Eu | 65 | CD25 (IL-2R) | 3C7 | | FDM | 13 |
| Mouse | Helios | 75 | 209 | 3152004B | 152Sm | 105 | CD3e | 145-2C11 | | FDM | 21 |
| Mouse | Helios | 75 | 209 | 3176002B | 176Yb | 136 | CD45R (B220) | RA3-6B2 | | FDM | 27 |
| Mouse | Helios | 75 | 209 | 3170002B | 170Er | 174 | CD161 (NK1.1) | PK136 | Feb. 23, 2021 16:31 | FDM | 35 |
| Mouse | Helios | 75 | 209 | 3142003B | 142Nd | 201 | CD11c | N418 | | FDM | 40 |
| Mouse | Helios | 75 | 209 | 3148003B | 148Nd | 340 | CD11b (Mac-1) | M1/70 | | FDM | 68 |
| Mouse | Helios | 75 | 209 | 3146003B | 146Nd | 282 | CD8a | 53-6.7 | | FDM | 57 |
| Mouse | Helios | 75 | 209 | 3145002B | 145Nd | 58 | CD4 | RM4-5 | | FDM | 12 |
| Mouse | Helios | 75 | 209 | 3155011B | 89Y | 467 | CD45 | 30-F11 | | FDM | 94 |
| Mouse | Helios | 75 | 209 | 3141005B | 141Pr | 1070 | Ly-6G/C (Gr-1) | RB6-8C5 | | FDM | 214 |
| Mouse | Helios | 75 | 209 | 3153016B | 153Eu | 37 | CD274 (PD-L1) | 10F.9G2 | | FDM | 8 |
| Mouse | Helios | 75 | 209 | 3154008B | 154Sm | 7 | CD152 (CTLA-4) | UC10-4B9 | | FDM | 3 |
| Mouse | Helios | 75 | 209 | 3158003A | 158Gd | 63 | FoxP3 | FJK-16s | | FDM | 13 |
| Mouse | Helios | 75 | 209 | 3159024B | 159Tb | 107 | CD279 (PD-1) | 29F.1A12 | | FDM | 21 |
| Mouse | Helios | 75 | 209 | 3173006B | 173Yb | 719 | Granzyme B | GB11 | Feb. 10, 2021 19:28 | FDM | 114 |
| Mouse | Helios | 75 | 209 | 3144016B | 144Nd | 106 | MHC Class I | 28-14-8 | | FDM | 21 |
| Mouse | Helios | 75 | 209 | 3166014B | 166Er | 1191 | CD326 (EpCAM) | G8.8 | | FDM | 238 |
| Mouse | Helios | 75 | 209 | 3165003B | 165Ho | 76 | IFNg | XMG1.2 | | FDM | 3 |
| Mouse | Helios | 75 | 209 | 3162012B | 162Dy | 1000 | Ki-67 | B56 | | FDM | 200 |

Two-dimensional maps of the data for a comprehensive view of the tumor-immune ecosystem were generated using the dimensionality reduction algorithm UMAP (Becht et al., Nat Biotechnol 2018; doi: 10.1038/nbt.4314). Tumor cells were the main population with a mean of 30% across samples and distinct from tumor-infiltrating leukocytes (TILs) (FIG. 10A), which were characterized by EpCAM and CD45, respectively. Heterogeneity of the markers was visualized. Levels of Ki67 in tumor cells were decreased after combination treatment (FIG. 11B). Further analysis was focused on CD45+ cells, which led to the identification of ten phenotypes of TILs (FIG. 10B). The expression profiles of the CD45+ cells were visualized in a heatmap (FIG. 12A). To gain a greater understanding of the relationships of 19 parameters, especially the relationships of functional markers and phenotypic markers, pairwise Spearman correlation coefficients were calculated, hierarchically clustered, and organized on a heatmap. Pairwise predominantly positive correlations were observed between several functional markers (in red) and phenotypic markers (in black), indicating cell type-dependent functionality (FIG. 12B). PD-L1 was expressed variably in the majority of TILs, both lymphoid and myeloid, and in tumor cells. Notably, no obvious changes of PD-L1 expression were observed after treatment (FIG. 11B, FIG. 12C).

The subtypes of CD45+ cells from different treatments were displayed in separated UMAPs (FIG. 10C). PD-L1 was most highly expressed in myeloid cells. PD-1 was tightly correlated on both CD8+ T cells and CD4+ T cells. IFN-γ was restricted to neutrophils and Granzyme B was mainly expressed in CD8+ and undefined T cells. (FIG. 12C). CyTOF analysis showed a significant decrease in the number of proliferating tumor cells after combination treatment. Notably, increased percentage of infiltrating CD8+ T cells, CD4+ T cells, EpCAM+ Macrophages and B cells were observed in the combination group, but not with either monotherapy (FIG. 10D). In contrast, regulatory T-cells (Tregs) and dendritic cells were decreased in the combination group, whereas the percentage of NK cells and expression of PD-L1 and Granzyme B were unaffected (FIG. 10D, FIG. 12D). Taken together, CyTOF data demonstrated that treatment with the combination of sulfopin and abemaciclib reprogrammed the tumor microenvironment towards an anti-tumor profile with decreased Tregs, increased cytotoxic T-cells and evidence for tumor cell phagocytosis (EpCAM+ Macrophages) (FIG. 10D).

To further support these findings, the anti-tumor activity of sulfopin and abemaciclib in this highly proliferative immunocompetent genetically engineered mouse model of TNBC were studied, which showed no response to chemotherapy (data not shown) and resistance to CDK4/6 and PARP inhibitors due to heterozygous state of BRCA1 (Pathania et al., Nat Commun 2014; 5:5496; Konishi et al., Proc Natl Acad Sci USA 2011; 108:17773-8), and explored further enhancement of the cytotoxic T-cell response through added blockade of PD-L1. A total of 86 FVB/N mice were grafted syngeneically with the K14cre; Brca1$^{+/-}$; p53"/tumors. Tumors were allowed to grow to 100-200 mm$^3$, prior to randomization. Treatment with sulfopin combined with abemaciclib was well-tolerated, significantly delayed tumor progression and increased survival compared to either monotherapy (FIG. 10E, FIG. 13A-FIG. 13D). Tumors were implanted in syngeneic FVB/N mice. Tumors were allowed to grow to 100-200 mm$^3$ prior to initiation of treatments as indicated. Time to mandatory euthanasia (tumor size 2 cm) was recorded. Survival curve generated from mice bearing K14cre; Brca1$^{+/-}$; p53$^{-/-}$-TNBC, treated with vehicle (n=7; median survival 20 days), sulfopin (n=12; median survival of 22.5 days), abemaciclib (n=12; median survival of 31 days) or a combination of the two drugs (n=12; median survival of 40.5 days). Anti-PD-L1 therapy further enhanced the efficacy of the combination of the two drugs and improved median survival from 20 to 46 days over control (FIG. 10F, FIG. 13E-FIG. 13H) for example, treatment as follows: anti programmed death-ligand 1 (anti-PD-L1) (n=7; median survival of 16 days), sulfopin plus anti-PD-L1 (n=12; median survival of 25 days), abemaciclib plus anti-PD-L1 (n=12; median survival of 33.5 days) or their triple combination (n=12; median survival of 46 days). Statistical significance was calculated using a two-sided log-rank test. These data confirm the in vivo synergy as predicted by the in vitro data (FIG. 8).

To further study the mechanism of anti-tumor immune response induced by combination treatment, RNA sequencing of Brca1-proficient tumors was performed, after treatment with sulfopin, abemaciclib or their combination. The heatmap of gene set enrichment analysis of biological process showed that the combination treatment had a larger effect on the gene sets of immune response signature and cell cycle signature. The gene set enrichment analysis revealed a more significant positive enrichment of adaptive immune response and enhanced tumor antigen presentation upon combination treatment compared with single-drug treatment, which was consistent with the CyTOF data, suggesting combination treatment increased tumor immunogenicity (FIG. 26A, FIG. 26B).

To determine the contribution of enhanced adaptive immunity on the effects of combination treatment, the anti-tumor activity of sulfopin and abemaciclib or palbociclib in immune-competent and immune-compromised mice, respectively was studied. Treatment with sulfopin combined with abemaciclib or palbociclib was well-tolerated, significantly delayed tumor progression and increased overall survival compared to either monotherapy in both of Brca1-proficient and Brca1-deficient cohorts (FIG. 18C, FIG. 18D, FIG. 27A, FIG. 27B, FIG. 18A, FIG. 18B). Combination treatment in immune-competent mice showed stronger synergistic anti-tumor effects than that in immune-compromised mice (FIG. 18C, FIG. 27C (*P<0.01, ** P<0.0001.), FIG. 27A). Effective anti-tumor activity of combination treatment in the Rb-deficient mouse tumor model was also observed, although to a lesser extent than that in the Rb-proficient mouse tumor model (FIG. 27C, FIG. 27D, FIG. 27**E (*P<0.05,  P<0.01, * P<0.001.)). Collectively, the pre-clinical activity of this regimen and its excellent safety profile with non-overlapping toxicity profiles make it a strong candidate for clinical development.

Example 7: Pin1 Inhibitors Synergize with CDK4/6 Inhibitors Against TNBC in PDOX Models The above results led to the proposal of the following model: APC/C$^{Cdh1}$ actively stabilizes the G1 phase by targeting mitotic cyclins and Pin1 for degradation. But as CDK4/6 activity garners momentum at the end of G1, Cdh1 is phosphorylated and becomes a substrate, rather than a regulator, of Pin1. The conformational change afforded by Pin1 catalyzed prolyl-isomerization stabilizes phosphorylated Cdh1, subsequently promotes its dissociation from APC core and renders APC/C$^{Cdh1}$ inactive, promoting S-phase entry (FIG. 14A). Pin1 inhibition abolishes prolyl isomerization of phosphorylated Cdh1 and cooperates with CDK4/6 inhibitors to reduce Cdh1 phosphorylation, leading to re-activation of the APC/C$^{Cdh1}$, which in turn targets Pin1 for degradation via its D-box motif, thereby creating insurmountable G1 arrest until tumor cell death. Combining Pin1 inhibitor and CDK4/6 inhibitor triggers an irreversible reactivation of APC/$C^{Cdh1}$, creating a negative feedback loop between Pin1 and APC/$C^{Cdh1}$ (FIG. 14B).

Figures 5K, 5L:
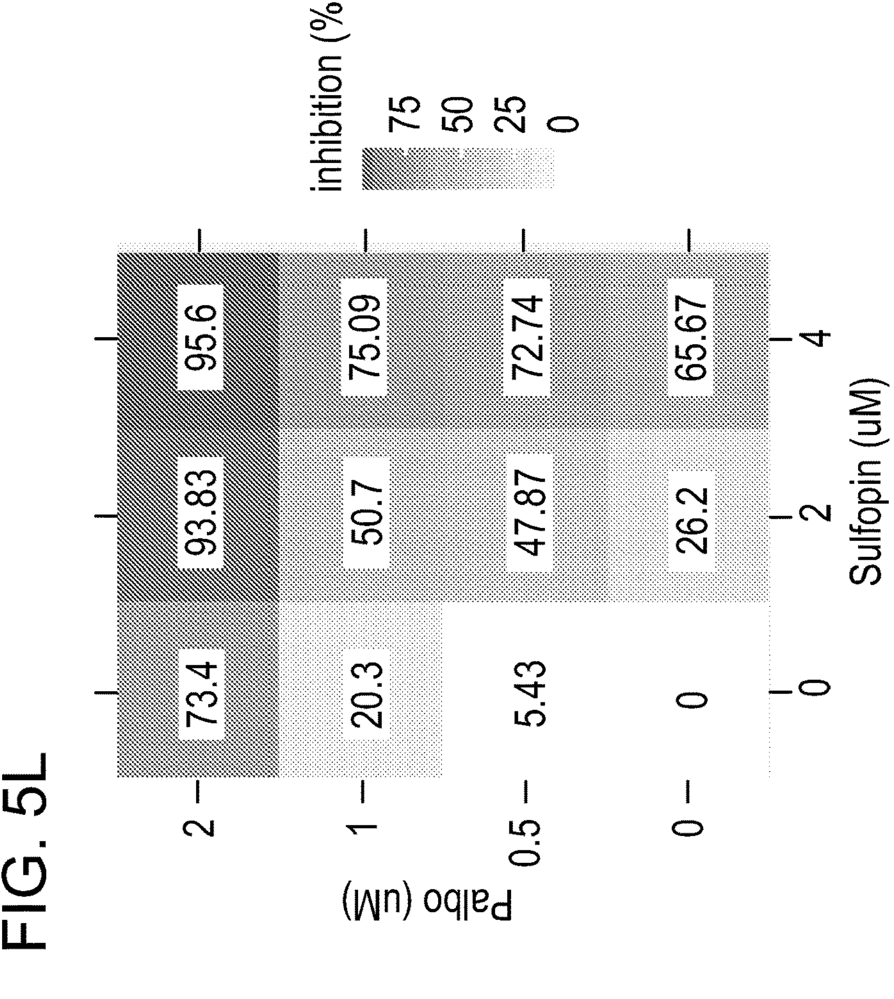
Figure 5M:
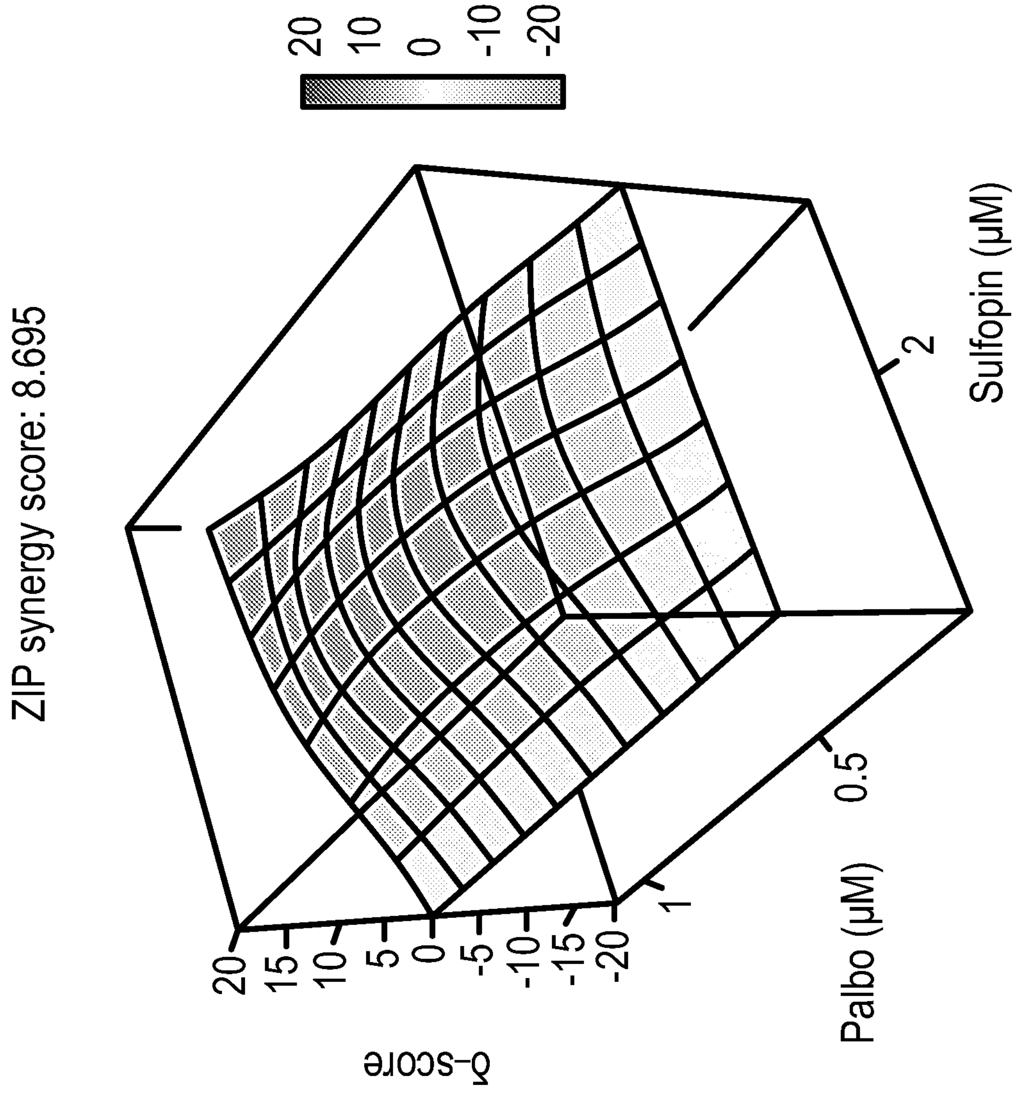

To gain structural insight into the interaction between the D-box of Pin1 and the WD40 domain of Cdh1, a docking model of the complex was generated using HADDOCK (FIG. 14C), based on the available structures of Pin1 (PDB: 1PIN) (Ranganathan et al., Cell 1997; 89:875-86) and the WD40 domain of Cdh1 (PDB: 4UI9_R) (Chang et al., Nature 2015; 522:450-54). D-box motif is marked in red. The molecular modeling suggested that the formation of the electrostatic interaction between R119 of the PPIase domain with the Cdh1 residues D180 and E465 drives a conformational change of the second β-strand of Pin1 PPIase domain, leading to L122 of the PPIase domain swinging in the hydrophobic pocket formed by Cdh1 residues L179, A181 and L467. Residues K117 and G123 of the PPIase domain mediated hydrogen bonds with the backbone of V219 and the side chain of W212, respectively (FIG. 14D). These modeling results further support the findings that the D-box in the Pin1 PPIase is critical for Cdh1 to interact with Pin1 and to target Pin1 degradation by APC/$C^{Cdh1}$ (FIG. 4G-FIG. 4I). The Pin1 PPIase domain in sulfopin complex closely resembles free PIN1 with a Root Mean Square Deviation (RMSD) of 0.231 Å. Notably, K117 is one of the very few residues that have significant different conformation between free Pin1 and Pin1-sulfopin complex (FIG. 15A), which are also consistent with the findings that sulfopin binding enhances Pin1 interaction with Cdh1 and eventually promotes ubiquitin-mediated proteasome degradation of Pin1 (FIG. 1L, FIG. 5L).

To further confirm whether the in vitro findings can be translated in vivo for antitumor treatment, a TNBC patient-derived orthotopic xenograft (PDOX) was used to evaluate the anti-tumor efficacy of the two-drug regimen. The TNBC PDOX was Rb-proficient and reached endpoint about 6 weeks post implantation. Sulfopin and palbociclib had limited single agent activity in this model. However, the combination of sulfopin and either of two CDK4/6 inhibitors suppressed tumor growth nearly completely (FIG. 14E-FIG. 14H), with 2/7 PDOX tumors achieving a complete remission. These results were supported by immunofluorescent analysis of tumors revealing a significant decrease in the levels of both Pin1 and APC/$C^{Cdh1}$ known substrates in tumors from mice treated with sulfopin and CDK4/6 inhibitors (FIG. 19A and FIG. 19B). With regard to safety and tolerability, the two-drug regimen showed no bone marrow suppression and was well tolerated with maintenance of body weight (FIG. 15B-FIG. 15K). These data demonstrate that Pin1 inhibitors synergize with CDK4/6 inhibitors against TNBC in human cells and PDOX mice.

To further support these findings, the anti-tumor activity of sulfopin and abemaciclib in Brca1-deficient cohort and in Brca1-proficient cohort were studied, and showed no response to chemotherapy (data not shown). Treatment with sulfopin combined with abemaciclib was well-tolerated, significantly delayed tumor progression and increased overall survival compared to either monotherapy in both of the cohorts (FIG. 18A-FIG. 18D). The preclinical activity of this regimen and its excellent safety profile with non-overlapping toxicity profiles make it a strong candidate for clinical development.

Collectively, the above data show two distinct modes of interaction. On the one hand, when phosphorylated in tumor cells, Cdh1 binds to the WW domain of Pin1, which catalyzes prolyl isomerization to stabilize phosphorylated Cdh1, thereby rendering APC/$C^{Cdh1}$ inactive. On the other, when unphosphorylated, Cdh1 is active and targets the D-box motif in the PPIase domain of Pin1 for degradation, which can be pharmacologically enhanced by Pin1 inhibitor engagement. Thus, depending on the binding modes, Pin1 is either a downstream substrate of APC/$C^{Cdh1}$ or its upstream regulator.

All patent publications and non-patent publications are indicative of the level of skill of those skilled in the art to which this disclosure pertains. All these publications are herein incorporated by reference to the same extent as if each individual publication were specifically and individually indicated as being incorporated by reference.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

SEQUENCE LISTING

```
Sequence total quantity: 30
SEQ ID NO: 1            moltype = DNA  length = 21
FEATURE                 Location/Qualifiers
source                  1..21
                        mol_type = other DNA
                        organism = synthetic construct
SEQUENCE: 1
cagaccgtgc agaatgttac a                                            21

SEQ ID NO: 2            moltype = DNA  length = 20
FEATURE                 Location/Qualifiers
source                  1..20
                        mol_type = other DNA
                        organism = synthetic construct
SEQUENCE: 2
tcctgaccgt atggcttagc                                              20

SEQ ID NO: 3            moltype = DNA  length = 23
FEATURE                 Location/Qualifiers
source                  1..23
                        mol_type = other DNA
```

-continued

```
                        organism = synthetic construct
SEQUENCE: 3
ggatgatgaa gatggagatg atg                                          23

SEQ ID NO: 4            moltype = DNA  length = 21
FEATURE                 Location/Qualifiers
source                  1..21
                        mol_type = other DNA
                        organism = synthetic construct
SEQUENCE: 4
cgcaacagct cagagtctct c                                            21

SEQ ID NO: 5            moltype = DNA  length = 22
FEATURE                 Location/Qualifiers
source                  1..22
                        mol_type = other DNA
                        organism = synthetic construct
SEQUENCE: 5
ttccagtaac gatgaccata gg                                           22

SEQ ID NO: 6            moltype = DNA  length = 21
FEATURE                 Location/Qualifiers
source                  1..21
                        mol_type = other DNA
                        organism = synthetic construct
SEQUENCE: 6
cagcatcaac atcaattccc t                                            21

SEQ ID NO: 7            moltype = DNA  length = 21
FEATURE                 Location/Qualifiers
source                  1..21
                        mol_type = other DNA
                        organism = synthetic construct
SEQUENCE: 7
ttcgagagac tccagtggaa c                                            21

SEQ ID NO: 8            moltype = DNA  length = 22
FEATURE                 Location/Qualifiers
source                  1..22
                        mol_type = other DNA
                        organism = synthetic construct
SEQUENCE: 8
gttgtgggtt catcattcac tg                                           22

SEQ ID NO: 9            moltype = DNA  length = 23
FEATURE                 Location/Qualifiers
source                  1..23
                        mol_type = other DNA
                        organism = synthetic construct
SEQUENCE: 9
tcatccacag attcagagca ttc                                          23

SEQ ID NO: 10           moltype = DNA  length = 24
FEATURE                 Location/Qualifiers
source                  1..24
                        mol_type = other DNA
                        organism = synthetic construct
SEQUENCE: 10
cagaacagtc agctgattga taca                                         24

SEQ ID NO: 11           moltype = DNA  length = 19
FEATURE                 Location/Qualifiers
source                  1..19
                        mol_type = other DNA
                        organism = synthetic construct
SEQUENCE: 11
gctgcatgtt ctgctgctg                                               19

SEQ ID NO: 12           moltype = DNA  length = 22
FEATURE                 Location/Qualifiers
source                  1..22
                        mol_type = other DNA
                        organism = synthetic construct
SEQUENCE: 12
atacgtcaag tcacattcca cg                                           22

SEQ ID NO: 13           moltype = DNA  length = 19
FEATURE                 Location/Qualifiers
source                  1..19
```

-continued

```
                        mol_type = other DNA
                        organism = synthetic construct
SEQUENCE: 13
tacgactgcg aacagcgac                                                19

SEQ ID NO: 14           moltype = DNA  length = 19
FEATURE                 Location/Qualifiers
source                  1..19
                        mol_type = other DNA
                        organism = synthetic construct
SEQUENCE: 14
gctgagcgac tgtcggaag                                                19

SEQ ID NO: 15           moltype = DNA  length = 27
FEATURE                 Location/Qualifiers
source                  1..27
                        mol_type = other DNA
                        organism = synthetic construct
SEQUENCE: 15
gggatccact agttctagtt agagcgg                                       27

SEQ ID NO: 16           moltype = DNA  length = 28
FEATURE                 Location/Qualifiers
source                  1..28
                        mol_type = other DNA
                        organism = synthetic construct
SEQUENCE: 16
ccagggctct taatccaatc attctcca                                      28

SEQ ID NO: 17           moltype = DNA  length = 17
FEATURE                 Location/Qualifiers
source                  1..17
                        mol_type = other DNA
                        organism = synthetic construct
SEQUENCE: 17
cagagagcct gtctcaa                                                  17

SEQ ID NO: 18           moltype = DNA  length = 25
FEATURE                 Location/Qualifiers
source                  1..25
                        mol_type = other DNA
                        organism = synthetic construct
SEQUENCE: 18
tgggcttgct gactagttat tacag                                         25

SEQ ID NO: 19           moltype = DNA  length = 31
FEATURE                 Location/Qualifiers
source                  1..31
                        mol_type = other DNA
                        organism = synthetic construct
SEQUENCE: 19
gctcttaatc caatcattct ccaccttatt t                                  31

SEQ ID NO: 20           moltype = DNA  length = 16
FEATURE                 Location/Qualifiers
source                  1..16
                        mol_type = other DNA
                        organism = synthetic construct
SEQUENCE: 20
caagccccgg gtgcag                                                   16

SEQ ID NO: 21           moltype = DNA  length = 37
FEATURE                 Location/Qualifiers
source                  1..37
                        mol_type = other DNA
                        organism = synthetic construct
SEQUENCE: 21
cgtataatgt atgctatacg aagttatctg cagcccg                            37

SEQ ID NO: 22           moltype = DNA  length = 21
FEATURE                 Location/Qualifiers
source                  1..21
                        mol_type = other DNA
                        organism = synthetic construct
SEQUENCE: 22
ggcacctttg atcccagcac a                                             21

SEQ ID NO: 23           moltype = DNA  length = 18
FEATURE                 Location/Qualifiers
```

-continued

```
source                1..18
                      mol_type = other DNA
                      organism = synthetic construct
SEQUENCE: 23
tccaactgtc tctgcctc                                            18

SEQ ID NO: 24         moltype = DNA  length = 27
FEATURE               Location/Qualifiers
source                1..27
                      mol_type = other DNA
                      organism = synthetic construct
SEQUENCE: 24
cagcagtaac ctcctgggaa tacttca                                  27

SEQ ID NO: 25         moltype = DNA  length = 27
FEATURE               Location/Qualifiers
source                1..27
                      mol_type = other DNA
                      organism = synthetic construct
SEQUENCE: 25
ctcaggaaaa caaattatga ttcgaac                                  27

SEQ ID NO: 26         moltype = DNA  length = 17
FEATURE               Location/Qualifiers
source                1..17
                      mol_type = other DNA
                      organism = synthetic construct
SEQUENCE: 26
cagtcagtcg ccctttc                                             17

SEQ ID NO: 27         moltype = AA  length = 23
FEATURE               Location/Qualifiers
source                1..23
                      mol_type = protein
                      organism = synthetic construct
NON_STD               3
                      note = phosphorylated serine 163
NON_STD               4
                      note = carbon and nitrogen isotope labeled proline 164
SEQUENCE: 27
LRSPRKPTRK ISKIPFKVLD APE                                      23

SEQ ID NO: 28         moltype = AA  length = 12
FEATURE               Location/Qualifiers
source                1..12
                      mol_type = protein
                      organism = Homo sapiens
SEQUENCE: 28
KARGDLGAFS RG                                                  12

SEQ ID NO: 29         moltype = AA  length = 12
FEATURE               Location/Qualifiers
source                1..12
                      mol_type = protein
                      organism = Homo sapiens
SEQUENCE: 29
KARGDLGPFS RG                                                  12

SEQ ID NO: 30         moltype = AA  length = 4
FEATURE               Location/Qualifiers
source                1..4
                      mol_type = protein
                      organism = Homo sapiens
SEQUENCE: 30
KLLR                                                           4
```

What is claimed is:

1. A method of treating a disease or disorder mediated by dysregulated cyclin-dependent kinase 4/6 (CDK4/6) activity, in a subject in need thereof, or a method of reducing the activity of CDK4/6 in a cell, either in vivo or in vitro, comprising co-administering a therapeutically effective amount of one or more CDK4/6 inhibitors, and a therapeutically effective amount of one or more peptidyl-prolyl cis-trans isomerase NIMA-interacting 1 (Pin1) inhibitors, or a pharmaceutically acceptable salt or salts thereof.

2. The method of claim 1, wherein the co-administering results in greater therapeutic effect than the effect of the one or more CDK4/6 inhibitors when administered as a monotherapy, without the one or more Pin1 inhibitors.

3. The method of claim 1, wherein the one or more CDK4/6 inhibitors is palbociclib, abemaciclib, ribociclib, or a combination thereof.

4. The method of claim 1, wherein the one or more CDK4/6 inhibitors is palbociclib.

5. The method of claim 1, wherein the one or more Pin1 inhibitors is sulfopin, all-trans retinoic acid (ATRA), arsenic trioxide (ATO), or a combination thereof, or a pharmaceutically acceptable salt or stereoisomer thereof.

6. The method of claim 1, wherein the one or more Pin1 inhibitors is sulfopin.

7. The method of claim 1, wherein the one or more Pin1 inhibitors is ATRA and ATO.

8. The method of claim 1, further comprising administering an immunotherapy, wherein the immunotherapy is anti-programmed cell death protein 1 (anti-PD-1) or anti programmed death-ligand 1 (anti-PD-L1).

9. The method of claim 8, wherein the immunotherapy is anti-PD-L1.

10. The method of claim 1, wherein the one or more CDK4/6 inhibitors is palbociclib and wherein the one or more Pin1 inhibitors is sulfopin; or wherein the one or more CDK4/6 inhibitors is palbociclib and wherein the one or more Pin1 inhibitors is ATRA and ATO; or wherein the one or more CDK4/6 inhibitors is abemaciclib and wherein the one or more Pin1 inhibitors is sulfopin; or wherein the one or more CDK4/6 inhibitors is abemaciclib and wherein the one or more Pin1 inhibitors is ATRA and ATO; or wherein the one or more CDK4/6 inhibitors is ribociclib and wherein the one or more Pin1 inhibitors is sulfopin or wherein the one or more CDK4/6 inhibitors is ribociclib and wherein the one or more Pin1 inhibitors is ATRA and ATO.

11. The method of claim 10, further comprising administering an immunotherapy, wherein the immunotherapy is anti-PD-L1.

12. The method of claim 1, wherein the disease is cancer.

13. The method of claim 12, wherein the cancer is breast cancer.

14. The method of claim 13, wherein the breast cancer is endocrine resistant estrogen receptor positive (ER+) breast cancer, or triple negative breast cancer; or wherein the breast cancer is either local, locally advanced, or metastatic endocrine resistant ER+ breast cancer; or wherein the breast cancer is either local, locally advanced, or metastatic triple negative breast cancer breast cancer.

15. A pharmaceutical composition, comprising a therapeutically effective amount of one or more CDK4/6 inhibitors, wherein the one or more CDK4/6 inhibitors is palbociclib, abemaciclib, ribociclib, or a combination thereof, and a therapeutically effective amount of one or more Pin1 inhibitors, wherein the one or more Pin1 inhibitors is sulfopin, ATRA, ATO, or a combination thereof, or a pharmaceutically acceptable salt or stereoisomer thereof.

16. The pharmaceutical composition of claim 15, which is in the form of a liquid or a solid.

17. The pharmaceutical composition of claim 16, wherein the solid is in the form of a tablet or capsule.

18. The pharmaceutical composition of claim 15, further comprising a therapeutically effective amount of one or more immunotherapies, wherein the one or more immunotherapies is anti-PD-1 or anti-PD-L1.

19. The method of claim 2, wherein the greater therapeutic effect is a synergistic effect or the reduction of tumor growth in triple negative breast cancer.

20. A kit comprising:

one or more CDK4/6 inhibitors and one or more Pin1 inhibitors, or a pharmaceutically acceptable salt or stereoisomer thereof, or the pharmaceutical composition of claim 15; and instructions for administering to a subject or instructions for contacting a biological sample with the one or more CDK4/6 inhibitors and the one or more Pin1 inhibitors or the pharmaceutical composition.

21. The kit of claim 20, further comprising one or more immunotherapies, wherein the one or more immunotherapies is anti-PD-1 or anti-PD-L1.

* * * * *